United States Patent
Hernandez et al.

(10) Patent No.: US 9,656,963 B2
(45) Date of Patent: May 23, 2017

(54) DIHYDROPYRAZOLE GPR40 MODULATORS

(71) Applicant: BRISTOL-MYERS SQUIBB COMPANY, Princeton, NJ (US)

(72) Inventors: Andres S. Hernandez, Lawrenceville, NJ (US); Bruce A. Ellsworth, Princeton, NJ (US); William R. Ewing, Yardley, NJ (US); Bin Chen, Lambertville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 56 days.

(21) Appl. No.: 14/442,624

(22) PCT Filed: Nov. 15, 2013

(86) PCT No.: PCT/US2013/070209
§ 371 (c)(1),
(2) Date: May 13, 2015

(87) PCT Pub. No.: WO2014/078608
PCT Pub. Date: May 22, 2014

(65) Prior Publication Data
US 2016/0280659 A1    Sep. 29, 2016

Related U.S. Application Data

(60) Provisional application No. 61/727,191, filed on Nov. 16, 2012.

(51) Int. Cl.
| | |
|---|---|
| C07D 231/06 | (2006.01) |
| C07D 403/12 | (2006.01) |
| C07D 231/08 | (2006.01) |
| C07D 401/10 | (2006.01) |
| C07D 403/04 | (2006.01) |
| C07D 401/04 | (2006.01) |
| C07D 401/12 | (2006.01) |
| C07D 403/10 | (2006.01) |
| C07D 413/04 | (2006.01) |
| A61K 45/06 | (2006.01) |
| A61K 31/4155 | (2006.01) |
| A61K 31/415 | (2006.01) |
| A61K 31/506 | (2006.01) |
| A61K 31/497 | (2006.01) |
| A61K 31/422 | (2006.01) |
| A61K 31/4439 | (2006.01) |

(52) U.S. Cl.
CPC .......... *C07D 231/06* (2013.01); *A61K 31/415* (2013.01); *A61K 31/4155* (2013.01); *A61K 31/422* (2013.01); *A61K 31/4439* (2013.01); *A61K 31/497* (2013.01); *A61K 31/506* (2013.01); *A61K 45/06* (2013.01); *C07D 231/08* (2013.01); *C07D 401/04* (2013.01); *C07D 401/10* (2013.01); *C07D 401/12* (2013.01); *C07D 403/04* (2013.01); *C07D 403/10* (2013.01); *C07D 403/12* (2013.01); *C07D 413/04* (2013.01)

(58) Field of Classification Search
None
See application file for complete search history.

(56) References Cited

U.S. PATENT DOCUMENTS

| | | |
|---|---|---|
| 5,614,492 A | 3/1997 | Habener |
| 8,791,091 B2 | 7/2014 | Turdi et al. |
| 2011/0082165 A1* | 4/2011 | Ellsworth ............ C07D 207/06 514/275 |

FOREIGN PATENT DOCUMENTS

| | | |
|---|---|---|
| EP | 1 743 894 A1 | 1/2007 |
| WO | WO 2004/099192 A2 | 11/2004 |
| WO | WO 2005/012249 | 2/2005 |
| WO | WO 2009/115515 | 9/2009 |
| WO | WO 2012/068529 | 5/2012 |

OTHER PUBLICATIONS

West, Anthony R., Solid State Chemistry and Its Applications, Wiley, New York, 1988, 358.*
Ainsworth, P.J. et al., "Intramolecular Diels-Alder Reactions of Silyl Acetal-tethered Trienes", Tetrahedron, vol. 51, No. 42, pp. 11601-11622 (1995).
Arbeeny, C. et al., "The Metabolic Syndrome: From Pathophysiology to Novel Treatment Strategies", Curr. Med. Chem.—Imm., Endoc. & Metab. Agents, vol. 1, No. 1, pp. 1-24 (2001).
Barlind, J.G. et al., "Identification and design of a novel series of MGAT2 inhibitors", Bioorganic & Medicinal Chemistry Letters, vol. 23, pp. 2721-2726 (2013).

(Continued)

*Primary Examiner* — Erich A Leeser
(74) *Attorney, Agent, or Firm* — Barry H. Jacobsen; Yong Lu

(57) ABSTRACT

The present invention provides compounds of Formula (I): or a stereoisomer, or a pharmaceutically acceptable salt thereof, wherein all of the variables are as defined herein. These compounds are GPR40 G protein-coupled receptor modulators which may be used as medicaments.

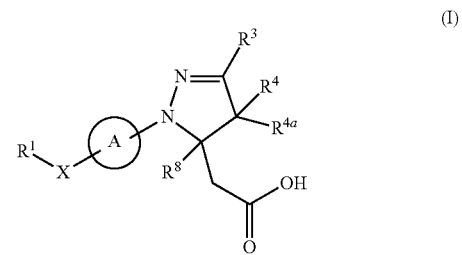

15 Claims, No Drawings

(56) References Cited

OTHER PUBLICATIONS

Bundgaard, H., Chapter 5: "Design and Application of Prodrugs", A Textbook of Drug Design and Development, pp. 113-191, Krogsgaard-Larsen, P. et al., eds., Harwood Academic Publishers, publ. (1991).

Bundgaard, H., ed., Design of Prodrugs, Elsevier Science Publishers B.V., publ. (1985).

Bundgaard, H., "Prodrugs as a means to improve the delivery of peptide drugs", Advanced Drug Delivery Reviews, vol. 8, pp. 1-38 (1992).

De Benassuti, L. et al., "Oxygenated monoterpenes as dipolarophiles for nitrilimine cycloadditions", Tetrahedron, vol. 60, pp. 4627-4633 (2004).

Edfalk, S. et al., "*Gpr40* is Expressed in Enteroendocrine Cells and Mediates Free Fatty Acid Stimulation of Incretin Secretion", Diabetes, vol. 57, pp. 2280-2287 (2008).

Elangbam, C.S., "Review Paper: Current Strategies in the Development of Anti-obesity Drugs and Their Safety Concerns", Vet. Pathol., vol. 46, No. 1, pp. 10-24 (2009).

Ford, E.S. et al., "Prevalence of the Metabolic Syndrome Among US Adults: Findings from the Third National Health and Nutrition Examination Survey", Journal of the American Medical Association, vol. 287, No. 3, pp. 356-359 (2002).

Fyfe, M.C.T. et al., "Glucokinase Activators as Potential Antidiabetic Agents Possessing Superior Glucose-Lowering Efficacy", Drugs of the Future, vol. 34, No. 8, pp. 641-653 (2009).

Garanti, L. et al., "Diastereoselective cycloadditions of nitrilimines to enantiopure acrylamides", Tetrahedron: Asymmetry, vol. 13, pp. 1285-1289 (2002).

Itoh, Y. et al., "Free fatty acids regulate insulin secretion from pancreatic β cells through GPR40", Nature, vol. 422, pp. 173-176 (2003).

Jones, D., "Novel pharmacotherapies for obesity poised to enter market", Nature Reviews: Drug Discovery, vol. 8, pp. 833-834 (2009).

Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).

Larock, R.C., Comprehensive Organic Transformations: A Guide to Functional Group Preparations, pp. xiii-xxviii, VCH Publishers, Inc., publ. (1989).

Lewis, Sr., R.J., Hawley's Condensed Chemical Dictionary, Thirteenth Edition, John Wiley & Sons, Inc., publ. (1997).

Luo, S. et al., "The Cotton Centromere Contains a Ty3-*gypsy*-like LTR Retroelement", PLoS ONE, vol. 7, No. 4, pp. 1-10 (2012).

Manyem, S. et al., "Solution-Phase Parallel Synthesis of a Library of Δ²-Pyrazikubes", J. Comb. Chem., vol. 9, No. 1, pp. 20-28 (2007).

Melnikova, I. et al., "Anti-obesity therapies", Nature Reviews Drug Discovery, 5, pp. 369-370 (2006).

Mizuno, C.S. et al., "Type 2 Diabetes and Oral Antihyperglycemic Drugs", Current Medicinal Chemistry, vol. 15, No. 1, pp. 61-74 (2008).

Mohler, M.L. et al., "Recent and Emerging Anti-Diabetes Targets", Medicinal Research Reviews, vol. 29, No. 1, pp. 125-195 (2009).

Molteni, G., "The first case of diastereoselective cycloadditions of enantiopure nitrilimines in aqueous media", Tetrahedron: Asymmetry, vol. 15, pp. 1077-1079 (2004).

NCBI Reference Sequence No. NM_005303, Kristinsson, H. et al., Feb. 20, 2014.

NCBI Reference Sequence No. NM_194057, Shen, X. et al., May 24, 2014.

Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).

Obici, S., "Minireview: Molecular Targets for Obesity Therapy in the Brain", Endocrinology, vol. 150, No. 6, pp. 2512-2517 (2009).

Semmelhack, M.F., ed., Comprehensive Organic Synthesis: Selectivity, Strategy & Efficiency in Modern Organic Chemistry, vol. 4: "Additions to and Substitutions at C—C π-Bonds", pp. v-vi, Pergamon Press, Inc., publ. (1991).

Shimizu, T. et al., "The Reaction of *N*-Aryl-*C*-ethoxycarbonylnitrilimine with Olefins", Bull. Chem. Soc. Jpn., vol. 57, No. 3, pp. 787-790 (1984).

Shimpukade, B. et al., "Discovery of a Potent and Selective GPR120 Agonist", Journal of Medicinal Chemistry, vol. 55, pp. 4511-4515 (2012).

Sibi, M.P. et al., "An Entry to a Chiral Dihydropyrazole Scaffold: Enantioselective [3+2] Cycloaddition of Nitrile Imines", J. Am. Chem. Soc., vol. 127, No. 23, pp. 8276-8277 (2005).

Sibi, M.P. et al., "Nitrile Ylides: Diastereoselective Cycloadditions using Chiral Oxzolidinones without Lewis Acid", Organic Letters, vol. 11, No. 23, pp. 5366-5369 (2009).

Simpkins, L.M. et al., "Potent non-nitrile dipeptidic dipeptidyl peptidase IV inhibitors", Bioorganic & Medicinal Chemistry Letters, vol. 17, pp. 6476-6480 (2007).

Smith, M.B. et al., March's Advanced Organic Chemistry: Reactions, Mechanisms, and Structure, Sixth Edition, John Wiley & Sons, Inc. (2007).

Tan, C.P. et al., "Selective Small-Molecule Agonists of G Protein-Coupled Receptor 40 Promote Glucose-Dependent Insulin Secretion and Reduce Blood Glucose in Mice", Diabetes, vol. 57, pp. 2211-2219 (2008).

Testa, B. et al., Hydrolysis in Drug and Prodrug Metabolism: Chemistry, Biochemistry, and Enzymology, pp. xi-xx, Wiley-VCH GmbH & Co., publ. (2003).

Widder, K.J. et al., eds., Section III: "Prodrugs", Methods in Enzymology, vol. 112, pp. 309-396, Academic Press, Inc., publ. (1985).

Yamashima, T., "A putative link of PUFA, GPR40 and adult-born hippocampal neurons for memory", Progress in Neurobiology, vol. 84, pp. 105-115 (2008).

\* cited by examiner

DIHYDROPYRAZOLE GPR40 MODULATORS

CROSS-REFERENCE TO RELATED APPLICATIONS

The present application is a 371 of International Application No. PCT/US2013/070209 filed on Nov. 15, 2013, which claims priority benefit of U.S. provisional application Ser. No. 61/727,191, filed Nov. 16, 2012; each of which is fully incorporated by reference herein.

FIELD OF THE INVENTION

The present invention provides novel carboxylic acid substituted dihydropyrazole compounds, and their analogues thereof, which are GPR40 G protein-coupled receptor modulators, compositions containing them, and methods of using them, for example, for the treatment or prophylaxis of diabetes and related conditions.

BACKGROUND OF THE INVENTION

Diabetes mellitus is a progressively debilitating disorder of epidemic proportions leading to various micro- and macrovascular complications and morbidity. The most common type of diabetes, type 2 diabetes, is characterized by increasing insulin resistance associated with inadequate insulin secretion after a period of compensatory hyperinsulinemia. Free fatty acids (FFAs) are evidenced to influence insulin secretion from β cells primarily by enhancing glucose-stimulated insulin secretion (GSIS). G-protein coupled receptors (GPCRs) expressed in β cells are known to modulate the release of insulin in response to changes in plasma glucose levels. GPR40, also known as fatty acid receptor 1 (FFAR1), is a membrane-bound FFA receptor which is preferentially expressed in the pancreatic islets and specifically in β cells and mediates medium to long chain fatty acid induced insulin secretion. GPR40 is also expressed in enteroendocrine cells wherein activation promotes the secretion of gut incretin hormones, such as GLP-1, GIP, CCK and PYY. To decrease medical burden of type 2 diabetes through enhanced glycemic control, GPR40 modulator compounds hold the promise of exerting an incretin effect to promote GSIS as well as potential combination with a broad range of antidiabetic drugs.

The present invention relates to novel substituted dihydropyrazole compounds which have the ability to modulate GPR40. Such compounds are therefore potentially useful for the treatment or prophylaxis of diabetes and related conditions.

SUMMARY OF THE INVENTION

The present invention provides substituted dihydropyrazole compounds, and their analogues thereof, which are useful as GPR40 modulators, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of multiple diseases or disorders associated with GPR40, such as diabetes and related conditions, microvascular complications associated with diabetes, the macrovascular complications associated with diabetes, cardiovascular diseases, Metabolic Syndrome and its component conditions, disorders of glucose metabolism, obesity and other maladies.

The compounds of the invention may be used in therapy.

The compounds of the invention may be used for the manufacture of a medicament for the treatment and/or prophylaxis of multiple diseases or disorders associated with GPR40.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

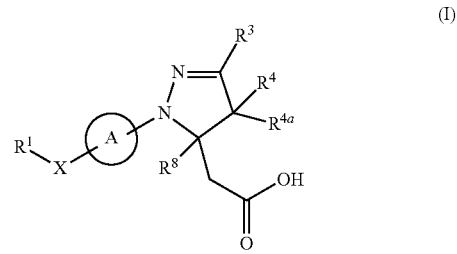

or a stereoisomer, a tautomer, a pharmaceutically acceptable salt, or a solvate thereof, wherein:

X is independently selected from: O, S, $CH_2$, and $CH(C_{1-4}$ alkyl);

ring A is independently

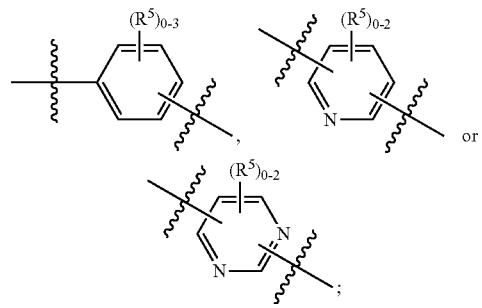

$R^1$ is

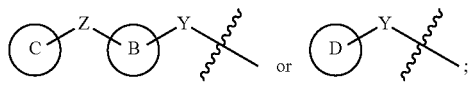

Y is independently selected from: a bond, $C_{1-4}$ alkylene, $C_{2-4}$ alkenylene, and $C_{2-4}$ alkynylene;
Z is independently selected from: a bond, W, $C_{1-4}$ alkylene, W—$C_{1-4}$ alkylene, and $C_{1-4}$ alkylene-W;
W is independently selected from: O, S and NH;
ring B and ring D are independently phenyl, naphthyl or a 5- to 6-membered heteroaryl containing carbon atoms and 1-4 heteroatoms selected from N, $NR^{11}$, O, and S; wherein said phenyl, naphthyl and heteroaryl are each substituted with 0-3 $R^2$;
ring C is independently phenyl, naphthyl or a 5- to 10-membered heteroaryl containing carbon atoms and 1-4 heteroatoms selected from N, $NR^{11}$, O, and S; wherein said phenyl, naphthyl and heteroaryl are each substituted with 0-3 $R^6$;
$R^2$, at each occurrence, is independently selected from: $C_{1-6}$ alkyl substituted with 0-2 $R^a$, $C_{2-6}$ alkenyl substituted with 0-2 $R^a$, $C_{1-6}$ alkoxy substituted with 0-2 $R^a$, $C_{1-6}$ alkylthio substituted with 0-2 $R^a$, halogen, $CHF_2$, $CF_3$, $OCF_3$, $OCHF_2$, $SCF_3$, CN, $NO_2$, $NH_2$, $NH(C_{1-4}$ alkyl), $N(C_{1-4}$ alkyl$)_2$, and a $C_{3-10}$ carbocycle substituted with 0-3 $R^b$;
$R^3$ is independently selected from: H, halogen, CN, OH, $CO_2H$, $C_{1-4}$ alkyl, $C_{1-4}$ alkenyl, $C_{1-4}$ alkynyl, $C_{1-4}$ haloalkyl, $OR^9$, $SR^9$, $C(O)OR^9$, $CO_2R^9$, $S(O)R^9$, $SO_2R^9$, $CONHR^9$, $CON(C_{1-4}$ alkyl$)_2$, —(O)$_n$—(CH$_2$)$_m$-phenyl, —(CH$_2$)$_m$-(5- to 10-membered heteroaryl containing carbon atoms and 1-4 heteroatoms selected from N, $NR^{11}$, O, and S); wherein said phenyl and heteroaryl are substituted with 0-2 $R^{10}$;
$R^4$ is independently selected from: H, $C_{1-4}$ alkyl substituted with 0-1 $R^c$, and —(CH$_2$)$_m$—$C_{3-6}$ carbocycle substituted with 0-2 $R^c$;
$R^{4a}$ is independently selected from: H, halogen, $C_{1-4}$ alkyl, and —(CH$_2$)$_m$—$C_{3-6}$ carbocycle;
$R^5$, at each occurrence, is independently selected from: halogen and $C_{1-4}$ alkyl;
$R^6$, at each occurrence, is independently selected from: halogen, OH, $C_{1-4}$ alkylthio, CN, $SO_2(C_{1-2}$ alkyl), $N(C_{1-4}$ alkyl$)_2$, $C_{1-4}$ haloalkyl, $C_{1-4}$ haloalkoxy, $C_{1-6}$ alkyl substituted with 0-1 $R^7$, $C_{1-4}$ alkoxy substituted with 0-1 $R^7$, —(O)$_n$—(CH$_2$)$_m$—(C$_{3-10}$ carbocycle substituted with 0-2 $R^7$), and —(CH$_2$)$_m$-(5- to 10-membered heteroaryl containing carbon atoms and 1-4 heteroatoms selected from N, $NR^{11}$, O, and S; wherein said heteroaryl is substituted with 0-2 $R^7$;
$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl$)_2$, $SO_2(C_{1-2}$ alkyl), and phenyl;
$R^8$ is independently selected from: H and $C_{1-4}$ alkyl;
$R^9$, at each occurrence, is independently selected from: $C_{1-4}$ alkyl, $C_{1-4}$ haloalkyl and —(CH$_2$)$_m$-phenyl;
$R^{10}$, at each occurrence, is independently selected from: halogen, CN, $C_{1-4}$ haloalkyl, $C_{1-4}$ haloalkoxy, $SCF_3$, $NO_2$, and $CO_2(C_{1-4}$ alkyl);
$R^{11}$, at each occurrence, is independently selected from: H, $C_{1-4}$ alkyl and benzyl;

$R^a$, at each occurrence, is independently selected from: OH, $C_{1-4}$ alkoxy, $C_{1-4}$ alkylthio, halogen, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl$)_2$, $SO_2(C_{1-2}$ alkyl) and phenyl;
$R^b$, at each occurrence, is independently selected from: OH, $C_{1-4}$ alkyl, $C_{2-4}$ alkenyl, $C_{1-4}$ alkoxy, $C_{1-4}$ alkylthio, halogen, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl$)_2$, and $SO_2(C_{1-2}$ alkyl);
$R^c$, at each occurrence, is independently selected from: OH, $C_{1-4}$ alkoxy, halogen, $CF_3$, $OCF_3$, and CN;
m, at each occurrence, is independently 0, 1, or 2; and
n, at each occurrence, is independently 0 or 1.

In a second aspect, the present disclosure provides a compound of Formula (I), wherein $R^{4a}$ is hydrogen and $R^8$ is hydrogen, further characterized by Formula (II):

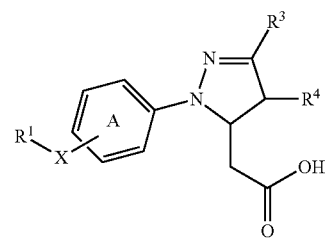

(II)

or a stereoisomer, a tautomer, a pharmaceutically acceptable salt, or a solvate thereof, wherein:
X is independently selected from: O, S, $CH_2$, and $CH(C_{1-4}$ alkyl);
ring A is independently

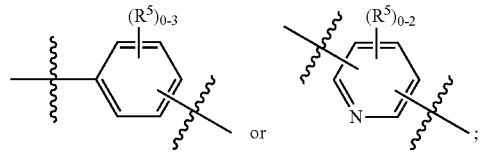

$R^1$ is

Y is independently selected from: a bond, $C_{1-4}$ alkylene, $C_{2-4}$ alkenylene, and $C_{2-4}$ alkynylene;
Z is independently selected from: a bond, W, $C_{1-4}$ alkylene, W—$C_{1-4}$ alkylene, and $C_{1-4}$ alkylene-W;
W is independently selected from: O, S and NH;
ring B and ring D are independently phenyl, naphthyl or a 5- to 6-membered heteroaryl containing carbon atoms and 1-4 heteroatoms selected from N, $NR^{11}$, O, and S; wherein said phenyl, naphthyl and heteroaryl are each substituted with 0-3 $R^2$;
ring C is independently phenyl, naphthyl or a 5- to 10-membered heteroaryl containing carbon atoms and 1-4 heteroatoms selected from N, $NR^{11}$, O, and S; wherein said phenyl, naphthyl and heteroaryl are each substituted with 0-3 $R^6$;

R² , at each occurrence, is independently selected from: $C_{1-6}$ alkyl substituted with 0-2 R^a, $C_{2-6}$ alkenyl substituted with 0-2 R^a, $C_{1-6}$ alkoxy substituted with 0-2 R^a, $C_{1-6}$ alkylthio substituted with 0-2 R^a, halogen, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl)$_2$, and a $C_{3-10}$ carbocycle substituted with 0-3 R^b;

R³ is independently selected from: H, halogen, CN, $SO_2(C_{1-4}$ alkyl), $CONH(C_{1-4}$ alkyl), $CON(C_{1-4}$ alkyl)$_2$, $C_{1-4}$ alkyl, $C_{1-4}$ alkoxy, $C_{1-4}$ alkylthio, $C_{1-4}$ haloalkyl, $C_{1-4}$ haloalkoxy, phenyl, benzyl, phenoxy, and a 5- to 10-membered heteroaryl containing carbon atoms and 1-4 heteroatoms selected from N, $NR^{11}$, O, and S; wherein said phenyl, benzyl, phenoxy and heteroaryl is substituted with 0-2 $R^{10}$;

R⁴ is independently selected from: H, $C_{1-4}$ alkyl substituted with 0-1 R^c, and —$(CH_2)_m$—$C_{3-6}$ carbocycle substituted with 0-2 R^c;

R⁵, at each occurrence, is independently selected from: halogen and $C_{1-4}$ alkyl;

R⁶, at each occurrence, is independently selected from: halogen, OH, $CH_2OH$, $C_{1-4}$ alkylthio, CN, $SO_2(C_{1-2}$ alkyl), $N(C_{1-4}$ alkyl)$_2$, $C_{1-6}$ alkyl substituted with 0-1 R⁷, $C_{1-4}$ haloalkyl, $C_{1-4}$ haloalkoxy, —$(CH_2)_m$-(phenyl substituted with 0-2 R⁷), —$O(CH_2)_m$-(phenyl substituted with 0-2 R⁷), —$(CH_2)_m$-(naphthyl substituted with 0-2 R⁷), and —$(CH_2)_m$-(5- to 10-membered heteroaryl containing carbon atoms and 1-4 heteroatoms selected from the group consisting of N, O, and S; wherein said heteroaryl is substituted with 0-2 R⁷;

R⁷, at each occurrence, is independently selected from: OH, $C_{1-4}$ alkyl, $C_{2-4}$ alkenyl, $C_{1-4}$ alkoxy, $C_{1-4}$ alkylthio, halogen, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl)$_2$, $SO_2(C_{1-2}$ alkyl), and phenyl;

$R^{10}$, at each occurrence, is independently selected from: halogen, CN, $C_{1-4}$ haloalkyl, $C_{1-4}$ haloalkoxy, $SCF_3$, $NO_2$, and $CO_2(C_{1-4}$ alkyl);

$R^{11}$, at each occurrence, is independently selected from: H, $C_{1-4}$ alkyl and benzyl;

R^a, at each occurrence, is independently selected from: OH, $C_{1-4}$ alkoxy, $C_{1-4}$ alkylthio, halogen, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl)$_2$, $SO_2(C_{1-2}$ alkyl) and phenyl;

R^b, at each occurrence, is independently selected from: OH, $C_{1-4}$ alkyl, $C_{2-4}$ alkenyl, $C_{1-4}$ alkoxy, $C_{1-4}$ alkylthio, halogen, $C_{1-4}$ haloalkyl, $C_{1-4}$ haloalkoxy $SCF_3$, CN, $NO_2$, $NH_2$, $NH(C_{1-4}$ alkyl), $N(C_{1-4}$ alkyl)$_2$, and $SO_2(C_{1-2}$ alkyl);

R^c, at each occurrence, is independently selected from: OH, $C_{1-4}$ alkoxy, halogen, $C_{1-4}$ haloalkyl, $C_{1-4}$ haloalkoxy, and CN; and m, at each occurrence, is independently 0, 1, or 2.

In a third aspect, the present disclosure provides a compound of Formula (I) or (II), or a stereoisomer, a tautomer, a pharmaceutically acceptable salt, or a solvate thereof, within the scope of the first or second aspect, wherein:

X is independently selected from: O, S, and $CH_2$;
ring A is independently

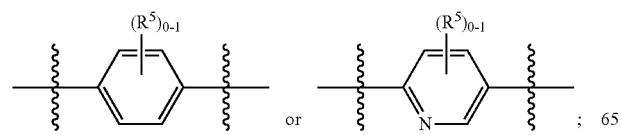

Y is independently selected from: a bond, $CH_2$, $CH_2CH_2$, and —CH=$CHCH_2$—;

Z is independently selected from: a bond, O, $CH_2$, $CH_2CH_2$, and $OCH_2$;

ring B and ring D are independently phenyl substituted with 0-3 R², or a heteroaryl substituted with 0-1 R² and selected from: thiazolyl, oxazolyl, pyrazolyl, pyridinyl, pyrimidinyl, pyrazinyl, and pyridazinyl;

ring C is independently phenyl substituted with 0-3 R⁶ or a heteroaryl substituted with 0-2 R⁶; wherein said heteroaryl is selected from: furanyl, oxazolyl, thiazolyl, pyrazolyl, pyridinyl, pyrimidinyl, pyrazinyl, and pyridazinyl;

R², at each occurrence, is independently selected from: $C_{1-6}$ alkyl, $C_{1-6}$ alkoxy, halogen, CN, cyclopropyl, and 5,5-diMe-cyclopent-1-enyl;

R³ is independently selected from: halogen, CN, $CF_3$, $CF_2CF_3$, $CO_2H$, $SO_2(C_{1-4}$ alkyl), $CONH(C_{1-4}$ alkyl), $CON(C_{1-4}$ alkyl)$_2$, oxazolyl,

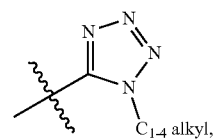

5-$C_{1-4}$ alkyl-isoxazol-3-yl, 1-$C_{1-4}$ alkyl-pyrazol-3-yl, pyridyl, pyrimidinyl, and phenyl substituted with 0-1 halo; and R⁶, at each occurrence, is independently selected from: halogen, OH, $CH_2OH$, $C_{1-4}$ alkylthio, CN, $SO_2(C_{1-2}$ alkyl), $N(C_{1-4}$ alkyl)$_2$, $C_{1-6}$ alkyl, $C_{1-4}$ alkoxy, $C_{1-4}$ haloalkyl, and $C_{1-4}$ haloalkoxy.

In a fourth aspect, the present disclosure provides a compound of Formula (I) or (II), or a stereoisomer, a tautomer, a pharmaceutically acceptable salt, or a solvate thereof, within the scope of the first, second or third aspect, wherein:

ring A is

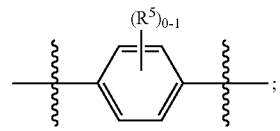

ring B and ring D are independently phenyl substituted with 0-3 R², pyridinyl substituted with 0-2 R² or pyrimidinyl substituted with 0-2 R²;

ring C is independently phenyl substituted with 0-3 R⁶, pyridinyl substituted with 0-2 R⁶, pyrimidinyl substituted with 0-2 R², or pyrazinyl substituted with 0-2 R⁶; and R⁴ is independently selected from: H, $C_{1-4}$ alkyl substituted with 0-1 R^c, $C_{3-6}$ carbocycle and —$CH_2$—$C_{3-6}$ carbocycle.

In a fifth aspect, the present disclosure provides a compound of Formula (III):

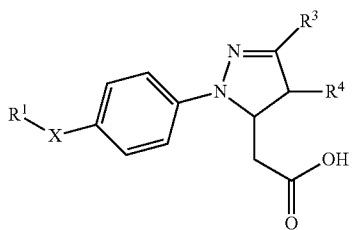

(III)

or a stereoisomer, a tautomer, a pharmaceutically acceptable salt, or a solvate thereof, wherein:
X is independently selected from: O and $CH_2$;
$R^1$ independently selected from: phenyl substituted with 0-3 $R^2$, benzyl substituted with 0-3 $R^2$,

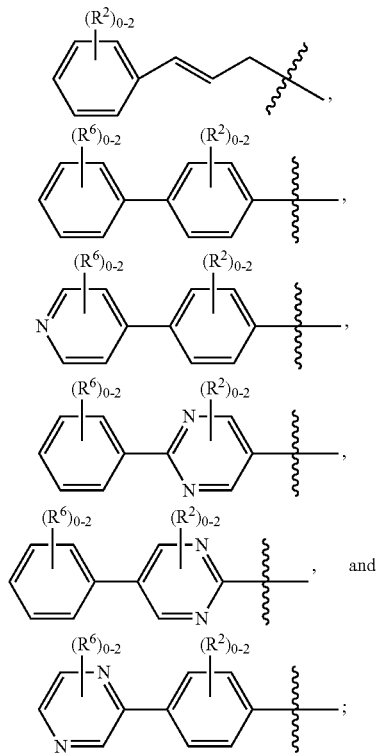

$R^2$, at each occurrence, is independently selected from: halogen, $C_{1-4}$ alkyl, and $C_{1-4}$ alkoxy;
$R^3$ is independently selected from: CN, $CF_3$, $SO_2(C_{1-4}$ alkyl), $CON(C_{1-4}$ alkyl$)_2$, oxazol-2-yl,

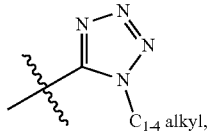

1-$C_{1-4}$ alkyl-pyrazol-3-yl, 5-$C_{1-4}$ alkyl-isoxazol-3-yl, pyrid-2-yl, pyrimidin-2-yl, and phenyl substituted with 0-1 halogen;
$R^4$ is independently selected from: H, $C_{1-4}$ alkyl substituted with 0-1 $R^c$, $C_{3-6}$ cycloalkyl, —$CH_2$—$C_{3-6}$ cycloalkyl, and Ph; and $R^6$, at each occurrence, is independently selected from: halogen, OH, CN, $C_{1-4}$ alkyl, $C_{1-4}$ alkoxy, $C_{1-4}$ haloalkyl, and $C_{1-4}$ haloalkoxy.

In a sixth aspect, the present disclosure provides a compound of Formula (III), or a stereoisomer, a tautomer, a pharmaceutically acceptable salt, or a solvate thereof, within the scope of the fifth aspect, wherein:
$R^1$ is independently

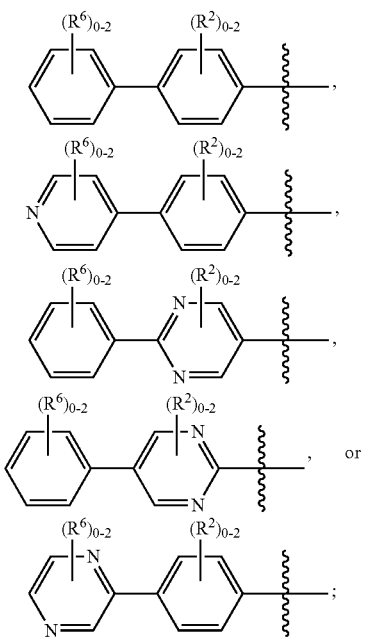

$R^2$, at each occurrence, is independently selected from: halo and $C_{1-4}$ alkyl;
$R^3$ is independently selected from: CN, $CF_3$, Ph, 3-halo-Ph, 4-halo-Ph, oxazolyl, 5-$C_{1-4}$ alkyl-isoxazol-3-yl, pyridyl and pyrimidinyl; and
$R^6$, at each occurrence, is independently selected from: halogen, OH, CN, $CF_3$, $OCF_3$, $C_{1-4}$ alkyl, and $C_{1-4}$ alkoxy.

In a seventh aspect, the present disclosure provides a compound of Formula (III), or a stereoisomer, a tautomer, a pharmaceutically acceptable salt, or a solvate thereof, within the scope of the fifth or sixth aspect, wherein:
$R^1$ is independently selected from: 4-(3-$C_{1-4}$ alkoxy-Ph)-2-$C_{1-4}$ alkyl-Ph, 4-(2-halo-5-OH-Ph)-2-$C_{1-4}$ alkyl-Ph, 4-(2-halo-5-$C_{1-4}$ alkoxy-Ph)-2-$C_{1-4}$ alkyl-Ph, 4-(2-halo-5-CN-Ph)-2-$C_{1-4}$ alkyl-Ph, 4-(2-halo-5-$C_{1-4}$ alkoxy-Ph)-3-$C_{1-4}$ alkyl-Ph, 4-(2-halo-5-$CF_3$-Ph)-3-$C_{1-4}$ alkyl-Ph, 4-(2-halo-5-$OCF_3$-Ph)-3-$C_{1-4}$ alkyl-Ph, 4-(2-halo-5-$C_{1-4}$ alkoxy-Ph)-2-halo-Ph, 4-(3-$C_{1-4}$ alkoxy-Ph)-2-$C_{1-4}$ alkyl-5-$C_{1-4}$ alkyl-Ph, 4-(2-halo-5-$C_{1-4}$ alkoxy-Ph)-2-$C_{1-4}$ alkyl-5-$C_{1-4}$ alkyl-Ph, 4-(2-halo-5-$C_{1-4}$ alkoxy-Ph)-2-$C_{1-4}$ alkyl-5-halo-Ph, 4-(2-halo-5-$C_{1-4}$ alkoxy-Ph)-2-$C_{1-4}$ alkyl-6-halo-Ph, 4-($C_{1-4}$ alkoxy-pyrid-4-yl)-2-$C_{1-4}$ alkyl-Ph, 4-(3-halo-6-$C_{1-4}$ alkoxy-pyrid-4-yl)-2-$C_{1-4}$ alkyl-Ph, 4-(pyrazin-2-yl)-2-$C_{1-4}$ alkyl-Ph, 2-Ph-4-$C_{1-4}$ alkyl-pyrimidin-5-yl, 5-(2-halo-5-$C_{1-4}$ alkoxy-Ph)-pyrimidin-2-yl, 2-(2-halo-5-$C_{1-4}$ alkoxy-Ph)-4-$C_{1-4}$ alkyl-pyrimidin-5-yl; and
$R^3$ is independently selected from: CN, $CF_3$, Ph, 3-halo-Ph, 4-halo-Ph, oxazol-2-yl, 5-$C_{1-4}$ alkyl-isoxazol-3-yl, pyrid-2-yl and pyrimidin-2-yl.

In an eighth aspect, the present invention includes a compound of Formula (III), or a stereoisomer, a tautomer, a pharmaceutically acceptable salt, or a solvate thereof, within the scope of any of the fifth, sixth and seventh aspects, wherein:

- $R^1$ is independently selected from: 4-(3-$C_{1-4}$ alkoxy-Ph)-2-$C_{1-4}$ alkyl-Ph, 4-(2-halo-5-OH-Ph)-2-$C_{1-4}$ alkyl-Ph, 4-(2-halo-5-$C_{1-4}$ alkoxy-Ph)-2-$C_{1-4}$ alkyl-Ph, 4-(2-halo-5-CN-Ph)-2-$C_{1-4}$ alkyl-Ph, 4-(2-halo-5-$C_{1-4}$ alkoxy-Ph)-3-$C_{1-4}$ alkyl-Ph, 4-(2-halo-5-OCF$_3$-Ph)-3-$C_{1-4}$ alkyl-Ph, 4-(2-halo-5-$C_{1-4}$ alkoxy-Ph)-2-halo-Ph, 4-(2-halo-5-$C_{1-4}$ alkoxy-Ph)-2-$C_{1-4}$ alkyl-5-$C_{1-4}$ alkyl-Ph, 4-(2-halo-5-$C_{1-4}$ alkoxy-Ph)-2-$C_{1-4}$ alkyl-6-halo-Ph, 4-(2-$C_{1-4}$ alkoxy-pyrid-4-yl)-2-$C_{1-4}$ alkyl-Ph, 4-(3-halo-6-$C_{1-4}$ alkoxy-pyrid-4-yl)-2-$C_{1-4}$ alkyl-Ph, and 2-(2-halo-5-$C_{1-4}$ alkoxy-Ph)-4-$C_{1-4}$ alkyl-pyrimidin-5-yl;
- $R^3$ is independently selected from: CN, CF$_3$, Ph, 3-halo-Ph, 4-halo-Ph, 5-$C_{1-4}$ alkyl-isoxazol-3-yl, pyrid-2-yl and pyrimidin-2-yl; and
- $R^4$ is independently selected from: H, $C_{1-4}$ alkyl, —CH$_2$OH, —CH$_2$O($C_{1-4}$ alkyl), —CH$_2$CN, $C_{3-6}$ cycloalkyl and —CH$_2$—$C_{3-6}$ cycloalkyl.

In a ninth aspect, the present disclosure provides a compound of Formula (III), or a stereoisomer, a tautomer, a pharmaceutically acceptable salt, or a solvate thereof, within the scope of the fifth aspect, wherein:

- $R^1$ is independently selected from: 4-(3-$C_{1-4}$ alkoxy-Ph)-2-$C_{1-4}$ alkyl-Ph, 4-(2-halo-5-OH-Ph)-2-$C_{1-4}$ alkyl-Ph, 4-(2-halo-5-$C_{1-4}$ alkoxy-Ph)-2-$C_{1-4}$ alkyl-Ph, 4-(2-halo-5-CN-Ph)-2-$C_{1-4}$ alkyl-Ph, 4-(2-halo-5-$C_{1-4}$ alkoxy-Ph)-2-halo-Ph, 4-(2-halo-5-$C_{1-4}$ alkoxy-Ph)-2-$C_{1-4}$ alkyl-5-$C_{1-4}$ alkyl-Ph, and 4-(3-halo-6-$C_{1-4}$ alkoxy-pyrid-4-yl)-2-$C_{1-4}$ alkyl-Ph;
- $R^3$ is independently selected from: CN, CF$_3$, Ph, 3-halo-Ph, 4-halo-Ph, 5-$C_{1-4}$ alkyl-isoxazol-3-yl, and pyrid-2-yl; and
- $R^4$ is independently selected from: H, $C_{1-4}$ alkyl, —CH$_2$OH, —CH$_2$O($C_{1-4}$ alkyl), $C_{3-6}$ cycloalkyl and —CH$_2$—$C_{3-6}$ cycloalkyl.

In another aspect, the present disclosure provides a compound of Formula (II), or a stereoisomer, a tautomer, a pharmaceutically acceptable salt, or a solvate thereof, within the scope of any of the fifth to eighth or tenth aspect, wherein:

- X is CH$_2$;
- $R^1$ is independently selected from: 4-(3-$C_{1-4}$ alkoxy-Ph)-2-$C_{1-4}$ alkyl-Ph, 4-(2-halo-5-$C_{1-4}$ alkoxy-Ph)-2-$C_{1-4}$ alkyl-Ph and 4-(2-halo-5-$C_{1-4}$ alkoxy-Ph)-2-halo-Ph;
- $R^3$ is independently selected from: CN, CF$_3$, Ph, 3-halo-Ph, 4-halo-Ph, 5-$C_{1-4}$ alkyl-isoxazol-3-yl, and pyrid-2-yl; and
- $R^4$ is independently selected from: H, $C_{1-4}$ alkyl, $C_{3-4}$ cycloalkyl and —CH$_2$—$C_{3-4}$ cycloalkyl.

In another aspect, the present disclosure provides a compound of Formula (III), or a stereoisomer, a tautomer, a pharmaceutically acceptable salt, or a solvate thereof, within the scope of the fifth aspect, wherein:

- X is independently selected from: O and CH$_2$;
- $R^1$ is independently selected from: phenyl substituted with 1-3 $R^2$ and benzyl substituted with 1-3 $R^2$;
- $R^2$, at each occurrence, is independently selected from: halogen, $C_{1-4}$ alkyl, and $C_{1-4}$ alkoxy;
- $R^3$ is independently selected from: CN, CF$_3$, SO$_2$($C_{1-4}$ alkyl), CON($C_{1-4}$ alkyl)$_2$, and

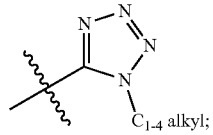
$C_{1-4}$ alkyl;

and $R^4$ is H.

In another aspect, the present disclosure provides a compound of Formula (IV):

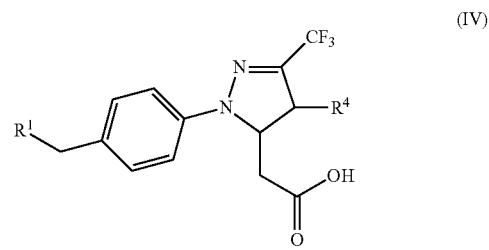

(IV)

or a stereoisomer, a tautomer, a pharmaceutically acceptable salt, or a solvate thereof, within the scope of any of the sixth to thirteenth aspect.

In another aspect, the present disclosure provides a process for preparing a compound of Formula (IVa):

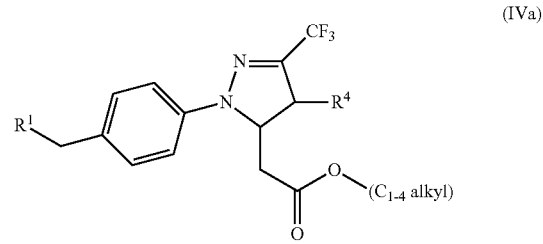

(IVa)

wherein $R^1$ and $R^4$ are defined within the scope of any one of the sixth to thirteenth aspect; in which either according to a process alternative:

[A] contacting a compound of Formula (IVb) with a compound of Formula (IVc) to form a compound of Formula (IVa) in the presence of optionally an activating reagent and/or a silver salt:

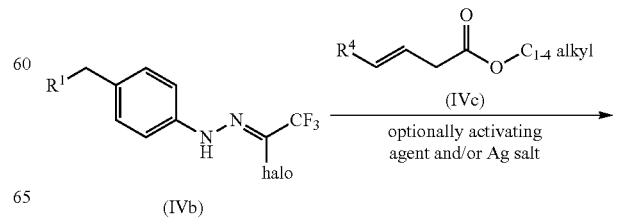

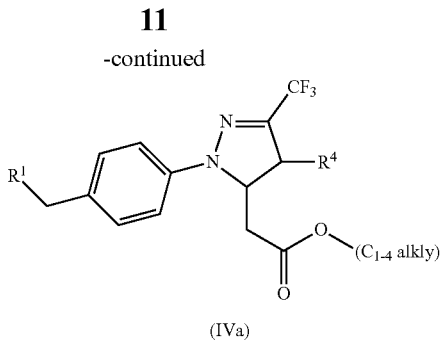

(IVa)

or else according to a process alternative:

[B] contacting a compound of Formula (IVb) with a compound of Formula (IVd) in presence of in the presence of an activating reagent and optionally a Ag salt to form a compound of Formula (IVe), followed by reduction via a reducing agent to give a compound of Formula (IVf), displacement with a cyanide reagent to give a compound of (IVg), and conversion in presence of an acid, alcohol and optionally acetate to form a compound of Formula (IVa):

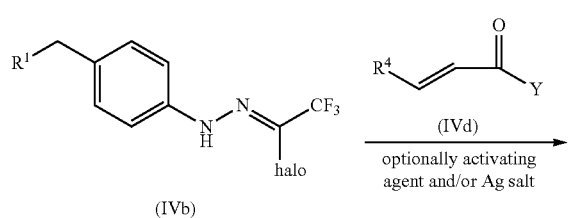

(IVb)

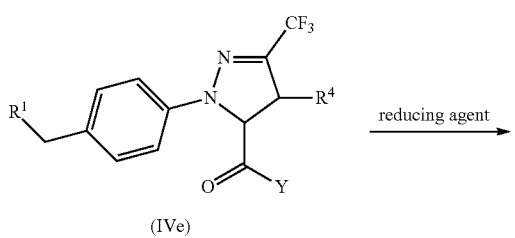

(IVe)

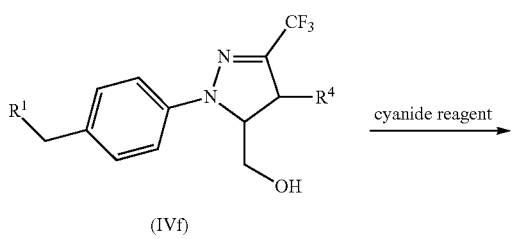

(IVf)

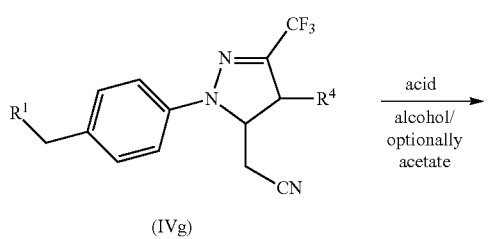

(IVg)

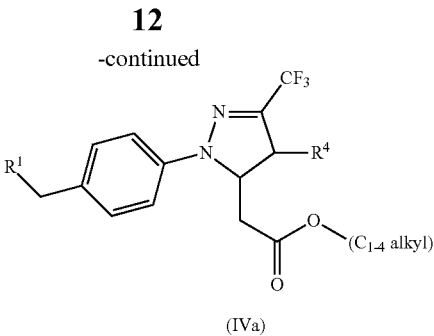

(IVa)

wherein Y is independently selected from the group consisting of:

$C_{1-4}$ alkoxy and a chiral auxiliary selected from

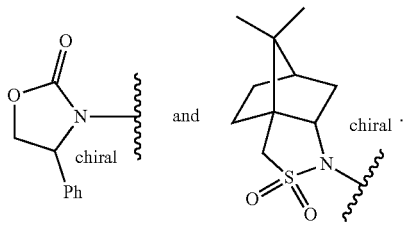 [SMILES: *N1C(=O)OCC1c1ccccc1 ; *N1C2CC3CCC2(CS1(=O)=O)C3(C)C]

In another aspect, the present invention provides a process for preparing a compound of Formula (IVa), wherein:
said activating reagent is independently triethylamine, carbonate or bicarbonate;
said silver salt is independently silver carbonate or silver acetate;
said reducing agent is independently $NaBH_4$ or $LiBH_4$;
said cyanide reagent is independently sodium cyanide, potassium cyanide or trimethylsilylcyanide;
said acid is independently HCl;
said alcohol is MeOH; and
said acetate is MeOAc.

In another aspect, the present invention provides a process for preparing a compound of Formula (IV), within the scope of any of the sixth to thirteen aspect, which comprises: converting a compound of Formula ((IVa) into a compound of Formula (IV) by hydrolysis in presence of a hydroxide reagent.

In another aspect, the present invention provides a process for preparing a compound of Formula (IV), wherein said hydroxide reagent is independently LiOH or NaOH.

In another aspect, the present disclosure provides a compound of Formula (V) or (VI):

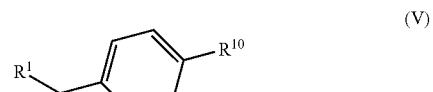

(V)

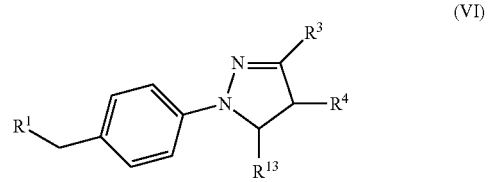

(VI)

or a stereoisomer or a tautomer thereof, wherein:
wherein $R^1$ and $R^4$ are defined within the scope of any one of the sixth to thirteenth aspect;
$R^{10}$ is independently selected from: halogen and —$NR^{11}R^{12}$;
$R^{11}$ is independently selected from: $NH_2$, —$NH(COCF_3)$, —$N=C(halo)(CN)$, and —$N=C(halo)(CF_3)$;
$R^{12}$ is independently selected from: H and an amine protecting group; and
$R^{13}$ is independently selected from:

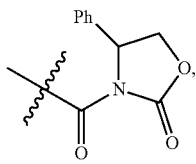 [SMILES: *C(=O)N1C(=O)OCC1c1ccccc1]

—$CH_2OH$, —$CH_2OSO_2(C_{1-4}$ alkyl), —$CH_2CN$, and —$CH_2CO_2(C_{1-4}$ alkyl).

In another aspect, the present disclosure provides a compound of Formula (V) or (VI), or a stereoisomer or a tautomer thereof, wherein:
$R^{12}$ is independently selected from: H and Cbz; and
$R^{13}$ is independently selected from:

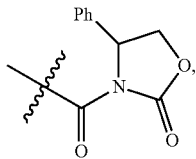

—$CH_2OH$, —$CH_2CN$, —$CH_2OSO_2Me$, and —$CH_2CO_2Me$.

In another aspect, the present disclosure provides a compound of Formula (III), or a stereoisomer, a tautomer, a pharmaceutically acceptable salt, or a solvate thereof, within the scope of any of the fourth or thirteenth aspect, wherein:
X is independently selected from: O and $CH_2$;
$R^1$ is independently selected from: 2-$C_{1-4}$ alkyl-Ph, 2-halo-Ph, 2-$C_{1-4}$ alkyl-4-$C_{1-4}$ alkoxy-Ph, 2-$C_{1-4}$ alkyl-4-halo-Ph, 2-$C_{1-4}$ alkyl-4-halo-5-halo-Ph, 2-$C_{1-4}$ alkyl-6-$C_{1-4}$ alkyl-4-halo-Ph, and 2-halo-4-halo-Bn;
$R^3$ is independently selected from: CN and $CF_3$; and
$R^4$ is H.

In a tenth aspect, the present invention provides a compound selected from the exemplified examples within the scope of the first aspect, or a stereoisomer, a tautomer, a pharmaceutically acceptable salt, or a solvate thereof.

In another aspect, the present invention provides a compound selected from any subset list of compounds within the scope of any of the above aspects.

In another embodiment, X is O, S or $CH_2$.
In another embodiment, X is O or $CH_2$.
In another embodiment, X is O.
In another embodiment, X is $CH_2$.
In another embodiment, Y is independently selected from the group consisting of: a bond and $C_{1-4}$ alkylene.
In another embodiment, Y is a bond, $CH_2$ or $CH_2CH_2$.
In another embodiment, Y is a bond or $CH_2$.
In another embodiment, Z is a bond, O, $CH_2$, $CH_2CH_2$, $CH_2O$, or $OCH_2$.

In another embodiment, Z is a bond, O, $CH_2$, $CH_2CH_2$, or $OCH_2$.
In another embodiment, Z is a bond, O, $CH_2$, or $CH_2O$.
In another embodiment, Z is a bond, O, or $CH_2$.
In another embodiment, Z is a bond.
In another embodiment, Z is O.
In another embodiment, Z is $CH_2$.
In another embodiment, Z is $CH_2O$.
In another embodiment, Z is $OCH_2$.
In another embodiment, Z is $CH_2CH_2$.
In another embodiment, ring A is independently

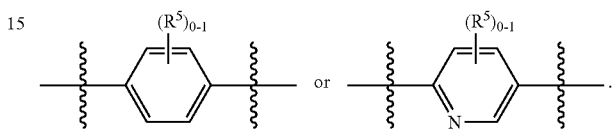

In another embodiment, ring A is

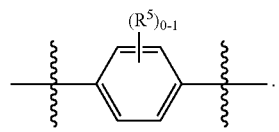

In another embodiment, ring A is

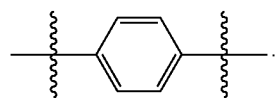

In another embodiment, $R^1$ is —$(CH_2)_n$-phenyl substituted with 0-3 $R^2$ or —$(CH_2)_n$-pyridyl substituted with 0-3 $R^2$.

In another embodiment, $R^1$ is —$(CH_2)_n$-phenyl substituted with 0-2 $R^2$.

In another embodiment, $R^1$ is

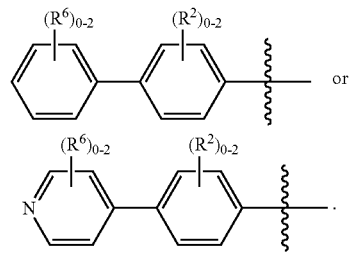

In another embodiment, $R^1$ is

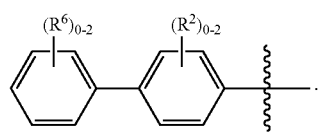

In another embodiment, $R^1$ is

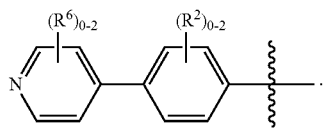

In another embodiment, $R^1$ is

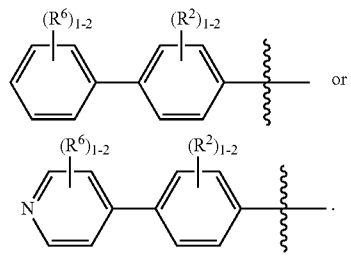 or

In another embodiment, $R^1$ is

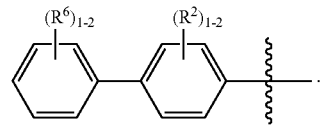

In another embodiment, $R^1$ is

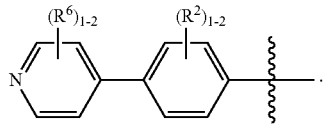

In another embodiment, $R^2$, at each occurrence, is independently selected from the group consisting of: halogen, $C_{1-4}$ alkyl, and $C_{1-4}$ alkoxy.

In another embodiment, $R^3$ is CN, $CF_3$, $SO_2(C_{1-4}$ alkyl), $CON(C_{1-4}$ alkyl$)_2$, oxazol-2-yl or

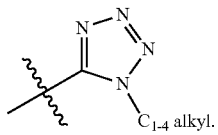

In another embodiment, $R^3$ is CN or $CF_3$.
In another embodiment, $R^3$ is CN.
In another embodiment, $R^3$ is $CF_3$.
In another embodiment, $R^4$ is H, $C_{1-4}$ alkyl, $C_{3-6}$ cycloalkyl or —$CH_2$—$C_{3-6}$ cycloalkyl.
In another embodiment, $R^4$ is H, $C_{1-4}$ alkyl, $C_{3-4}$ cycloalkyl or —$CH_2$—$C_{3-4}$ cycloalkyl.
In another embodiment, $R^4$ is H or $C_{1-4}$ alkyl.
In another embodiment, $R^4$ is H.
In another embodiment, $R^4$ is $C_{1-4}$ alkyl.
In another embodiment, $R^4$ is $C_{3-6}$ cycloalkyl or —$CH_2$—$C_{3-6}$ cycloalkyl.

In another embodiment, $R^4$ is $C_{3-4}$ cycloalkyl or —$CH_2$—$C_{3-4}$ cycloalkyl.

In another embodiment, $R^6$, at each occurrence, is independently selected from the group consisting of: halogen, CN, $CF_3$, $OCF_3$, $C_{1-4}$ alkyl, and $C_{1-4}$ alkoxy;

In another embodiment, $R^6$, at each occurrence, is independently selected from the group consisting of: halogen, CN, $CF_3$, $OCF_3$, and $C_{1-4}$ alkoxy.

In another embodiment, the compounds of the present invention have hGPR40 $EC_{50}$ values ≤10 μM.

In another embodiment, the compounds of the present invention have hGPR40 $EC_{50}$ values ≤5 μM.

In another embodiment, the compounds of the present invention have hGPR40 $EC_{50}$ values ≤1 μM.

In another embodiment, the compounds of the present invention have hGPR40 $EC_{50}$ values ≤0.5 μM.

In another embodiment, the compounds of the present invention have hGPR40 $EC_{50}$ values ≤0.2 μM.

In another embodiment, the compounds of the present invention have hGPR40 $EC_{50}$ values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a pharmaceutical composition further comprising additional therapeutic agent(s). Examples of additional therapeutic agent(s), according to the present invention include, but are not limited to, anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease and anti-inflammatory agents.

In a preferred embodiment, the present invention provides pharmaceutical composition, wherein the additional therapeutic agents are, for example, a dipeptidyl peptidase-IV (DPP4) inhibitor (for example a member selected from saxagliptin, sitagliptin, vildagliptin, linagliptin, alogliptin, and "BMS DPP4i"), and/or a sodium-glucose transporter-2 (SGLT2) inhibitor (for example a member selected from dapagliflozin, canagliflozin, empagliflozin and remagliflozin).

In a preferred embodiment, the present invention provides pharmaceutical composition, wherein the additional therapeutic agents are, for example, a DPP4 inhibitor (for example a member selected from saxagliptin, sitagliptin, vildagliptin, linagliptin, alogliptin, and "BMS DPP4i").

In a preferred embodiment, the present invention provides pharmaceutical composition, wherein the additional therapeutic agents are, for example, an SGLT2 inhibitor (for example a member selected from dapagliflozin, canagliflozin, empagliflozin and remagliflozin).

In another embodiment, the present invention provides a method for the treatment and/or prophylaxis of multiple diseases or disorders associated with GPR40, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the GPR40 that can be prevented, modulated, or treated according to the present invention include, but are not limited to, diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), non-cardiac ischemia, pancreatitis, lipid disorders, neurodegenerative disease, cognitive impairment, dementia, and liver diseases such as NASH (Non-Alcoholic SteatoHepatitis), NAFLD (Non-Alcoholic Fatty Liver Disease) and liver cirrhosis.

In another embodiment, the present invention provides a method for the treatment and/or prophylaxis of diabetes, hyperglycemia, gestational diabetes, obesity, dyslipidemia, hypertension and cognitive impairment, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of diabetes, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hyperglycemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of cognitive impairment, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with GPR40.

In another embodiment, the present invention also provides the use of a compound of the present invention for the manufacture of a medicament for the treatment and/or prophylaxis of multiple diseases or disorders associated with GPR40.

In another embodiment, the present invention provides a method for the treatment and/or prophylaxis of multiple diseases or disorders associated with GPR40, comprising: administering to a patient in need thereof a therapeutically effective amount of a first and second therapeutic agent, wherein the first therapeutic agent is a compound of the present invention. Preferably, the second therapeutic agent, for example, a DPP4 inhibitor (for example a member selected from saxagliptin, sitagliptin, vildagliptin, linagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with GPR40.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR40 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the GPR40 receptor modulator of the present invention include, but are not limited to, insulin secretagogues or insulin sensitizers, other GPR40 receptor modulators, or other antidiabetic agents. These agents include, but are not limited to, DPP4 inhibitors (for example, sitagliptin, saxagliptin, alogliptin, linagliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, tesaglitazar and aleglitazar), glucokinase activators, GPR119 receptor modulators (for example, MBX-2952, PSN821, and APD597), GPR120 receptor modulators (for example, as described in Shimpukade, B. et al. *J. Med. Chem.* 2012, 55 (9), 4511-4515), SGLT2 inhibitors (for example, dapagliflozin, canagliflozin, empagliflozin and remagliflozin), MGAT inhibitors (for example, as described in Barlind, J. G. et al. *Bioorg. Med. Chem. Lett.* 2013, 23 (9), 2721-2726; or US20130143843A1), amylin analogs such as pramlintide, and/or insulin.

The GPR40 receptor modulator of the present invention may also be optionally employed in combination with agents for treating complication of diabetes. These agents include PKC inhibitors and/or AGE inhibitors.

The GPR40 receptor modulator of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The GPR40 receptor modulator of the present invention may also be employed in combination with an agonist of the glucagon-like peptide-1 receptor (GLP-1 R), such as exenatide, liraglutide, GLP-1 (1-36) amide, GLP-1(7-36) amide, GLP-1(7-37), which may be administered via injection, intranasal, or by transdermal or buccal devices.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of stereoisomeric forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle," "carbocyclyl," or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in *Hawley's Condensed Chemical Dictionary* (13th ed.), R. J. Lewis, ed., J. Wiley & Sons, Inc., New York, 1997. "$C_{6-10}$ aryl" refers to phenyl and naphthyl.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, imidazopyridazinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolopyrimidinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, pyrimidinyl, pyrazinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, imidazolopyridinyl, imidazopyridazinyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, pyrazolopyridinyl and pyrazolopyrimidinyl.

Examples of 5- to 6-membered heterocycles include, but are not limited to, pyridinyl, furanyl, thienyl, pyrrolyl, pyrazolyl, pyrazinyl, piperazinyl, piperidinyl, pyrimidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), calcium ($Ca^{2+}$)ammonium ($R_nNH_m+$ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington: *The Science and Practice of Pharmacy*, $22^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, Bundgaard, H., ed., Elsevier (1985), and *Methods in Enzymology*, 112:309-396, Widder, K. et al., eds., Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd edition, Academic Press, San Diego, Calif. (2008).

The present invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H (also represented as 'ID' for deuterium) and $^3$H, carbon such as $^{11}$C, $^{13}$C, and $^{14}$C, nitrogen, such as $^{13}$N and $^{15}$N, oxygen, such as $^{15}$O, $^{17}$O, and $^{18}$O. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increase in vivo half-life or reduced dosage requirements, and hence may be preferred in some circumstances. Substitution with positron emitting isotopes, such as $^{11}$C, $^{15}$O, $^{18}$F, and $^{13}$N, can be useful in Positron Emission Topography (PET) studies for examining substrate receptor occupancy. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
$Ag_2CO_3$ silver carbonate
AgOAc silver acetate
$CDCl_3$ deutero-chloroform
$CHCl_3$ chloroform
cDNA complimentary DNA
DMF dimethyl formamide
DMSO dimethyl sulfoxide
EDTA ethylenediaminetetraacetic acid
EtOAc ethyl acetate
$Et_2O$ diethyl ether
$AlCl_3$ aluminum chloride
Boc tert-butyloxycarbonyl
$CH_2Cl_2$ dichloromethane
$CH_3CN$ or ACN acetonitrile
$Cs_2CO_3$ cesium carbonate
HCl hydrochloric acid
$H_2SO_4$ sulfuric acid
$K_2CO_3$ potassium carbonate
KCN potassium cyanide
mCPBA or m-CPBA meta-chloroperbenzoic acid
Pd/C palladium on carbon
$PhSO_2Cl$ benzenesulfonyl chloride
i-$Pr_2$NEt diisopropylethylamine
PS polystyrene
$SiO_2$ silica oxide
$SnCl_2$ tin(II) chloride
TEA triethylamine
TFA trifluoroacetic acid
TFAA trifluoroacetic anhydride
THF tetrahydrofuran
$TMSCHN_2$ trimethylsilyldiazomethane
KOAc potassium acetate
$MgSO_4$ magnesium sulfate
MsCl methanesulfonyl chloride
MsOH or MSA methylsulfonic acid
NaCl sodium chloride
NaH sodium hydride
$NaHCO_3$ sodium bicarbonate
NaOH sodium hydroxide
$Na_2SO_3$ sodium sulfite
$Na_2SO_4$ sodium sulfate
$NH_3$ ammonia
$NH_4Cl$ ammonium chloride
$NH_4OH$ ammonium hydroxide
LG leaving group The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Wuts, P. G. M. and Greene, T. W. *Protecting Groups in Organic Synthesis*, 4th Edition, Wiley (2007)). General methods of organic synthesis and functional group transformations are found in: Trost, B. M. and Fleming, I., eds., *Comprehensive Organic Synthesis: Selectivity, Strategy & Efficiency in Modern Organic Chemistry*, Pergamon Press, New York, N.Y. (1991); Smith, M. B. and March, J., *March's Advanced Organic Chemistry: Reactions, Mechanisms, and Structure*. 6th Edition, Wiley & Sons, New York, N.Y. (2007); Katritzky, A. R. and Taylor, R. J. K., eds., *Comprehensive Organic Functional Groups Transformations II*, 2nd Edition, Elsevier Science Inc., Tarrytown, N.Y. (2004); Larock, R. C., *Comprehensive Organic Transformations*, VCH Publishers, Inc., New York, N.Y. (1999), and references therein.

Methods for synthesis of a large variety of substituted dihydropyrazole compounds useful as starting materials for the preparation of compounds of the present invention are well known in the art. For examples of methods useful for the preparation of dihydropyrazole materials see the following references and citations therein: Katritzky et al., eds., *Comprehensive Heterocyclic Chemistry*, Pergamon Press Inc., New York (1996); Sibi, M. P. et al., *Organic Letters*, 11(23): 5366 (2009); Sibi, M. P. et al., *J. Am. Chem. Soc.* 127(23): 8276 (2005); Manyem, S. et al., *J. Comb. Chem.* 9: 20 (2007); Garanti, L. et al., *Tetrahedron: Asymmetry*, 13: 1285 (2002); Molteni, G. *Tetrahedron: Asymmetry*, 15: 1077 (2004); Benassuti, L. D. et al., *Tetrahedron*, 60:4627 (2004); Shimizu, T. et al. *Bull. Chem. Soc. Jpn.*, 57: 787 (1984).

Compounds for Formula (I) can be prepared as shown in Scheme 1. Conversion of the hydrazine A to the hydrazide B with trifluoroacetic anhydride followed by treatment with a phenylsulfonyl chloride forms the hydrazonoyl chloride C. A [3+2] cycloaddition of hydrazonoyl chloride C with methyl but-3-enoate mediated by optionally an activating agent and/or a silver salt forms the dihydropyrazole D. Intermediate D could be converted to compounds of Formula (I) by hydrolysis, via a hydroxide reagent, e.g., LiOH or NaOH.

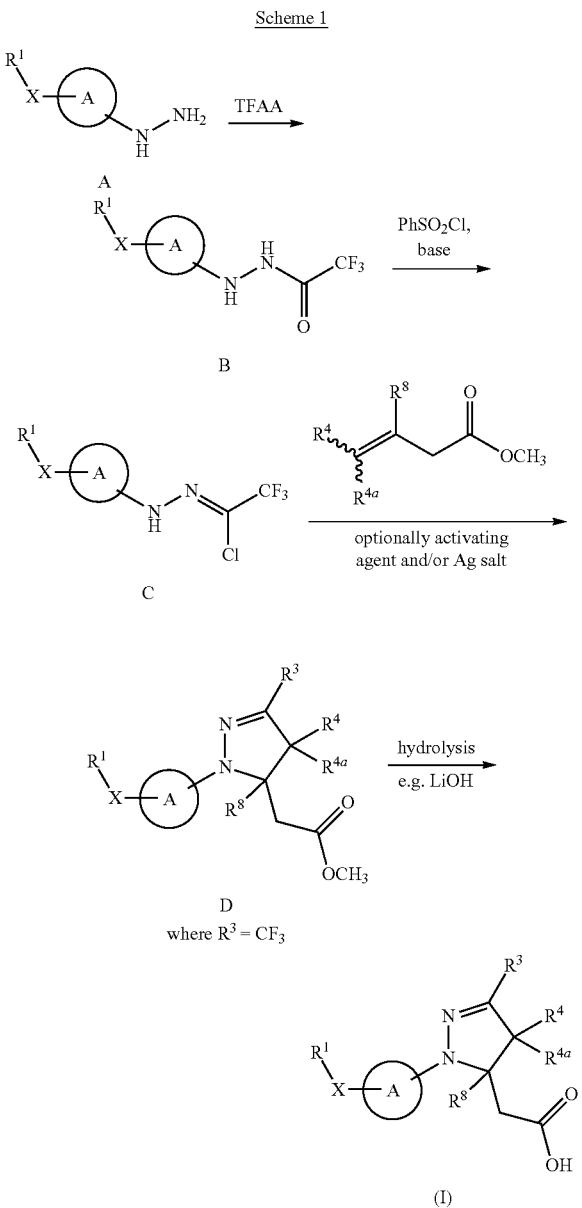

Alternatively, hydrazonoyl chloride C could undergo a [3+2] cyclization with an α,β-unsaturated carbonyl compound where Y is a chiral auxiliary or alkoxy group to give dihydropyrazole E as depicted in Scheme 2. Reduction of the carbonyl E, via a reducing agent, e.g., NaBH$_4$ or LiBH$_4$, leads to hydroxyl F. Activation of the hydroxyl F, via methanesulfonyl chloride, for example, and displacement with a cyanide reagent, e.g., sodium cyanide, potassium cyanide or trimethylsilylcyanide, leads to nitrile G. The nitrile G can be converted to the methyl ester D by acidic methanolysis. Intermediate D could be converted to compounds of Formula (I) by hydrolysis, via a hydroxide reagent, e.g., LiOH or NaOH.

Scheme 2

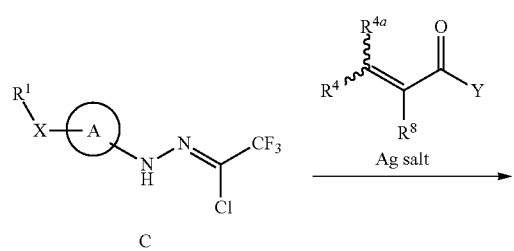

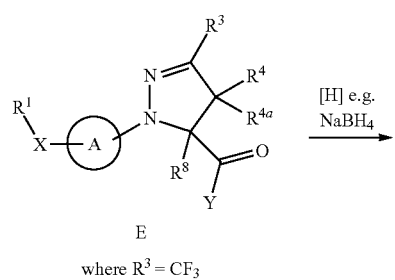

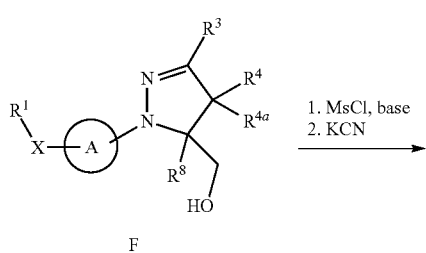

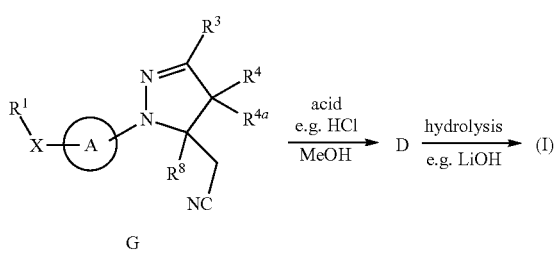

Exemplary activating agents include, but are not limited to, triethylamine, carbonate and bicarbonate. Exemplary silver salts include, but are not limited to, silver carbonate and silver acetate.

Compounds of Formula (I) may be synthesized starting with aniline H, which can be diazotized with $NaNO_2$ and HCl and then converted to the hydrazonoyl chloride I via reaction with 2-chloro-3-oxobutanenitrile as shown in Scheme 3. A [3+2] cycloaddition of hydrazonoyl chloride I with methyl but-3-enoate mediated by an Ag salt forms the dihydropyrazole D. Intermediate D could be converted to compounds of Formula (I) by hydrolysis, via a hydroxide reagent, e.g., LiOH or NaOH.

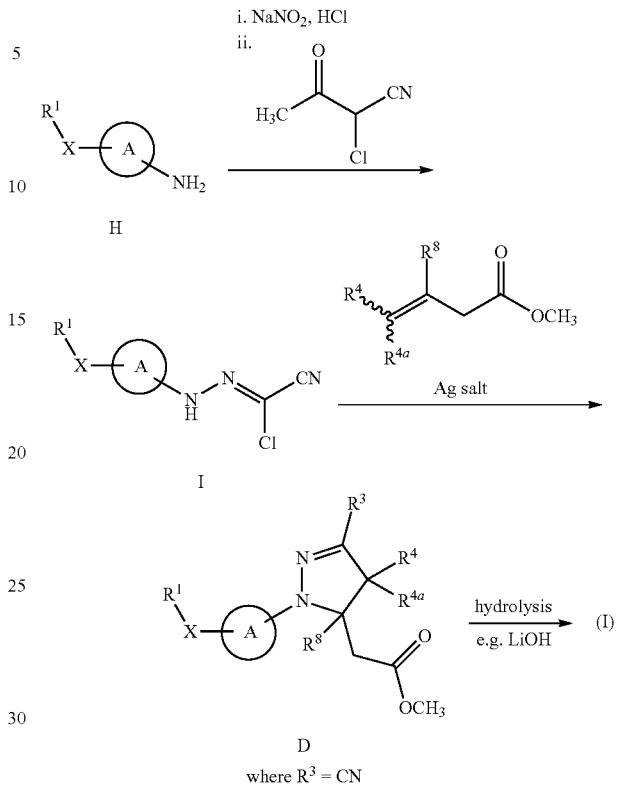

Alternatively, compounds of Formula (I) can be synthesized via reaction of intermediate C or I with a substituted acrylate J in the presence of a Ag salt to provide dihydropyrazole E as depicted in Scheme 4. The methyl ester E is hydrolyzed, via LiOH, for example, to afford carboxylic acid K. The carboxylic acid K can be converted to the ester D, via an Arndt-Eistert homologation. Intermediate D could be converted to compounds of Formula (I) by hydrolysis, via a hydroxide reagent, e.g, LiOH or NaOH.

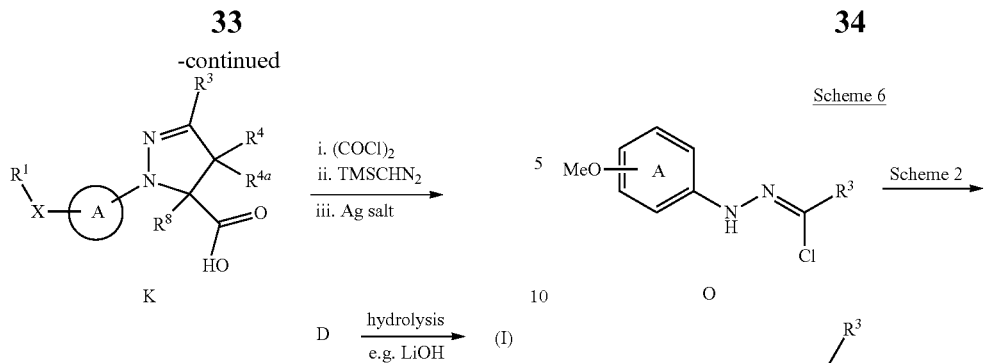

Compounds of Formula (I) may be synthesized starting with hydrazonoyl chlorides L containing a L.G. such as =F, Cl, Br and the like, which can be converted to dihydropyrazoles M according to the sequence depicted in Scheme 2. The LG can be coupled via a Pd-catalyzed coupling to intermediate N that contains an organometallic, e.g. organozinc to generate intermediate D as shown in Scheme 5.

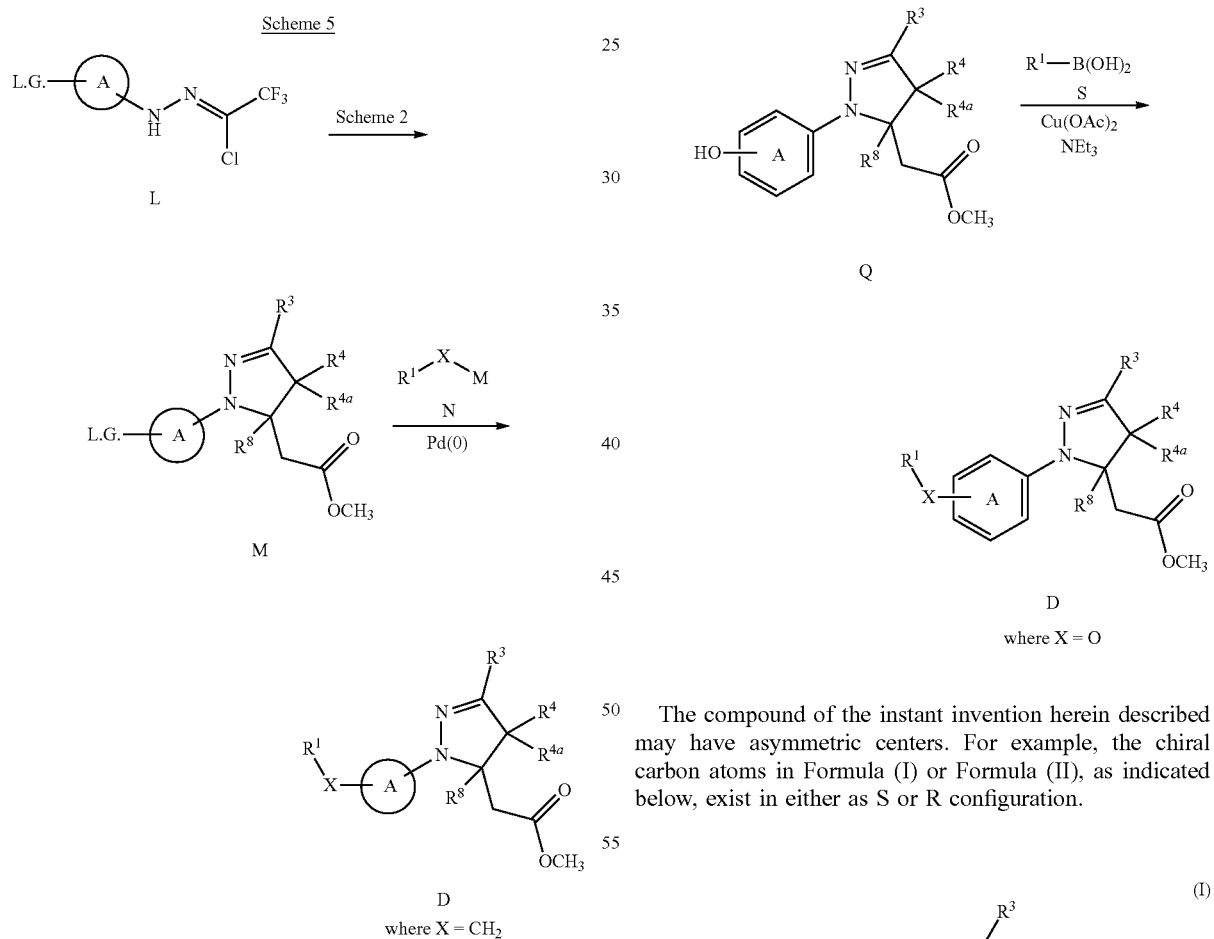

Alternatively, the hydrazonoyl chloride could contain a methyl ether O, which could be converted to dihydropyrazole P according to the synthetic steps described in Scheme 2. Methyl ether P can be deprotected via a boron trihalide, e.g. BF$_3$·SMe$_2$ to give phenol Q, which could be coupled boronic acids S to give biaryl ethers D as shown in Scheme 6.

The compound of the instant invention herein described may have asymmetric centers. For example, the chiral carbon atoms in Formula (I) or Formula (II), as indicated below, exist in either as S or R configuration.

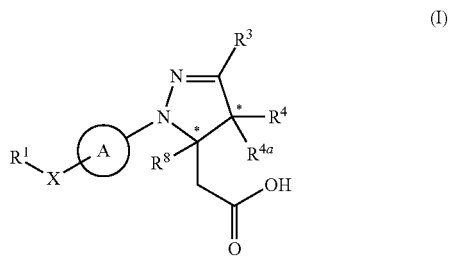

-continued

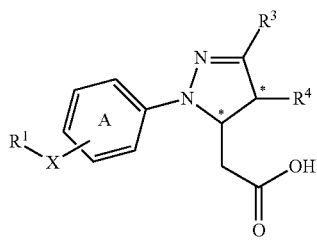
(II)

Thus, the stereoisomeric configurations of each compound of Formula (I) or Formula (II) are considered part of the invention. In structures where the stereochemistry of an intermediate or final compound is not indicated, it has not been determined.

IV. Biology

Diabetes mellitus is a serious disease afflicting over 100 million people worldwide. It is diagnosed as a group of disorders characterized by abnormal glucose homeostasis resulting in elevated blood glucose. Diabetes is a syndrome with interrelated metabolic, vascular, and neuropathic components. The metabolic abnormality is generally characterized by hyperglycemia and alterations in carbohydrate, fat and protein metabolism caused by absent or reduced insulin secretion and/or ineffective insulin secretion. The vascular syndrome consists of abnormalities in the blood vessels leading to cardiovascular, retinal and renal complications. Abnormalities in the peripheral and autonomic nervous systems are also part of diabetic syndrome. Strikingly, diabetes is the fourth leading cause of global death by disease, the largest cause of kidney failure in developed countries, the leading cause of vision loss in industrialized countries and has the greatest prevalence increase in developing countries.

Type 2 diabetes, which accounts for 90% of diabetes cases, is characterized by increasing insulin resistance associated with inadequate insulin secretion after a period of compensatory hyperinsulinemia. The reasons for β cell secondary failure are not completely understood. Acquired pancreatic islet damage or exhaustion and/or genetic factors causing susceptibility to islet secretory insufficiency have been hypothesized.

Free fatty acids (FFAs) are evidenced to influence insulin secretion from β cells primarily by enhancing glucose-stimulated insulin secretion (GSIS). Although glucose is recognized as the major stimulator of insulin secretion from β cells, other stimuli, such as amino acids, hormones, and FFAs, also regulate insulin secretion. Thus, under normal settings, insulin secretion from β cells in response to food intake is evoked by the collective stimuli of nutrients, such as glucose, amino acids, and FFAs, and hormones like the incretin glucagon-like peptide 1 (GLP-1). Fatty acids are also known to stimulate the secretion of several gut satiety hormones, including cholocystokinine (CCK), GLP-1, and peptide YY (PYY).

G-protein coupled receptors (GPCRs) expressed in β cells are known to modulate the release of insulin in response to changes in plasma glucose levels. GPR40, also known as fatty acid receptor 1 (FFAR1), is a membrane-bound FFA receptor which is preferentially expressed in the pancreatic islets and specifically in β cells. GPR40 (e.g., human GPR40, RefSeq mRNA ID NM_005303; e.g., mouse GPR40 RefSeq mRNA ID NM_194057) is a GPCR located at chromosome 19q13.12. GPR40 is activated by medium to long chain fatty acids and thereby triggering a signaling cascade that results in increased levels of $[Ca^{2+}]_i$ in β cells and subsequent stimulation of insulin secretion (Itoh et al., *Nature*, 422:173-176 (2003)). Selective small molecule agonists of GPR40 have been shown to promote GSIS and reduce blood glucose in mice (Tan et al., *Diabetes*, 57:2211-2219 (2008)). Briefly, when activators of GPR40 are administered to either normal mice or mice that are prone to diabetes due to genetic mutation, prior to a glucose tolerance test, improvements in glucose tolerance are observed. A short-lived increase in plasma insulin levels are also observed in these treated mice. It has also been shown that GPR40 agonists restore GSIS in pancreatic β-cells from the neonatal STZ rats suggesting that GPR40 agonists will be efficacious in diabetics with compromised β-cell function and mass. Fatty acids are known to stimulate the secretion of several gut satiety hormones, including cholocystokinine (CCK), GLP-1, and peptide YY (PYY), and GPR40 has been shown to colocalize with cells that secrete such hormones (Edfalk et al., *Diabetes*, 57:2280-2287 (2008) Luo et al. *PLOSone*, 7:1-12 (2012)). Fatty acids are also known to play a role in neuronal development and function, and GPR40 has been reported as a potential modulator of the fatty acid effects on neurons (Yamashima, T., *Progress in Neurobiology*, 84:105-115 (2008)).

Given the increase in the worldwide patient population afflicted by type 2 diabetes, there is a need for novel therapies which are effective with minimal adverse events. To decrease medical burden of type 2 diabetes through enhanced glycemic control, GPR40 modulator compounds of the present invention are being investigated here for their incretin effect to promote GSIS as well as the potential combination with a broad range of anti-diabetic drugs.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a GPR40 modulator. Exemplary subjects include human beings of any age with risk factors for metabolic disease. Common risk factors include, but are not limited to, age, sex, weight, family history, or signs of insulin resistance such as acanthosis nigricans, hypertension, dislipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate GPR40 and/or to prevent or treat the disorders listed herein. When applied to a combination, the term refers to combined amounts of the active ingredients that result in the preventive or therapeutic effect, whether administered in combination, serially, or simultaneously.

In Vitro GPR40 Assays
FDSS-Based Intracellular Calcium Assay

Cell lines expressing GPR40 are generated using the pDEST 3× flag gene expression system and are cultured in culture medium comprising the following components: F12 (Gibco #11765), 10% lipid deprived fetal bovine serum, 250 µg/ml zeocin and 500 µg/ml G418. To conduct the fluorescent imaging plate reader (FLIPR)-based calcium flux assay to measure intracellular $Ca^{2+}$ response, cells expressing GPR40 are plated on 384 well plates (BD Biocoat #356697) at a density of 20,000 cells/20 µL medium per well in phenol red and serum-free DMEM (Gibco #21063-029) and incubated overnight. Using BD kit #s 80500-310 or -301, the cells are incubated with 20 µL per well of Hank's buffered salt solution with 1.7 mM probenecid and Fluo-3 at 37° C. for 30 min. Compounds are dissolved in DMSO and diluted to desired concentrations with assay buffer and added to the cells as 3× solution (20 µL per well). Run fluorescence/luminescence reader FDSS (Hamamatsu) to read intracellular $Ca^{2+}$ response.

The exemplified Examples disclosed below were tested in the Human GRP40 In Vitro assay described above and found having hGRP40 modulating activity.

GPR40 IP-One HTRF Assays in HEK293/GPR40 Inducible Cell Lines

Human, mouse and rat GPR40-mediated intracellular IP-One HTRF assays were established using human embryonic kidney HEK293 cells stably transfected with a tetracycline-inducible human, mouse or rat GPR40 receptor. Cells were routinely cultured in growth medium containing DMEM (Gibco Cat. #:12430-047), 10% qualified FBS (Sigma, Cat. #: F2442), 200 µg/mL hygromycin (Invitrogen, Cat. #: 16087-010) and 1.5 µg/mL blasticidin (Invitrogen, Cat. # R210-01). About 12-15 million cells were passed into a T175 tissue culture flask (BD Falcon 353112) with growth medium and incubated for 16-18 hours (overnight) at 370 C with 5% CO2. The next day, assay medium was exchanged with growth medium containing 1000 µg/mL of tetracycline (Fluka Analytical, Cat. #87128) to induce GPR40 expression for 18-24 hours at 370 C incubator with 5% CO2. After induction, the cells were washed with PBS (Gibco, Cat. #14190-036) and detached with Cell Stripper (Cellgro, Cat. #25-056-CL). 10-20 mL growth medium were added to the flask and cells were collected in 50 mL tubes (Falcon, Cat.#:352098) and spun at 1000 RPM for 5 minutes. Culture medium was aspirated and the cells were resuspended in 10 mL of 1× IP-One Stimulation Buffer from the Cisbio IP-One kit (Cisbio, Cat. #62IPAPEJ). The cells were diluted to 1.4×106 cells/mL in Stimulation Buffer.

Test compounds were 3-fold, 11-point serially diluted in DMSO in a REMP assay plate (Matrix Cat. #: 4307) by BioCel (Agilent). The compounds were transferred into an Echo plate (LABCYTE, Cat. #: LP-0200) and 20 nL of diluted compounds were transferred to an assay plate (proxiplate from Perkin Elmer, Cat. #6008289) by Echo acoustic nano dispenser (LABCYTE, model ECHO550). 14 µL of the diluted cells were then added to the assay plate by Thermo (SN 836 330) Combi Drop and incubated at room temperature for 45 minutes. Then 3 µL of IP1 coupled to dye D2 from the Cisbio IP-One kit were added to the assay plate followed by 3 µL of Lumi4TM-Tb cryptate K from the kit. The plate was further incubated at room for 1 hour before reading on the Envision (Perkin Elmer Mode12101) with an HTRF protocol. Activation data for the test compound over a range of concentrations was plotted as percentage activation of the test compound (100%=maximum response). After correcting for background [(sample read-mean of low control)/(mean of high control−mean of low control)] (low control is DMSO without any compound), EC50 values were determined. The EC50 is defined as the concentration of test compound which produces 50% of the maximal response and was quantified using the 4 parameter logistic equation to fit the data. The maximal Y value observed (% Ymax) was calculated relative to a BMS standard reference compound at a final concentration of 0.625 µM.

Some of the exemplified Examples disclosed below were tested in the Human GRP40 In Vitro assay described above and found having hGRP40 modulating activity reported as hGPR40 IP1 $EC_{50}$.

In Vivo GPR40 Assays
Acute Oral Glucose Tolerance Test

Ten week old C57BL6 mice were housed individually and fasted for 5 hours on the day of study. Tail vein sampling was performed from nicked tails to obtain plasma samples. Baseline plasma samples were taken at t=0. Mice were orally treated with vehicle or compounds co-administered with glucose (2 g/kg). Sampling thereafter from tails of treated mice at 20, 40, 60, 120 and 180 min provided data used for generating glucose excursion curves from which 0-180 min blood glucose excursion profiles were generated. The area under the curve (AUC) allowed for assessment of glucose lowering by compound treatments. Blood samples were collected in EDTA-treated tubes (microvette CB300, Sarstedt, Numbrecht, Germany), stored on ice and spun @ 6000 rpm for 10 minutes. Plasma glucose was analyzed on the same day using an AU680 Clinical Chemistry Analyzer (Beckman Coulter, Brea, Calif.). Statistical analysis is a one way ANOVA with Dunnett's post hoc test or two-way student's t test where appropriate. P values less than 0.05 were considered statistically significant. Glucose reduction is reported as a % change in AUC (0-180 min) from the vehicle treatment group. For example, "Acute oral glucose tolerance: −50% @ 0.3 mg/kg" represents the results of a study as described above, whereupon administration of 0.3 mg/kg of the specified example results in a 50% reduction in glucose AUC (0-180 min) relative to vehicle treated animals.

Acute Oral Glucose Tolerance Test in Rats

Male Sprague Dawley rats (CRL, Wilmington Mass.) were used. Rats were delivered to the vivarium and acclimated for 1 week. Rats were fasted from 5 PM on the night before study. Overnight fasted rats were 180-200 grams at time of study. Tail vein sampling was performed to obtain baseline plasma samples. Rats were randomized to treatment groups based on fasting plasma glucose readings determined by Accu-Chek® glucometer (Roche, Indianapolis, Ind.). Rats were dosed at 4 mL/Kg body weight with 40% PEG400 (Sigma, St. Louis, Mo.) 10% Cremophore (Sigma, St. Louis, Mo.) and 50% distilled water with or without compounds. For rats that received BMS DPP4i combined with GPR40 agonist, administration was performed by co-dosing compounds. Plasma samples were collected one hour after compound dosing to determine baseline changes in glucose and active GLP-1 levels in the presence and absence of BMS DPP4i. Sampling thereafter from tail veins provided time point data to calculate $AUC_{0-120}$, glucose as a marker of two hour glucose lowering efficacy. Blood samples were collected in EDTA-treated tubes (microvette CB300, Sarstedt, Numbrecht, Germany), stored on ice and spun @ 6000 rpm for 10 minutes. Plasma glucose was analyzed on the same day using an AU680 Clinical Chemistry Analyzer (Beckman Coulter, Brea, Calif.). Statistical analysis is a one way ANOVA with Dunnett's post hoc test or two-way student's t test where appropriate. P values less than 0.05 were considered statistically significant. Glucose reduction is reported as a % change in AUC (0-120 min) from the vehicle treatment group. Fasting hormone responses are the difference from basal levels 1 hour post dose. Active GLP-1 levels (GLP-1 (7-36) amide and GLP-1 (7-37)) were measured by ELISA (Millipore, Billerica, Mass.).

BMS DPP4i—Reference Compound

BMS DPP4i is disclosed in Simpkins, L. et al. *Bioorganic Medicinal Chemistry Letters* 2007, 17(23), 6476-80 (compound 48) and in WO2005012249 (Example 3). BMS DPP4i has the following formula:

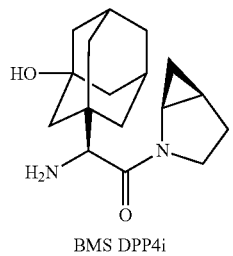 [SMILES: N[C@H](C(=O)N1CC[C@@H]2C[C@@H]21)C12CC3CC(CC(O)(C3)C1)C2]

BMS DPP4i

BMS DPP4i was administered to rats alone, and in combination with Example 81, Isomer 2 of the present invention, at 10 mg/kg, as depicted in FIG. 1 and FIG. 2. As depicted in FIG. 1, the combination of BMS DPP4i with Example 81, Isomer 2 demonstrated greater reductions in plasma glucose during an oral glucose tolerance test than either Example 81, Isomer 2 or BMS DPP4i alone. As depicted in FIG. 2, the combination of BMS DPP4i with Example 81, Isomer 2 shows greater increases in active GLP-1 during an oral glucose tolerance test than either Example 81, Isomer 2 or BMS DPP4i alone.

The compounds of the present invention possess activity as modulators of GPR40, and, therefore, may be used in the treatment of diseases associated with GPR40 activity. Via modulation of GPR40, the compounds of the present invention may preferably be employed to modulate the production/secretion of insulin and/or gut hormones, such as GLP-1, GIP, PYY, CCK and amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, fatty liver disease, dyslipidemia, hyperlipidemia, hypertriglyceridemia, hypercholesterolemia, low HDL, high LDL, vascular restenosis, peripheral arterial disease, lipid disorders, liver diseases such as NASH (Non-Alcoholic SteatoHepatitis), NAFLD (Non-Alcoholic Fatty Liver Disease) and liver cirrhosis, neurodegenerative disease, cognitive impairment, dementia, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

GPR40 is expressed in neuronal cells, and is associated with development and maintenance of neuronal health in brain, as described in Yamashima, T. *Progress in Neurobiology* 2008, 84, 105-115.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 Volumes), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR40 modulators or one or more other suitable therapeutic agents useful in the treatment of the aforementioned disorders including: antidiabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, or cognition promoting agents, appetite suppressants, treatments for heart failure, treatments for peripheral arterial disease and anti-inflammatory agents.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR40 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the compound of the present invention include, but are not limited to, insulin secretagogues or insulin sensitizers, other GPR40 receptor modulators, or other antidiabetic agents. These agents include, but are not limited to, dipeptidyl peptidase IV inhibitors (DPP4i; for example, sitagliptin, saxagliptin, alogliptin, vildagliptin), biguanides (for example, metformin, phenformin), sulfonyl ureas (for example, gliburide, glimepiride, glipizide), glucosidase inhibitors (for example, acarbose, miglitol), PPARγ agonists such as thiazolidinediones (for example, rosiglitazone, pioglitazone), PPAR α/γ dual agonists (for example, muraglitazar, tesaglitazar, aleglitazar), glucokinase activators (as described in Fyfe, M. C. T. et al., *Drugs of the Future*, 34(8):641-653 (2009) and incorporated herein by reference), other GPR40 receptor modulators (e.g. TAK-875), GPR119 receptor modulators (for example, MBX-2952, PSN821, APD597), GPR120 receptor modulators (for example, as described in Shimpukade, B. et al. *J. Med. Chem.* 2012, 55 (9), 4511-4515), sodium-glucose transporter-2 (SGLT2) inhibitors (for example dapagliflozin, canagliflozin, empagliflozin, remagliflozin), 11b-HSD-1 inhibitors (for example MK-0736, BI35585, BMS-823778, and LY2523199), MGAT inhibitors (for example, as described in Barlind, J. G. et al. *Bioorg. Med. Chem. Leu.* 2013, 23(9), 2721-2726; or US20130143843A1), amylin analogs such as pramlintide, and/or insulin. Reviews of current and emerging therapies for the treatment of diabetes can be found in: Mohler, M. L. et al., *Medicinal Research Reviews*, 29(1):125-195 (2009), and Mizuno, C. S. et al., *Current Medicinal Chemistry*, 15:61-74 (2008).

The GPR40 receptor modulator of formula I may also be optionally employed in combination with agents for treating complication of diabetes. These agents include PKC inhibitors and/or AGE inhibitors.

The GPR40 receptor modulator of formula I way also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The compound of structure I may also be employed in combination with an agonist of the glucagon-like peptide-1 receptor (GLP-1 R), such as exenatide, liraglutide, GPR-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., *Nature Reviews Drug Discovery*, 5:369-370 (2006); Jones, D., *Nature Reviews: Drug Discovery*, 8:833-834 (2009); Obici, S., *Endocrinology*, 150(6):2512-2517 (2009); and Elangbam, C. S., *Vet. Pathol.*, 46(1):10-24 (2009).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the GPR40 receptor. Such compounds may be provided in a commercial kit, for example, for use in pharmaceutical research involving GPR40 or anti-diabetic activity. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving GPR40.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment and/or prophylaxis of multiple diseases or disorders associated with GPR40 (as defined previously). In another embodiment, the package insert states that the pharmaceutical composition can be used in combination (as defined previously) with a second therapeutic agent for the treatment and/or prophylaxis of multiple diseases or disorders associated with GPR40. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS and Preparatory/Analytical HPLC Methods Employed in Characterization or Purification of Examples Analytical HPLC/MS (unless otherwise noted) was performed on Shimadzu SCL-10A liquid chromatographs and Waters MICROMASS® ZQ Mass Spectrometers (Desalvation Gas: Nitrogen; Desalvation Temp. 250° C.; Ion Source Temp: 120° C.; Positive Electrospray conditions) using the following method:
  Linear Gradient of 0% to 100% solvent B over 2 min, with 1 minute hold at 100% B;
  UV visualization at 220 nm;
  Column: PHENOMENEX® Luna C18 (2) 30 mm×4.60 mm; 5 m particle (Heated to Temp. 40° C.);
  Flow rate: 5 ml/min;
  Solvent A: 10% ACN, 90% Water, 0.1% TFA; or, 10% MeOH, 90% water, 0.1% TFA; and
  Solvent B: 90% ACN, 10% Water, 0.1% TFA; or, 90% MeOH, 10% water, 0.1% TFA.

Preparatory HPLC (unless otherwise noted) was performed on a Shimadzu SCL-10A liquid chromatograph with a linear gradient of 20-100% Solvent B over 10 or 30 min, with either a 2 or 5 min (respectively) hold at 100% Solvent B;
  UV visualization at 220 nm;
  Column: PHENOMENEX® Luna Axia 5u C18 30×100 mm;
  Flow rate: 20 mL/min;
  Solvent A: 10% ACN, 90% water, 0.1% trifluoroacetic Acid; and
  Solvent B: 90% ACN, 10% water, 0.1% trifluoroacetic Acid.

Analytical HPLC (unless otherwise noted) was performed to determine compound purity on a Shimadzu SIL-10A using the following method (Unless otherwise stated, retention times listed in Examples refer the retention times of Column 1):
  Linear Gradient of 10% to 100% solvent B over 15 min;
  UV visualization at 220 nm and 254 nm;
  Column 1: SunFire C18 3.5 µm, 4.6×150 mm;
  Column 2: Xbridge Phenyl 3.5 m, 4.6×150 mm;
  Flow rate: 1 ml/min (for both columns);
  Solvent A: 5% MeCN—95% H2O—0.05% TFA; and
  Solvent B: 95% MeCN—5% H2O—0.05% TFA.
  or
  Linear Gradient of stated starting percentage to 100% solvent B over 8 min;
  UV visualization at 220 nm;
  Column: Zorbax SB C18 3.5 µm, 4.6×75 mm;
  Flow rate: 2.5 ml/min;
  Solvent A: 10% MeOH—90% H2O—0.2% $H_3PO_4$; and
  Solvent B: 90% MeOH—10% H2O—00.2% $H_3PO_4$.

Preparatory chiral SFC chromatography (unless otherwise noted) was performed on a Berger Multigram II SFC chromatograph using the following method:
  UV visualization at 220 nm;
  Column: Chiralpak AD-H SFC, 250×21 mm ID, 5 µm;
  Flow rate: 60.0 mL/min, 150 bar backpressure; and
  Mobile Phase: 60/40, $CO_2$/MeOH.

Analytical chiral SFC chromatography (unless otherwise noted) was performed on an Aurora Analytical SFC chromatography using the following method:
  UV visualization at 220 nm;
  Column: Chiralpak AD-H, 250×4.6 mm ID, 5 µm;
  Flow rate: 3 mL/min, 150 bar backpressure; and
  Mobile Phase: 60/40, $CO_2$/MeOH.

NMR Employed in Characterization of Examples $^1$H NMR spectra (unless otherwise noted) were obtained with JEOL or Bruker FOURIER® transform spectrometers operating at 400 MHz or 500 MHz. $^1$H-nOe experiments were performed in some cases for regiochemistry elucidation with a 400 MHz Bruker FOURIER® Transform spectrometer.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$).

Example 1

2-(1-(4-(benzyloxy)phenyl)-3-(trifluoromethyl)-4,5-dihydro-1H-pyrazol-5-yl)acetic acid

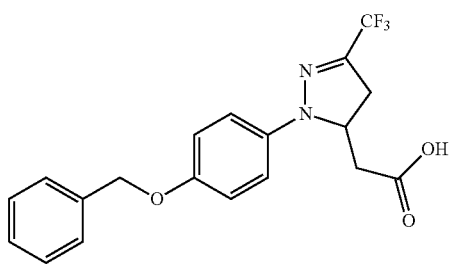 [SMILES: O=C(O)CC1CC(C(F)(F)F)=NN1c1ccc(OCc2ccccc2)cc1]

1A. methyl 2-(1-(4-(benzyloxy)phenyl)-3-(trifluoromethyl)-4,5-dihydro-1H-pyrazol-5-yl)acetate: N'-(4-(benzyloxy)phenyl)-2,2,2-trifluoroacetohydrazonoyl chloride (white solid, 52 mg) was prepared following the procedure of Example 17. To a solution of N'-(4-(benzyloxy)phenyl)-2,2,2-trifluoroacetohydrazonoyl chloride (62 mg, 0.19 mmol) in toluene (1.0 mL) was added methyl but-3-enoate (0.022 mL, 0.21 mmol) and then AgOAc (31 mg, 0.19 mmol). The resulting mixture was stirred at rt in the dark for 7 h. The reaction mixture was filtered and the filter cake was washed with EtOAc and CH$_2$Cl$_2$. The combined organic layers were concentrated and purified flash chromatography to afford 1A (yellow solid, 4 mg, 10 μmol, 5% yield). LC-MS Anal. Calc'd for C$_{20}$H$_{19}$F$_3$N$_2$O$_3$ 392.37. found [M+H] 393.2.

Example 1 (white solid, 2 mg, 6.1 μmol, 59% yield) was prepared as a racemate from 1A following the procedure of Example 17. LC-MS Anal. Calc'd for C$_{19}$H$_{17}$F$_3$N$_2$O$_3$ 378.35. found [M+H] 379.1. $^1$H NMR (500 MHz, CDCl$_3$) δ 7.43 (d, J=7.3 Hz, 2H), 7.38 (t, J=7.5 Hz, 2H), 7.32 (t, J=7.3 Hz, 1H), 7.06 (d, J=9.0 Hz, 2H), 6.95 (d, J=9.1 Hz, 2H), 5.04 (s, 2H), 4.82-4.71 (m, 1H), 3.39-3.30 (m, 1H), 2.94 (ddd, J=17.6, 6.0, 1.5 Hz, 1H), 2.84 (dd, J=16.2, 3.0 Hz, 1H), 2.43 (dd, J=16.2, 10.4 Hz, 1H). Analytical HPLC (orthogonal method): RT=11.3 min, HI: 95%. hGPR40 EC$_{50}$=1960 nM.

Example 2

2-(1-(4-(2,4-dichlorobenzyloxy)phenyl)-3-(trifluoromethyl)-4,5-dihydro-1H-pyrazol-5-yl)acetic acid

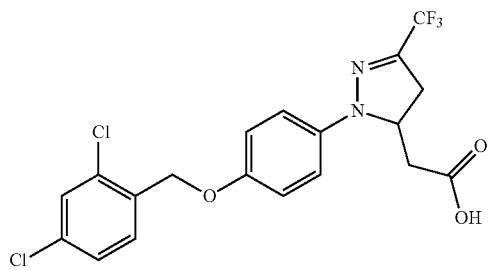 [SMILES: O=C(O)CC1CC(C(F)(F)F)=NN1c1ccc(OCc2ccc(Cl)cc2Cl)cc1]

Example 2 (white solid, 4 mg) was prepared as a racemate following the procedure for Example 1. LC-MS Anal. Calc'd for C$_{19}$H$_{15}$Cl$_2$F$_3$N$_2$O$_3$ 447.24. found [M+H] 447.1. $^1$H NMR (500 MHz, CDCl$_3$) δ 7.49 (d, J=8.3 Hz, 1H), 7.42 (d, J=2.1 Hz, 1H), 7.27 (dd, J=8.5, 2.1 Hz 1H), 7.07 (d, J=9.1 Hz, 2H), 6.94 (d, J=9.1 Hz, 2H), 5.09 (s, 2H), 4.83-4.71 (m, 1H), 3.46-3.30 (m, 1H), 2.95 (ddd, J=17.7, 5.8, 1.5 Hz, 1H), 2.85 (dd, J=16.2, 3.0 Hz, 1H), 2.45 (dd, J=16.2, 10.4 Hz, 1H). Analytical HPLC (orthogonal method): RT=12.9 min, HI: 95%. hGPR40 EC$_{50}$=800 nM.

Example 3

Isomer 1 and Isomer 2

2-(3-cyano-1-(4-(o-tolyloxy)phenyl)-4,5-dihydro-1H-pyrazol-5-yl)acetic acid

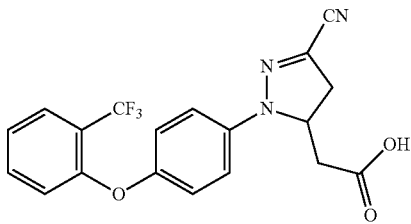

Example 3, Isomer 1 and Isomer 2 were prepared as single enantiomers following the procedure of Example 29. Example 3, Isomer 1 (yellow solid, 25 mg). LC-MS Anal. Calc'd for C$_{19}$H$_{17}$N$_3$O$_3$ 335.36. found [M+H] 336.1. $^1$H NMR (500 MHz, CDCl$_3$) δ 7.24 (dd, J=8.1, 1.2 Hz, 1H), 7.15 (td, J=7.6, 1.3 Hz, 1H), 7.08 (d, J=9.1 Hz, 2H), 7.05 (td, J=7.3, 0.9 Hz, 1H), 6.90 (d, J=9.0 Hz, 2H), 6.85 (dd, J=8.0, 0.7 Hz, 1H), 4.95-4.83 (m, 1H), 3.41 (dd, J=17.4, 11.9 Hz, 1H), 3.00 (dd, J=17.5, 5.1 Hz, 1H), 2.90 (dd, J=16.5, 3.0 Hz, 1H), 2.54 (dd, J=16.5, 10.1 Hz, 1H), 2.24 (s, 3H). Analytical HPLC (orthogonal method): RT=10.9 min, HI: 98%. hGPR40 EC$_{50}$=37 nM. Example 3, Isomer 2 (yellow solid, 25 mg). LC-MS Anal. Calc'd for C$_{19}$H$_{17}$N$_3$O$_3$ 335.36. found [M+H] 336.1. $^1$H NMR (500 MHz, CDCl$_3$) δ 7.24 (dd, J=8.1, 1.2 Hz, 1H), 7.15 (td, J=7.6, 1.3 Hz, 1H), 7.08 (d, J=9.1 Hz, 2H), 7.05 (td, J=7.3, 0.9 Hz, 1H), 6.90 (d, J=9.0 Hz, 2H), 6.85 (dd, J=8.0, 0.7 Hz, 1H), 4.95-4.83 (m, 1H), 3.41 (dd, J=17.4, 11.9 Hz, 1H), 3.00 (dd, J=17.5, 5.1 Hz, 1H), 2.90 (dd, J=16.5, 3.0 Hz, 1H), 2.54 (dd, J=16.5, 10.1 Hz, 1H), 2.24 (s, 3H). Analytical HPLC (orthogonal method): RT=10.9 min, HI: 99%. hGPR40 EC$_{50}$=560 nM.

Example 4

2-(1-(4-(3-chlorophenoxy)phenyl)-3-cyano-4,5-dihydro-1H-pyrazol-5-yl)acetic acid

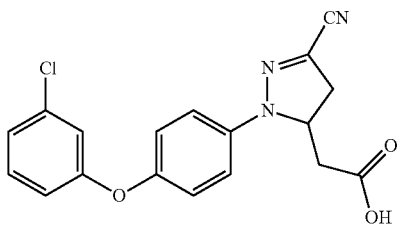 [SMILES: N#CC1=NN(c2ccc(Oc3cccc(Cl)c3)cc2)C(CC(=O)O)C1]

Example 4 (white solid, 4 mg) was prepared as a racemate following the procedure for Example 29. LC-MS Anal.

Calc'd for $C_{18}H_{14}ClN_3O_3$ 355.78. found [M+H] 356.1. $^1$H NMR (500 MHz, CDCl$_3$) δ 7.24 (t, J=8.2 Hz, 1H), 7.14 (d, J=9.1 Hz, 2H), 7.08-7.04 (m, 1H), 7.03 (d, J=9.0 Hz, 2H), 6.94 (t, J=2.1 Hz, 1H), 6.86 (ddd, J=8.3, 2.4, 0.8 Hz, 1H), 4.99-4.88 (m, 1H), 3.45 (dd, J=17.5, 11.9 Hz, 1H), 3.03 (dd, J=17.5, 4.9 Hz, 1H), 2.94 (dd, J=16.6, 2.9 Hz, 1H), 2.57 (dd, J=16.6, 10.2 Hz, 1H). Analytical HPLC (orthogonal method): RT=11.2 min, HI: 98%. hGPR40 EC$_{50}$=220 nM.

Example 5

2-(3-(methylsulfonyl)-1-(4-(o-tolyloxy)phenyl)-4,5-dihydro-1H-pyrazol-5-yl)acetic acid

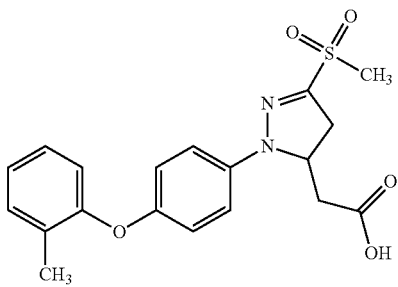 [SMILES: Cc1ccccc1Oc1ccc(N2N=C(S(C)(=O)=O)CC2CC(=O)O)cc1]

Example 5 (white solid, 2 mg) was prepared as a racemate following the procedure for Example 29. LC-MS Anal. Calc'd for $C_{19}H_{20}N_2O_5S$, 388.44. found [M+H] 387.1. $^1$H NMR (500 MHz, CDCl$_3$) δ 7.24 (d, J=7.2 Hz, 1H), 7.15 (t, J=7.4 Hz, 1H), 7.10-7.02 (m, 3H), 6.91 (d, J=9.0 Hz, 2H), 6.85 (d, J=7.3 Hz, 1H), 4.99-4.85 (m, 1H), 3.58 (dd, J=17.6, 11.7 Hz, 1H), 3.22 (s, 3H), 3.21 (dd, J=17.5, 5.5 Hz, 1H), 2.91 (dd, J=16.6, 2.9 Hz, 1H), 2.62 (dd, J=16.6, 9.8 Hz, 1H), 2.25 (s, 3H). Analytical HPLC (orthogonal method): RT=9.6 min, HI: 95%. hGPR40 EC$_{50}$=1650 nM.

Example 6

2-(3-(dimethylcarbamoyl)-1-(4-(o-tolyloxy)phenyl)-4,5-dihydro-1H-pyrazol-5-yl)acetic acid

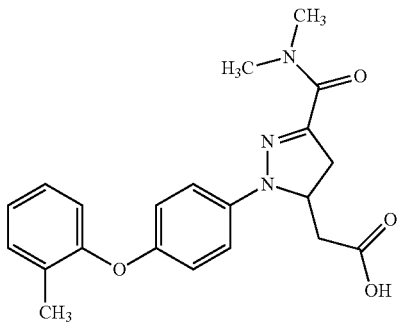 [SMILES: Cc1ccccc1Oc1ccc(N2N=C(C(=O)N(C)C)CC2CC(=O)O)cc1]

6A. ethyl 5-(cyanomethyl)-1-(4-methoxyphenyl)-4,5-dihydro-1H-pyrazole-3-carboxylate: To a solution of ethyl 2-chloro-2-(2-(4-methoxyphenyl)hydrazono)acetate, which was prepared following the procedure for Example 29 (2.0 g, 7.8 mmol) in toluene (15 mL) at rt was added AgOAc (1.3 g, 7.8 mmol) under argon followed by but-3-enenitrile (0.94 mL, 12 mmol). The resulting mixture was stirred at rt under argon overnight. The reaction mixture was filtered and the filtrate was concentrated and purified by flash chromatography to afford 6A (dark red solid, 1.18 g, 4.09 mmol, 53% yield). LC-MS Anal. Calc'd for $C_{15}H_{17}N_3O_3$ 287.31. found [M+H] 288.0.

6B. ethyl 5-(cyanomethyl)-1-(4-hydroxyphenyl)-4,5-dihydro-1H-pyrazole-3-carboxylate: To a solution of 6A (1.16 g, 4.02 mmol) in CH$_2$Cl$_2$ (15 mL) at 0° C. under argon was added BF$_3$.SMe$_2$ (2.54 mL, 24.1 mmol) dropwise. The resulting mixture was stirred at ambient temperature for 2 h and then allowed to warm to rt for 4 h. The reaction mixture was quenched with MeOH and then concentrated. The crude product was purified by flash chromatography to provide 6B (yellow solid, 694 mg, 1.78 mmol, 44% yield). LC-MS Anal. Calc'd for $C_{14}H_{15}N_3O_3$ 273.29. found [M+H] 274.0.

6C. ethyl 5-(cyanomethyl)-1-(4-(o-tolyloxy)phenyl)-4,5-dihydro-1H-pyrazole-3-carboxylate: To a solution of 6B (694 mg, 2.54 mmol) in CH$_2$Cl$_2$ (10 mL) was added o-tolylboronic acid (691 mg, 5.08 mmol), copper (II) acetate (923 mg, 5.08 mmol), NEt$_3$ (1.77 mL, 12.7 mmol) and 4 Å mol. sieves (500 mg). The resulting mixture was stirred overnight under air. The reaction mixture was filtered and the filter cake was washed with CH$_2$Cl$_2$/EtOAc (3×). The combined filtrates were concentrated and purified by flash chromatography to afford 6C (yellow solid, 317 mg, 0.872 mmol, 34% yield). LC-MS Anal. Calc'd for $C_{21}H_{21}N_3O_3$ 363.41. found [M+H] 364.2.

6D. 5-(cyanomethyl)-N,N-dimethyl-1-(4-(o-tolyloxy)phenyl)-4,5-dihydro-1H-pyrazole-3-carboxamide: To a solution 6C (47 mg, 0.13 mmol) in MeOH (1.0 mL) was added KCN (4 mg, 0.065 mmol) and dimethylamine (2.0 M in MeOH) (0.19 mL, 0.39 mmol). The resulting mixture was sealed in a vial and heated to 45° C. overnight. The reaction mixture was concentrated and purified by flash chromatography to afford 6D (yellow oil, 6 mg, 0.018 mmol, 14% yield). LC-MS Anal. Calc'd for $C_{21}H_{22}N_4O_2$ 362.42. found [M+H] 363.2.

6E. methyl 2-(3-(dimethylcarbamoyl)-1-(4-(o-tolyloxy)phenyl)-4,5-dihydro-1H-pyrazol-5-yl)acetate: A 3 M solution of HCl in MeOAc/MeOH solution was prepared by adding 0.13 mL AcCl dropwise into 1.0 mL MeOH at 0° C. The solution was allowed to warm to rt for 30 min and then transferred to a flask containing 6D (6 mg, 0.018 mmol) and stirred for 2 days under argon. The mixture was concentrated and was treated with another batch of 3 M HCl solution in MeOAc/MeOH (1.20 mL, 3.59 mmol). The resulting mixture was stirred overnight under argon for 2 days. The reaction mixture was then heated to 40° C. overnight. The above solution was concentrated and treated with an additional batch of 3 M HCl (1.20 mL, 3.59 mmol). The resulting mixture was stirred at rt for 3 days. The reaction mixture was concentrated, diluted with THF, and then adjusted to pH ~2 with aq. 1 N NaOH solution. The solution was extracted with EtOAc. The combined organic extracts were dried over Na$_2$SO$_4$ and concentrated to give 6E (red residue, 5 mg, 0.014 mmol, 76% yield), which was used without further purification. LC-MS Anal. Calc'd for $C_{22}H_{25}N_3O_4$ 395.45. found [M+H] 396.2.

Example 6: To a solution of 6E (5 mg, 0.014 mmol) in THF (1.0 mL) was added LiOH (1 mg, 0.027 mmol) in water (0.5 mL). The resulting mixture was stirred at rt for 2 h. The reaction mixture was adjusted to pH ~2 with aq. 1 N HCl solution and then purified by RP-prep HPLC to afford Example 6 as a racemate (yellow solid, 2 mg, 5.2 μmol, 38% yield). LC-MS Anal. Calc'd for $C_{21}H_{23}N_3O_4$ 381.43. found [M+H] 382.2. $^1$H NMR (500 MHz, CDCl$_3$) δ 7.23 (d, J=7.1 Hz, 1H), 7.13 (t, J=7.7 Hz, 1H), 7.06-7.01 (m, 3H), 6.91 (d, J=9.0 Hz, 2H), 6.83 (d, J=8.2 Hz, 1H), 4.81-4.65 (m, 1H), 3.55-3.38 (m, 4H), 3.20-3.05 (m, 4H), 2.91 (dd, J=16.1, 3.0 Hz, 1H), 2.44 (dd, J=16.0, 10.5 Hz, 1H), 2.27 (s, 3H). Analytical HPLC (Zorbax method, 50% Solvent B start): RT=6.0 min, HI: 99%. hGPR40 $EC_{50}$=1810 nM.

Example 7

2-(3-(1-methyl-1H-tetrazol-5-yl)-1-(4-(o-tolyloxy) phenyl)-4,5-dihydro-1H-pyrazol-5-yl)acetic acid

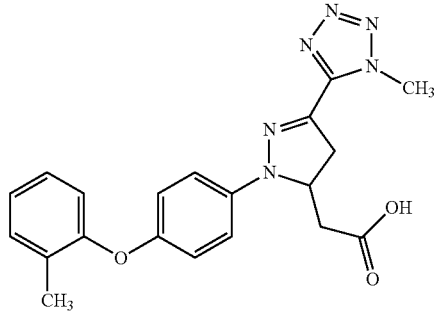 [SMILES: Cc1ccccc1Oc1ccc(N2N=C(c3nnnn3C)CC2CC(=O)O)cc1]

7A. 5-(cyanomethyl)-N-methyl-1-(4-(o-tolyloxy)phenyl)-4,5-dihydro-1H-pyrazole-3-carboxamide: To a solution of 6C (70 mg, 0.19 mmol) in MeOH (1.0 mL) was added KCN (6 mg, 0.096 mmol) and methanamine (0.24 mL, 1.9 mmol). The resulting mixture was heated to 45° C. in a sealed vial overnight. The mixture was concentrated and purified by flash chromatography to afford 7A (yellow solid, 39 mg, 0.11 mmol, 58% yield). LC-MS Anal. Calc'd for $C_{20}H_{20}N_4O_2$ 348.4. found [M+H] 349.2.

7B. 2-(3-(1-methyl-1H-tetrazol-5-yl)-1-(4-(o-tolyloxy)phenyl)-4,5-dihydro-1H-pyrazol-5-yl)acetonitrile: To a solution of 8A (39 mg, 0.11 mmol) in $CH_3CN$ (1.0 mL) was added sodium azide (8 mg, 0.12 mmol). The reaction mixture was cooled to 0° C. under argon and to the mixture was added trifluoromethanesulfonic anhydride (0.028 mL, 0.17 mmol) dropwise. The reaction mixture was then stirred at rt for 4 h. The reaction mixture was concentrated. The crude residue was purified by flash chromatography to afford 8B (yellow solid, 13 mg, 0.035 mmol, 31% yield). LC-MS Anal. Calc'd for $C_{20}H_{19}N_7O$, 373.41. found [M+H] 374.2.

Example 7: To a flask of 7B (13 mg, 0.035 mmol) was added a solution of 3 M HCl in $MeOAc/MeOH/CH_2Cl_2$ (prepared by adding 1.3 mL AcCl into MeOH (3.0 mL) and $CH_2Cl_2$ (2.0 mL) at 0° C. and then stirring at rt for 30 min) The reaction mixture was stirred at rt overnight. The reaction mixture was concentrated and dissolved in THF (1.0 mL) and water (1.0 mL). To the solution was added a solution of LiOH (2 mg, 0.070 mmol) in water (0.5 mL). The resulting mixture was stirred at rt for 2 h. The reaction mixture was quenched with aq. 1 N HCl solution, concentrated, and purified by RP-prep HPLC to afford Example 7 as a racemate (yellow oil, 3 mg, 7.3 µmol, 21% yield). LC-MS Anal. Calc'd for $C_{20}H_{20}N_6O_3$ 392.41. found [M+H] 393.1. $^1$H NMR (500 MHz, $CDCl_3$) δ 7.25 (d, J=8.0 Hz, 1H), 7.16 (td, J=8.0, 1.5 Hz, 1H), 7.12 (d, J=9.0 Hz, 2H), 7.05 (td, J=7.4, 1.0 Hz, 1H), 6.95 (d, J=9.0 Hz, 2H), 6.87 (d, J=8.0 Hz, 1H), 5.00-4.90 (m, 1H), 4.37 (s, 3H), 3.83-3.71 (m, 1H), 3.42 (dd, J=17.9, 5.3 Hz, 1H), 3.05 (dd, J=16.4, 3.0 Hz, 1H), 2.55 (dd, J=16.4, 10.7 Hz, 1H), 2.28 (s, 3H). Analytical HPLC (orthogonal method): RT=10.2 min, HI: 96%. hGPR40 $EC_{50}$=3200 nM.

Example 8, Isomer 1 and Isomer 2

2-(1-(4-(2'-fluoro-5'-methoxy-3-methylbiphenyl-4-yloxy)phenyl)-3-(oxazol-2-yl)-4,5-dihydro-1H-pyrazol-5-yl)acetic acid

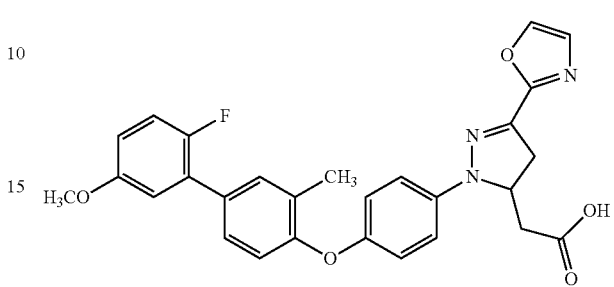

8A. 5-(cyanomethyl)-N-(2,2-dimethoxyethyl)-1-(4-methoxyphenyl)-4,5-dihydro-1H-pyrazole-3-carboxamide: To a suspension of methyl 5-(cyanomethyl)-1-(4-methoxyphenyl)-4,5-dihydro-1H-pyrazole-3-carboxylate prepared following the procedure of Example 6 (1.22 g, 4.46 mmol) in MeOH (6 mL) was added 2,2-dimethoxyethanamine (1.99 mL, 44.6 mmol). The resulting mixture was heated to 50° C. and stirred for 2 days. The reaction mixture was diluted with water and extracted with $CH_2Cl_2$. The combined organic extracts were dried over $Na_2SO_4$, concentrated, and purified by flash chromatography to afford 8A (yellow solid, 1.26 g, 3.64 mmol, 81% yield).

8B. 5-(cyanomethyl)-1-(4-methoxyphenyl)-N-(2-oxoethyl)-4,5-dihydro-1H-pyrazole-3-carboxamide: To a solution of 8A (1.26 g, 2.18 mmol) in THF (5.0 mL) was added aq. 1 N HCl (8.7 mL, 8.7 mmol). The resulting mixture was stirred at rt for 2.5 days. The reaction mixture was extracted with $CH_2Cl_2$. The combined organic extracts were dried over $Na_2SO_4$, concentrated, and purified by flash chromatography to provide 8B (yellow solid, 724 mg, 1.50 mmol, 69% yield). LC-MS Anal. Calc'd for $C_{15}H_{16}N_4O_3$ 300.31. found [M+H] 301.1.

8C. 2-(1-(4-methoxyphenyl)-3-(oxazol-2-yl)-4,5-dihydro-1H-pyrazol-5-yl)acetonitrile: To a solution of 8B (500 mg, 1.67 mmol) in $CH_3CN$ (4.0 mL) was added perchloroethane (118 mg, 4.99 mmol) in $CH_3CN$ (2.0 mL). The reaction mixture was cooled to 0° C. and to the mixture was added $NEt_3$ (1.39 mL, 9.99 mmol) and $PPh_3$ (131 mg, 4.99 mmol) portionwise. The cold bath was removed and the resulting mixture was stirred at rt overnight. The reaction mixture was purified by RP-prep HPLC to afford 8C (dark red solid, 250 mg, 0.886 mmol, 53% yield). LC-MS Anal. Calc'd for $C_{15}H_{14}N_4O_2$ 282.30. found [M+H] 283.1.

8D. 2-(1-(4-hydroxyphenyl)-3-(oxazol-2-yl)-4,5-dihydro-1H-pyrazol-5-yl)acetonitrile: To a solution of 8C (331 mg, 1.17 mmol) in $CH_2Cl_2$ (5.0 mL) at 0° C. was added $BF_3.SMe_2$ (0.74 mL, 7.0 mmol) under argon. The reaction mixture was allowed to warm to rt and stirred for 2 h. The reaction mixture was cooled to 0° C., and quenched with MeOH (5 mL). The mixture was stirred at rt for 30 min and then concentrated. The crude product was purified by flash chromatography to afford 8D (yellow solid, 79 mg, 0.29 mmol, 25% yield). LC-MS Anal. Calc'd for $C_{14}H_{12}N_4O_2$ 268.27. found [M+H] 269.1.

8E. 2-(1-(4-(4-bromo-2-methylphenoxy)phenyl)-3-(oxazol-2-yl)-4,5-dihydro-1H-pyrazol-5-yl)acetonitrile: A mixture of 4-bromo-2-methylphenylboronic acid (127 mg, 0.589 mmol), 8D (79 mg, 0.29 mmol), copper (II) acetate (107 mg, 0.589 mmol), NEt$_3$ (0.21 mL, 1.5 mmol) and 4 Å mol. sieves (100 mg, 0.294 mmol) in CH$_2$Cl$_2$ (5.0 mL) was stirred under air overnight. The reaction mixture was filtered through a pad of silica gel and the filtrate was concentrated and purified by flash chromatography to afford 8E (yellow solid, 92 mg, 0.21 mmol, 71% yield). LC-MS Anal. Calc'd for C$_{21}$H$_{17}$BrN$_4$O$_2$ 437.29. found [M+H] 437.0, 439.0.

8F. 2-(1-(4-(2'-fluoro-5'-methoxy-3-methylbiphenyl-4-yloxy)phenyl)-3-(oxazol-2-yl)-4,5-dihydro-1H-pyrazol-5-yl)acetonitrile: To a solution of 8E (92 mg, 0.21 mmol) in 1,4-dioxane (2.0 mL) was added 2-fluoro-5-methoxyphenylboronic acid (72 mg, 0.421 mmol), 2.0 M aq. NaHCO$_3$ (0.32 mL, 0.63 mmol) and Pd(PPh$_3$)$_4$ (24 mg, 0.021 mmol). The resulting mixture was heated to 90° C. and stirred under argon overnight. The reaction mixture was diluted with water and extracted with CH$_2$Cl$_2$. The combined organic extracts were dried over Na$_2$SO$_4$, concentrated, and purified by flash chromatography to provide 8F (orange oil, 101 mg, 0.209 mmol, 99% yield). LC-MS Anal. Calc'd for C$_{28}$H$_{23}$FN$_4$O$_3$ 482.51. found [M+H] 483.2.

Example 8, Isomer 1 and Isomer 2 were prepared from 8F as single enantiomers following the procedure of Example 6. Example 8, Isomer 1 (yellow solid, 6 mg). LC-MS Anal. Calc'd for C$_{28}$H$_{24}$FN$_3$O$_5$ 501.51. found [M+H] 502.2. $^1$H NMR (500 MHz, CDCl$_3$) δ 7.71 (s, 1H), 7.41 (s, 1H), 7.29 (d, J=8.8 Hz, 1H), 7.23 (s, 1H), 7.19 (d, J=8.3 Hz, 2H), 7.05 (t, J=9.5 Hz, 1H), 6.98 (d, J=8.1 Hz, 2H), 6.92 (dd, J=6.2, 3.1 Hz, 1H), 6.85 (d, J=8.4 Hz, 1H), 6.80 (dt, J=8.9, 3.4 Hz, 1H), 4.90 (m, 1H), 3.82 (s, 3H), 3.63 (t, J=13.8 Hz, 1H), 3.29 (d, J=13.3 Hz, 1H), 2.97 (t, J=13.6 Hz, 1H), 2.46 (t, J=13.5 Hz, 1H), 2.33 (s, 3H). Analytical HPLC (orthogonal method): RT=10.2 min, HI: 97%. hGPR40 EC$_{50}$=910 nM. Example 8, Isomer 2 (yellow solid, 5 mg). LC-MS Anal. Calc'd for C$_{28}$H$_{24}$FN$_3$O$_5$ 501.51. found [M+H] 502.2. $^1$H NMR (500 MHz, CDCl$_3$) δ 7.71 (s, 1H), 7.41 (s, 1H), 7.29 (d, J=8.8 Hz, 1H), 7.23 (s, 1H), 7.19 (d, J=8.3 Hz, 2H), 7.05 (t, J=9.5 Hz, 1H), 6.98 (d, J=8.1 Hz, 2H), 6.92 (dd, J=6.2, 3.1 Hz, 1H), 6.85 (d, J=8.4 Hz, 1H), 6.80 (dt, J=8.9, 3.4 Hz, 1H), 4.90 (m, 1H), 3.82 (s, 3H), 3.63 (t, J=13.8 Hz, 1H), 3.29 (d, J=13.3 Hz, 1H), 2.97 (t, J=13.6 Hz, 1H), 2.46 (t, J=13.5 Hz, 1H), 2.33 (s, 3H). Analytical HPLC (orthogonal method): RT=10.2 min, HI: 97%. hGPR40 EC$_{50}$=1160 nM.

Example 9, Isomer 1 and Isomer 2

2-(1-(4-(3'-methoxy-3-methylbiphenyl-4-yloxy)phenyl)-3-(trifluoromethyl)-4,5-dihydro-1H-pyrazol-5-yl)acetic acid

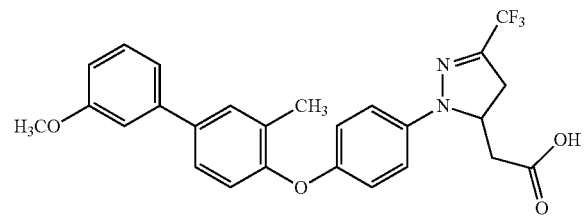 [SMILES: COc1cccc(-c2ccc(Oc3ccc(N4N=C(C(F)(F)F)CC4CC(=O)O)cc3)c(C)c2)c1]

9A. methyl 1-(4-methoxyphenyl)-3-(trifluoromethyl)-4,5-dihydro-1H-pyrazole-5-carboxylate: 9A (yellow solid, 11.5 g, 38.1 mmol, 78% yield) was prepared from 2,2,2-trifluoro-N'-(4-methoxyphenyl)acetohydrazonoyl chloride following the procedure of Example 17 Isomer 2. LC-MS Anal. Calc'd for C$_{13}$H$_{13}$F$_3$N$_2$O$_3$ 302.25. found [M+H] 303.0.

9B. (1-(4-methoxyphenyl)-3-(trifluoromethyl)-4,5-dihydro-1H-pyrazol-5-yl)methanol: To a solution of 9A (11.5 g, 38.1 mmol) in THF (20 mL) at 0° C. was added LiBH$_4$ (2.0 M in THF) (19.1 mL, 38.1 mmol) dropwise. The resulting mixture was stirred at ambient temperature for 30 min and then allowed to warm to rt for another 3 h. The reaction mixture was cooled to 0° C. and quenched with MeOH (10 mL) dropwise. The reaction mixture was allowed to warm to rt and stirred for 1 h. The reaction mixture was concentrated and purified by flash chromatography to give 9B (yellow solid, 11.0 g, 40.2 mmol, 100% yield). LC-MS Anal. Calc'd for C$_{12}$H$_{13}$F$_3$N$_2$O$_2$ 274.24. found [M+H] 275.0.

9C. methyl 2-(1-(4-(3'-methoxy-3-methylbiphenyl-4-yloxy)phenyl)-3-(trifluoromethyl)-4,5-dihydro-1H-pyrazol-5-yl)acetate: To a solution of 9B (11.0 g, 40.2 mmol) in CH$_2$Cl$_2$ (50 mL) at 0° C. was added MsCl (4.70 mL, 60.3 mmol) and NEt$_3$ (16.8 mL, 121 mmol). The resulting mixture was stirred at 0° C. for 10 min and then allowed to warm to rt overnight. The reaction mixture was diluted with CH$_2$Cl$_2$ and washed with aq. sat. NaHCO$_3$ solution. The organic layer was dried over Na$_2$SO$_4$ and concentrated to give a thick red oil, which was dissolved in DMSO (50.0 mL) and to the solution was added KCN (5.2 g, 80 mmol). The reaction mixture was heated to 60° C. for 4 h and then cooled to rt and stirred overnight. The reaction mixture was diluted with water and extracted with CH$_2$Cl$_2$. The combined organic extracts were dried over Na$_2$SO$_4$, concentrated, and purified by flash chromatography to afford 2-(1-(4-methoxyphenyl)-3-(trifluoromethyl)-4,5-dihydro-1H-pyrazol-5-yl)acetonitrile (red solid, 9.88 g, 34.9 mmol, 87% yield). To a solution of 2-(1-(4-methoxyphenyl)-3-(trifluoromethyl)-4,5-dihydro-1H-pyrazol-5-yl)acetonitrile (4.60 g, 16.2 mmol) in CH$_2$Cl$_2$ (16 mL) at −78° C. under argon was added BBr$_3$ (3.07 mL, 32.5 mmol) dropwise. The reaction mixture was kept at −78° C. for 1 h and then was allowed to warm to 0° C. After stirring for 1 h at 0° C., the reaction mixture was diluted with 200 mL CH$_2$Cl$_2$ and quenched by adding aq. sat. NaHCO$_3$ solution slowly at 0° C. The resulting mixture was stirred for 10 min, diluted with water, and extracted with CH$_2$Cl$_2$. The combined organic extracts were dried over Na$_2$SO$_4$ overnight. The solution was filtered, concentrated, and purified by flash chromatography to afford 2-(1-(4-hydroxyphenyl)-3-(trifluoromethyl)-4,5-dihydro-1H-pyrazol-5-yl)acetonitrile (yellow solid, 3.13 g, 11.2 mmol, 69% yield). A mixture of 2-(1-(4-hydroxyphenyl)-3-(trifluoromethyl)-4,5-dihydro-1H-pyrazol-5-yl)acetonitrile (3.12 g, 11.6 mmol), 4-bromo-2-methylphenylboronic acid (5.23 g, 24.3 mmol), copper (II) acetate (4.21 g, 23.2 mmol), NEt$_3$ (8.08 mL, 57.9 mmol) and 4 Å mol. sieves (5.0 g) in CH$_2$Cl$_2$ (40 mL) was stirred for 2.5 days under air. The reaction mixture was filtered and the filter cake was washed with CH$_2$Cl$_2$. The combined filtrates were concentrated and purified by flash chromatography to afford 2-(1-(4-(4-bromo-2-methylphenoxy)phenyl)-3-(trifluoromethyl)-4,5-dihydro-1H-pyrazol-5-yl)acetonitrile (yellow solid, 853 mg, 1.95 mmol, 17% yield) and 1.83 g recovered phenol. A 3 M HCl solution was prepared by adding AcCl (15 mL) slowly into a mixture of CH$_2$Cl$_2$ (20 mL) and MeOH (30 mL) at 0° C. The mixture was allowed to warm to rt for 1 h. To the above solution was added a solution of 2-(1-(4-(4-bromo-2-methylphenoxy)phenyl)-3-(trifluoromethyl)-4,5-dihydro-1H-pyrazol-5-yl)acetonitrile (1.57 g, 3.58 mmol) in MeOH (5 mL) at 0° C. The resulting mixture was stirred at 0° C. for 30 min and then allowed to warm to rt and stirred for 2 days. The reaction mixture was concentrated, diluted with CH$_2$Cl$_2$, and washed with aq. sat. NaHCO$_3$ solution. The aq. solution was back extracted with CH$_2$Cl$_2$. The combined organic extracts were dried over Na$_2$SO$_4$, concentrated, and purified by flash chromatography to afford methyl 2-(1-(4-(4-bromo-2-methylphenoxy)phenyl)-3-(trifluoromethyl)-4,5-dihydro-1H-pyrazol-5-yl)acetate (off white solid, 1.27 g, 2.69 mmol, 75% yield). To a solution of methyl 2-(1-(4-(4-bromo-2-methylphenoxy)phenyl)-3-(trifluoromethyl)-4,5-dihydro-1H-pyrazol-5-yl)acetate (100 mg, 0.212 mmol) in 1,4-dioxane (2.0 mL) was added 3-methoxyphenylboronic acid (64 mg, 0.424 mmol), Pd(PPh$_3$)$_4$ (25 mg, 0.021 mmol) and NaHCO$_3$ (2.0 M aq.) (0.32 mL, 0.64 mmol). The resulting mixture was degassed with argon (3×), and then heated to 120° C. for 2.5 h. The reaction mixture was cooled to rt, diluted with water, and extracted with CH$_2$Cl$_2$. The combined organic extracts were dried over Na$_2$SO$_4$, concentrated, and purified by flash chromatography to afford 9C (white film, 43 mg, 0.086 mmol, 41% yield). LC-MS Anal. Calc'd for C$_{27}$H$_{25}$F$_3$N$_2$O$_4$ 498.49. found [M+H] 499.2.

Example 9, Isomer 1 and Isomer 2 were prepared as single enantiomers from 9C following the procedure of Example 17. Example 9, Isomer 1 (white solid, 45 mg). LC-MS Anal. Calc'd for C$_{26}$H$_{23}$F$_3$N$_2$O$_4$ 484.47. found [M+H] 485.1. $^1$H NMR (500 MHz, CDCl$_3$) δ 7.46 (d, J=1.9 Hz, 1H), 7.34 (t, J=7.9 Hz, 2H), 7.15 (d, J=7.7 Hz, 1H), 7.13-7.06 (m, 3H), 6.96 (d, J=8.6 Hz, 2H), 6.87 (d, J=8.3 Hz, 2H), 4.92-4.73 (m, 1H), 3.87 (s, 3H), 3.53-3.33 (m, 1H), 3.09-2.86 (m, 2H), 2.69-2.45 (m, 1H), 2.33 (s, 3H). Analytical HPLC (orthogonal method): RT=13.1 min, HI: 96%. hGPR40 EC$_{50}$=190 nM. Example 9, Isomer 2 (white solid, 40 mg). LC-MS Anal. Calc'd for C$_{26}$H$_{23}$F$_3$N$_2$O$_4$ 484.47. found [M+H] 485.2. $^1$H NMR (500 MHz, CDCl$_3$) δ 7.46 (d, J=1.9 Hz, 1H), 7.34 (t, J=7.9 Hz, 2H), 7.15 (d, J=7.7 Hz, 1H), 7.13-7.06 (m, 3H), 6.96 (d, J=8.6 Hz, 2H), 6.87 (d, J=8.3 Hz, 2H), 4.92-4.73 (m, 1H), 3.87 (s, 3H), 3.53-3.33 (m, 1H), 3.09-2.86 (m, 2H), 2.69-2.45 (m, 1H), 2.33 (s, 3H). Analytical HPLC (orthogonal method): RT=13.1 min, HI: 99%. hGPR40 EC$_{50}$=290 nM.

Example 10

2-(1-(4-(4-bromo-5-fluoro-2-methylphenoxy)phenyl)-3-(trifluoromethyl)-4,5-dihydro-1H-pyrazol-5-yl)acetic acid

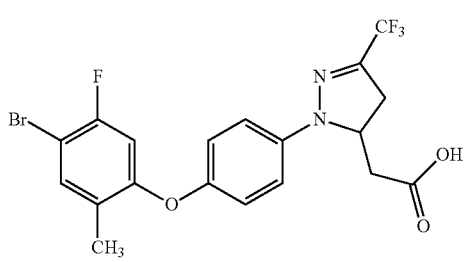 [SMILES: Cc1cc(Br)c(F)cc1Oc1ccc(N2N=C(C(F)(F)F)CC2CC(=O)O)cc1]

Example 10 (white powder, 15 mg) was prepared as a racemate following the procedure of Example 9. LC-MS Anal. Calc'd for C$_{19}$H$_{15}$BrF$_4$N$_2$O$_3$ 475.23. found [M+H] 474.9, 476.9. $^1$H NMR (500 MHz, CDCl$_3$) δ 7.38 (d, J=7.7 Hz, 1H), 7.11 (d, J=9.0 Hz, 2H), 6.95 (d, J=9.0 Hz, 2H), 6.54 (d, J=9.7 Hz, 1H), 4.88-4.81 (m, 1H), 3.52-3.35 (m, 1H), 3.05-2.90 (m, 2H), 2.57 (dd, J=16.5, 10.1 Hz, 1H), 2.24 (s, 3H). Analytical HPLC (orthogonal method): RT=13.1 min, HI: 99%. hGPR40 EC$_{50}$=230 nM.

Example 11, Isomer 1 and Isomer 2

2-(1-(4-(o-tolyloxy)phenyl)-3-(trifluoromethyl)-4,5-dihydro-1H-pyrazol-5-yl)acetic acid

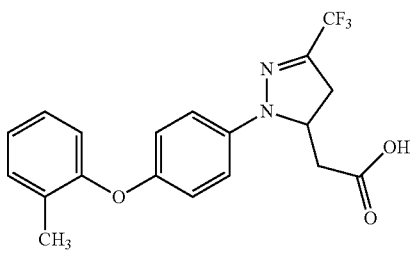 [SMILES: Cc1ccccc1Oc1ccc(N2N=C(C(F)(F)F)CC2CC(=O)O)cc1]

Example 11, Isomer 1 and Isomer 2 were prepared as single enantiomers following the procedure of Example 9. Example 11, Isomer 1 (white solid, 13 mg). LC-MS Anal. Calc'd for C$_{19}$H$_{17}$F$_3$N$_2$O$_3$ 378.35. found [M+H] 379. $^1$H NMR (500 MHz, CDCl$_3$) δ 7.24 (d, J=7.5 Hz, 1H), 7.14 (td, J=7.6, 1.4 Hz, 1H), 7.07 (d, J=9.0 Hz, 2H), 7.03 (td, J=7.4, 1.1 Hz, 1H), 6.91 (d, J=9.0 Hz, 2H), 6.83 (dd, J=8.0, 0.9 Hz, 1H), 4.85-4.74 (m, 1H), 3.45-3.33 (m, 1H), 3.02-2.89 (m, 2H), 2.54 (dd, J=16.4, 10.2 Hz, 1H), 2.26 (s, 3H). Analytical HPLC (orthogonal method): RT=12.1 min, HI: 95%. hGPR40 EC$_{50}$=70 nM. Example 11, Isomer 2 (white solid, 26 mg). LC-MS Anal. Calc'd for C$_{19}$H$_{17}$F$_3$N$_2$O$_3$ 378.35. found [M+H] 379. $^1$H NMR (500 MHz, CDCl$_3$) δ 7.24 (d, J=7.5 Hz, 1H), 7.14 (td, J=7.6, 1.4 Hz, 1H), 7.07 (d, J=9.0 Hz, 2H), 7.03 (td, J=7.4, 1.1 Hz, 1H), 6.91 (d, J=9.0 Hz, 2H), 6.83 (dd, J=8.0, 0.9 Hz, 1H), 4.85-4.74 (m, 1H), 3.45-3.33 (m, 1H), 3.02-2.89 (m, 2H), 2.54 (dd, J=16.4, 10.2 Hz, 1H), 2.26 (s, 3H). Analytical HPLC (orthogonal method): RT=12.1 min, HI: 95%. hGPR40 EC$_{50}$=1850 nM.

Example 12

2-(1-(4-(2,2'-difluoro-5'-methoxy-5-methylbiphenyl-4-yloxy)phenyl)-3-(trifluoromethyl)-4,5-dihydro-1H-pyrazol-5-yl)acetic acid

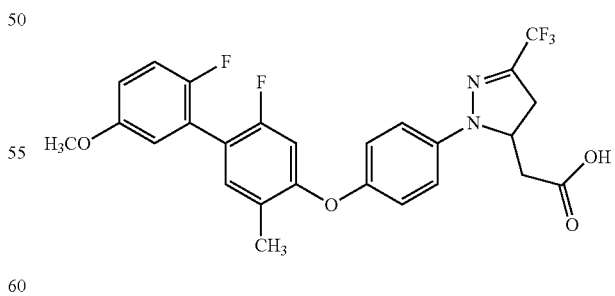

Example 12 (white solid, 7 mg) was prepared as a racemate following the procedure of Example 9. LC-MS Anal. Calc'd for C$_{26}$H$_{21}$F$_5$N$_2$O$_4$ 520.45. found [M+H] 521. $^1$H NMR (500 MHz, CDCl$_3$) δ 7.23 (d, J=8.2 Hz, 1H), 7.13 (d, J=9.0 Hz, 2H), 7.06 (t, J=9.1 Hz, 1H), 7.02 (d, J=9.0 Hz, 2H), 6.90-6.83 (m, 2H), 6.57 (d, J=11.0 Hz, 1H), 4.92-4.79 (m, 1H), 3.81 (s, 3H), 3.51-3.36 (m, 1H), 3.05-2.91 (m, 2H), 2.57 (dd, J=16.5, 10.2 Hz, 1H), 2.30 (s, 3H). Analytical HPLC (orthogonal method): RT=13.1 min, HI: 96%. hGPR40 EC$_{50}$=510 nM.

Example 13

2-(1-(4-(4-bromo-2-methylphenoxy)phenyl)-3-(trifluoromethyl)-4,5-dihydro-1H-pyrazol-5-yl)acetic acid

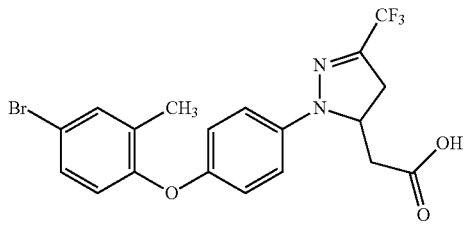 [SMILES: Cc1cc(Br)ccc1Oc1ccc(N2N=C(C(F)(F)F)CC2CC(=O)O)cc1]

Example 13 (white solid, 8 mg) was prepared as a racemate following the procedure of Example 9. LC-MS Anal. Calc'd for C$_{19}$H$_{16}$BrF$_3$N$_2$O$_3$ 457.24. found [M+H] 456.9, 458.9. $^1$H NMR (500 MHz, CDCl$_3$) δ 7.37 (d, J=1.9 Hz, 1H), 7.23 (dd, J=8.7, 2.3 Hz, 1H), 7.08 (d, J=9.0 Hz, 2H), 6.90 (d, J=9.0 Hz, 2H), 6.68 (d, J=8.6 Hz, 1H), 4.89-4.75 (m, 1H), 3.46-3.35 (m, 1H), 3.02-2.88 (m, 2H), 2.55 (dd, J=16.5, 10.1 Hz, 1H), 2.24 (s, 3H). Analytical HPLC (orthogonal method): RT=13.2 min, HI: 96%. hGPR40 EC$_{50}$=160 nM.

Example 14, Isomer 1 and Isomer 2

2-(1-(4-(2'-fluoro-5'-methoxy-3-methylbiphenyl-4-yloxy)phenyl)-3-(trifluoromethyl)-4,5-dihydro-1H-pyrazol-5-yl)acetic acid

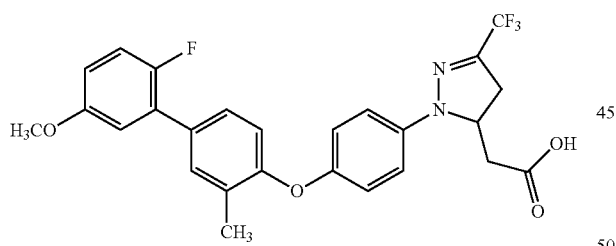

Example 14, Isomer 1 and Isomer 2 were prepared as single enantiomers following the procedure of Example 9. Example 14, Isomer 1 (white solid, 96 mg). LC-MS Anal. Calc'd for C$_{26}$H$_{22}$F$_4$N$_2$O$_4$ 502.46. found [M+H] 503.1. $^1$H NMR (500 MHz, CDCl$_3$) δ 7.42 (s, 1H), 7.30 (d, J=8.4 Hz, 1H), 7.10 (d, J=9.0 Hz, 2H), 7.08-7.02 (m, 1H), 6.98 (d, J=9.0 Hz, 2H), 6.92 (dd, J=6.3, 3.1 Hz, 1H), 6.86 (d, J=8.4 Hz, 1H), 6.81 (dt, J=8.9, 3.4 Hz, 1H), 4.91-4.75 (m, 1H), 3.82 (s, 3H), 3.41 (ddd, J=17.6, 11.4, 2.0 Hz, 1H), 3.04-2.88 (m, 2H), 2.55 (dd, J=16.5, 10.2 Hz, 1H), 2.33 (s, 3H). Analytical HPLC (orthogonal method): RT=11.4 min, HI: 97%. hGPR40 EC$_{50}$=165 nM. Example 14, Isomer 2 (white solid, 98 mg). LC-MS Anal. Calc'd for C$_{26}$H$_{22}$F$_4$N$_2$O$_4$ 502.46. found [M+H] 503.1. $^1$H NMR (500 MHz, CDCl$_3$) δ 7.42 (s, 1H), 7.30 (d, J=8.4 Hz, 1H), 7.10 (d, J=9.0 Hz, 2H), 7.08-7.02 (m, 1H), 6.98 (d, J=9.0 Hz, 2H), 6.92 (dd, J=6.3, 3.1 Hz, 1H), 6.86 (d, J=8.4 Hz, 1H), 6.81 (dt, J=8.9, 3.4 Hz, 1H), 4.91-4.75 (m, 1H), 3.82 (s, 3H), 3.41 (ddd, J=17.6, 11.4, 2.0 Hz, 1H), 3.04-2.88 (m, 2H), 2.55 (dd, J=16.5, 10.2 Hz, 1H), 2.33 (s, 3H). Analytical HPLC (orthogonal method): RT=11.4 min, HI: 98%. hGPR40 EC$_{50}$=160 nM.

Example 15, Isomer 1 and Isomer 2

2-(1-(4-(5-fluoro-2-methoxypyridin-4-yl)-2-methylphenoxy)phenyl)-3-(trifluoromethyl)-4,5-dihydro-1H-pyrazol-5-yl)acetic acid

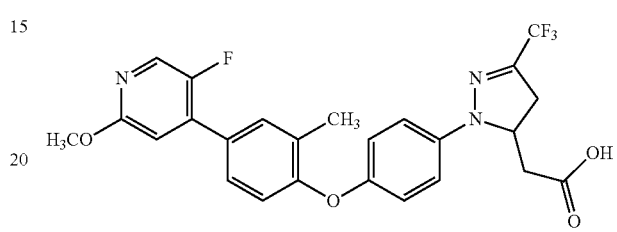

Example 15, Isomer 1 and Isomer 2 were prepared as single enantiomers following the procedure of Example 9. Example 15, Isomer 1 (white solid, 47 mg). LC-MS Anal. Calc'd for C$_{25}$H$_{21}$F$_4$N$_3$O$_4$ 503.45. found [M+H] 504.3. $^1$H NMR (500 MHz, CDCl$_3$) δ 8.12 (s, 1H), 7.48 (s, 1H), 7.35 (d, J=8.5 Hz, 1H), 7.12 (d, J=9.0 Hz, 2H), 6.99 (d, J=9.0 Hz, 2H), 6.85 (d, J=8.5 Hz, 2H), 4.88-4.82 (m, 1H), 3.96 (s, 3H), 3.47-3.36 (m, 1H), 2.97-2.94 (m, 2H), 2.56 (dd, J=16.5, 10.2 Hz, 1H), 2.36 (s, 3H). Analytical HPLC (orthogonal method): RT=13.1 min, HI: 97%. hGPR40 EC$_{50}$=270 nM. Example 15, Isomer 2 (slightly yellow solid, 34 mg). LC-MS Anal. Calc'd for C$_{25}$H$_{21}$F$_4$N$_3$O$_4$ 503.45. found [M+H] 504.2. $^1$H NMR (500 MHz, CDCl$_3$) δ 8.12 (s, 1H), 7.48 (s, 1H), 7.35 (d, J=8.5 Hz, 1H), 7.12 (d, J=9.0 Hz, 2H), 6.99 (d, J=9.0 Hz, 2H), 6.85 (d, J=8.5 Hz, 2H), 4.88-4.82 (m, 1H), 3.96 (s, 3H), 3.47-3.36 (m, 1H), 2.97-2.94 (m, 2H), 2.56 (dd, J=16.5, 10.2 Hz, 1H), 2.36 (s, 3H). Analytical HPLC (orthogonal method): RT=13.1 min, HI: 97%. hGPR40 EC$_{50}$=530 nM.

Example 16, Isomer 1 and Isomer 2

2-(1-(4-(2'-fluoro-5'-methoxy-2-methylbiphenyl-4-yloxy)phenyl)-3-(trifluoromethyl)-4,5-dihydro-1H-pyrazol-5-yl)acetic acid

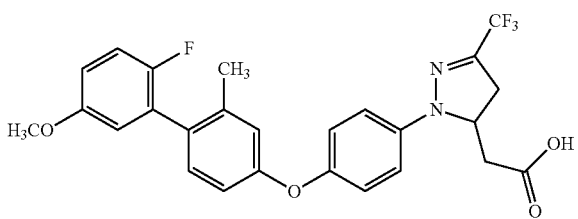 [SMILES: COc1ccc(F)c(-c2ccc(Oc3ccc(N4N=C(C(F)(F)F)CC4CC(=O)O)cc3)cc2C)c1]

Example 16, Isomer 1 and Isomer 2 were prepared as single enantiomers following the procedure of Example 9. Example 16, Isomer 1 (white solid, 7 mg). LC-MS Anal. Calc'd for C$_{26}$H$_{22}$F$_4$N$_2$O$_4$ 502.46. found [M+H] 503.2. $^1$H NMR (500 MHz, CDCl$_3$) δ 7.14 (d, J=8.4 Hz, 1H), 7.12 (d, J=9.0 Hz, 2H), 7.08-7.00 (m, 3H), 6.87 (d, J=2.5 Hz, 1H), 6.86-6.80 (m, 2H), 6.74 (dd, J=5.9, 3.2 Hz, 1H), 4.84 (m, 1H), 3.80 (s, 3H), 3.41 (dd, J=16.1, 10.2 Hz, 1H), 3.07-2.86 (m, 2H), 2.56 (dd, J=16.1, 10.2 Hz, 1H), 2.17 (s, 3H). Analytical HPLC (orthogonal method): RT=12.9 min, HI: 99%. hGPR40 $EC_{50}$=670 nM. Example 16, Isomer 2 (white solid, 4 mg). LC-MS Anal. Calc'd for $C_{26}H_{22}F_4N_2O_4$ 502.46. found [M+H] 503.2. $^1$H NMR (500 MHz, $CDCl_3$) δ 7.14 (d, J=8.4 Hz, 1H), 7.12 (d, J=9.0 Hz, 2H), 7.08-7.00 (m, 3H), 6.87 (d, J=2.5 Hz, 1H), 6.86-6.80 (m, 2H), 6.74 (dd, J=5.9, 3.2 Hz, 1H), 4.84 (m, 1H), 3.80 (s, 3H), 3.41 (dd, J=16.1, 10.2 Hz, 1H), 3.07-2.86 (m, 2H), 2.56 (dd, J=16.1, 10.2 Hz, 1H), 2.17 (s, 3H). Analytical HPLC (orthogonal method): RT=12.9 min, HI: 99%. hGPR40 $EC_{50}$=340 nM.

Example 17, Isomer 1 and Isomer 2

2-(1-(4-((2'-fluoro-5'-methoxy-3-methylbiphenyl-4-yl)methyl)phenyl)-3-(trifluoromethyl)-4,5-dihydro-1H-pyrazol-5-yl)acetic acid

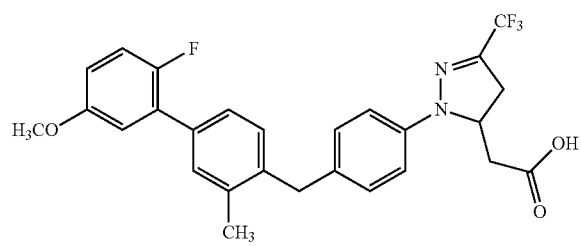 [SMILES: COc1ccc(F)c(-c2ccc(Cc3ccc(N4N=C(C(F)(F)F)CC4CC(=O)O)cc3)c(C)c2)c1]

17A. N'-(4-bromophenyl)-2,2,2-trifluoroacetohydrazide: The HCl salt of (4-bromophenyl)hydrazine was dissolved in THF (50 mL) and treated with aq. 1 N NaOH solution. The mixture was stirred for 30 min, and then was extracted with EtOAc. The combined organic extracts were dried over $Na_2SO_4$ and concentrated to give a slightly yellow solid, which was dried under high vacuum overnight to afford (4-bromophenyl)hydrazine (4.45 g, 23.8 mmol). To a black solution of the above solid in THF (25 mL) at 0° C. was added TFAA (3.80 mL, 27.4 mmol) dropwise by syringe pump. The resulting mixture was stirred at ambient temperature for 2 h. The mixture was concentrated to give a solid, which was purified by flash chromatography to afford 17A (grey solid, 5.41 g, 19.1 mmol, 80% yield). LC-MS Anal. Calc'd for $C_8H_6BrF_3N_2O$, 283.05. found [M+Na] 304.9, 306.9.

17B. methyl 1-(4-bromophenyl)-3-(trifluoromethyl)-4,5-dihydro-1H-pyrazole-5-carboxylate: To a solution of 17A (5.41 g, 19.1 mmol) in EtOAc (20 mL) was added $PhSO_2Cl$ (2.95 mL, 22.9 mmol). The reaction mixture was cooled to 0° C. and i-$Pr_2NEt$ (5.00 mL, 28.6 mmol) was added. The resulting mixture was stirred for 3 h at ambient temperature and white solids precipitated during the reaction. The reaction mixture was concentrated and purified by flash chromatography to afford N'-(4-bromophenyl)-2,2,2-trifluoroacetohydrazonoyl chloride (yellow oil, 5.69 g, 18.9 mmol, 99% yield), which was dissolved in toluene (20 mL). Methyl acrylate (6.79 mL, 75.0 mmol) and $NEt_3$ (5.78 mL, 41.5 mmol) were added to the reaction mixture, which was heated to 40° C. overnight. The reaction mixture was concentrated and purified by flash chromatography to afford 17B (yellow solid, 5.96 g, 17.0 mmol, 90% yield). LC-MS Anal. Calc'd for $C_{12}H_{10}BrF_3N_2O_2$ 351.12. found [M+H] 350.9, 352.9.

17C. (1-(4-bromophenyl)-3-(trifluoromethyl)-4,5-dihydro-1H-pyrazol-5-yl)methanol: To a solution of 17B (5.96 g, 17.0 mmol) in THF (20 mL) at 0° C. was added $LiBH_4$ (2.0 M in THF) (8.49 mL, 17.0 mmol) dropwise. The resulting mixture was stirred at 0° C. for 30 min and then allowed to warm to rt for another 3 h. The reaction mixture was cooled to 0° C. and MeOH (10 mL) was added dropwise. The reaction mixture was allowed to warm to rt and stirred for 1 h. The reaction mixture was concentrated and purified by flash chromatography to give 17C (yellow solid, 5.03 g, 15.6 mmol, 92% yield). LC-MS Anal. Calc'd for $C_{11}H_{10}BrF_3N_2O$, 323.109. found [M+H] 323.0, 325.0.

17D. 2-(1-(4-bromophenyl)-3-(trifluoromethyl)-4,5-dihydro-1H-pyrazol-5-yl)acetonitrile: To a solution of 17C (5.03 g, 15.6 mmol) in $CH_2Cl_2$ (40 mL) at 0° C. was added methanesulfonyl chloride (1.40 mL, 17.9 mmol) and $NEt_3$ (6.51 mL, 46.7 mmol). The resulting mixture was allowed to warm to rt and stirred overnight. The reaction mixture was diluted with $CH_2Cl_2$ and washed with aq. sat. $NaHCO_3$ and water. The organic extracts were dried over $Na_2SO_4$ and concentrated to give the mesylate as a red oil, which was used without further purification. The mesylate was dissolved in DMSO (10 mL) and to the solution was added KCN (3.04 g, 46.7 mmol). The resulting mixture was heated to 60° C. for 4 h. The reaction mixture was cooled to rt, diluted with water, and extracted with EtOAc. The combined organic extracts were dried over $Na_2SO_4$, concentrated, and purified by flash chromatography to afford 17D (yellow solid, 3.00 g, 9.03 mmol, 58% yield). LC-MS Anal. Calc'd for $C_9H_5BrF_3N_3$ 292.06. found [M+H] 291.0, 293.0.

17E. methyl 2-(1-(4-bromophenyl)-3-(trifluoromethyl)-4,5-dihydro-1H-pyrazol-5-yl)acetate: A 3 M HCl solution (160 mL) in MeOH/$CH_2Cl_2$/MeOAc was prepared as follows: 40 mL AcCl was added dropwise into a mixture of $CH_2Cl_2$ (40 mL) and MeOH (80 mL) at 0° C. The mixture was allowed to warm to rt for 60 min and then used for the reaction. The above solution was added to 17D (3.00 g, 9.03 mmol) and the resulting mixture was stirred at rt overnight. The reaction mixture was concentrated and the crude material was purified by flash chromatography to give 17E (colorless oil, 2.02 g, 5.53 mmol, 61% yield). LC-MS Anal. Calc'd for $C_{13}H_{12}BrF_3N_2O_2$ 365.15. found [M+H] 365.0, 367.0.

17F. 2'-fluoro-5'-methoxy-3-methylbiphenyl-4-carboxylic acid: 2-Fluoro-5-methoxyphenylboronic acid (1.04 g, 6.14 mmol), 4-bromo-2-methylbenzoic acid (1.2 g, 5.6 mmol), tetrabutylammonium bromide (1.80 g, 5.58 mmol), $Pd(Ph_3P)_4$ (0.129 g, 0.112 mmol), and $Na_2CO_3$ (2.37 g, 22.3 mmol) were combined in a microwave tube and degassed water (11.2 mL) was added. The vial was sealed and microwaved at 130° C. for 20 min. The reaction mixture was diluted with EtOAc/water and acidified to pH 1 with 1 N HCl (aq.). The layers were separated and the aqueous layer was extracted with EtOAc (2×). The combined organic layers were dried ($MgSO_4$) and concentrated to give 17F (pale yellow solid, 1.33 g, 5.11 mmol, 92% yield), which was used without further purification. LC-MS Anal. Calc'd for $C_{15}H_{13}FO_3$ 260.26. found [M+H] 261.0.

17G. (2'-fluoro-5'-methoxy-3-methylbiphenyl-4-yl)methanol: 17F (3.066 g, 11.78 mmol) was dissolved in THF (50 mL) and cooled to 0° C. LAH (0.984 g, 25.9 mmol) was added in several portions. The reaction mixture was warmed to rt and stirred for 1 h. The reaction mixture was recooled to 0° C. and quenched by the sequential addition of water (0.98 mL), 15% aq. NaOH (0.98 mL), and water (2.9 mL). The reaction mixture was warmed to rt and stirred for 30 min. The solids were filtered off and the organic layer was dried (MgSO$_4$) and concentrated. The crude product was purified by flash chromatography to afford 17G (colorless oil, 2.57 g, 10.4 mmol, 89% yield). LC-MS Anal. Calc'd for C$_{15}$H$_{15}$FO$_2$ 246.28. found [M-OH] 229.0.

17H. 4'-(bromomethyl)-2-fluoro-5-methoxy-3'-methylbiphenyl: Lithium bromide (1.06 g, 12.2 mmol) was added to dry THF (12.2 mL) and stirred for 10 min until dissolved. The solution was cannulated into a flask containing 17G (0.300 g, 1.22 mmol) and NEt$_3$ (0.85 mL, 6.1 mmol) was added. The reaction mixture was cooled to 0° C. and MsCl (0.24 mL, 3.1 mmol) was added dropwise. The reaction mixture was stirred at 0° C. for 1.5 h. The reaction mixture was diluted with hexanes and washed with water and brine. The organic layer was dried (MgSO$_4$) and concentrated. The crude product was purified by flash chromatography to afford 17H (white solid, 0.333 g, 1.08 mmol, 89% yield). $^1$H NMR (400 MHz, CDCl$_3$) δ 7.32-7.43 (3H, m), 7.06 (1H, dd, J=9.85, 9.09 Hz), 6.93 (1H, dd, J=6.32, 3.03 Hz), 6.83 (1H, dt, J=8.84, 3.41 Hz), 4.57 (2H, s), 3.82 (3H, s), 2.48 (3H, s).

17I. methyl 2-(1-(4-((2'-fluoro-5'-methoxy-3-methylbiphenyl-4-yl)methyl)phenyl)-3-(trifluoromethyl)-4,5-dihydro-1H-pyrazol-5-yl)acetate: A oven dried flask of zinc dust (98 mg, 1.5 mmol) in THF (1.0 mL) was purged with argon (3×), and then to the flask was added ethylene dibromide (3.4 μl, 0.040 mmol) and TMS-Cl (2.6 μl, 0.020 mmol). The resulting mixture was heated to 65° C. for 20 min. To the mixture at ambient temperature was added 17H (308 mg, 0.996 mmol) in THF (2.0 mL) dropwise. The resulting mixture was stirred at 65° C. for 2 h. A flask of 17E (200 mg, 0.548 mmol) and Pd(PPh$_3$)$_4$ (63 mg, 0.055 mmol) was purged with argon (3×). Then to the flask was added THF (1.5 mL), and the solution was added dropwise into the organozinc solution at 65° C. The resulting mixture was heated to 80° C. for 1 h and then stirred at rt overnight. The reaction mixture was diluted with water and extracted with EtOAc (3×) and CH$_2$Cl$_2$ (3×). The combined organic extracts were dried over Na$_2$SO$_4$, concentrated, and purified by flash chromatography to afford 17I (yellow solid, 203 mg, 0.383 mmol, 70% yield). LC-MS Anal. Calc'd for C$_{28}$H$_{26}$F$_4$N$_2$O$_3$ 514.51. found [M+H] 515.1.

Example 17, Isomer 1 and Isomer 2: To a solution of 17I (203 mg, 0.395 mmol) in THF (4.0 mL) was added LiOH (18.9 mg, 0.789 mmol) in water (4 mL). The resulting mixture was stirred at rt overnight. The reaction mixture was adjusted to pH ~2 by the addition of aq. 1 N HCl solution and extracted with CH$_2$Cl$_2$. The combined organic extracts were concentrated and purified by RP-Prep HPLC to afford 155 mg of racemic product. The enantiomers were separated by chiral Prep. SFC to provide Example 17, Isomer 1 and Isomer 2 as single enantiomers. Example 17, Isomer 1 (white solid, 70 mg, 0.137 mmol, 35% yield). LC-MS Anal. Calc'd for C$_{27}$H$_{24}$F$_4$N$_2$O$_3$ 500.49. found [M+H] 501.1. $^1$H NMR (400 MHz, CDCl$_3$) δ 7.34 (s, 1H), 7.32 (d, J=10.5 Hz, 1H), 7.16-7.06 (m, 3H), 7.07-7.02 (m, 3H), 6.93 (dd, J=6.2, 3.1 Hz, 1H), 6.80 (dt, J=8.8, 3.4 Hz, 1H), 4.89-4.74 (m, 1H), 3.95 (s, 2H), 3.80 (s, 3H), 3.36 (dd, J=16.6, 12.4 Hz, 1H), 2.93 (d, J=16.7 Hz, 2H), 2.51 (dd, J=16.3, 10.2 Hz, 1H), 2.29 (s, 3H). Analytical HPLC (orthogonal method): RT=13.3 min, HI: 98%. hGPR40 EC$_{50}$=150 nM. Example 17, Isomer 2 (white solid, 69 mg, 0.136 mmol, 35% yield). LC-MS Anal. Calc'd for C$_{27}$H$_{24}$F$_4$N$_2$O$_3$ 500.49. found [M+H] 501.1. $^1$H NMR (400 MHz, CDCl$_3$) δ 7.34 (s, 1H), 7.32 (d, J=10.5 Hz, 1H), 7.16-7.06 (m, 3H), 7.07-7.02 (m, 3H), 6.93 (dd, J=6.2, 3.1 Hz, 1H), 6.80 (dt, J=8.8, 3.4 Hz, 1H), 4.89-4.74 (m, 1H), 3.95 (s, 2H), 3.80 (s, 3H), 3.36 (dd, J=16.6, 12.4 Hz, 1H), 2.93 (d, J=16.7 Hz, 2H), 2.51 (dd, J=16.3, 10.2 Hz, 1H), 2.29 (s, 3H). Analytical HPLC (orthogonal method): RT=13.3 min, HI: 99%. hGPR40 EC$_{50}$=90 nM.

Example 18

2-(1-(4-(4-bromo-3-methylbenzyl)phenyl)-3-(trifluoromethyl)-4,5-dihydro-1H-pyrazol-5-yl)acetic acid

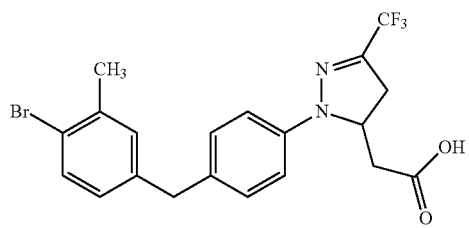 [SMILES: Cc1cc(Cc2ccc(N3N=C(C(F)(F)F)CC3CC(=O)O)cc2)ccc1Br]

Example 18 (white solid, 5 mg) was prepared as a racemate following the procedure of Example 17. LC-MS Anal. Calc'd for C$_{20}$H$_{18}$BrF$_3$N$_2$O$_2$ 455.27. found [M+H] 454.9, 456.9. $^1$H NMR (400 MHz, CDCl$_3$) δ 7.42 (d, J=8.1 Hz, 1H), 7.11 (d, J=8.6 Hz, 2H), 7.04 (s, 1H), 7.03 (d, J=8.6 Hz, 2H), 6.85 (dd, J=8.1, 1.9 Hz, 1H), 4.88-4.81 (m, 1H), 3.84 (s, 2H), 3.46-3.32 (m, 1H), 2.95 (dd, J=16.5, 2.8 Hz, 2H), 2.52 (dd, J=16.5, 10.3 Hz, 1H), 2.35 (s, 3H). Analytical HPLC (Zorbax method, 50% Solvent B start): RT=7.7 min, HI: 99%. hGPR40 EC$_{50}$=455 nM.

Example 19, Isomer 1 and Isomer 2

2-(1-(4-((2',3-difluoro-5'-methoxybiphenyl-4-yl)methyl)phenyl)-3-(trifluoromethyl)-4,5-dihydro-1H-pyrazol-5-yl)acetic acid

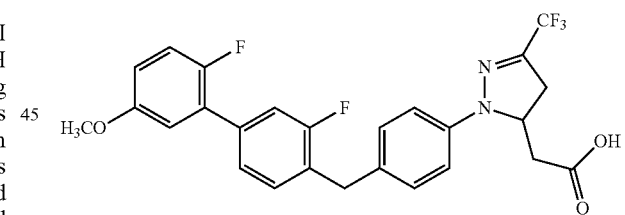

Example 19, Isomer 1 and Isomer 2 were prepared as single enantiomers following the procedure of Example 17. Example 19, Isomer 1 (white solid, 41 mg). LC-MS Anal. Calc'd for C$_{26}$H$_{21}$F$_5$N$_2$O$_3$ 504.45. found [M+H] 505.2. $^1$H NMR (500 MHz, CDCl$_3$) δ 7.25 (s, 1H), 7.23 (d, J=1.4 Hz, 1H), 7.22-7.16 (m, 3H), 7.09-7.02 (m, 3H), 6.90 (dd, J=6.2, 3.2 Hz, 1H), 6.83 (dt, J=8.9, 3.5 Hz, 1H), 4.93-4.79 (m, 1H), 3.98 (s, 2H), 3.81 (s, 3H), 3.39 (dd, J=16.6, 12.5 Hz, 1H), 2.95 (d, J=18.9 Hz, 2H), 2.52 (dd, J=16.5, 10.2 Hz, 1H). Analytical HPLC (orthogonal method): RT=12.9 min, HI: 96%. hGPR40 EC$_{50}$=580 nM. Example 19, Isomer 2 (white solid, 43 mg). LC-MS Anal. Calc'd for C$_{26}$H$_{21}$F$_5$N$_2$O$_3$ 504.45. found [M+H] 505.2. $^1$H NMR (500 MHz, CDCl$_3$) δ 7.25 (s, 1H), 7.23 (d, J=1.4 Hz, 1H), 7.22-7.16 (m, 3H), 7.09-7.02 (m, 3H), 6.90 (dd, J=6.2, 3.2 Hz, 1H), 6.83 (dt, J=8.9, 3.5 Hz, 1H), 4.93-4.79 (m, 1H), 3.98 (s, 2H), 3.81 (s, 3H), 3.39 (dd, J=16.6, 12.5 Hz, 1H), 2.95 (d, J=18.9 Hz, 2H), 2.52 (dd, J=16.5, 10.2 Hz, 1H). Analytical HPLC (orthogonal method): RT=12.9 min, HI: 99%. hGPR40 $EC_{50}$=90 nM.

Example 20, Isomer 1

2-(1-(4-((3-chloro-2'-fluoro-5'-methoxybiphenyl-4-yl)methyl)phenyl)-3-(trifluoromethyl)-4,5-dihydro-1H-pyrazol-5-yl)acetic acid

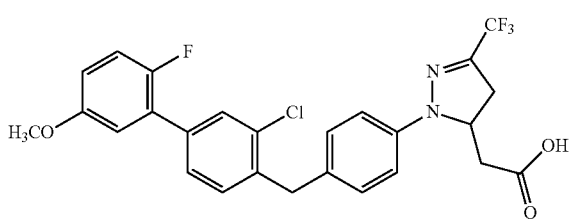 [SMILES: COc1ccc(F)c(-c2ccc(Cc3ccc(N4N=C(C(F)(F)F)CC4CC(=O)O)cc3)c(Cl)c2)c1]

and

Example 20, Isomer 2

(R)-2-(1-(4-((3-chloro-2'-fluoro-5'-methoxybiphenyl-4-yl)methyl)phenyl)-3-(trifluoromethyl)-4,5-dihydro-1H-pyrazol-5-yl)acetic acid

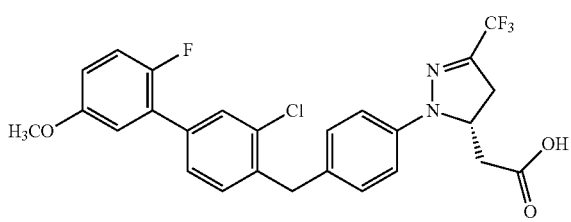 [SMILES: COc1ccc(F)c(-c2ccc(Cc3ccc(N4N=C(C(F)(F)F)C[C@@H]4CC(=O)O)cc3)c(Cl)c2)c1]

Example 20, Isomer 1 and Isomer 2 were prepared as single enantiomers following the procedure of Example 17. Example 20, Isomer 1 (white solid, 43 mg). LC-MS Anal. Calc'd for $C_{26}H_{21}ClF_4N_2O_3$ 520.91. found [M+H] 521.1. $^1$H NMR (500 MHz, $CDCl_3$) δ 7.57 (s, 1H), 7.36 (d, J=7.9 Hz, 1H), 7.22-7.16 (m, 3H), 7.11-7.01 (m, 3H), 6.90 (dd, J=6.2, 3.1 Hz, 1H), 6.83 (dt, J=8.9, 3.5 Hz, 1H), 4.94-4.78 (m, 1H), 4.08 (s, 2H), 3.81 (s, 3H), 3.39 (dd, J=15.9, 11.6 Hz, 1H), 2.96 (d, J=16.3 Hz, 2H), 2.53 (dd, J=16.5, 10.6 Hz, 1H). Analytical HPLC (orthogonal method): RT=13.4 min, HI: 96%. hGPR40 $EC_{50}$=470 nM. Example 20, Isomer 2 (white solid, 50 mg). LC-MS Anal. Calc'd for $C_{26}H_{21}ClF_4N_2O_3$ 520.91. found [M+H] 521.1. $^1$H NMR (500 MHz, $CDCl_3$) δ 7.57 (s, 1H), 7.36 (d, J=7.9 Hz, 1H), 7.22-7.16 (m, 3H), 7.11-7.01 (m, 3H), 6.90 (dd, J=6.2, 3.1 Hz, 1H), 6.83 (dt, J=8.9, 3.5 Hz, 1H), 4.94-4.78 (m, 1H), 4.08 (s, 2H), 3.81 (s, 3H), 3.39 (dd, J=15.9, 11.6 Hz, 1H), 2.96 (d, J=16.3 Hz, 2H), 2.53 (dd, J=16.5, 10.6 Hz, 1H). Analytical HPLC (orthogonal method): RT=13.4 min, HI: 97%. hGPR40 $EC_{50}$=50 nM.

Example 21, Isomer 1 and Isomer 2

2-(1-(4-((2',3-difluoro-5'-methoxy-5-methylbiphenyl-4-yl)methyl)phenyl)-3-(trifluoromethyl)-4,5-dihydro-1H-pyrazol-5-yl)acetic acid

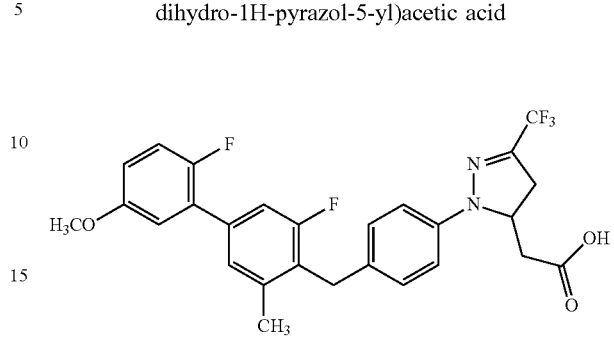

Example 21, Isomer 1 and Isomer 2 were prepared as single enantiomers following the procedure of Example 17. Example 21, Isomer 1 (white solid, 18 mg). LC-MS Anal. Calc'd for $C_{27}H_{23}F_5N_2O_3$ 518.48. found [M+H] 519.2. $^1$H NMR (500 MHz, $CDCl_3$) δ 7.15 (d, J=6.2 Hz, 2H), 7.13 (d, J=8.6 Hz, 2H), 7.06 (dd, J=10.0, 9.0 Hz, 1H), 7.02 (d, J=8.6 Hz, 2H), 6.92 (dd, J=6.2, 3.1 Hz, 1H), 6.83 (dt, J=8.9, 3.5 Hz, 1H), 4.81 (m, 1H), 4.01 (s, 1H), 3.82 (s, 2H), 3.43-3.30 (m, 1H), 2.99-2.87 (m, 1H), 2.50 (dd, J=16.4, 10.3 Hz, 1H), 2.32 (s, 2H). Analytical HPLC (orthogonal method): RT=13.2 min, HI: 95%. hGPR40 $EC_{50}$=500 nM. Example 21, Isomer 2 (white solid, 20 mg). LC-MS Anal. Calc'd for $C_{27}H_{23}F_5N_2O_3$ 518.48. found [M+H] 519.2. $^1$H NMR (500 MHz, $CDCl_3$) δ 7.15 (d, J=6.2 Hz, 2H), 7.13 (d, J=8.6 Hz, 2H), 7.06 (dd, J=10.0, 9.0 Hz, 1H), 7.02 (d, J=8.6 Hz, 2H), 6.92 (dd, J=6.2, 3.1 Hz, 1H), 6.83 (dt, J=8.9, 3.5 Hz, 1H), 4.81 (m, 1H), 4.01 (s, 1H), 3.82 (s, 2H), 3.43-3.30 (m, 1H), 2.99-2.87 (m, 1H), 2.50 (dd, J=16.4, 10.3 Hz, 1H), 2.32 (s, 2H). Analytical HPLC (orthogonal method): RT=13.2 min, HI: 95%. hGPR40 $EC_{50}$=270 nM.

Example 22, Isomer 1 and Isomer 2

2-(1-(4-((2'-fluoro-5'-methoxy-2-methylbiphenyl-4-yl)methyl)phenyl)-3-(trifluoromethyl)-4,5-dihydro-1H-pyrazol-5-yl)acetic acid

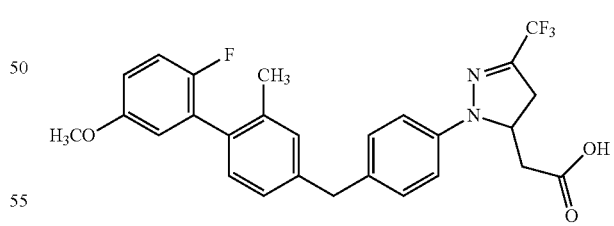

22A. methyl 2-(1-(4-(4-bromo-2-methylbenzyl)phenyl)-3-(trifluoromethyl)-4,5-dihydro-1H-pyrazol-5-yl)acetate: 22A (130 mg, 0.194 mmol, 35% yield) was prepared from 1-bromo-4-(bromomethyl)-2-methylbenzene and 17E following the procedure of Example 17. LC-MS Anal. Calc'd for $C_{21}H_{20}BrF_3N_2O_2$ 469.30. found [M+H] 469.0, 471.0.

Example 22, Isomer 1 and Isomer 2 were prepared from 22A following the procedure of Example 9. Example 22, Isomer 1 (white solid, 15 mg). LC-MS Anal. Calc'd for $C_{27}H_{24}F_4N_2O_3$ 500.49. found [M+H] 501.2. $^1$H NMR (500

MHz, CDCl$_3$) δ 7.19 (d, J=8.6 Hz, 2H), 7.13 (d, J=7.7 Hz, 1H), 7.09 (s, 1H), 7.06 (d, J=8.6 Hz, 2H), 7.04 (s, 1H), 7.03 (t, J=9.0 Hz, 1H), 6.86-6.81 (m, 1H), 6.74 (dd, J=5.9, 3.2 Hz, 1H), 4.95-4.77 (m, 1H), 3.94 (s, 2H), 3.79 (s, 3H), 3.48-3.33 (m, 1H), 3.05-2.89 (m, 2H), 2.53 (dd, J=16.5, 10.3 Hz, 1H), 2.17 (s, 3H). Analytical HPLC (orthogonal method): RT=11.3 min, HI: 98%. hGPR40 EC$_{50}$=770 nM. Example 22, Isomer 2 (white solid, 11 mg). LC-MS Anal. Calc'd for C$_{27}$H$_{24}$F$_4$N$_2$O$_3$ 500.49. found [M+H] 501.2. $^1$H NMR (500 MHz, CDCl$_3$) δ 7.19 (d, J=8.6 Hz, 2H), 7.13 (d, J=7.7 Hz, 1H), 7.09 (s, 1H), 7.06 (d, J=8.6 Hz, 2H), 7.04 (s, 1H), 7.03 (t, J=9.0 Hz, 1H), 6.86-6.81 (m, 1H), 6.74 (dd, J=5.9, 3.2 Hz, 1H), 4.95-4.77 (m, 1H), 3.94 (s, 2H), 3.79 (s, 3H), 3.48-3.33 (m, 1H), 3.05-2.89 (m, 2H), 2.53 (dd, J=16.5, 10.3 Hz, 1H), 2.17 (s, 3H). Analytical HPLC (orthogonal method): RT=11.3 min, HI: 98%. hGPR40 EC$_{50}$=350 nM.

Example 23

2-(1-(4-((2'-chloro-5'-methoxy-2-methylbiphenyl-4-yl)methyl)phenyl)-3-(trifluoromethyl)-4,5-dihydro-1H-pyrazol-5-yl)acetic acid

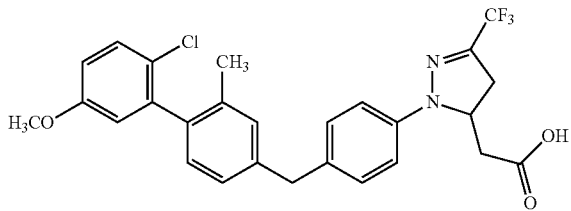

Example 23 (white solid, 17 mg) was prepared as a racemate following the procedure of Example 22. LC-MS Anal. Calc'd for C$_{27}$H$_{24}$ClF$_3$N$_2$O$_3$ 516.95. found [M+H] 517.1. $^1$H NMR (400 MHz, CDCl$_3$) δ 7.33 (d, J=8.8 Hz, 1H), 7.20 (d, J=8.5 Hz, 2H), 7.11-7.02 (m, 5H), 6.83 (dd, J=8.8, 3.0 Hz, 1H), 6.75 (d, J=3.1 Hz, 1H), 4.93-4.78 (m, 1H), 3.95 (s, 2H), 3.78 (s, 3H), 3.47-3.32 (m, 1H), 3.04-2.90 (m, 2H), 2.54 (dd, J=16.5, 10.3 Hz, 1H), 2.10 (s, 3H). Analytical HPLC (orthogonal method): RT=13.4 min, HI: 98%. hGPR40 EC$_{50}$=350 nM.

Example 24

2-(1-(4-((2'-fluoro-2-methyl-5'-(trifluoromethyl)biphenyl-4-yl)methyl)phenyl)-3-(trifluoromethyl)-4,5-dihydro-1H-pyrazol-5-yl)acetic acid

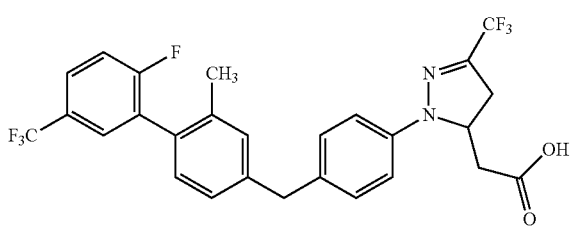 [SMILES: Cc1cc(Cc2ccc(N3N=C(C(F)(F)F)CC3CC(=O)O)cc2)ccc1-c1cc(C(F)(F)F)ccc1F]

Example 24 (slightly yellow solid, 5 mg) was prepared as a racemate following the procedure of Example 22. LC-MS Anal. Calc'd for C$_{27}$H$_{21}$F$_7$N$_2$O$_2$ 538.46. found [M+H] 539.1. $^1$H NMR (500 MHz, CDCl$_3$) δ 7.64-7.58 (m, 1H), 7.53 (dd, J=6.6, 2.2 Hz, 1H), 7.23 (t, J=8.8 Hz, 1H), 7.18 (d, J=8.6 Hz, 2H), 7.13 (d, J=8.0 Hz, 1H), 7.11 (s, 1H), 7.08 (d, J=8.0 Hz, 1H), 7.06 (d, J=8.6 Hz, 2H), 4.90-4.81 (m, 1H), 3.95 (s, 2H), 3.45-3.34 (m, 1H), 3.02-2.92 (m, 2H), 2.54 (dd, J=16.5, 10.3 Hz, 1H), 2.15 (s, 3H). Analytical HPLC (orthogonal method): RT=13.6 min, HI: 91%. hGPR40 EC$_{50}$=570 nM.

Example 25

2-(1-(4-((2'-chloro-2-methyl-5'-(trifluoromethoxy)biphenyl-4-yl)methyl)phenyl)-3-(trifluoromethyl)-4,5-dihydro-1H-pyrazol-5-yl)acetic acid

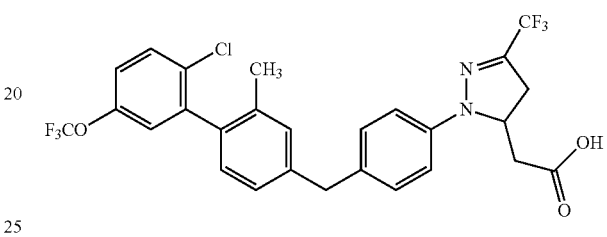

Example 25 (white solid, 2 mg) was prepared as a racemate following the procedure of Example 22. LC-MS Anal. Calc'd for C$_{27}$H$_{21}$ClF$_6$N$_2$O$_3$ 570.92. found [M+H] 571. $^1$H NMR (500 MHz, CDCl$_3$) δ 7.47 (d, J=8.7 Hz, 1H), 7.19 (d, J=8.6 Hz, 2H), 7.15 (dd, J=8.8, 2.1 Hz, 1H), 7.12-7.04 (m, 6H), 4.94-4.77 (m, 1H), 3.95 (s, 2H), 3.46-3.35 (m, 1H), 3.02-2.91 (m, 2H), 2.54 (dd, J=16.5, 10.3 Hz, 1H), 2.08 (s, 3H). Analytical HPLC (orthogonal method): RT=14.1 min, HI: 98%. hGPR40 EC$_{50}$=280 nM.

Example 26, Isomer 1 and Isomer 2

2-(1-(4-((3'-methoxy-3-methylbiphenyl-4-yl)methyl)phenyl)-3-(trifluoromethyl)-4,5-dihydro-1H-pyrazol-5-yl)acetic acid

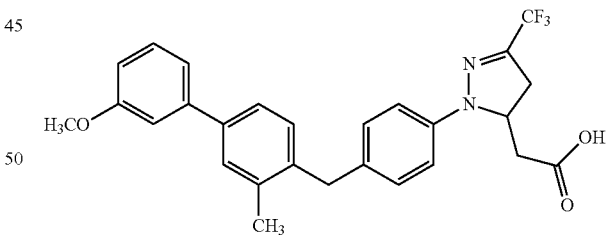

26A. methyl 2-(1-(4-(4-chloro-2-methylbenzyl)phenyl)-3-(trifluoromethyl)-4,5-dihydro-1H-pyrazol-5-yl)acetate:
26A (1.63 g, 3.84 mmol, 64% yield) was prepared from 1-(bromomethyl)-4-chloro-2-methylbenzene and 17E following the procedure of Example 17. LC-MS Anal. Calc'd for C$_{21}$H$_{20}$ClF$_3$N$_2$O$_2$ 424.84. found [M+H] 425.0. 26B. methyl 2-(1-(4-((3'-methoxy-3-methylbiphenyl-4-yl)methyl)phenyl)-3-(trifluoromethyl)-4,5-dihydro-1H-pyrazol-5-yl)acetate: A mixture of 26A (300 mg, 0.706 mmol), 3-methoxyphenylboronic acid (215 mg, 1.41 mmol), SPhos (232 mg, 0.565 mmol), K$_3$PO$_4$ (320 mg, 1.836 mmol), and Pd(OAc)$_2$ (63 mg, 0.282 mmol) in dioxane (6 mL) and water (0.6 mL) was purged with argon and then heated to 100° C.

overnight. The reaction mixture was filtered and purified by flash chromatography to afford 26B (yellow oil, 274 mg, 0.552 mmol, 78% yield). LC-MS Anal. Calc'd for $C_{28}H_{27}F_3N_2O_3$ 496.52. found [M+H] 497.2.

Example 26, Isomer 1 and Isomer 2 were prepared as single enantiomers from 26B following the procedure of Example 17. Example 26, Isomer 1 (slightly yellow solid, 91 mg). LC-MS Anal. Calc'd for $C_{27}H_{25}F_3N_2O_3$ 482.5. found [M+H] 483.2. $^1$H NMR (500 MHz, CDCl$_3$) δ 7.39 (s, 1H), 7.37 (d, J=7.9 Hz, 1H), 7.33 (t, J=7.9 Hz, 1H), 7.17 (d, J=8.0 Hz, 1H), 7.14 (d, J=7.8 Hz, 1H), 7.11 (m, 3H), 7.04 (d, J=8.6 Hz, 2H), 6.87 (dd, J=8.2, 1.9 Hz, 1H), 4.91-4.76 (m, 1H), 3.96 (s, 2H), 3.86 (s, 3H), 3.39 (dd, J=17.7, 11.3 Hz, 1H), 2.95 (d, J=18.9 Hz, 2H), 2.52 (dd, J=16.6, 10.1 Hz, 1H), 2.31 (s, 3H). Analytical HPLC (orthogonal method): RT=13.1 min, HI: 98%. hGPR40 EC$_{50}$=330 nM. Example 26, Isomer 2 (white solid, 91 mg). LC-MS Anal. Calc'd for $C_{27}H_{25}F_3N_2O_3$ 482.5. found [M+H] 483.2. $^1$H NMR (500 MHz, CDCl$_3$) δ 7.39 (s, 1H), 7.37 (d, J=7.9 Hz, 1H), 7.33 (t, J=7.9 Hz, 1H), 7.17 (d, J=8.0 Hz, 1H), 7.14 (d, J=7.8 Hz, 1H), 7.11 (m, 3H), 7.04 (d, J=8.6 Hz, 2H), 6.87 (dd, J=8.2, 1.9 Hz, 1H), 4.91-4.76 (m, 1H), 3.96 (s, 2H), 3.86 (s, 3H), 3.39 (dd, J=17.7, 11.3 Hz, 1H), 2.95 (d, J=18.9 Hz, 2H), 2.52 (dd, J=16.6, 10.1 Hz, 1H), 2.31 (s, 3H). Analytical HPLC (orthogonal method): RT=13.1 min, HI: 97%. hGPR40 EC$_{50}$=120 nM.

Example 27, Isomer 1 and Isomer 2

2-(1-(4-(4-(5-fluoro-2-methoxypyridin-4-yl)-2-methylbenzyl)phenyl)-3-(trifluoromethyl)-4,5-dihydro-1H-pyrazol-5-yl)acetic acid

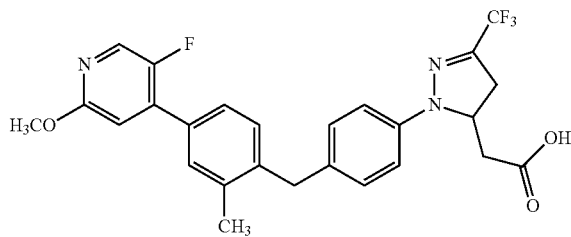

Example 27, Isomer 1 and Isomer 2 were prepared as single enantiomers following the procedure of Example 26. Example 27, Isomer 1 (white solid, 94 mg). LC-MS Anal. Calc'd for $C_{26}H_{23}F_4N_3O_3$ 501.48. found [M+H] 502.2. $^1$H NMR (500 MHz, CDCl$_3$) δ 8.04 (d, J=2.4 Hz, 1H), 7.38 (s, 1H), 7.36 (d, J=7.9 Hz, 1H), 7.17 (d, J=7.8 Hz, 1H), 7.10 (d, J=8.6 Hz, 2H), 7.05 (d, J=8.6 Hz, 2H), 6.80 (d, J=5.3 Hz, 1H), 4.91-4.78 (m, 1H), 3.97 (s, 2H), 3.94 (s, 3H), 3.39 (dd, J=16.7, 10.5 Hz, 1H), 3.02-2.88 (m, 2H), 2.52 (dd, J=16.5, 10.3 Hz, 1H), 2.31 (s, 3H). Analytical HPLC (orthogonal method): RT=13.0 min, HI: 99%. hGPR40 EC$_{50}$=360 nM. Example 27, Isomer 2 (white solid, 95 mg). LC-MS Anal. Calc'd for $C_{26}H_{23}F_4N_3O_3$ 501.48. found [M+H] 502.3. $^1$H NMR (500 MHz, CDCl$_3$) δ 8.04 (d, J=2.4 Hz, 1H), 7.38 (s, 1H), 7.36 (d, J=7.9 Hz, 1H), 7.17 (d, J=7.8 Hz, 1H), 7.10 (d, J=8.6 Hz, 2H), 7.05 (d, J=8.6 Hz, 2H), 6.80 (d, J=5.3 Hz, 1H), 4.91-4.78 (m, 1H), 3.97 (s, 2H), 3.94 (s, 3H), 3.39 (dd, J=16.7, 10.5 Hz, 1H), 3.02-2.88 (m, 2H), 2.52 (dd, J=16.5, 10.3 Hz, 1H), 2.31 (s, 3H). Analytical HPLC (orthogonal method): RT=13.1 min, HI: 99%. hGPR40 EC$_{50}$=150 nM.

Example 28, Isomer 1

2-(1-(4-((2'-fluoro-5'-methoxy-3-methylbiphenyl-4-yl)methyl)phenyl)-4-methyl-3-(trifluoromethyl)-4,5-dihydro-1H-pyrazol-5-yl)acetic acid

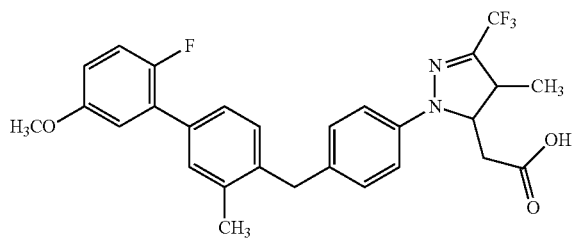 [SMILES: COc1ccc(F)c(-c2ccc(Cc3ccc(N4N=C(C(F)(F)F)C(C)C4CC(=O)O)cc3)c(C)c2)c1]

Example 28, Isomer 1 (white solid, 28 mg) was prepared as a single enantiomer following the procedure of Example 46 except (E)-methyl but-2-enoate was used instead of (E)-benzyl 4-cyclopropylbut-2-enoate. LC-MS Anal. Calc'd for $C_{28}H_{26}F_4N_2O_3$ 514.52. found [M+H] 515.2. $^1$H NMR (500 MHz, CD$_2$Cl$_2$) δ 7.35 (s, 1H), 7.32 (d, J=8.2 Hz, 1H), 7.17 (d, J=7.7 Hz, 1H), 7.13 (d, J=8.2 Hz, 2H), 7.09-7.01 (m, 3H), 6.94 (dd, J=6.1, 3.3 Hz, 1H), 6.82 (dt, J=8.8, 3.3 Hz, 1H), 4.44 (d, J=9.9 Hz, 1H), 3.97 (s, 2H), 3.80 (s, 3H), 3.24 (broad s, 1H), 2.88 (d, J=15.9 Hz, 1H), 2.47 (dd, J=15.9, 9.9 Hz, 1H), 2.31 (s, 3H), 1.33 (d, J=6.6 Hz, 3H). Analytical HPLC (Zorbax method, 50% Solvent B start): RT=8.4 min, HI: 99%. Analytical HPLC (orthogonal method): RT=14.3 min, HI: 100%. hGPR40 EC$_{50}$=710 nM.

Example 28, Isomer 2

2-((4S,5S)-1-(4-((2'-fluoro-5'-methoxy-3-methylbiphenyl-4-yl)methyl)phenyl)-4-methyl-3-(trifluoromethyl)-4,5-dihydro-1H-pyrazol-5-yl)acetic acid

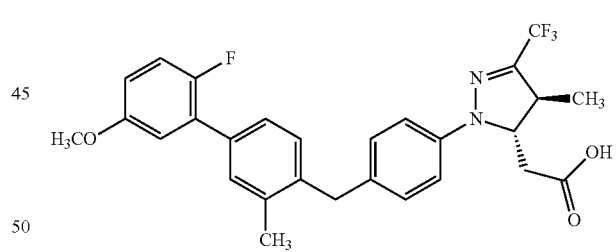

28A. (4-bromo-2-methylphenyl)methanol: To a solution of 4-bromo-2-methylbenzoic acid (40.0 g, 186 mmol) in THF (800 mL) was added a 1 M solution of BH$_3$.THF in THF (558 mL, 558 mmol) at 0° C. The reaction mixture was stirred rt for 2 h. The reaction mixture was quenched with 1 N aq. HCl and extracted with EtOAc (3×200 mL). The combined organic layers were washed with 1 N aq. HCl, water, sat. aq. NaHCO$_3$, and brine. The organic layer was dried (Na$_2$SO$_4$) and concentrated to give 28A (37.8 g, 186 mmol, 100% yield). $^1$H NMR (400 MHz, CDCl$_3$) δ 7.29-7.36 (m, 2H), 7.20-7.25 (m, 1H), 4.66 (d, J=5.77 Hz, 2H), 2.32 (s, 3H).

28B. 4-bromo-2-methylbenzaldehyde: To a solution of oxalyl chloride (249 mL, 497 mmol) in CH$_2$Cl$_2$ (150 mL) at −78° C. under argon was added a solution of DMSO (42.4 mL, 597 mmol) in CH$_2$Cl$_2$ (75 mL) dropwise with a venting needle (Note: gas was generated, slow addition was necessary). After the addition, the venting needle was removed. The reaction mixture was stirred at −78° C. under argon for 30 min. Then, a solution of 28A (20.0 g, 99.0 mmol) in CH$_2$Cl$_2$ (203 mL) was added. The resulting solution was stirred at −78° C. for 30 min and then TEA (166 mL, 1190 mmol) was added dropwise. The reaction mixture was warmed to rt and stirred for 12 h. The reaction mixture was diluted with water (20 mL) and CH$_2$Cl$_2$ (30 mL). The layers were separated and the aqueous layer was extracted with CH$_2$Cl$_2$ (3×50 mL). The combined organic extracts were washed with water and brine, dried (MgSO$_4$), filtered, and concentrated. The crude product was purified by flash chromatography to provide 28B (15.4 g, 78 mmol, 78% yield) as a yellow oil. $^1$H NMR (400 MHz, CDCl$_3$) δ 10.22 (s, 1H), 7.66 (d, J=8.28 Hz, 1H), 7.51 (dd, J=8.28, 1.76 Hz, 1H), 7.45 (s, 1H), 2.65 (s, 3H).

28C. 2'-fluoro-5'-methoxy-3-methyl-[1,1'-biphenyl]-4-carbaldehyde: To a solution of 28B (18 g, 86 mmol) in THF (250 mL) was added (2-fluoro-5-methoxyphenyl)boronic acid (15 g, 90 mmol) and a 2 M aq. solution of K$_2$CO$_3$ (193 mL, 387 mmol). The reaction mixture was purged with nitrogen for 5 min and then Pd(Ph$_3$P)$_4$ (3.57 g, 3.09 mmol) was added. The reaction mixture was heated at 66° C. for 3 h and then cooled to rt. The layers were separated. The aqueous layer was extracted with EtOAc (800 mL). The organic layers were combined and washed with brine, sat. aq. NaH$_2$PO$_4$, and brine, dried (Na$_2$SO$_4$), and concentrated to an oil containing an orange precipitate. The material was diluted with EtOAc and the precipitate was filtered and washed with EtOAc. The filtrate was concentrated to give the crude product, which was purified by flash chromatography to afford 28C (17 g, 71 mmol, 83% yield) as a yellow oil. LC-MS Anal. Calc'd for C$_{15}$H$_{13}$FO$_2$ 244.26. found [M+H] 245.0. $^1$H NMR (400 MHz, CDCl$_3$) δ 10.3 (s, 1H), 7.87 (d, J=8 Hz, 1H), 7.54 (d, J=8 Hz, 1H), 7.44 (s, 1H), 7.10 (dd, J=9.6, 8.8 Hz, 1H), 6.95 (dd, J=6.4, 3.2 Hz, 1H), 6.88 (dt, J=8.8, 3.4, 1H), 3.84 (s, 3H), 2.73 (s, 3H). $^{13}$C NMR (101 MHz, CDCl$_3$) δ 192.1, 155.7, 154.0 (d, J$_{C-F}$=240.1 Hz), 140.9, 140.5, 133.1, 132.1, 132.1, 132.0, 128.1 (d, J$_{C-F}$=14.8 Hz), 126.8, 126.7, 116.7 (d, J$_{C-F}$=24.5 Hz), 115.2 (d, J$_{C-F}$=2.2 Hz), 114.6 (d, J$_{C-F}$=8 Hz), 55.7, 19.5.

28D. 2-fluoro-4'-(4-iodobenzyl)-5-methoxy-3'-methylbiphenyl: To a 2 L round-bottom flask equipped with a reflux condenser was added 28C (37.6 g, 154 mmol), 1,4-dioxane (600 mL) and 4-methylbenzenesulfonylhydrazide (28.7 g, 154 mmol). The resulting solution was heated to 80° C. for 20 min. The heating was stopped and (4-iodophenyl)boronic acid (38.1 g, 154 mmol) and K$_2$CO$_3$ (25.5 g, 185 mmol) were added. The reaction mixture was then heated to 90° C. for 80 min to give a white suspension. The reaction mixture was cooled to rt and stored in a refrigerator overnight. The reaction mixture was diluted with EtOAc and water and the layers were separated. The aqueous layer was extracted with EtOAc (2×1.5 L) and the combined organic extracts were washed with water and brine, dried (MgSO$_4$), filtered, and concentrated to give an orange oil. Upon standing at at rt, the residual 4-idophenylboronic acid precipitated as white crystals. The white solid was removed by filtration and washed with EtOAc. The filtrate was concentrated. The filtration and concentration were repeated (3×). The crude product was purified by flash chromatography to provide 28D (34.4 g, 80.0 mmol, 52% yield) as a white solid. $^1$H NMR (400 MHz, CDCl$_3$) δ 7.58-7.65 (m, 2H), 7.31-7.39 (m, 2H), 7.15 (d, J=7.5 Hz, 1H), 7.02-7.10 (m, 1H), 6.90-6.97 (m, 3H), 6.82 (dt, J=9.0, 3.4 Hz, 1H), 3.97 (s, 2H), 3.83 (s, 3H), 2.29 (s, 3H).

28E. benzyl 1-(4-((2'-fluoro-5'-methoxy-3-methylbiphenyl-4-yl)methyl)phenyl)hydrazinecarboxylate: A flask containing 28D (8.50 g, 19.7 mmol), benzyl hydrazinecarboxylate (3.92 g, 23.6 mmol), Cs$_2$CO$_3$ (9.30 g, 28.5 mmol), anhydrous 1,10-phenanthroline (0.748 g, 4.15 mmol) and copper(I) iodide (0.386 g, 2.03 mmol) was evacuated and backfilled with argon. DMF (17 mL) was added under argon and the mixture was degassed with argon for 5 min. The mixture was stirred and heated at 80° C. After 1 h 40 min, the reaction mixture was cooled to rt, diluted with EtOAc (200 mL) and filtered through a pad of silica gel. The filter cake was rinsed with EtOAc and the combined filtrate and rinse were concentrated. The residue was co-evaporated with toluene. The crude product was purified by flash chromatography to give 28E as a yellow oil, (8.15 g, 17.0 mmol, 86% yield). LC-MS Anal. Calc'd for C$_{29}$H$_{27}$FN$_2$O$_3$ 470.54. found [M+H] 471.2. $^1$H NMR (400 MHz, CDCl$_3$) δ 7.41-7.29 (m, 9H), 7.18-7.10 (m, 3H), 7.05 (t, J=9.3 Hz, 1H), 6.93 (dd, J=6.1, 3.3 Hz, 1H), 6.80 (dt, J=8.8, 3.3 Hz, 1H), 5.22 (2, 2H), 4.52 (s, 2H), 4.00 (s, 2H), 3.82 (s, 3H), 2.30 (s, 3H). $^{13}$C NMR (101 MHz, CDCl$_3$) δ 156.1, 155.7, 154.2 (d, J$_{C-F}$=239.1 Hz), 140.6, 138.5, 137.3, 136.7, 136.0, 134.0, 130.7 (d, J$_{C-F}$=2.5 Hz), 129.9, 129.4 (d, J$_{C-F}$=15.3 Hz), 128.8 (2C), 128.5 (2C), 128.2, 128.0 (2C), 126.5 (d, J$_{C-F}$=3.8 Hz), 128.4 (2C), 116.5 (d, J$_{C-F}$=25.4 Hz), 115.3 (d, J$_{C-F}$=3.8 Hz), 113.6 (d, J$_{C-F}$=7.6 Hz), 68.0, 55.8, 38.6, 19.8. $^{19}$F NMR (376 MHz, CDCl$_3$) δ −128.6.

28F. benzyl 1-(4-((2'-fluoro-5'-methoxy-3-methylbiphenyl-4-yl)methyl)phenyl)-2-(2,2,2-trifluoroacetyl)hydrazinecarboxylate: To a stirred solution of 28E (10.0 g, 21.3 mmol) in CH$_2$Cl$_2$ (49.0 mL) at 0° C. was added TFAA (3.47 ml, 24.9 mmol) and i-Pr$_2$NEt (1.47 ml, 8.50 mmol). The reaction mixture was stirred at 0° C. for 1 h. The reaction mixture was slowly warmed to rt and stirred for 30 min. The reaction mixture was concentrated. The residue was diluted with EtOAc, washed with aq. sat. NaHCO$_3$, water, and brine, dried (MgSO$_4$), and concentrated. The crude product was purified by flash chromatography to provide 28F as a yellow gum (11.6 g, 19.9 mmol, 93% yield). LC-MS Anal. Calc'd for C$_{31}$H$_{26}$F$_4$N$_2$O$_4$ 566.54. found [M−H]$^-$ 565.4. $^1$H NMR (500 MHz, CDCl$_3$) δ 8.71 (s, 1H), 7.39-7.25 (m, 9H), 7.18-7.13 (m, 3H), 7.05 (t, J=9.4 Hz, 1H), 6.93 (dd, J=6.1, 3.3 Hz, 1H), 6.81 (dt, J=8.8, 3.3 Hz, 1H), 5.21 (s, 2H), 4.01 (s, 2H), 3.81 (s, 3H), 2.28 (s, 3H). $^{13}$C NMR (101 MHz, CDCl$_3$) δ 156.5 (q, J$_{C-F}$=38.0 Hz), 155.6, 154.1 (d, J$_{C-F}$=239.1 Hz), 153.7, 140.0, 137.9, 137.8, 136.6, 135.1, 134.1, 130.8 (2C), 130.0, 129.4 (2C), 129.3 (d, J$_{C-F}$=17.8 Hz), 128.5 (2C), 128.3, 127.7, 126.6, 125.2 (2C), 116.5 (d, J$_{C-F}$=25.4 Hz), 115.5 (q, J$_{C-F}$=290.9 Hz), 115.3, 113.6 (d, J$_{C-F}$=7.5 Hz), 68.8, 55.7, 38.6, 19.7. $^{19}$F NMR (376 MHz, CDCl$_3$) δ −74.8, −128.5.

28G. 2,2,2-trifluoro-N'-(4-((2'-fluoro-5'-methoxy-3-methylbiphenyl-4-yl)methyl)phenyl)acetohydrazide: To a stirred solution of 28F (11.6 g, 20.5 mmol) in EtOAc (160 mL) was added Pd/C (5% dry basis, Degussa type: 50% water content, 523 mg) and the suspension was hydrogenated (1 atm, balloon) for 2 h. The suspension was filtered through Celite and the filter cake was rinsed with EtOAc. The filtrate was concentrated. The crude material was dissolved in EtOAc (160 mL) and Pd/C (5% dry basis, Degussa type: 50% water content, 400 mg) was added. The suspension was hydrogenated for an additional 2 h 45 min, filtered, and concentrated to provide crude 28G, which was used in the next reaction without further purification. LC-MS Anal. Calc'd for $C_{23}H_{20}F_4N_2O_2$ 432.41. found [M+H] 433.0. $^1$H NMR (500 MHz, CDCl$_3$) δ 8.04 (s, 1H), 7.34 (s, 1H), 7.32 (d, J=7.7 Hz, 1H), 7.13 (d, J=8.2 Hz, 1H), 7.11-7.02 (m, 3H), 6.93 (dd, J=6.6, 3.3 Hz, 1H), 6.83-6.77 (m, 3H), 6.01 (d, J=3.6 Hz, 1H), 3.95 (s, 2H), 3.82 (s, 3H), 2.29 (s, 3H). $^{13}$C NMR (101 MHz, CDCl$_3$) δ 157.3 (q, $J_{C-F}$=37.7 Hz), 155.6, 154.2 (d, $J_{C-F}$=240.9 Hz), 144.1, 138.8, 136.6, 134.1, 133.9, 130.7, 129.8, 129.7 (2C), 129.4 (d, $J_{C-F}$=15.2 Hz), 126.5, 116.5 (d, $J_{C-F}$=25.3 Hz), 115.7 (q, $J_{C-F}$=289.0 Hz), 115.3, 114.1 (2C), 113.6 (d, $J_{C-F}$=7.7 Hz), 55.8, 38.3, 19.7. $^{19}$F NMR (376 MHz, CDCl$_3$) δ −74.9, −128.6.

28H. 2,2,2-trifluoro-N'-(4-((2'-fluoro-5'-methoxy-3-methylbiphenyl-4-yl)methyl)phenyl)acetohydrazonoyl chloride: To a stirred solution of crude 28G from the previous step in EtOAc (58 mL) at 0° C. under argon was added PhSO$_2$Cl (2.81 mL, 21.9 mmol) followed by i-Pr$_2$NEt (3.80 mL, 22.0 mmol) dropwise. The reaction mixture was stirred while slowly warming to rt and was stirred overnight. The reaction mixture was diluted with EtOAc, washed with water and brine, dried (MgSO$_4$), and concentrated. The crude product was purified by flash chromatography to give 28H as a white solid (7.77 g, 16.7 mmol, 82% yield over two steps). LC-MS Anal. Calc'd for $C_{23}H_{19}ClF_4N_2O$, 450.86. found [M−H]$^-$ 449.1. $^1$H NMR (500 MHz, CDCl$_3$) δ 7.98 (s, 1H), 7.35 (s, 1H), 7.33 (d, J=8.2 Hz, 1H), 7.16-7.10 (m, 3H), 7.09-7.02 (m, 3H), 6.93 (dd, J=6.1, 3.3 Hz, 1H), 6.81 (dt, J=8.8, 3.3 Hz, 1H), 3.98 (s, 2H), 3.81 (s, 3H), 2.29 (s, 3H). $^{13}$C NMR (101 MHz, CDCl$_3$) δ 155.7, 154.2 (d, $J_{C-F}$=239.9 Hz), 139.8, 138.7, 136.7 (2C), 134.7, 134.0, 130.8, 129.8 (2C), 129.4 (d, $J_{C-F}$=15.3 Hz), 126.6, 118.5 (q, $J_{C-F}$=271.9 Hz), 116.5 (d, $J_{C-F}$=25.4 Hz), 115.3, 114.1 (2C), 113.6 (d, $J_{C-F}$=7.7 Hz), 111.1 (q, $J_{C-F}$=43.6 Hz), 55.8, 38.5, 19.8. $^{19}$F NMR (376 MHz, CDCl$_3$) δ −67.6, −128.6.

28I. (S)-3-((4S,5R)-1-(4-(2'-fluoro-5'-methoxy-3-methylbiphenyl-4-yl)methyl)phenyl)-4-methyl-3-(trifluoromethyl)-4,5-dihydro-1H-pyrazole-5-carbonyl)-4-phenyloxazolidin-2-one: A flask containing a solution of 28H (7.77 g, 17.2 mmol) and (4S)-3-((2E)-2-butenoyl)-4-phenyl-1,3-oxazolidin-2-one (4.58 g, 19.8 mmol) in dioxane (160 mL) was evacuated and backfilled with argon. Ag$_2$CO$_3$ (11.9 g, 43.1 mmol) was added to the solution and the resulting suspension was heated to 50° C. for 23 h. (S,E)-3-but-2-enoyl-4-phenyloxazolidin-2-one (400 mg, 1.73 mmol) was added and the reaction was heated to 55° C. for 18 h. The reaction mixture was cooled to rt and filtered through Celite®. The filter cake was rinsed with EtOAc and, the combined filtrate and rinse were concentrated. The crude product was purified using an ISCO flash chromatography system. A 330 g silica gel column was used with a gradient of CH$_2$Cl$_2$/hexanes (0% to 100%). Impure fractions were repurified using a 330 g silica gel column with the same solvent system. Remaining impure fractions were repurified using an 80 g silica gel column. The clean fractions were combined and concentrated to afford 28I as a colorless foam (6.50 g, 9.73 mmol, 56% yield). LC-MS Anal. Calc'd for $C_{36}H_{31}F_4N_3O_4$ 645.64, found [M+H] 646.2. $^1$H NMR (400 MHz, CDCl$_3$) δ 7.41-7.29 (m, 5H), 7.25 (m, 2H), 7.14 (d, J=7.7 Hz, 1H), 7.10-7.02 (m, 3H), 6.96-6.91 (m, 3H), 6.81 (dt, J=8.8, 3.3 Hz, 1H), 5.82 (d, J=2.7 Hz, 1H), 5.40 (dd, J=8.8, 3.9 Hz, 1H), 4.80 (t, J=8.8 Hz, 1H), 4.41 (dd, J=8.8, 3.9 Hz, 1H), 3.94 (s, 2H), 3.82 (s, 3H), 3.15 (m, 1H), 2.29 (s, 3H), 1.48 (d, J=7.2 Hz, 3H). $^{13}$C NMR (101 MHz, CDCl$_3$) δ 167.1, 155.7, 154.2 (d, $J_{C-F}$=240.3 Hz), 153.9, 141.1, 139.8 (q, $J_{C-F}$=36.9 Hz), 139.0, 137.7, 136.7, 133.9, 132.9, 130.7 (d, $J_{C-F}$=2.5 Hz), 129.9, 129.8 (2C), 129.6 (d, $J_{C-F}$=15.3 Hz), 129.4 (2C), 129.3, 126.5 (d, $J_{C-F}$=2.5 Hz), 125.8 (2C), 120.8 (q, $J_{C-F}$=269.6 Hz), 116.5 (d, $J_{C-F}$=24.2 Hz), 115.4 (d, $J_{C-F}$=3.8 Hz), 113.6 (3C), 70.8, 68.9, 57.6, 55.8, 44.9, 38.4, 19.8, 17.4. $^{19}$F NMR (376 MHz, CDCl$_3$) δ −63.6, −128.6.

28J. ((4S,5R)-1-(4-((2'-fluoro-5'-methoxy-3-methylbiphenyl-4-yl)methyl)phenyl)-4-methyl-3-(trifluoromethyl)-4,5-dihydro-1H-pyrazol-5-yl)methanol: To a solution of 28I (6.28 g, 9.72 mmol) in THF (200 mL) at rt was added a solution of NaBH$_4$ (2.22 g, 58.3 mmol) in water (40.0 mL). The reaction mixture was stirred at rt for 1.5 h. The reaction mixture was cooled to 0° C. and the reaction was quenched with 10% aq. KHSO$_4$ (100 mL). The resulting aqueous mixture was stirred for 0.5 h. The mixture was extracted with CH$_2$Cl$_2$ and the combined organic extracts were washed with water and brine, dried (MgSO$_4$), and concentrated. The crude product was purified by flash chromatography to provide 28J as a white foam (4.07 g, 8.37 mmol, 86% yield). LC-MS Anal. Calc'd for $C_{27}H_{26}F_4N_2O_2$ 486.50. found [M+H] 487.1. $^1$H NMR (500 MHz, CDCl$_3$) δ 7.34 (s, 1H), 7.32 (d, J=7.7 Hz, 1H), 7.14 (d, J=7.7 Hz, 1H), 7.02-7.12 (m, 5H), 6.93 (dd, J=6.6, 3.3 Hz, 1H), 6.80 (dt, J=8.8, 3.3 Hz, 1H), 4.05 (m, 1H), 3.96 (s, 2H), 3.88 (dt, J=11.6, 4.9 Hz, 1H), 3.81 (s, 3H), 3.73 (m, 1H), 3.48 (m, 1H), 2.31 (s, 3H), 1.52 (dd, J=7.7, 4.4 Hz, 1H), 1.34 (d, J=7.2 Hz, 3H). $^{13}$C NMR (101 MHz, CDCl$_3$) δ 156.7, 154.2 (d, $J_{C-F}$=240.3 Hz), 141.8 (q, $J_{C-F}$=36.9 Hz), 141.6, 138.9, 136.6, 133.9, 133.1, 130.8 (d, $J_{C-F}$=2.5 Hz), 129.8, 129.7 (2C), 129.5 (d, $J_{C-F}$=15.3 Hz), 126.5 (d, $J_{C-F}$=2.5 Hz), 121.3 (q, $J_{C-F}$=269.6 Hz), 116.5 (d, $J_{C-F}$=25.4 Hz), 115.4 (d, $J_{C-F}$=2.5 Hz), 114.5 (2C), 113.6 (d, $J_{C-F}$=7.6 Hz), 70.6, 61.1, 55.8, 42.0, 38.4, 19.8, 17.9. $^{19}$F NMR (376 MHz, CDCl$_3$) δ −63.6, −128.6.

28K. ((4S,5R)-1-(4-((2'-fluoro-5'-methoxy-3-methylbiphenyl-4-yl)methyl)phenyl)-4-methyl-3-(trifluoromethyl)-4,5-dihydro-1H-pyrazol-5-yl)methyl methanesulfonate: To a solution of 28J (4.07 g, 8.37 mmol) and MsCl (0.971 mL, 12.6 mmol) in CH$_2$Cl$_2$ (83.7 mL) at 0° C. was added TEA (2.33 mL, 16.7 mmol). The reaction mixture was stirred for 30 min at 0° C. and at rt for 2.5 h. The reaction mixture was concentrated, diluted with EtOAc, washed with water and brine, dried (MgSO$_4$), and concentrated. The crude product was purified by flash chromatography to give 28K as a colorless gum (4.47 g, 7.91 mmol, 95% yield). $^1$H NMR (400 MHz, CDCl$_3$) δ 7.35 (s, 1H), 7.33 (d, J=7.7 Hz, 1H), 7.17-7.01 (m, 6H), 6.93 (dd, J=6.6, 3.3 Hz, 1H), 6.81 (dt, J=8.8, 3.3 Hz, 1H), 4.40 (dd, J=10.6, 3.5 Hz, 1H), 4.33 (m, 1H), 4.15 (m, 1H), 3.97 (s, 2H), 3.82 (s, 3H), 3.42 (m, 1H), 2.95 (s, 3H), 2.30 (s, 3H), 1.36 (d, J=7.2 Hz, 3H). $^{13}$C NMR (101 MHz, CDCl$_3$) δ 155.7, 154.2 (d, $J_{C-F}$=239.1 Hz), 141.3 (q, $J_{C-F}$=36.9 Hz), 140.5, 138.9, 136.6, 133.9, 133.5, 130.8 (d, $J_{C-F}$=2.5 Hz), 129.9 (2C), 129.8, 129.4 (d, $J_{C-F}$=15.3 Hz), 126.5 (d, $J_{C-F}$=2.5 Hz), 121.1 (q, $J_{C-F}$=270.1 Hz), 116.5 (d, $J_{C-F}$=25.4 Hz), 115.3 (d, $J_{C-F}$=2.5 Hz), 114.3 (2C), 113.6 (d, $J_{C-F}$=7.6 Hz), 67.1, 66.0, 55.8, 42.6, 38.3, 37.6, 19.7, 17.9. $^{19}$F NMR (376 MHz, CDCl$_3$) δ−63.4, −128.6.

28L. 2-((4S,5S)-1-(4-((2'-fluoro-5'-methoxy-3-methylbiphenyl-4-yl)methyl)phenyl)-4-methyl-3-(trifluoromethyl)-4,5-dihydro-1H-pyrazol-5-yl)acetonitrile: To a solution of 28K (4.37 g, 7.73 mmol) in DMSO (26 mL) was added KCN (0.665 g, 9.90 mmol). The reaction mixture was heated to 60° C. for 1.3 h. Additional KCN (0.300 g, 4.61 mmol) was added. The reaction mixture was stirred at 60° C. for 4.5 h. The reaction mixture was diluted with EtOAc, washed with sat. aq. NaHCO$_3$ and brine, dried (MgSO$_4$), and concentrated. The crude product was purified by flash chromatography to give 28L as a white solid (3.27 g, 6.60 mmol, 85% yield). LC-MS Anal. Calc'd for $C_{28}H_{25}F_4N_3O$, 495.51. found [M+H] 496.1. $^1$H NMR (400 MHz, CDCl$_3$) δ 7.35 (s, 1H), 7.33 (d, J=8.2 Hz, 1H), 7.17-7.11 (m, 3H), 7.09-7.00 (m, 3H), 6.93 (dd, J=6.1, 3.3 Hz, 1H), 6.81 (dt, J=8.8, 3.3 Hz, 1H), 4.28 (dt, J=9.3, 3.3 Hz, 1H), 3.97 (s, 2H), 3.82 (s, 3H), 3.37 (m, 1H), 2.80 (dd, J=17.0, 3.3 Hz, 1H), 2.48 (dd, J=17.0, 9.3 Hz, 1H), 2.30 (s, 3H), 1.40 (d, J=7.2 Hz, 3H). $^{13}$C NMR (101 MHz, CDCl$_3$) δ 155.7, 154.2 (d, $J_{C-F}$=240.3 Hz), 141.4 (q, $J_{C-F}$=36.9 Hz), 140.0, 138.6, 136.6, 134.2, 134.0, 130.8 (d, $J_{C-F}$=2.5 Hz), 130.0 (2C), 129.8, 129.4 (d, $J_{C-F}$=14.0 Hz), 126.6 (d, $J_{C-F}$=2.5 Hz), 121.0 (q, $J_{C-F}$=268.3 Hz), 116.5 (d, $J_{C-F}$=25.4 Hz), 115.8, 115.4 (d, $J_{C-F}$=3.8 Hz), 114.9 (2C), 113.6 (d, $J_{C-F}$=8.9 Hz), 65.0, 55.8, 44.9, 38.4, 19.8 (2C), 17.6. $^{19}$F NMR (376 MHz, CDCl$_3$) δ −63.5, −128.6.

28M. methyl 2-((4S,5S)-1-(4-((2'-fluoro-5'-methoxy-3-methylbiphenyl-4-yl)methyl)phenyl)-4-methyl-3-(trifluoromethyl)-4,5-dihydro-1H-pyrazol-5-yl)acetate: The 28L (3.26 g, 6.58 mmol) was dissolved in a ~3 M solution of HCl in MeOH/CH$_2$Cl$_2$/MeOAc (230 mL, prepared by addition of AcCl (47.5 mL) to a 3/2 CHCl$_2$/MeOH solution (182.5 mL) at 0° C. and then stirring at rt for 30 min) The reaction mixture was stirred at rt for 22 h and heated to 35° C. for 3 h. The reaction mixture was concentrated, diluted with EtOAc, washed with sat. NaHCO$_3$, water, and brine, dried (MgSO$_4$), and concentrated. The crude product was purified by flash chromatography to provide 28M as a colorless gum (2.77 g, 5.24 mmol, 80% yield). LC-MS Anal. Calc'd for $C_{29}H_{28}F_4N_2O_3$ 528.54. found [M+H] 529.1. $^1$H NMR (400 MHz, CDCl$_3$) δ 7.35 (s, 1H), 7.32 (d, J=8.2 Hz, 1H), 7.14 (d, J=7.7 Hz, 1H), 7.11 (d, J=8.8 Hz, 2H), 7.08-7.11 (m, 3H), 6.93 (dd, J=6.1, 3.3 Hz, 1H), 6.80 (dt, J=8.8, 3.3 Hz, 1H), 4.43 (m, 1H), 3.96 (s, 2H), 3.81 (s, 3H), 3.70 (s, 3H), 3.17 (m, 1H), 2.84 (dd, J=13.7, 2.8 Hz, 1H), 2.41 (dd, J=16.4, 10.4 Hz, 1H), 2.31 (s, 3H), 1.33 (d, J=7.2 Hz, 3H). $^{13}$C NMR (101 MHz, CDCl$_3$) δ 170.8, 155.7, 154.2 (d, $J_{C-F}$=240.3 Hz), 141.1 (q, $J_{C-F}$=36.9 Hz), 140.3, 138.9, 136.6, 133.9, 133.0, 130.8 (d, $J_{C-F}$=2.5 Hz), 129.83 (2C), 129.79, 129.5 (d, $J_{C-F}$=15.3 Hz), 126.5 (d, $J_{C-F}$=2.5 Hz), 121.5 (q, $J_{C-F}$=269.6 Hz), 116.5 (d, $J_{C-F}$=25.4 Hz), 115.4 (d, $J_{C-F}$=3.8 Hz), 114.4 (2C), 113.6 (d, $J_{C-F}$=7.6 Hz), 65.2, 55.8, 52.0, 45.3, 38.4, 34.9, 19.8, 17.8. $^{19}$F NMR (376 MHz, CDCl$_3$) δ −63.3, −128.6.

Example 28, Isomer 2: To a stirred solution of 28M (3.26 g, 6.17 mmol) in THF (134 mL) and water (13.4 mL) at rt was added a solution of 1.0 M aq. LiOH (13.6 mL, 13.6 mmol) dropwise. After stirring at rt for 3.5 h, half of the THF was evaporated and the reaction mixture was partitioned between water (150 mL) and hexanes (600 mL). The layers were separated and the organic layer was extracted with 0.5 N LiOH (2×40 mL). The combined aqueous layers were cooled to 0° C. and acidified to pH<7 by the addition of 3 M aq. HCl and then extracted with EtOAc (3×400 mL). The combined organic extracts were dried (MgSO$_4$), concentrated, and dried under vacuum to afford a colorless foam. The foam was dissolved in EtOAc (200 mL), washed with 1 N aq. HCl (50 mL) and brine, dried (MgSO$_4$), and concentrated to give Example 28, Isomer 2 (3.03 g, 5.77 mmol, 94% yield) as a off-white foam. LC-MS Anal. Calc'd for $C_{28}H_{26}F_4N_2O_3$ 514.51. found [M+H] 514.9. $^1$H NMR (500 MHz, CD$_2$Cl$_2$) δ 7.39 (s, 1H), 7.36 (dt, J=7.8, 1.8 Hz, 1H), 7.21 (d, J=7.8 Hz, 1H), 7.17 (d, J=8.6 Hz, 2H), 7.12-7.08 (m, 1H), 7.08 (d, J=8.4 Hz, 2H), 6.98 (dd, J=6.3, 3.2 Hz, 1H), 6.86 (dt, J=8.9, 3.5 Hz, 1H), 4.49 (dt, J=9.9, 3.1 Hz, 1H), 4.02 (s, 2H), 3.85 (s, 3H), 3.34-3.23 (m, 1H), 2.93 (dd, J=16.6, 2.9 Hz, 1H), 2.54 (dd, J=16.2, 10.2 Hz, 1H), 2.36 (s, 3H), 1.38 (d, J=7.1 Hz, 3H). $^{13}$C NMR (126 MHz, CD$_2$Cl$_2$) δ 175.5, 156.5, 154.7 (d, J=239.3 Hz), 141.6 (q, J=35.8 Hz), 140.9, 139.8, 137.3, 134.4, 133.9, 131.3 (d, J=3.5 Hz), 130.4 (3C), 130.0 (d, J=15.0 Hz), 127.1 (d, J=3.5 Hz), 122.2 (q, J=269.3 Hz), 117.0 (d, J=25.4 Hz), 115.9 (d, J=3.5 Hz), 115.0 (2C), 114.2 (d, J=8.1 Hz), 65.6, 56.4, 45.8, 38.9, 35.2, 20.1, 18.2. $^{19}$F NMR (471 MHz, CD$_2$Cl$_2$) δ −63.8, −129.5. Analytical HPLC (orthogonal method): RT=12.8 min, HI: 98%. Elemental Anal. Calc'd for $C_{28}H_{26}F_4N_2O_3$: C, 65.20; H, 5.16; N, 5.36. Found C, 65.35; H, 5.26; N, 5.38. hGPR40 EC$_{50}$=30 nM.

Example 29

2-(3-cyano-1-(4-(2-isopropylphenoxy)phenyl)-4,5-dihydro-1H-pyrazol-5-yl)acetic acid

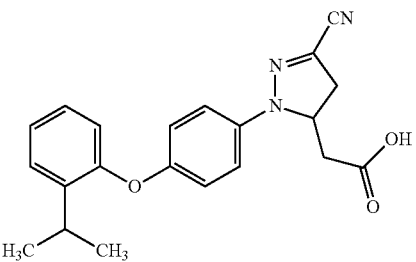

29A. (4-methoxyphenyl)carbonocyanidohydrazonic chloride: A solution of NaNO$_2$ (8.89 g, 125 mmol) in water (55 mL) was added to a stirred mixture ofp-anisidine (14.8 g, 119 mmol), aq. HCl, 37% (37 mL), and water (92 mL) cooled to −5° C. The resulting mixture was stirred for 20 min and then 2-chloro-3-oxobutanenitrile (6.34 g, 53.9 mmol), EtOH (92 mL), NaOAc (29.4 g, 355 mmol), and water (368 mL) were added sequentially. The reaction mixture was allowed to warm to rt and stirred for an additional 5.0 h. The reaction mixture was filtered and the collected solid was thoroughly rinsed with water. The sticky solid obtained above was dissolved in CH$_2$Cl$_2$ (300 mL). The solution was dried (Na$_2$SO$_4$), filtered, and concentrated to provide 29A (brown solid, 11.2 g, 37.8 mmol, 70% yield). LC-MS Anal. Calc'd for $C_9H_8ClN_3O$, 209.63. found [M+H] 210.0.

29B. methyl 2-(3-cyano-1-(4-methoxyphenyl)-4,5-dihydro-1H-pyrazol-5-yl)acetate: A solution of 29A (11.1 g, 37.7 mmol) and methyl 3-butenoate (4.35 mL, 38.8 mmol) in anhydrous toluene (255 mL) was treated with AgOAc (6.54 g, 38.8 mmol) and stirred at rt for 3.3 h. The reaction mixture was filtered through Celite® and the filter cake was rinsed with EtOAc (300 mL). The EtOAc solution was washed with aq. 5% NaHCO$_3$ (225 mL) and water (225 ml), dried (Na$_2$SO$_4$), and concentrated. The dark residue was purified by flash chromatography to provide 29B (brown oil, 2.75 g, 7.45 mmol, 20% yield). LC-MS Anal. Calc'd for $C_{14}H_{15}N_3O_3$ 273.29. found [M+H] 274.1.

29C. methyl 2-(3-cyano-1-(4-hydroxyphenyl)-4,5-dihydro-1H-pyrazol-5-yl)acetate: To a solution of 29B (2.74 g, 10.0 mmol) in CH$_2$Cl$_2$ (15.2 mL) at 0° C. was added BF$_3$.SMe$_2$ (6.4 mL, 61 mmol) and the reaction mixture was allowed to warm to rt. After stirring at rt for 2.5 h, the reaction was cooled to 0° C. and quenched with MeOH (4.0 mL) followed by AcCl (0.1 mL). The mixture was allowed to warm to rt while stirring. After stirring at rt for 12 h, the reaction mixture was evaporated and the residue was purified by flash chromatography to give crude methyl 2-(3-cyano-1-(4-hydroxyphenyl)-4,5-dihydro-1H-pyrazol-5-yl)

acetate (1.50 g) as a brown solid. The crude solid was dissolved in MeOH/CH$_2$Cl$_2$ and allowed to stand at rt for 2 days. After two days at rt, the solid that formed was collected by filtration and rinsed with ether. Drying under vacuum afforded 29 C (yellow solid, 895 mg, 34% yield, single isomer). The mother liquor and the ether rinses were combined and allowed to stand at rt. After 5 days, a second filtration gave 44 C (brown solid, 148 mg, 6% yield, contains 2% of an isomeric dihydropyrazole). The remaining solution was concentrated to give 29C (dark oil, 416 mg, 7% yield, 2/3 mixture of dihydropyrazole and isomer). LC-MS Anal. Calc'd for C$_{13}$H$_{13}$N$_3$O$_3$ 259.26. found [M+H] 260.1.

29D. methyl 2-(3-cyano-1-(4-(2-isopropylphenoxy)phenyl)-4,5-dihydro-1H-pyrazol-5-yl)acetate: To a stirred suspension of 2-isopropylphenylboronic acid (30 mg, 0.18 mmol), 29C (23 mg, 0.089 mmol), anhydrous copper(II) acetate (33 mg, 0.18 mmol) and powdered mol. sieves (4 Å, <5 micron, activated, 103 mg) in CH$_2$Cl$_2$ (1.0 mL) at rt was added pyridine (51 µL, 0.63 mmol). The reaction mixture was stirred at rt under an air atmosphere (balloon). After stirring at rt for 11.3 h, the reaction mixture was filtered through Celite® and the filter cake was rinsed with EtOAc (100 mL). The combined filtrate and rinses were concentrated and stripped from toluene (2×5 mL). The residue was purified by flash chromatography to afford 29D (yellow oil, 8 mg, 0.019 mmol, 22% yield). LC-MS Anal. Calc'd for C$_{22}$H$_{23}$N$_3$O$_3$ 377.44. found [M+H] 378.2.

Example 29: To a stirred solution of 29D (7 mg, 0.019 mmol) in THF (0.30 mL) at rt was added 0.46 M aq. LiOH (0.11 mL, 0.051 mmol) dropwise. The resulting solution was stirred at rt for 1.0 h. The final solution was cooled to 0° C. and acidified with aq. 1 M HCl (0.07 mL). The organic solvents were mostly evaporated and the remaining aqueous mixture was purified by RP-Prep HPLC to afford Example 29 as a racemate (yellow solid, 7 mg, 0.018 mmol, 96% yield). LC-MS Anal. Calc'd for C$_{21}$H$_{21}$N$_3$O$_3$ 363.42. found [M+H] 364.1. $^1$H NMR (500 MHz, CD$_2$Cl$_2$) δ 7.33 (dd, J=7.7. 1.7 Hz, 1H), 7.17-7.09 (m, 4H), 6.93 (d, J=8.8 Hz, 2H), 6.83 (dd, J=7.7, 1.7 Hz, 1H), 4.92 (m, 1H), 3.43 (dd, J=17.6, 12.1 Hz, 1H), 3.38 (m, 1H), 3.02 (dd, J=17.6, 4.9 Hz, 1H), 2.90 (dd, J=16.5, 2.8 Hz, 1H), 2.58 (dd, J=16.5, 9.9 Hz, 1H), 1.22 (d, J=6.6 Hz, 6H). Analytical HPLC (Zorbax method, 0% Solvent B start): RT=7.9 min, HI: 98%. hGPR40 EC$_{50}$=430 nM.

Example 30

2-(1-(4-(2-bromophenoxy)phenyl)-3-cyano-4,5-dihydro-1H-pyrazol-5-yl)acetic acid

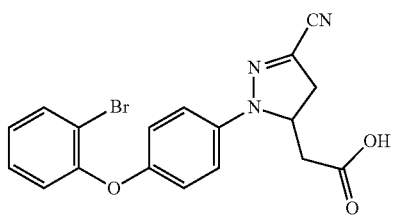 [SMILES: N#CC1=NN(c2ccc(Oc3ccccc3Br)cc2)C(CC(=O)O)C1]

Example 30 (yellow solid, 6 mg) was prepared as a racemate following the procedure for Example 29. LC-MS Anal. Calc'd for C$_{18}$H$_{14}$BrN$_3$O$_3$ 400.23. found [M+H] 399.9, 401.9. $^1$H NMR (500 MHz CD$_2$Cl$_2$) δ 7.55 (d, J=7.7 Hz, 1H), 6.63 (t, J=7.7 Hz, 1H), 7.06 (d, J=8.8, 2H), 6.95 (t, J=7.7 Hz, 1H), 6.89 (d, J=8.8, 2H), 6.85 (d, J=8.3 Hz, 1H), 4.85 (m, 1H), 3.36 (dd, J=17.6, 12.1 Hz, 1H), 2.95 (dd, J=17.6, 4.9 Hz, 1H), 2.83 (d, J=16.5 Hz, 1H), 2.50 (dd, J=16.5, 9.9 Hz, 1H), 2.11 (s, 3H). Analytical HPLC (Zorbax method, 0% Solvent B start): RT=7.4 min, HI: 98%. hGPR40 EC$_{50}$=180 nM.

Example 31

2-(1-(4-(4-bromo-2,5-dimethylphenoxy)phenyl)-3-cyano-4,5-dihydro-1H-pyrazol-5-yl)acetic acid

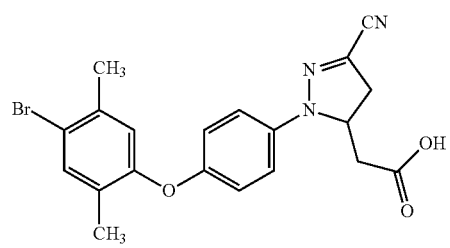 [SMILES: Cc1cc(Oc2ccc(N3N=C(C#N)CC3CC(=O)O)cc2)c(C)cc1Br]

Example 31 (yellow solid, 4 mg) was prepared as a racemate following the procedure for Example 29. LC-MS Anal. Calc'd for C$_{20}$H$_{18}$BrN$_3$O$_3$ 428.28. found [M+H] 428.0, 430.0. $^1$H NMR (500 MHz, CD$_2$Cl$_2$) δ 7.32 (s, 1H), 7.02 (d, J=8.7 Hz, 2H), 6.81 (d, J=8.4 Hz, 2H), 6.65 (s, 1H), 4.82 (broad s, 1H), 3.34 (dd, J=17.0, 12.6 Hz, 1H), 2.94 (dd, J=17.0, 3.3 Hz, 1H), 2.80 (d, J=16.0, 1H), 2.48 (broad s, J=16.5, 1H), 2.19 (s, 3H), 2.09 (s, 3H). Analytical HPLC (Zorbax method, 0% Solvent B start): RT=8.3 min, HI: 100%. hGPR40 EC$_{50}$=360 nM.

Example 32

2-(3-cyano-1-(4-(2'-fluoro-5'-methoxy-3-methylbiphenyl-4-yloxy)phenyl)-4,5-dihydro-1H-pyrazol-5-yl)acetic acid

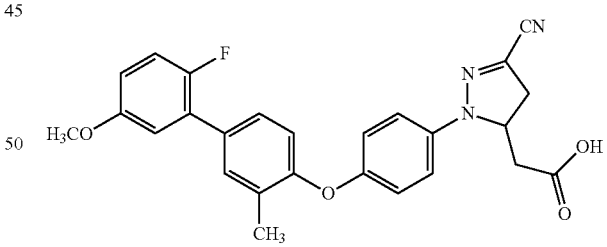

Example 32 (yellow solid, 27 mg) was prepared as a racemate following the procedure for Example 29. LC-MS Anal. Calc'd for C$_{26}$H$_{22}$FN$_3$O$_4$ 459.48. found [M+H] 460.1. $^1$H NMR (500 MHz, CD$_2$Cl$_2$) δ 7.43 (s, 1H), 7.32 (d, J=8.2 Hz, 1H), 7.13 (d, J=9.3 Hz, 2H), 7.06 (t, J=9.7 Hz, 1H), 6.98 (d, J=9.3 Hz, 2H), 6.93 (dd, J=6.2, 3.1 Hz, 1H), 6.88 (d, J=8.2 Hz, 1H), 6.81 (dt, J=8.8, 3.3 Hz, 1H), 4.92 (m, 1H), 3.80 (s, 3H), 3.43 (dd, J=17.6, 12.1 Hz, 1H), 3.02 (dd, J=17.6, 5.5 Hz, 1H), 2.91 (dd, J=16.5, 3.3 Hz, 1H), 2.57 (dd, J=16.5, 10.1 Hz, 1H), 2.30 (s, 3H). Analytical HPLC (Zorbax method, 50% Solvent B start): RT=7.1 min, HI: 100%. hGPR40 EC$_{50}$=190 nM.

Example 33

2-(3-cyano-1-(4-(2,4-dichlorobenzyloxy)phenyl)-4,5-dihydro-1H-pyrazol-5-yl)acetic acid

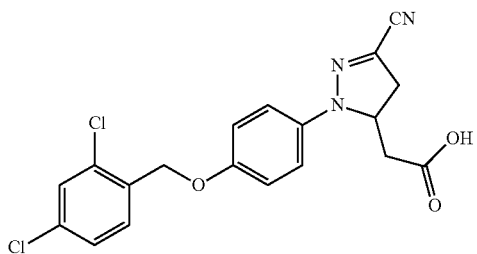 [SMILES: N#CC1=NN(c2ccc(OCc3ccc(Cl)cc3Cl)cc2)C(CC(=O)O)C1]

33A. methyl 2-(3-cyano-1-(4-(2,4-dichlorobenzyloxy)phenyl)-4,5-dihydro-1H-pyrazol-5-yl)acetate: To a stirred suspension of 29C (15 mg, 0.058 mmol) and $Cs_2CO_3$ (73 mg, 0.22 mmol) in MeCN (1.0 mL) at 50° C. was added 2,4-dichloro-1-(chloromethyl)benzene (9.4 μL, 0.067 mmol). The reaction mixture was stirred at 50° C. for 1.0 h and then cooled to rt and partitioned between $CH_2Cl_2$ (40 mL) and water (6 mL). The aqueous layer was extracted with $CH_2Cl_2$ (2×20 mL) and the combined organic layers were dried ($Na_2SO_4$) and concentrated. The crude product was purified by flash chromatography to provide 33A (yellow oil, 14 mg, 0.032 mmol, 56% yield). LC-MS Anal. Calc'd for $C_{20}H_{17}Cl_2N_3O_3$ 418.27. found [M+] 418.1. $^1$H NMR (400 MHz, $CDCl_3$) δ 7.48 (d, J=8.2 Hz, 1H), 7.42 (d, J=2.2 Hz, 1H), 7.28 (dd, J=8.2, 1.7 Hz, 1H), 7.09 (d, J=9.1 Hz, 2H), 6.95 (d, J=9.2 Hz, 2H), 5.09 (s, 2H), 4.89 (m, 1H), 4.65 (s, 1H), 3.71 (s, 3H), 3.38 (dd, J=17.6, 12.1 Hz, 1H), 2.96 (dd, J=17.6, 5.3 Hz, 1H), 2.82 (dd, J=16.0, 3.0 Hz, 1H), 2.45 (dd, J=15.9, 10.4 Hz, 1H).

Example 33 (yellow solid, 11 mg, 0.027 mmol, 80% yield) was prepared as a racemate from 33A following the procedure of Example 29. LC-MS Anal. Calc'd for $C_{19}H_{15}Cl_2N_3O_3$ 404.25. found [M+H] 404.1. $^1$H NMR (400 MHz, $CDCl_3$) δ 7.48 (d, J=8.8 Hz, 1H), 7.42 (d, J=2.2 Hz, 1H), 7.28 (dd, J=8.2, 1.7 Hz, 1H), 7.09 (d, J=8.9 Hz, 2H), 6.96 (d, J=9.1 Hz, 2H), 5.01 (s, 2H), 4.89 (m, 1H), 3.41 (dd, J=17.6, 12.1 Hz, 1H), 3.00 (dd, J=17.6, 4.9 Hz, 1H), 2.88 (dd, J=16.5, 2.8 Hz, 1H), 2.53 (dd, J=16.5, 9.9 Hz, 1H). Analytical HPLC (Zorbax method, 50% Solvent B start): RT=6.6 min, HI: 100%. hGPR40 $EC_{50}$=300 nM.

Example 34, Isomer 1 and Isomer 2

2-(3-cyano-1-(4-((2'-fluoro-5'-methoxy-3-methylbiphenyl-4-yl)methyl)phenyl)-4,5-dihydro-1H-pyrazol-5-yl)acetic acid

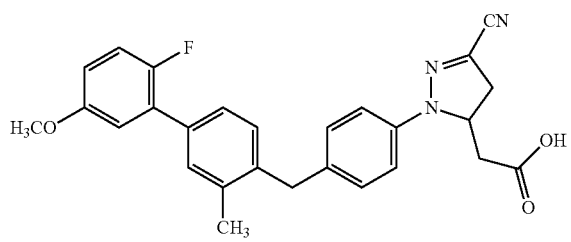 [SMILES: COc1ccc(F)c(-c2ccc(Cc3ccc(N4N=C(C#N)CC4CC(=O)O)cc3)c(C)c2)c1]

34A. methyl 2-(1-(4-bromophenyl)-3-cyano-4,5-dihydro-1H-pyrazol-5-yl)acetate: 34A (contaminated with methyl 2-(1-(4-bromophenyl)-3-cyano-4,5-dihydro-1H-pyrazol-4-yl)acetate) was prepared following the procedure of Example 29. LC-MS Anal. Calc'd for $C_{13}H_{12}BrN_3O_2$ 322.157. found [M+H] 322.0, 324.0.

Example 34, Isomer 1 and Isomer 2 were prepared from 34A as single enantiomers following the procedure of Example 17. Example 34, Isomer 1 (yellow solid, 7 mg). LC-MS Anal. Calc'd for $C_{27}H_{24}FN_3O_3$ 457.5. found [M+H] 458.2. $^1$H NMR (400 MHz, $CD_2Cl_2$) δ 7.27 (s, 1H), 7.24 (d, J=7.7 Hz, 1H), 7.11-7.05 (m, 3H), 7.03-6.95 (m, 3H), 6.86 (dd, J=6.1, 3.2 Hz, 1H), 6.74 (dt, J=8.8, 3.5 Hz, 1H), 4.85 (m, 1H), 3.90 (s, 2H), 3.72 (s, 3H), 3.34 (dd, J=17.6, 12.1 Hz, 1H), 2.93 (dd, J=17.6, 4.7 Hz, 1H), 2.84 (dd, J=16.5, 2.8 Hz, 1H), 2.47 (dd, J=16.5, 9.9 Hz, 1H), 2.22 (s, 3H). Analytical HPLC (Zorbax method, 50% Solvent B start): RT=7.4 min, HI: 99%. hGPR40 $EC_{50}$=150 nM. Example 34, Isomer 2 (yellow solid, 7 mg). LC-MS Anal. Calc'd for $C_{27}H_{24}FN_3O_3$ 457.5. found [M+H] 458.1. $^1$H NMR (400 MHz, $CD_2Cl_2$) δ 7.27 (s, 1H), 7.24 (d, J=7.7 Hz, 1H), 7.11-7.05 (m, 3H), 7.03-6.95 (m, 3H), 6.86 (dd, J=6.1, 3.2 Hz, 1H), 6.74 (dt, J=8.8, 3.5 Hz, 1H), 4.85 (m, 1H), 3.90 (s, 2H), 3.72 (s, 3H), 3.34 (dd, J=17.6, 12.1 Hz, 1H), 2.93 (dd, J=17.6, 4.7 Hz, 1H), 2.84 (dd, J=16.5, 2.8 Hz, 1H), 2.47 (dd, J=16.5, 9.9 Hz, 1H), 2.22 (s, 3H). Analytical HPLC (Zorbax method, 50% Solvent B start): RT=7.4 min, HI: 100%. hGPR40 $EC_{50}$=560 nM.

Example 35

2-(3-cyano-1-(4-(2'-fluoro-5'-methoxy-2,5-dimethylbiphenyl-4-yloxy)phenyl)-4,5-dihydro-1H-pyrazol-5-yl)acetic acid

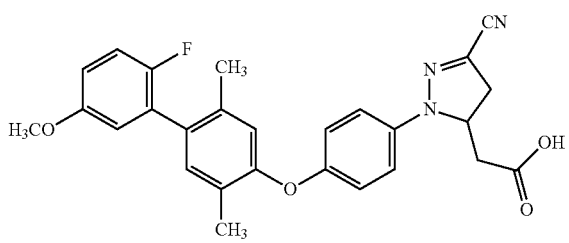

35A. methyl 2-(3-cyano-1-(4-(2'-fluoro-5'-methoxy-2,5-dimethylbiphenyl-4-yloxy)phenyl)-4,5-dihydro-1H-pyrazol-5-yl)acetate: To a stirred solution of methyl 2-(1-(4-(4-bromo-2,5-dimethylphenoxy)phenyl)-3-cyano-4,5-dihydro-1H-pyrazol-5-yl)acetate (prepared following the procedure for Example 29) (18 mg, 0.040 mmol) in toluene (0.3 mL) under argon was added a solution of 2-fluoro-5-methoxyphenylboronic acid (10 mg, 0.059 mmol) in MeOH (62 μl) and a solution of $Na_2CO_3$ (14 mg, 0.132 mmol) in water (0.24 mL). The reaction mixture was degassed by ultrasound irradiation (5 min) under argon and then $Pd(PPh_3)_2Cl_2$ (3 mg, 4.3 μmol) was added. The resulting mixture was stirred at 87° C. for 2.5 h. After cooling to rt, the reaction mixture was diluted with water (6 mL) and extracted with $CH_2Cl_2$ (3×20 mL). The combined organic extracts were dried ($Na_2SO_4$) and evaporated. The crude mixture was purified by flash chromatography to afford 35A (5 mg, 10 μmol, 26% yield) as a yellowish oil. LC-MS Anal. Calc'd for $C_{28}H_{26}FN_3O_4$ 487.52. found [M+H] 488.2.

Example 35 (yellow solid, 5 mg, 10.14 µmol, 95% yield) was prepared as a racemate from 35A following the procedure of Example 29. LC-MS Anal. Calc'd for $C_{27}H_{24}FN_3O_4$ 473.5. found [M+H] 474.1. $^1$H NMR (500 MHz, $CD_2Cl_2$) δ 7.06 (d, J=9.3 Hz, 2H), 7.02 (s, 1H), 6.97 (t, J=9.1 Hz, 1H), 6.90 (d, J=9.3 Hz, 2H), 6.78 (dt, J=8.8, 3.6 Hz, 1H), 6.68 (m, 2H), 4.85 (m, 1H), 3.72 (s, 3H), 3.36 (dd, J=17.6, 12.1 Hz, 1H), 2.95 (dd, J=17.6, 5.5 Hz, 1H), 2.85 (dd, J=16.5, 2.9 Hz, 1H), 2.50 (dd, J=16.5, 10.0 Hz, 1H), 2.15 (s, 3H), 2.01 (s, 3H). Analytical HPLC (Zorbax method, 0% Solvent B start): RT=8.3 min, HI: 100%. hGPR40 $EC_{50}$=180 nM.

Example 36

2-(3-cyano-1-(4-(3'-methoxy-2,5-dimethylbiphenyl-4-yloxy)phenyl)-4,5-dihydro-1H-pyrazol-5-yl)acetic acid

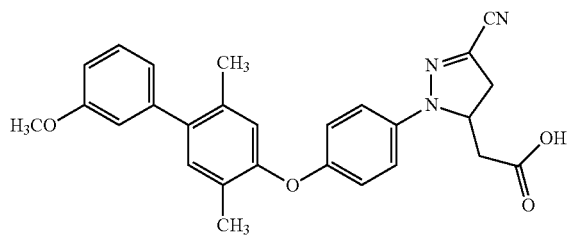 [SMILES: COc1cccc(-c2cc(C)c(Oc3ccc(N4N=C(C#N)CC4CC(=O)O)cc3)cc2C)c1]

Example 36 (yellow solid, 5 mg) was prepared as a racemate following the procedure of Example 35. LC-MS Anal. Calc'd for $C_{27}H_{25}N_3O_4$ 455.51. found [M+H] 456.1. $^1$H NMR (500 MHz, $CD_2Cl_2$) δ 7.31 (t, J=8.0 Hz, 1H), 7.14-7.09 (m, 3H), 6.97-6.93 (m, 2H), 6.91-6.82 (m, 3H), 6.75 (s, 1H), 4.92 (m, 1H), 3.81 (s, 3H), 3.43 (dd, J=17.6, 12.1 Hz, 1H), 3.02 (dd, J=17.6, 4.9 Hz, 1H), 2.91 (dd, J=16.5, 3.0 Hz, 1H), 2.57 (dd, J=16.5, 10.4 Hz, 1H), 2.20 (s, 3H), 2.16 (s, 3H). Analytical HPLC (Zorbax method, 0% Solvent B start): RT=8.4 min, HI: 98%. hGPR40 $EC_{50}$=590 nM.

Example 37

2-(3-cyano-1-(4-(4-methoxy-2-methylbenzyl)phenyl)-4,5-dihydro-1H-pyrazol-5-yl)acetic acid

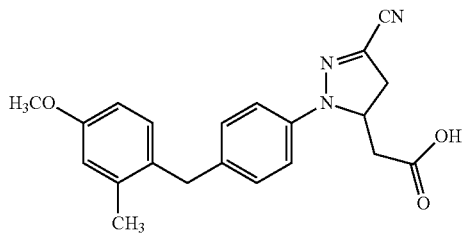 [SMILES: COc1ccc(Cc2ccc(N3N=C(C#N)CC3CC(=O)O)cc2)c(C)c1]

37A. 4-(4-methoxy-2-methylbenzyl)aniline: 37A (yellow solid, 371 mg, 1.551 mmol, 97% yield) was prepared from 28A following the procedure of Example 46. LC-MS Anal. Calc'd for $C_{15}H_{17}NO$, 227.302. found [M+H] 228.2.

Example 37 (white solid, 9 mg) was prepared as a racemate from 37A following the procedure of Example 29. LC-MS Anal. Calc'd for $C_{21}H_{21}N_3O_3$ 363.42. found [M+H] 364. $^1$H NMR (400 MHz, $CD_2Cl_2$) δ 7.04-6.89 (m, 5H), 6.63 (d, J=2.8 Hz, 1H), 6.59 (dd, J=8.3, 2.8 Hz, 1H), 4.83 (m, 1H), 3.79 (s, 2H), 3.67 (s, 3H), 3.33 (dd, J=17.6, 12.1 Hz, 1H), 2.91 (dd, J=17.6, 4.9 Hz, 1H), 2.82 (dd, J=16.5, 2.8 Hz, 1H), 2.46 (dd, J=16.5, 9.9 Hz, 1H), 2.11 (s, 3H). Analytical HPLC (Zorbax method, 0% Solvent B start): RT=7.6 min, HI: 100%. hGPR40 $EC_{50}$=150 nM.

Example 38

2-(3-cyano-1-(4-((3'-methoxy-3-methylbiphenyl-4-yl)methyl)phenyl)-4,5-dihydro-1H-pyrazol-5-yl)acetic acid

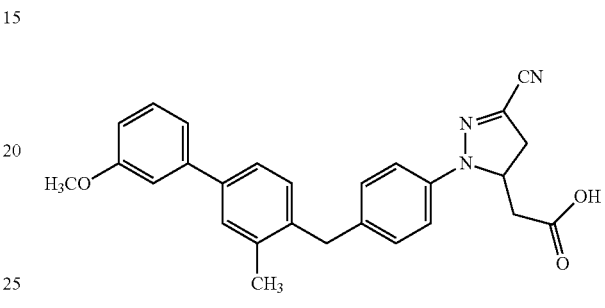

38A. methyl 2-(3-cyano-1-(4-(4-hydroxy-2-methylbenzyl)phenyl)-4,5-dihydro-1H-pyrazol-5-yl)acetate: 38A (yellow solid, 140 mg, 0.385 mmol, 75% yield) was prepared from 37A following the procedure of Example 29. LC-MS Anal. Calc'd for $C_{21}H_{21}N_3O_3$ 363.41. found [M+H] 364.0.

38B. methyl 2-(3-cyano-1-(4-(2-methyl-4-(trifluoromethylsulfonyloxy)benzyl)phenyl)-4,5-dihydro-1H-pyrazol-5-yl)acetate: 38B (yellow oil, 182 mg, 0.363 mmol, 96% yield) was prepared from 38A following the procedure of Example 46. LC-MS Anal. Calc'd for $C_{22}H_{20}F_3N_3O_5S$, 495.47. found [M+H] 496.0.

38C. methyl 2-(3-cyano-1-(4-((3'-methoxy-3-methylbiphenyl-4-yl)methyl)phenyl)-4,5-dihydro-1H-pyrazol-5-yl) acetate: A mixture of 38B (28 mg, 0.057 mmol), 3-methoxyphenylboronic acid (18 mg, 0.12 mmol), $K_3PO_4$ (70 mg, 0.32 mmol) and DMF (0.4 mL) was degassed by ultrasound irradiation under argon for 5 min. Then, $Pd(PPh_3)_4$ (4.0 mg, 3.5 µmol) was added and the resulting mixture was heated to 105° C. while stirring. After stirring at 105° C. for 2.2 h, the reaction mixture was cooled to rt and partitioned between water (8 mL) and EtOAc (30 mL). The organic layer was separated and the aqueous layer was extracted with EtOAc (2×20 mL). The combined organic layers were washed with aq. sat. $NaHCO_3$ (2×20 mL) and water (20 mL), dried ($Na_2SO_4$) and evaporated. The crude product was purified by flash chromatography to afford 38C (8 mg, 30% yield) as a yellowish oil. LC-MS Anal. Calc'd for $C_{28}H_{27}N_3O_3$ 453.53. found [M+H] 454.1.

Example 38 (off white solid, 6 mg, 0.014 mmol, 88% yield) was prepared as a racemate from 38C following the procedure for Example 29. LC-MS Anal. Calc'd for $C_{27}H_{25}N_3O_3$ 439.51. found [M+H] 440.2. $^1$H NMR (400 MHz, $CD_2Cl_2$) δ 7.33 (s, 1H), 7.30 (dd, J=7.7, 2.2 Hz, 1H), 7.25 (t, J=8.0 Hz, 1H), 7.11-7.05 (m, 4H), 7.03 (t, J=2.2 Hz, 1H), 7.00 (d, J=8.7 Hz, 2H), 6.79 (dd, J=8.0, 2.4 Hz, 1H), 4.85 (m, 1H), 3.90 (s, 2H), 3.76 (s, 3H), 3.34 (dd, J=17.6, 12.1 Hz, 1H), 2.92 (dd, J=17.6, 4.9 Hz, 1H), 2.83 (dd, J=16.5, 2.8 Hz, 1H), 2.47 (dd, J=16.5, 10.1 Hz, 1H), 2.23 (s, 3H). Analytical HPLC (Zorbax method, 50% Solvent B start): RT=7.4 min, HI: 100%. hGPR40 $EC_{50}$=190 nM.

Example 39

2-(3-cyano-1-(4-((5'-cyano-2'-fluoro-3-methylbiphenyl-4-yl)methyl)phenyl)-4,5-dihydro-1H-pyrazol-5-yl)acetic acid

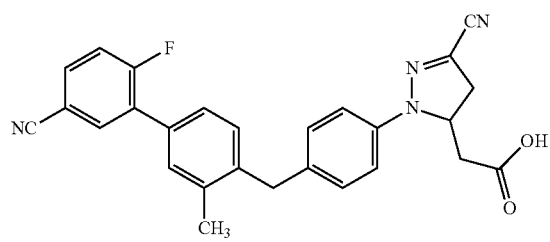 [SMILES: Cc1cc(-c2cc(C#N)ccc2F)ccc1Cc1ccc(N2N=C(C#N)CC2CC(=O)O)cc1]

Example 39 (white solid, 6 mg) was prepared as a racemate following the procedure of Example 38. LC-MS Anal. Calc'd for $C_{27}H_{21}FN_4O_2$ 452.49. found [M+H] 453.1. $^1$H NMR (400 MHz, $CD_2Cl_2$) δ 7.71 (d, J=7.2 Hz, 1H), 7.56 (m, 1H), 7.28-7.16 (m, 3H), 7.13 (d, J=7.7 Hz, 1H), 7.06 (d, J=8.2 Hz, 2H), 7.01 (d, J=8.2 Hz, 2H), 4.85 (m, 1H), 3.91 (s, 2H), 3.31 (dd, J=17.6, 12.1 Hz, 1H), 2.93 (dd, J=17.6, 4.9 Hz, 1H), 2.76 (dd, J=16.5, 2.2 Hz, 1H), 2.38 (dd, J=16.5, 10.4 Hz, 1H), 2.24 (s, 3H). Analytical HPLC (Zorbax method, 0% Solvent B start): RT=8.1 min, HI: 100%. hGPR40 $EC_{50}$=200 nM.

Example 40

2-(1-(4-((2'-chloro-5'-methoxy-3-methylbiphenyl-4-yl)methyl)phenyl)-3-cyano-4,5-dihydro-1H-pyrazol-5-yl)acetic acid

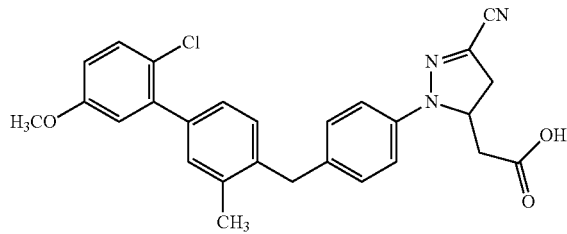

Example 40 (off-white solid, 2 mg) was prepared as a racemate following the procedure of Example 38. LC-MS Anal. Calc'd for $C_{27}H_{24}ClN_3O_3$ 473.96. found [M+H] 474.1. $^1$H NMR (400 MHz, $CD_2Cl_2$) δ 7.27 (d, J=8.8 Hz, 1H), 7.18-7.05 (m, 5H), 7.02 (d, J=8.8 Hz, 2H), 6.79 (d, J=3.3 Hz, 1H), 6.75 (dd, J=8.8, 3.3 Hz, 1H), 4.86 (m, 1H), 3.91 (s, 2H), 3.72 (s, 3H), 3.35 (dd, J=17.6, 12.1 Hz, 1H), 2.93 (dd, J=17.6, 4.9 Hz, 1H), 2.84 (dd, J=16.5, 3.1 Hz, 1H), 2.47 (dd, J=16.5, 10.2 Hz, 1H), 2.23 (s, 3H). Analytical HPLC (Zorbax method, 50% Solvent B start): RT=7.7 min, HI: 100%. hGPR40 $EC_{50}$=120 nM.

Example 41, Isomer 2

2-(1-(4-((2'-fluoro-5'-methoxy-3-methylbiphenyl-4-yl)methyl)phenyl)-4-isobutyl-3-(trifluoromethyl)-4,5-dihydro-1H-pyrazol-5-yl)acetic acid

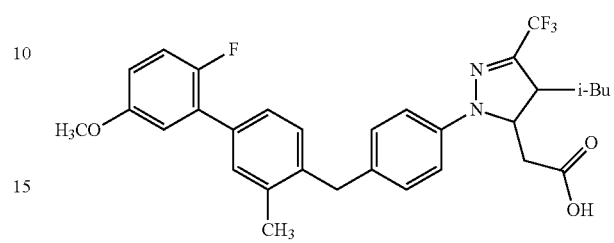

Example 41, Isomer 2 (light yellow oil, 6 mg) was prepared as single enantiomers following the procedure of Example 46. LC-MS Anal. Calc'd for $C_{31}H_{32}F_4N_2O_3$ 556.6. found [M+H] 557.4. $^1$H NMR (400 MHz, $CD_2Cl_2$) δ 7.28-7.42 (2H, m), 7.10-7.22 (3H, m), 7.02-7.09 (3H, m), 6.94 (1H, dd, J=6.3, 3.0 Hz), 6.77-6.87 (1H, m), 4.52-4.66 (1H, m), 3.97 (2H, s), 3.80 (3H, s), 3.15-3.30 (1H, m), 2.69-2.85 (1H, m), 2.46 (1H, dd, J=15.9, 9.9 Hz), 2.31 (3H, s), 1.72-1.93 (1H, m), 1.36-1.59 (2H, m), 0.93 (6H, dd, J=8.7, 6.7 Hz). Analytical HPLC (orthogonal method): RT=8.8 min, HI: 98.0%. hGPR40 $EC_{50}$=95 nM.

Example 42, Isomer 1 and Isomer 2

2-(1-(4-(3-chloro-2'-fluoro-5'-methoxybiphenyl-4-yloxy)phenyl)-3-(trifluoromethyl)-4,5-dihydro-1H-pyrazol-5-yl)acetic acid

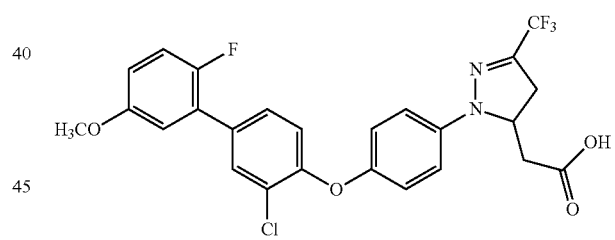

42A. 4-bromo-2-chloro-1-(4-nitrophenoxy)benzene: To a stirred suspension of NaH (0.997 g, 24.9 mmol) in DMF (26.4 ml) was added portionwise 4-bromo-2-chlorophenol (4.27 g, 20.6 mmol). The mixture was stirred at rt under argon for 15 min and then 4-fluoronitrobenzene (3.51 g, 24.9 mmol) was added in one portion. The reaction mixture was heated to 100° C. for 3.5 h and then cooled to rt and quenched with ice. The aqueous mixture was allowed to warm to rt while stirring. After stirring at rt overnight, the mixture was cooled to 0° C. and filtered. The collected solid was rinsed with water (4.0 mL) and MeOH (3×4 mL), and dried to afford 42A (6.90 g, 20.6 mmol, 100% yield) as a yellow solid. LC-MS Anal. Calc'd for $C_{12}H_7BrClNO_3$ 328.55. found [M+H] 329.9.

42B. 3'-chloro-2-fluoro-5-methoxy-4'-(4-nitrophenoxy)biphenyl: A mixture of 42A (763 mg, 2.32 mmol), 2-fluoro-5-methoxyphenylboronic acid (534 mg, 3.08 mmol), $K_2CO_3$ (600 mg, 4.25 mmol) and toluene (18 mL) was degassed by ultrasound irradiation under argon for 5 min. Then, Pd(PPh$_3$)$_4$ (139 mg, 0.120 mmol) was added and the resulting mixture was stirred at 90° C. for 3.7 h. Additional amounts of 2-fluoro-5-methoxyphenylboronic acid (534 mg, 3.08 mmol) and K$_2$CO$_3$ (600 mg, 4.25 mmol) were added. Stirring at 90° C. was continued for an additional 11.5 h at 90° C. The mixture was cooled to rt and diluted with EtOAc (50 mL). The organic layer was washed with 5% aq. NaHCO$_3$ (40 mL), water (40 mL), 10% aq. KHSO$_4$ (30 mL), water (30 mL), and brine (30 mL). The organic phase was dried (Na$_2$SO$_4$) and evaporated. The crude material was purified by flash chromatography to afford 42B (yellow oil, 638 mg, 1.50 mmol, 65% yield). LC-MS Anal. Calc'd for C$_{19}$H$_{13}$ClFNO$_4$ 373.76. found [M+H] 374.0.

42C. N'-(4-(3-chloro-2'-fluoro-5'-methoxybiphenyl-4-yloxy)phenyl)-2,2,2-trifluoroacetohydrazonoyl chloride: 42C (brown oil, 94 mg, 0.197 mmol) was prepared from 42B following the procedure for Example 46. LC-MS Anal. Calc'd for C$_{21}$H$_{1-4}$Cl$_2$F$_4$N$_2$O$_2$ 473.25. found [M−H]⁻ 471.1.

Example 42, Isomer 1 and Isomer 2 were prepared as single enantiomers from 42C following the procedure for Example 17. Example 42, Isomer 1 (off-white solid, 18 mg). LC-MS Anal. Calc'd for C$_{25}$H$_{19}$ClF$_4$N$_2$O$_4$ 522.88. found [M+H] 523.2. $^1$H NMR (500 MHz, CD$_2$Cl$_2$) δ 8.01 (s, 1H), 7.65 (s, 1H), 7.37 (dt, J=8.3, 1.6 Hz, 1H), 7.16 (d, J=9.3 Hz, 2H), 7.16 (t, J=9.3 Hz, 1H), 7.04 (d, J=8.8 Hz, 2H), 6.95 (d, J=8.3 Hz, 1H), 6.90 (dd, J=6.6, 3.3 Hz, 1H), 6.84 (dt, J=8.8, 3.3 Hz, 1H), 4.85 (m, 1H), 3.80 (s, 3H), 3.41 (dd, J=16.5, 12.1 Hz, 1H), 3.00 (dd, J=16.5, 4.1 Hz, 1H), 2.93 (d, J=16.5 Hz, 1H), 2.47 (dd, J=16.5, 9.6 Hz, 1H). Analytical HPLC (Zorbax, 70% Solvent B start): RT=6.5 min, HI: 97%. hGPR40 EC$_{50}$=620 nM. Example 42, Isomer 2 (off-white solid, 19 mg). LC-MS Anal. Calc'd for C$_{25}$H$_{19}$ClF$_4$N$_2$O$_4$ 522.88. found [M+H] 523.2. $^1$H NMR (500 MHz, CD$_2$Cl$_2$) δ 8.01 (s, 1H), 7.65 (s, 1H), 7.37 (dt, J=8.3, 1.6 Hz, 1H), 7.16 (d, J=9.3 Hz, 2H), 7.16 (t, J=9.3 Hz, 1H), 7.04 (d, J=8.8 Hz, 2H), 6.95 (d, J=8.3 Hz, 1H), 6.90 (dd, J=6.6, 3.3 Hz, 1H), 6.84 (dt, J=8.8, 3.3 Hz, 1H), 4.85 (m, 1H), 3.80 (s, 3H), 3.41 (dd, J=16.5, 12.1 Hz, 1H), 3.00 (dd, J=16.5, 4.1 Hz, 1H), 2.93 (d, J=16.5 Hz, 1H), 2.47 (dd, J=16.5, 9.6 Hz, 1H). Analytical HPLC (orthogonal method): RT=10.9 min, HI: 95%. hGPR40 EC$_{50}$=290 nM.

Example 43, Isomer 1 and Isomer 2

2-(4-cyclopropyl-1-(4-((2'-fluoro-5'-methoxy-3-methylbiphenyl-4-yl)methyl)phenyl)-3-(trifluoromethyl)-4,5-dihydro-1H-pyrazol-5-yl)acetic acid

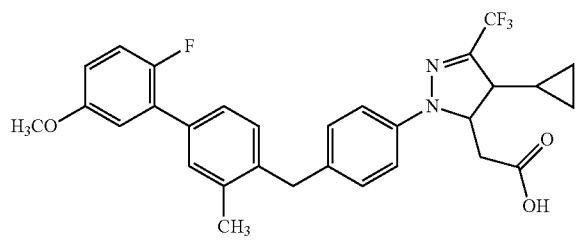 [SMILES: COc1ccc(F)c(-c2ccc(Cc3ccc(N4N=C(C(F)(F)F)C(C5CC5)C4CC(=O)O)cc3)c(C)c2)c1]

Example 43, Isomer 1 and Isomer 2 were prepared as single enantiomers following the procedure of Example 46. Example 43, Isomer 1 (colorless oil, 4 mg). LC-MS Anal. Calc'd for C$_{30}$H$_{28}$F$_4$N$_2$O$_3$ 540.55. found [M+H] 541.3. 1H NMR (400 MHz, CD$_3$OD) δ 7.27-7.38 (2H, m), 7.19 (1H, d, J=7.8 Hz), 7.03-7.15 (5H, m), 6.96 (1H, dd, J=6.3, 3.3 Hz), 6.86 (1H, dt, J=9.0, 3.4 Hz), 4.72 (1H, d, J=10.0 Hz), 3.98 (2H, s), 3.81 (3H, s), 2.70 (1H, dd, J=15.2, 2.6 Hz), 2.53 (1H, dd, J=9.9, 1.4 Hz), 2.21-2.36 (4H, m), 0.87-1.00 (1H, m), 0.62-0.73 (1H, m), 0.51-0.62 (1H, m), 0.36-0.49 (2H, m), Analytical HPLC (orthogonal method): RT=14.71 min, HI: 98%. hGPR40 EC$_{50}$=3280 nM. Example 43, Isomer 2 (colorless oil, 6 mg). LC-MS Anal. Calc'd for C$_{30}$H$_{28}$F$_4$N$_2$O$_3$ 540.55. found [M+H] 541.3. $^1$H NMR (400 MHz, CD$_3$OD) δ 7.27-7.36 (2H, m), 7.19 (1H, d, J=7.8 Hz), 7.02-7.15 (5H, m), 6.96 (1H, dd, J=6.3, 3.3 Hz), 6.86 (1H, ddd, J=8.9, 3.6, 3.5 Hz), 4.72 (1H, d, J=10.0 Hz), 3.98 (2H, s), 3.81 (3H, s), 2.70 (1H, d, J=13.3 Hz), 2.53 (1H, d, J=9.3 Hz), 2.21-2.38 (4H, m), 0.85-1.01 (1H, m), 0.61-0.74 (1H, m), 0.51-0.60 (1H, m), 0.43 (2H, d, J=3.0 Hz). Analytical HPLC (orthogonal method): RT=14.71 min, HI: 98%. hGPR40 EC$_{50}$=90 nM.

Example 44, Isomer 1 and Isomer 2

2-(4-ethyl-1-(4-((2'-fluoro-5'-methoxy-3-methylbiphenyl-4-yl)methyl)phenyl)-3-(trifluoromethyl)-4,5-dihydro-1H-pyrazol-5-yl)acetic acid

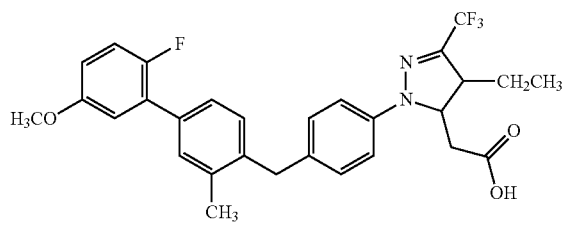 [SMILES: CCC1C(C(F)(F)F)=NN(c2ccc(Cc3ccc(-c4cc(OC)ccc4F)cc3C)cc2)C1CC(=O)O]

Example 44, Isomer 1 and Isomer 2 were prepared as single enantiomers following the procedure of Example 46. Example 44, Isomer 1 (colorless oil, 90 mg).

LC-MS Anal. Calc'd for C$_{29}$H$_{28}$F$_4$N$_2$O$_3$ 528.54. found [M+H] 529.2. $^1$H NMR (500 MHz, CDCl$_3$) δ 7.37 (s, 1H), 7.35 (d, J=7.8 Hz, 1H), 7.20-7.11 (m, 3H), 7.11-7.04 (m, 3H), 6.96 (dd, J=6.3, 3.2 Hz, 1H), 6.83 (dt, J=8.9, 3.5 Hz, 1H), 4.58 (d, J=10.2 Hz, 1H), 3.99 (s, 2H), 3.84 (s, 3H), 3.23-3.12 (m, 1H), 2.90 (dd, J=16.2, 2.7 Hz, 1H), 2.48 (dd, J=16.2, 10.4 Hz, 1H), 2.34 (s, 3H), 1.86-1.72 (m, 1H), 1.72-1.58 (m, 1H), 0.97 (t, J=7.4 Hz, 3H). Analytical HPLC (orthogonal method): RT=13.7 min, HI: 99%. hGPR40 EC$_{50}$=1310 nM. Example 44, Isomer 2 (colorless oil, 71 mg). LC-MS Anal. Calc'd for C$_{29}$H$_{28}$F$_4$N$_2$O$_3$ 528.54. found [M+H] 529.2. $^1$H NMR (500 MHz, CDCl$_3$) δ 7.37 (s, 1H), 7.35 (d, J=7.8 Hz, 1H), 7.20-7.11 (m, 3H), 7.11-7.04 (m, 3H), 6.96 (dd, J=6.3, 3.2 Hz, 1H), 6.83 (dt, J=8.9, 3.5 Hz, 1H), 4.58 (d, J=10.2 Hz, 1H), 3.99 (s, 2H), 3.84 (s, 3H), 3.23-3.12 (m, 1H), 2.90 (dd, J=16.2, 2.7 Hz, 1H), 2.48 (dd, J=16.2, 10.4 Hz, 1H), 2.34 (s, 3H), 1.86-1.72 (m, 1H), 1.72-1.58 (m, 1H), 0.97 (t, J=7.4 Hz, 3H). Analytical HPLC (orthogonal method): RT=13.7 min, HI: 98%. hGPR40 EC$_{50}$=20 nM.

Example 45, Isomer 1 and Isomer 2

2-(1-(4-((2'-fluoro-5'-methoxy-3-methylbiphenyl-4-yl)methyl)phenyl)-4-isopropyl-3-(trifluoromethyl)-4,5-dihydro-1H-pyrazol-5-yl)acetic acid

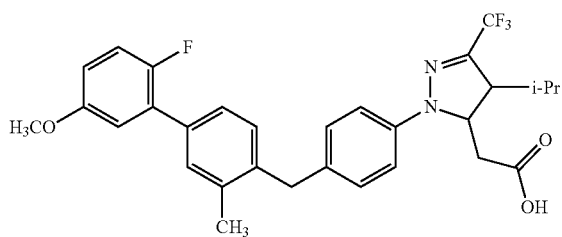 [SMILES: COc1ccc(F)c(-c2ccc(Cc3ccc(N4N=C(C(F)(F)F)C(C(C)C)C4CC(=O)O)cc3)c(C)c2)c1]

Example 45, Isomer 1 and Isomer 2 were prepared as single enantiomers following the procedure of Example 46. Example 45, Isomer 1 (colorless oil, 93 mg). LC-MS Anal. Calc'd for $C_{30}H_{30}F_4N_2O_3$ 542.57. found [M+H] 543.2. $^1$H NMR (500 MHz, CDCl$_3$) δ 7.37 (s, 1H), 7.35 (d, J=7.8 Hz, 1H), 7.18 (d, J=7.8 Hz, 1H), 7.13 (d, J=8.6 Hz, 2H), 7.10-7.04 (m, 3H), 6.96 (dd, J=6.3, 3.2 Hz, 1H), 6.83 (dt, J=8.9, 3.5 Hz, 1H), 4.61 (d, J=9.8 Hz, 1H), 3.98 (s, 2H), 3.84 (s, 3H), 3.18 (s, 1H), 2.84 (dd, J=15.3, 2.5 Hz, 1H), 2.46 (dd, J=15.3, 10.0 Hz, 1H), 2.34 (s, 3H), 2.16-2.04 (m, 1H), 1.02 (d, J=6.9 Hz, 3H), 0.82 (d, J=6.9 Hz, 3H). Analytical HPLC (orthogonal method): RT=13.9 min, HI: 98%. hGPR40 EC$_{50}$=3820 nM. Example 45, Isomer 2 (colorless oil, 74 mg). LC-MS Anal. Calc'd for $C_{30}H_{30}F_4N_2O_3$ 542.57. found [M+H] 543.2. $^1$H NMR (500 MHz, CDCl$_3$) δ 7.37 (s, 1H), 7.35 (d, J=7.8 Hz, 1H), 7.18 (d, J=7.8 Hz, 1H), 7.13 (d, J=8.6 Hz, 2H), 7.10-7.04 (m, 3H), 6.96 (dd, J=6.3, 3.2 Hz, 1H), 6.83 (dt, J=8.9, 3.5 Hz, 1H), 4.61 (d, J=9.8 Hz, 1H), 3.98 (s, 2H), 3.84 (s, 3H), 3.18 (s, 1H), 2.84 (dd, J=15.3, 2.5 Hz, 1H), 2.46 (dd, J=15.3, 10.0 Hz, 1H), 2.34 (s, 3H), 2.16-2.04 (m, 1H), 1.02 (d, J=6.9 Hz, 3H), 0.82 (d, J=6.9 Hz, 3H). Analytical HPLC (orthogonal method): RT=13.9 min, HI: 96%. hGPR40 EC$_{50}$=70 nM.

Example 46, Isomer 1 and Isomer 2

2-(4-(cyclopropylmethyl)-1-(4-((2'-fluoro-5'-methoxy-3-methylbiphenyl-4-yl)methyl)phenyl)-3-(trifluoromethyl)-4,5-dihydro-1H-pyrazol-5-yl)acetic acid

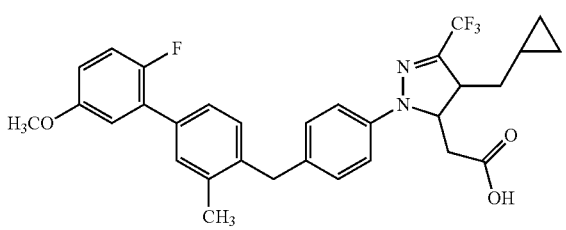 [SMILES: COc1ccc(F)c(-c2ccc(Cc3ccc(N4N=C(C(F)(F)F)C(CC5CC5)C4CC(=O)O)cc3)c(C)c2)c1]

46A. benzyl 4-(cyclopropylmethyl)-1-(4-(2'-fluoro-5'-methoxy-3-methylbiphenyl-4-yl)methyl)phenyl)-3-(trifluoromethyl)-4,5-dihydro-1H-pyrazole-5-carboxylate: A solution of 60% NaH in mineral oil (0.271 g, 6.78 mmol) in THF (10 mL) was cooled to 0° C. and treated with benzyl 2-(dimethoxyphosphoryl)acetate (1.44 mL, 6.78 mmol). The reaction stirred at 0° C. for 15 minutes until all the solids were dissolved and the solution was clear. Then, a solution of 2-cyclopropylacetaldehyde (0.475 g, 5.65 mmol) in CH$_3$CN (9 mL) and CH$_2$Cl$_2$ (3 mL) was added, and the reaction stirred at rt overnight. The reaction mixture was quenched with water and then concentrated to partially remove the solvent. The reaction mixture was then diluted with EtOAc, the layers were separated, and the aqueous layer extracted with EtOAc (2×). The combined organic extracts were dried (Na$_2$SO$_4$), filtered, and concentrated. The crude product was purified by flash chromatography to yield (E)-benzyl 4-cyclopropylbut-2-enoate (305 mg, 1.41 mmol, 25% yield) as a colorless liquid. A solution of 28D (320 mg, 0.710 mmol), (E)-benzyl 4-cyclopropylbut-2-enoate (200 mg, 0.925 mmol), and Ag$_2$CO$_3$ (489 mg, 1.77 mmol) in dioxane (4 mL) was heated to 70° C. and stirred overnight. The reaction mixture was filtered through Celite® and rinsed with EtOAc, and then concentrated. The crude product was purified by flash chromatography to provide 46A (262 mg, 0.415 mmol, 59% yield). LC-MS Anal. Calc'd for $C_{37}H_{34}F_4N_2O_3$ 630.67. found [M+H] 631.3.

46B. (4-(cyclopropylmethyl)-1-(4-((2'-fluoro-5'-methoxy-3-methylbiphenyl-4-yl)methyl)phenyl)-3-(trifluoromethyl)-4,5-dihydro-1H-pyrazol-5-yl)methanol: A solution of 46A (262 mg, 0.415 mmol) in EtOH (3 mL) and THF (0.6 mL) was treated with NaBH$_4$ (23.6 mg, 0.623 mmol) and stirred at rt overnight. The reaction mixture was quenched with water, diluted with EtOAc, and the aqueous layer was further extracted with EtOAc (3×). The combined organic extracts were washed with water and brine, dried (Na$_2$SO$_4$), filtered, and concentrated. The crude material was purified by flash chromatography to afford 46B (240 mg, 0.456 mmol, 110% yield). LC-MS Anal. Calc'd for $C_{30}H_{30}F_4N_2O_2$ 526.57. found [M+H] 527.2.

Example 46, Isomer 1 and Isomer 2 were prepared as single enantiomers following the procedure of Example 28, Isomer 2 except that (E)-benzyl 4-cyclopropylbut-2-enoate was used instead of (4S)-3-((2E)-2-butenoyl)-4-phenyl-1,3-oxazolidin-2-one during the cyclization step and a chiral separation was used to separate the enantiomers following the final hydrolysis. Example 46, Isomer 1 (colorless oil, 18 mg). LC-MS Anal. Calc'd for $C_{31}H_{30}F_4N_2O_3$ 554.58. found [M+H] 555.2. $^1$H NMR (400 MHz, CD$_2$Cl$_2$) δ 7.28-7.38 (2H, m), 7.10-7.21 (3H, m), 7.01-7.10 (3H, m), 6.94 (1H, dd, J=6.4, 3.1 Hz), 6.82 (1H, dt, J=9.0, 3.4 Hz), 4.80 (1H, d, J=9.8 Hz), 3.97 (2H, s), 3.81 (3H, s), 3.26-3.41 (1H, m), 2.83 (1H, dd, J=15.8, 2.5 Hz), 2.48 (1H, dd, J=15.9, 9.9 Hz), 2.31 (3H, s), 1.64 (1H, dt, J=14.3, 7.2 Hz), 1.40-1.54 (1H, m), 0.67-0.82 (1H, m), 0.35-0.59 (2H, m), 0.02-0.21 (2H, m). Analytical HPLC (orthogonal method): RT=13.9 min, HI: 95%. hGPR40 EC$_{50}$=50 nM. Example 46, Isomer 2 (colorless oil, 18 mg). LC-MS Anal. Calc'd for $C_{31}H_{30}F_4N_2O_3$ 554.58. found [M+H] 555.2. $^1$H NMR (400 MHz, CD$_2$Cl$_2$) δ 7.30-7.38 (2H, m), 7.14-7.21 (2H, m), 7.13 (1H, s), 7.02-7.10 (3H, m), 6.95 (1H, dd, J=6.4, 3.1 Hz), 6.82 (1H, ddd, J=8.9, 3.6, 3.5 Hz), 4.82 (1H, d, J=9.3 Hz), 3.98 (2H, s), 3.81 (3H, s), 3.33 (1H, dd, J=7.5, 3.5 Hz), 2.85 (1H, dd, J=16.1, 3.0 Hz), 2.51 (1H, dd, J=16.1, 10.0 Hz), 2.32 (3H, s), 1.65 (1H, ddd, J=14.4, 8.0, 6.4 Hz), 1.48 (1H, ddd, J=14.2, 7.7, 4.0 Hz), 0.69-0.80 (1H, m), 0.35-0.57 (2H, m), 0.03-0.24 (2H, m). Analytical HPLC (orthogonal method): RT=13.9 min, HI: 95%. hGPR40 EC$_{50}$=1910 nM.

Example 47, Isomer 1 and Isomer 2

2-(1-(4-((2'-fluoro-5'-methoxy-3-methylbiphenyl-4-yl)methyl)phenyl)-4-phenyl-3-(trifluoromethyl)-4,5-dihydro-1H-pyrazol-5-yl)acetic acid

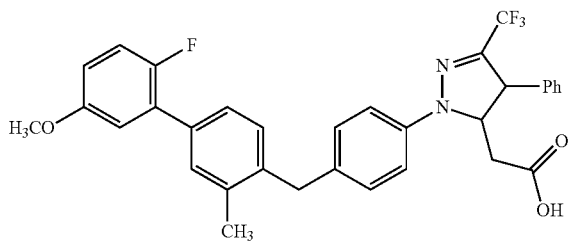 [SMILES: COc1ccc(F)c(-c2ccc(Cc3ccc(N4N=C(C(F)(F)F)C(c5ccccc5)C4CC(=O)O)cc3)c(C)c2)c1]

Example 47, Isomer 1 and Isomer 2 were prepared as single enantiomers following the procedure of Example 46. Example 47, Isomer 1 (colorless oil, 3 mg). LC-MS Anal. Calc'd for $C_{33}H_{28}F_4N_2O_3$ 576.59. found [M+H] 577.2. $^1$H NMR (400 MHz, $CD_2Cl_2$) δ 7.28-7.43 (5H, m), 7.12-7.23 (5H, m), 7.02-7.12 (3H, m), 6.94 (1H, dd, J=6.3, 3.0 Hz), 6.82 (1H, ddd, J=8.7, 3.6, 3.5 Hz), 4.72 (1H, d, J=10.0 Hz), 4.31 (1H, d, J=2.3 Hz), 3.99 (2H, s), 3.81 (3H, s), 2.97 (1H, dd, J=16.4, 2.9 Hz), 2.66 (1H, dd, J=16.4, 10.2 Hz), 2.32 (3H, s). Analytical HPLC (orthogonal method): RT=11.8 min, HI: 97.8%. hGPR40 $EC_{50}$=890 nM. Example 47, Isomer 2 (colorless oil, 3 mg). LC-MS Anal. Calc'd for $C_{33}H_{28}F_4N_2O_3$ 576.59. found [M+H] 577.2. $^1$H NMR (400 MHz, $CD_2Cl_2$) δ 7.29-7.40 (5H, m), 7.12-7.22 (5H, m), 7.02-7.11 (3H, m), 6.94 (1H, dd, J=6.3, 3.0 Hz), 6.76-6.86 (1H, m), 4.72 (1H, d, J=9.9 Hz), 4.31 (1H, br. s.), 3.98 (2H, s), 3.80 (3H, s), 2.97 (1H, dd, J=16.5, 2.7 Hz), 2.66 (1H, dd, J=16.5, 10.4 Hz), 2.32 (3H, s). Analytical HPLC (orthogonal method): RT=11.9 min, HI: 97.4%. hGPR40 $EC_{50}$=5929 nM.

Example 48, Isomer 1 and Isomer 2

2-(1-(4-((2'-fluoro-5'-methoxy-3-methylbiphenyl-4-yl)methyl)phenyl)-4-(methoxymethyl)-3-(trifluoromethyl)-4,5-dihydro-1H-pyrazol-5-yl)acetic acid

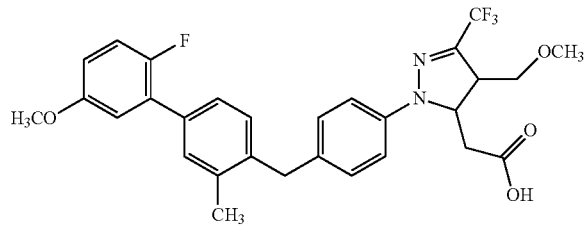 [SMILES: COCC1C(C(F)(F)F)=NN(c2ccc(Cc3ccc(-c4cc(OC)ccc4F)cc3C)cc2)C1CC(=O)O]

Example 48, Isomer 1 and Isomer 2 were prepared as single enantiomers following the procedure of Example 46. Example 48, Isomer 1 (colorless oil, 3 mg). LC-MS Anal. Calc'd for $C_{29}H_{28}F_4N_2O_4$ 544.54. found [M+H] 545.3. $^1$H NMR (400 MHz, $CD_2Cl_2$) δ 7.29-7.39 (2H, m), 7.11-7.22 (3H, m), 7.02-7.10 (3H, m), 6.94 (1H, dd, J=6.3, 3.3 Hz), 6.82 (1H, dt, J=8.8, 3.5 Hz), 4.75 (1H, d, J=9.5 Hz), 3.97 (2H, s), 3.81 (3H, s), 3.55-3.64 (1H, m), 3.43-3.55 (2H, m), 3.33 (3H, s), 2.92 (1H, dd, J=16.3, 2.8 Hz), 2.59 (1H, dd, J=16.3, 9.5 Hz), 2.31 (3H, s). Analytical HPLC (Zorbax method, 50% Solvent B start): RT=8.0 min, HI: 98%. hGPR40 $EC_{50}$=170 nM. Example 48, Isomer 2 (colorless oil, 3 mg). LC-MS Anal. Calc'd for $C_{29}H_{28}F_4N_2O_4$ 544.54. found [M+H] 545.3. $^1$H NMR (400 MHz, $CD_2Cl_2$) δ 7.28-7.40 (2H, m), 7.10-7.22 (3H, m), 7.01-7.09 (3H, m), 6.94 (1H, dd, J=6.3, 3.3 Hz), 6.82 (1H, ddd, J=8.9, 3.6, 3.5 Hz), 4.75 (1H, d, J=9.5 Hz), 3.97 (2H, s), 3.80 (3H, s), 3.55-3.64 (1H, m), 3.43-3.55 (2H, m), 3.33 (3H, s), 2.92 (1H, dd, J=16.2, 2.9 Hz), 2.59 (1H, dd, J=16.3, 9.5 Hz), 2.31 (3H, s). Analytical HPLC (Zorbax method, 50% Solvent B start): RT=8.0 min, HI: 98%. hGPR40 $EC_{50}$=920 nM.

Example 49, Isomer 1 and Isomer 2

2-(3-cyano-1-(4-((2',5'-dimethoxy-3-methylbiphenyl-4-yl)methyl)phenyl)-4,5-dihydro-1H-pyrazol-5-yl)acetic acid

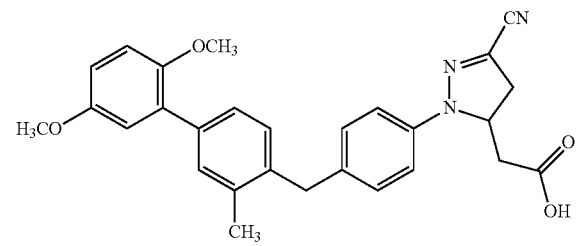 [SMILES: COc1ccc(OC)c(-c2ccc(Cc3ccc(N4N=C(C#N)CC4CC(=O)O)cc3)c(C)c2)c1]

Example 49, Isomer 1 and Isomer 2 were prepared as single enantiomers following the procedure of Example 46. Example 49, Isomer 1 BMS-983142 (off-white solid, 1.8 mg). LC-MS Anal. Calc'd for $C_{28}H_{27}N_3O_4$ 469.54. found [M+H] 470.1. $^1$H NMR (400 MHz, $CD_2Cl_2$) δ 7.20 (m, 2H), 7.09 (d, J=8.8 Hz, 2H), 7.04 (d, J=7.7 Hz, 1H), 7.01 (d, J=8.8 Hz, 2H), 6.83 (d, J=8.8 Hz, 1H), 6.78 (d, J=2.8 Hz, 1H), 6.75 (dd, J=8.8, 2.8 Hz, 1H), 4.86 (m, 1H), 3.89 (s, 2H), 3.69 (s, 3H), 3.65 (s, 3H), 3.34 (dd, J=17.6, 12.1 Hz, 1H), 2.93 (dd, J=17.6, 4.9 Hz, 1H), 2.84 (dd, J=16.5, 2.8 Hz, 1H), 2.47 (dd, J=16.5, 9.9 Hz, 1H), 2.21 (s, 3H). Analytical HPLC (orthogonal method): RT=13.4 min, HI: 99.0%. hGPR40 $EC_{50}$=225 nM. Example 49, Isomer 2 BMS-983145 (off-white solid, 1.5 mg). LC-MS Anal. Calc'd for $C_{28}H_{27}N_3O_4$ 469.54. found [M+H] 470.1. $^1$H NMR (400 MHz, $CD_2Cl_2$) δ 7.20 (m, 2H), 7.09 (d, J=8.8 Hz, 2H), 7.04 (d, J=7.7 Hz, 1H), 7.01 (d, J=8.8 Hz, 2H), 6.83 (d, J=8.8 Hz, 1H), 6.78 (d, J=2.8 Hz, 1H), 6.75 (dd, J=8.8, 2.8 Hz, 1H), 4.86 (m, 1H), 3.89 (s, 2H), 3.69 (s, 3H), 3.65 (s, 3H), 3.34 (dd, J=17.6, 12.1 Hz, 1H), 2.93 (dd, J=17.6, 4.9 Hz, 1H), 2.84 (dd, J=16.5, 2.8 Hz, 1H), 2.47 (dd, J=16.5, 9.9 Hz, 1H), 2.21 (s, 3H). Analytical HPLC (orthogonal method): RT=13.3 min, HI: 99.0%. hGPR40 $EC_{50}$=3110 nM.

Example 50, Isomer 1 and Isomer 2

2-(1-(4-((2'-fluoro-5'-methoxy-3-methylbiphenyl-4-yl)methyl)phenyl)-4,4-dimethyl-3-(trifluoromethyl)-4,5-dihydro-1H-pyrazol-5-yl)acetic acid

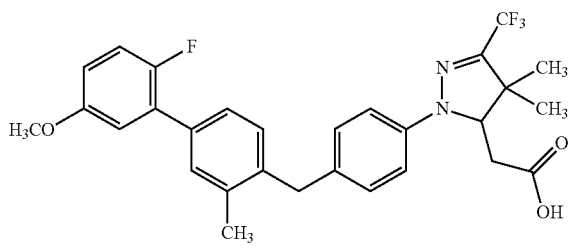 [SMILES: COc1ccc(F)c(-c2ccc(Cc3ccc(N4N=C(C(F)(F)F)C(C)(C)C4CC(=O)O)cc3)c(C)c2)c1]

Example 50, Isomer 1 and Isomer 2 were prepared as single enantiomers following the procedure of Example 46. Example 50, Isomer 1 (colorless oil, 0.6 mg). LC-MS Anal. Calc'd for $C_{29}H_{28}F_4N_2O_3$ 528.54. found [M+H] 529.2. $^1$H NMR (400 MHz, CDCl$_3$) δ 7.31-7.41 (3H, m), 7.10-7.20 (3H, m), 7.07 (2H, d, J=8.8 Hz), 6.94 (1H, dd, J=6.3, 3.3 Hz), 6.81 (1H, dt, J=9.0, 3.4 Hz), 4.50 (1H, dd, J=10.3, 1.5 Hz), 3.98 (2H, s), 3.83 (3H, s), 2.68-2.78 (1H, m), 2.55-2.66 (1H, m), 2.32 (3H, s), 1.40 (3H, s), 1.36 (3H, s). Analytical HPLC (Zorbax method, 0% Solvent B start): RT=9.1 min, HI: 95.0%. hGPR40 EC$_{50}$=220 nM. Example 50, Isomer 2 (colorless oil, 1 mg). LC-MS Anal. Calc'd for $C_{29}H_{28}F_4N_2O_3$ 528.54. found [M+H] 529.2. $^1$H NMR (400 MHz, CDCl$_3$) δ 7.31-7.41 (3H, m), 7.10-7.20 (3H, m), 7.07 (2H, d, J=8.8 Hz), 6.94 (1H, dd, J=6.3, 3.3 Hz), 6.81 (1H, dt, J=9.0, 3.4 Hz), 4.50 (1H, dd, J=10.3, 1.5 Hz), 3.98 (2H, s), 3.83 (3H, s), 2.68-2.78 (1H, m), 2.55-2.66 (1H, m), 2.32 (3H, s), 1.40 (3H, s), 1.36 (3H, s). Analytical HPLC (Zorbax method, 0% Solvent B start): RT=9.1 min, HI: 95.0%. hGPR40 EC$_{50}$=1340 nM.

Example 51, Isomer 1 and Isomer 2

2-(1-(4-((2'-fluoro-5'-methoxy-3-methylbiphenyl-4-yl)methyl)phenyl)-5-methyl-3-(trifluoromethyl)-4,5-dihydro-1H-pyrazol-5-yl)acetic acid

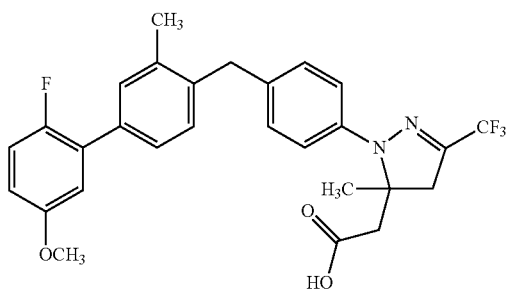 [SMILES: COc1ccc(F)c(-c2ccc(Cc3ccc(N4N=C(C(F)(F)F)CC4(C)CC(=O)O)cc3)c(C)c2)c1]

Example 51, Isomer 1 and Isomer 2 were prepared as single enantiomers following the procedure of Example 46. Example 51, Isomer 1 (white solid, 1.2 mg). LC-MS Anal. Calc'd for $C_{28}H_{26}F_4N_2O_3$ 514.52. found [M+H] 515.1. $^1$H NMR (400 MHz, CD$_3$OD) δ 7.35-7.28 (m, 2H), 7.24-7.16 (m, 3H), 7.14-7.03 (m, 3H), 6.96 (dd, J=6.4, 3.1 Hz, 1H), 6.86 (dt, J=8.8, 3.5 Hz, 1H), 4.05-3.96 (m, 3H), 3.81 (s, 3H), 3.44 (d, J=12.3 Hz, 1H), 2.84 (d, J=17.8 Hz, 1H), 2.36-2.18 (m, 4H), 1.33 (s, 3H). Analytical HPLC (orthogonal method, 12 min gradient, 6 minute hold): RT=16.9 min, HI: 99.0%. hGPR40 EC$_{50}$=1550 nM. Example 51, Isomer 2 (white solid, 1.4 mg). LC-MS Anal. Calc'd for $C_{28}H_{26}F_4N_2O_3$ 514.52. found [M+H] 515.1. $^1$H NMR (400 MHz, CD$_3$OD) δ 7.35-7.28 (m, 2H), 7.24-7.16 (m, 3H), 7.14-7.03 (m, 3H), 6.96 (dd, J=6.4, 3.1 Hz, 1H), 6.86 (dt, J=8.8, 3.5 Hz, 1H), 4.05-3.96 (m, 3H), 3.81 (s, 3H), 3.44 (d, J=12.3 Hz, 1H), 2.84 (d, J=17.8 Hz, 1H), 2.36-2.18 (m, 4H), 1.33 (s, 3H). Analytical HPLC (orthogonal method, 12 min gradient, 6 minute hold): RT=17.4 min, HI: 96.0%. hGPR40 EC$_{50}$=1490 nM.

Example 52, Isomer 1 and Isomer 2

2-(3-cyano-1-(4-((2'-fluoro-5'-methoxy-3-methylbiphenyl-4-yl)methyl)phenyl)-4-methyl-4,5-dihydro-1H-pyrazol-5-yl)acetic acid

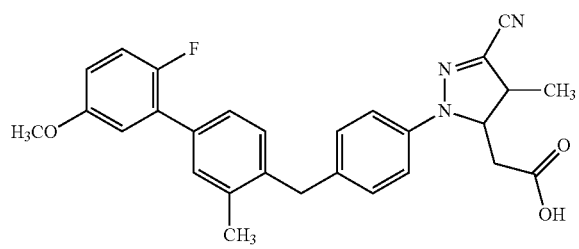 [SMILES: COc1ccc(F)c(-c2ccc(Cc3ccc(N4N=C(C#N)C(C)C4CC(=O)O)cc3)c(C)c2)c1]

Example 52, Isomer 1 and Isomer 2 were prepared as single enantiomers following the procedure of Example 46. Example 52, Isomer 1 (off-white solid, 4.6 mg). LC-MS Anal. Calc'd for $C_{28}H_{26}FN_3O_3$ 471.53. found [M+H] 472.0. $^1$H NMR (400 MHz, CDCl$_3$) δ 7.26 (d, J=7.9 Hz, 1H), 7.18 (s, 1H), 7.07 (dd, J=8.3, 2.6 Hz, 2H), 7.06 (S, 1H), 7.02-6.94 (m, 3H), 6.86 (dd, J=6.3, 3.1 Hz, 1H), 6.73 (dt, J=8.9, 3.5 Hz, 1H), 4.40 (dt, J=10.4, 3.1 Hz, 1H), 3.90 (s, 2H), 3.74 (s, 3H), 3.16-3.02 (m, 1H), 2.86 (dd, J=16.8, 2.7 Hz, 1H), 2.43 (dd, J=16.8, 10.5 Hz, 1H), 2.23 (s, 3H), 1.28 (d, J=7.1 Hz, 3H). Analytical HPLC (orthogonal method): RT=12.6 min, HI: 99.0%. hGPR40 EC$_{50}$=1050 nM. Example 52, Isomer 2 (off-white solid, 4.8 mg). LC-MS Anal. Calc'd for $C_{28}H_{26}FN_3O_3$ 471.53. found [M+H] 472.0. $^1$H NMR (400 MHz, CDCl$_3$) δ 7.26 (d, J=7.9 Hz, 1H), 7.18 (s, 1H), 7.07 (dd, J=8.3, 2.6 Hz, 2H), 7.06 (S, 1H), 7.02-6.94 (m, 3H), 6.86 (dd, J=6.3, 3.1 Hz, 1H), 6.73 (dt, J=8.9, 3.5 Hz, 1H), 4.40 (dt, J=10.4, 3.1 Hz, 1H), 3.90 (s, 2H), 3.74 (s, 3H), 3.16-3.02 (m, 1H), 2.86 (dd, J=16.8, 2.7 Hz, 1H), 2.43 (dd, J=16.8, 10.5 Hz, 1H), 2.23 (s, 3H), 1.28 (d, J=7.1 Hz, 3H). Analytical HPLC (orthogonal method): RT=12.6 min, HI: 96.0%. hGPR40 EC$_{50}$=300 nM.

Example 53, Isomer 1 and Isomer 2

2-(1-(4-((2'-fluoro-5'-methoxy-3-methyl-[1,1'-biphenyl]-4-yl)methyl)phenyl)-4-(hydroxymethyl)-3-(trifluoromethyl)-4,5-dihydro-1H-pyrazol-5-yl)acetic acid, trans-diastereomer

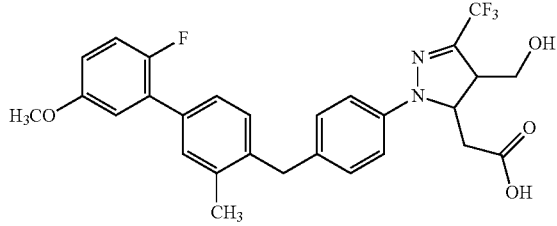 [SMILES: COc1ccc(F)c(-c2ccc(Cc3ccc(N4N=C(C(F)(F)F)C(CO)C4CC(=O)O)cc3)c(C)c2)c1]

53A. (E)-methyl 4-hydroxybut-2-enoate was prepared following the procedure described in *Tetrahedron*. 1995, 51, 11601.

53B. methyl 1-(4-((2'-fluoro-5'-methoxy-3-methyl-[1,1'-biphenyl]-4-yl)methyl)phenyl)-4-(hydroxymethyl)-3-(trifluoromethyl)-4,5-dihydro-1H-pyrazole-5-carboxylate: Example 53B (colorless oil, 497 mg) was prepared from example 53A and example 28G following the procedure of example 28 to obtain 53B: LC-MS Anal. Calc'd for $C_{28}H_{26}F_4N_2O_4$ 530.18. found [M+H]=531.

53C. methyl 4-(((tert-butyldimethylsilyl)oxy)methyl)-1-(4-((2'-fluoro-5'-methoxy-3-methyl-[1,1'-biphenyl]-4-yl)methyl)phenyl)-3-(trifluoromethyl)-4,5-dihydro-1H-pyrazole-5-carboxylate: To a solution of 53B (496 mg, 0.935 mmol) and imidazole (167 mg, 2.431 mmol) in dichloromethane (3.0 mL) at rt was added a solution of tert-butyldimethylsilyl chloride (189 mg, 1.215 mmol) in dichloromethane (1.5 mL) dropwise. The reaction mixture was stirred at rt for 15 h, the mixture was diluted with EtOAc (50 mL) and washed with sat'd NaHCO₃ (2×30 mL) and brine (20 mL). The organic layer was dried (Na₂SO₄) and evaporated. Chromatography (SiO₂ 230-400 mesh, 4/1Hex/EtOAc) of the crude provided example 53C (597 mg, 0.926 mmol, 99% yield) as a colorless oil: LC-MS Anal. Calc'd for $C_{34}H_{40}F_4N_2O_4Si$, 644.27. found [M+H]=645.

53D. (4-(((tert-butyldimethylsilyl)oxy)methyl)-1-(4-((2'-fluoro-5'-methoxy-3-methyl-[1,1'-biphenyl]-4-yl)methyl)phenyl)-3-(trifluoromethyl)-4,5-dihydro-1H-pyrazol-5-yl)methanol: To a solution of 53C (596 mg, 0.924 mmol) in EtOH (6.0 mL) and THF (1.2 mL) at RT was added sodium borohydride (71 mg, 1.858 mmol). The mixture was stirred at RT for 9.0 h. After cooling to 0° C., phosphate buffer (25 mL, 1M KH₂PO₄+H₃PO₄ added to pH 3) was added and the resulting aqueous mixture was stirred for 2.8 h. The mixture was extracted with CH₂Cl₂ (3×40 mL) and, the combined organic extracts were dried (Na₂SO₄) and concentrated. Chromatography (SiO₂ 230-400 mesh, 4/1 Hex/EtOAc) of the crude afforded 53D (482 mg, 0.782 mmol, 85% yield) as a colorless oil: LC-MS Anal. Calc'd for $C_{33}H_{40}F_4N_2O_3Si$, 616.27. found [M+H]=617.

53E. (4-(((tert-butyldimethylsilyl)oxy)methyl)-1-(4-((2'-fluoro-5'-methoxy-3-methyl-[1,1'-biphenyl]-4-yl)methyl)phenyl)-3-(trifluoromethyl)-4,5-dihydro-1H-pyrazol-5-yl)methyl methanesulfonate: To a solution of the compound 53D (480 mg, 0.778 mmol) and methanesulfonyl chloride (80 µl, 1.028 mmol) in dichloromethane (8.4 mL) at 0° C. was added triethylamine (190 µl, 1.356 mmol). The mixture was stirred for 40 min at 0° C. and for 3.5 h while warming to RT. Then, the mixture was diluted with EtOAc (80 mL) and washed with sat'd NaHCO₃ (2×40 mL) and brine (30 mL). The EtOAc solution was dried (Na₂SO₄) and evaporated. Chromatography (SiO₂ 230-400 mesh, 7/3 Hex/EtOAc) of the crude provided 53E (550 mg, 0.776 mmol, quantitative) as a colorless oil: LC-MS Anal. Calc'd for $C_{34}H_{42}F_4N_2O_5SSi$, 694.25. found [M+H]=695.

53F. 2-(4-(((tert-butyldimethylsilyl)oxy)methyl)-1-(4-((2'-fluoro-5'-methoxy-3-methyl-[1,1'-biphenyl]-4-yl)methyl)phenyl)-3-(trifluoromethyl)-4,5-dihydro-1H-pyrazol-5-yl)acetonitrile: To a solution of 53E (549 mg, 0.774 mmol) in DMSO (2.8 mL) was added potassium cyanide (107 mg, 1.594 mmol). The mixture was heated to 60° C. and stirred for 3.0 h. Then, the mixture was cooled to RT and diluted with EtOAc (100 mL). The EtOAc solution was washed with sat'd NaHCO₃ (2×50 mL), water (60 mL) and brine (40 mL), dried (Na₂SO₄) and concentrated. The crude was chromatographed (SiO₂ 230-400 mesh, 4/1 Hex/EtOAc) to give the nitrile 53F (401 mg, 0.641 mmol, 83% yield) as a colorless oil: LC-MS Anal. Calc'd for $C_{34}H_{39}F_4N_3O_2Si$, 625.27. found [M+H]=626.

53G. methyl 2-(1-(4-((2'-fluoro-5'-methoxy-3-methyl-[1,1'-biphenyl]-4-yl)methyl)phenyl)-4-(hydroxymethyl)-3-(trifluoromethyl)-4,5-dihydro-1H-pyrazol-5-yl)acetate: Example 53F (399 mg, 0.638 mmol) was dissolved in ~2.4M HCl/MeOH, CH₂Cl₂, MeOTMS [10 mL, prepared by addition of TMSCl (3.0 mL) to a 4/3 CH₂Cl₂/MeOH solution (7.0 mL) at 0° C. and then stirring at rt for 1 h]. The resulting solution was allowed to stand at RT for 24 h, then evaporated under reduced pressure and the residue was stripped from MeCN (10 mL). The resulting oily material was taken up in EtOAc (70 mL) and, washed with sat'd NaHCO₃ (2×40 mL) and brine (30 mL). The organic layer was dried (Na₂SO₄) and concentrated. The residue was dissolved in ~3M HCl/MeOH, MeOTMS solution [16 mL, prepared by addition of TMSCl (6.0 mL) to MeOH (10 mL) at 0° C. and then stirring at rt for 1 h]. The resulting solution was heated to 40° C. and allowed to stand at this temperature for 22 h. The solution was cooled to RT, diluted with MeCN (10 mL) and evaporated. The residue was taken up in EtOAc (60 mL) and, washed with 5% NaHCO₃ (2×30 mL) and brine (20 mL). The organic layer was dried (Na₂SO₄) and concentrated. The crude was chromatographed (SiO₂ 230-400 mesh, 7/3 to 3/2 Hex/EtOAc) to give 53G (156 mg, 0.29 mmol, 45% yield) as a colorless oil: LC-MS Anal. Calc'd for $C_{29}H_{28}F_4N_2O_4$ 544.20. found [M+H]=545.

Example 53, Isomer 1 and Isomer 2: To a stirred solution of 53G (29 mg, 0.053 mmol) in THF (1.2 mL) and water (0.12 mL) at rt was added 1.0M aqueous lithium hydroxide (0.12 mL, 0.120 mmol) dropwise. After stirring at rt for 3.5 h, the reaction mixture was partitioned between water (6 mL) and Hex (20 mL). The aqueous layer was acidified by addition of 1M HCl (0.12 mL+drops to pH 2.5) and then extracted with CH₂Cl₂ (3×30 mL). The combined organic extracts were dried (Na₂SO₄) and concentrated. Drying under vacuum afforded the racemic product (29.3 mg, quant) as a white solid. The enantiomers were separated by chiral Prep. SFC to provide Example 53, Isomer 1 (white solid, 12.5 mg, 0.023 mmol, 44% yield) Analytical HPLC (Zorbax method): RT=7.35 min, HI: 99.0%. LC-MS Anal. Calc'd for $C_{28}H_{26}F_4N_2O_4$ 530. found [M+H] 531. ¹H NMR (400 MHz, CD₃CN) δ 7.29 (s, 1H), 7.25 (d, J=7.7 Hz, 1H), 7.11 (d, J=7.7 Hz, 1H), 7.03 (m, 3H), 6.96 (d, J=8.3 Hz, 1H), 6.91 (dd, J=6.6, 3.3 Hz, 1H), 6.80 (dt, J=8.8, 3.3 Hz, 1H), 4.66 (m, 1H), 3.87 (s, 2H), 3.72 (s, 3H), 3.63 (m, 2H), 3.34 (broad s, 1H), 2.74 (d, J=15.9 Hz, 1H), 2.21 (m, 1H), 2.21 (s, 3H). hGPR40 EC₅₀=170 nM; and Example 53, Isomer 2 (white solid, 12.4 mg, 0.023 mmol, 44% yield). Analytical HPLC (Zorbax method): RT=7.39 min, HI: 100%. LC-MS Anal. Calc'd for $C_{28}H_{26}F_4N_2O_4$ 530. found [M+H] 531. $^1$H NMR (400 MHz, $CD_3CN$) δ 7.29 (s, 1H), 7.25 (d, J=7.7 Hz, 1H), 7.11 (d, J=7.7 Hz, 1H), 7.03 (m, 3H), 6.96 (d, J=8.3 Hz, 1H), 6.91 (dd, J=6.6, 3.3 Hz, 1H), 6.80 (dt, J=8.8, 3.3 Hz, 1H), 4.66 (m, 1H), 3.87 (s, 2H), 3.72 (s, 3H), 3.63 (m, 2H), 3.34 (broad s, 1H), 2.74 (d, J=15.9 Hz, 1H), 2.21 (m, 1H), 2.21 (s, 3H). hGPR40 $EC_{50}$=1100 nM.

Example 54, Isomer 1 and Isomer 2

2-(4-(cyanomethyl)-1-(4-((2'-fluoro-5'-methoxy-3-methyl-[1,1'-biphenyl]-4-yl)methyl)phenyl)-3-(trifluoromethyl)-4,5-dihydro-1H-pyrazol-5-yl)acetic acid, trans-diastereomer

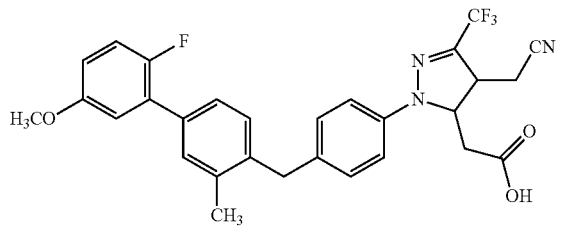 [SMILES: COc1ccc(F)c(-c2ccc(Cc3ccc(N4N=C(C(F)(F)F)C(CC#N)C4CC(=O)O)cc3)c(C)c2)c1]

54A. methyl 2-(1-(4-((2'-fluoro-5'-methoxy-3-methyl-[1,1'-biphenyl]-4-yl)methyl)phenyl)-4-(((methylsulfonyl)oxy)methyl)-3-(trifluoromethyl)-4,5-dihydro-1H-pyrazol-5-yl)acetate: To a solution of 53G (126 mg, 0.231 mmol) and methanesulfonyl chloride (0.023 mL, 0.301 mmol) in dichloromethane (2.5 mL) at 0° C. was added triethylamine (0.062 mL, 0.440 mmol). The mixture was stirred for 30 min at 0° C. and for 2.0 h while warming to RT. Then, the mixture was diluted with EtOAc (60 mL) and washed with 5% $NaHCO_3$ (2×20 mL) and brine (20 mL). The EtOAc solution was dried ($Na_2SO_4$) and evaporated. Chromatography ($SiO_2$ 230-400 mesh, 3/2 Hex/EtOAc) of the crude material provided 54A (149 mg, 0.22 mmol, 96% yield) as a colorless oil: LC-MS Anal. Calc'd for $C_{30}H_{30}F_4N_2O_6S$, 622. found [M+H]=623.

54B. methyl 2-((4S,5S)-4-(cyanomethyl)-1-(4-((2'-fluoro-5'-methoxy-3-methyl-[1,1'-biphenyl]-4-yl)methyl)phenyl)-3-(trifluoromethyl)-4,5-dihydro-1H-pyrazol-5-yl)acetate: To a solution of 54A (81 mg, 0.12 mmol) in DMSO (0.23 mL) was added a solution of sodium cyanide (8.0 mg, 0.16 mmol) and 15-crown 5-ether (0.029 mL, 0.14 mmol) in DMSO (0.20 mL). The reaction mixture was stirred at rt for 4.3 h and then diluted with 4/1 EtOAc/Hex (50 mL) and washed with 5% $NaHCO_3$ (25 mL), water (2×30 mL) and brine (20 mL). The organic phase was dried ($Na_2SO_4$) and concentrated under reduced pressure. The crude was chromatographed ($SiO_2$ 230-400 mesh, 4/1 to 7/3 Hex/EtOAc) to give 54B (11.3 mg, 0.020 mmol, 17% yield) as a colorless oil: LC-MS Anal. Calc'd for $C_{30}H_{27}F_4N_3O_3$ 553. found [M+H]=554.

Example 54. By following the procedure used for the preparation of Example 53, Example 54B was hydrolyzed and the resulting racemate resolved to afford Example 54, isomer 1 (white solid, 10 mg) Analytical HPLC (Zorbax method): RT=7.34 min, HI: 99%. LC-MS Anal. Calc'd for $C_{29}H_{25}F_4N_3O_3$ 539. found [M+H] 540. $^1$H NMR (400 MHz, $CD_2Cl_2$) δ 7.35 (s, 1H), 7.33 (d, J=8.3 Hz, 1H), 7.20-7.15 (m, 3H), 7.11-7.03 (m, 3H), 6.94 (dd, J=6.6, 3.3 Hz, 1H), 6.82 (dt, J=8.8, 3.3 Hz, 1H), 4.74 (m, 1H), 3.99 (s, 2H), 3.81 (s, 3H), 3.58 (m, 1H), 2.98 (dd, J=17.0, 3.3 Hz, 1H), 2.98, (dd, J=17.0, 3.3 Hz, 1H), 2.85 (dd, J=17.0, 4.4 Hz, 1H), 2.71 (dd, J=17.0, 7.2 Hz, 1H), 2.60 (dd, J=17.0, 10.4 Hz, 1H), 2.31 (s, 3H). hGPR40 $EC_{50}$=380 nM; and Example 54, Isomer 2 (white solid, 8 mg) Analytical HPLC (Zorbax method): RT=7.33 min, HI: 100%. LC-MS Anal. Calc'd for $C_{29}H_{25}F_4N_3O_3$ 539. found [M+H] 540. $^1$H NMR (400 MHz, $CD_2Cl_2$) δ 7.35 (s, 1H), 7.33 (d, J=8.3 Hz, 1H), 7.20-7.15 (m, 3H), 7.11-7.03 (m, 3H), 6.94 (dd, J=6.6, 3.3 Hz, 1H), 6.82 (dt, J=8.8, 3.3 Hz, 1H), 4.74 (m, 1H), 3.99 (s, 2H), 3.81 (s, 3H), 3.58 (m, 1H), 2.98 (dd, J=17.0, 3.3 Hz, 1H), 2.98, (dd, J=17.0, 3.3 Hz, 1H), 2.85 (dd, J=17.0, 4.4 Hz, 1H), 2.71 (dd, J=17.0, 7.2 Hz, 1H), 2.60 (dd, J=17.0, 10.4 Hz, 1H), 2.31 (s, 3H) (s, 1H). hGPR40 $EC_{50}$=1100 nM.

Example 55, Isomer 1 and Isomer 2

2-((1-(4-((2'-fluoro-5'-methoxy-3-methyl-[1,1'-biphenyl]-4-yl)methyl)phenyl)-1',4-dimethyl-4,5-dihydro-1H,1'H-[3,3'-bipyrazol]-5-yl)acetic acid, trans-diastereomer

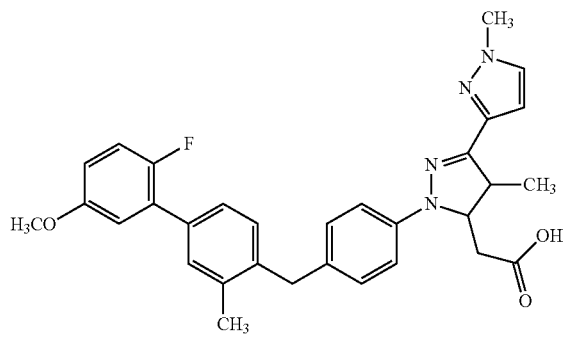 [SMILES: COc1ccc(F)c(-c2ccc(Cc3ccc(N4N=C(c5ccn(C)n5)C(C)C4CC(=O)O)cc3)c(C)c2)c1]

55A. 3-((2-(4-bromophenyl)hydrazono)methyl)-1-methyl-1H-pyrazole: To a solution of (4-bromophenyl)hydrazine hydrochloride (1150 mg, 5.04 mmol) and 1-methyl-1H-pyrazole-3-carbaldehyde (580 mg, 5.00 mmol) in DMF (5.1 mL) was added triethylamine (0.84 mL, 6.00 mmol). The mixture was stirred at rt under argon for 21 h, water (9 mL) was added and stirring was continued for 1 h. The solid that resulted was filtered, rinsed with water (5 mL) and dissolved in $CH_2Cl_2$ (120 mL). The $CH_2Cl_2$ solution was dried ($Na_2SO_4$) and concentrated to provide 55A (1400 mg, 5.02 mmol, 100% yield) as a yellowish solid: $^1$H NMR (400 MHz, $CDCl_3$) d 7.76 (s, 1H), 7.63 (s, 1H), 7.34 (m, 3H), 6.97 (d, J=8.8 Hz, 2H), 3.91 (s, 3H).

55B. N-(4-bromophenyl)-1-methyl-1H-pyrazole-3-carbohydrazonoyl bromide: N-Bromosuccinimide (0.99 g, 5.51 mmol) was added to a stirred solution of 55A (1.39 g, 4.98 mmol) in THF (8.2 ml) at 0° C. under argon. The mixture was stirred at 0° C. for 2.0 h and then evaporated under reduced pressure. The residue was chromatographed ($SiO_2$ 230-400 mesh, 7/3 to 3/2 Hex//EtOAc) to afford 55B (793.2 mg, 2.22 mmol, 45% yield) as a brownish solid: $^1$H NMR (400 MHz, $CDCl_3$) d 8.00 (s, 1H), 7.38 (m, 3H), 6.68 (d, J=8.2 Hz, 2H), 3.96 (s, 3H).

55C. methyl 1-(4-bromophenyl)-1',4-dimethyl-4,5-dihydro-1H,1'H-[3,3'-bipyrazole]-5-carboxylate: A flask containing a solution of 55B (790 mg, 2.207 mmol) in dioxane (10 mL) was evacuated and backfilled with argon. Methyl crotonate (0.39 mL, 3.61 mmol) and silver carbonate (1230 mg, 4.42 mmol) were added to the solution and the resulting suspension was degassed by ultrasound irradiation under Ar for 5 min. The mixture was heated to 47° C. and stirred at this temperature for 8.0 h. The rxn mixture was cooled to rt and filtered through Celite. The filter cake was rinsed with EtOAc (100 mL) and, the combined filtrate and rinse were concentrated. The crude was chromatographed (SiO$_2$ 230-400 mesh, 3/2 Hex/EtOAc) to afford 55C (565 mg, 1.393 mmol, 63.1% yield) as a yellow solid: LC-MS Anal. Calc'd for $C_{16}H_{17}BrN_4O_2$ 376. found [M+H]=377, 379.

55D. 1-(4-bromophenyl)-1',4-dimethyl-4,5-dihydro-1H,1'H-[3,3'-bipyrazol]-5-yl)methanol: To a solution of 55 C (556 mg, 1.371 mmol) in EtOH (8.9 mL) and THF (1.8 mL) at rt was added sodium borohydride (106 mg, 2.77 mmol). After stirring at rt for 12 h, additional sodium borohydride (49 mg, 1.28 mmol) was added and stirring at rt was continued for an additional 15.5 h, the mixture was cooled to 0° C., 1M H$_3$PO$_4$ (20 mL) was added and the resulting aqueous mixture was stirred for 20 min while warming to rt. The mixture was partitioned between CH$_2$Cl$_2$ (50 mL) and water (15 mL) and the aqueous layer was extracted with CH$_2$Cl$_2$ (2×30 mL). The combined organic layers were dried (Na$_2$SO$_4$) and concentrated. Chromatography (SiO$_2$ 230-400 mesh, 4/1 to 7/3 CH$_2$Cl$_2$/EtOAc) of the crude afforded 55D (353 mg, 1.011 mmol, 73.7% yield) as a colorless foam: HPLC (RT 6.80, Area % 100); LC-MS Anal. Calc'd for $C_{15}H_{17}BrN_4O$, 348. found [M+H]=349, 351.

55E. 1-((4-bromophenyl)-1',4-dimethyl-4,5-dihydro-1H,1'H-[3,3'-bipyrazol]-5-yl)methyl methanesulfonate: To a solution of 55D (352 mg, 1.008 mmol) and methanesulfonyl chloride (110 µl, 1.414 mmol) in dichloromethane (11 mL) at 0° C. was added triethylamine (280 µl, 1.999 mmol). The mixture was stirred for 30 min at 0° C. and for 4.0 h while warming to RT. Then, the mixture was diluted with EtOAc (70 mL) and washed with sat'd NaHCO$_3$ (2×40 mL) and brine (30 mL). The EtOAc solution was dried (Na$_2$SO$_4$) and evaporated. Drying under vacuum gave 55E (431 mg, 1.009 mmol, 100% yield) as a colorless oil: LC-MS Anal. Calc'd for $C_{16}H_{19}BrN_4O_3S$, 426. found [M+H]=427, 429.

55F. 2-(1-(4-bromophenyl)-1',4-dimethyl-4,5-dihydro-1H,1'H-[3,3'-bipyrazol]-5-yl)acetonitrile: To a solution of the compound 55E (431 mg, 1.009 mmol) in DMSO (4.5 mL) was added potassium cyanide (83 mg, 1.241 mmol). The mixture was heated to 40° C. and stirred for 12.0 h. Then, the mixture was cooled to rt and diluted with 4/1 EtOAc/Hex (120 mL) and, washed with sat'd NaHCO$_3$ (60 mL), water (2×60 mL) and brine (30 mL). The organic layer was dried (Na$_2$SO$_4$) and concentrated. The crude was chromatographed (SiO$_2$ 230-400 mesh, 1/1 Hex/EtOAc) to give 55F (339 mg, 0.946 mmol, 94% yield) as a colorless foam: LC-MS Anal. Calc'd for $C_{16}H_{16}BrN_5$ 357. found [M+H]=358, 360.

55G. 2-((1',4-dimethyl-1-(4-(4,4,5,5-tetramethyl-1,3,2-dioxaborolan-2-yl)phenyl)-4,5-dihydro-1H,1'H-[3,3'-bipyrazol]-5-yl)acetonitrile: A flask containing a suspension of 55F (94 mg, 0.262 mmol), bis(pinacolato)diboron (112 mg, 0.437 mmol) and potassium acetate (83 mg, 0.845 mmol)in DMF (1.0 mL) was evacuated and backfilled with Ar. 1,1'-bis(diphenylphosphino)ferrocenepalladium(II) dichloride (10 mg, 0.013 mmol) was added to the suspension and the mixture was degassed by ultrasound irradiation under argon for 5 min. The mixture was heated to 78° C. and stirred at this temperature for 13.2 h. Then, the rxn mixture was cooled to rt and filtered through Celite. The filter cake was rinsed with EtOAc (100 mL) and, the combined filtrate and rinse were concentrated. Chromatography (SiO$_2$ 230-400 mesh, 95/5 CH$_2$Cl$_2$/Ether) of the crude afforded 55G (54.7 mg, 0.13 mmol, 49% yield) as a colorless oil: LC-MS Anal. Calc'd for $C_{22}H_{28}BN_5O_2$ 405. found [M+H]=406.

55H. 2-((1',4-dimethyl-1-(4-(4,4,5,5-tetramethyl-1,3,2-dioxaborolan-2-yl)phenyl)-4,5-dihydro-1H,1'H-[3,3'-bipyrazol]-5-yl)acetonitrile: A flask containing a mixture of example 17H (50 mg, 0.162 mmol), 55G (54 mg, 0.133 mmol), 1.0M potassium carbonate (0.7 mL, 0.700 mmol) and toluene (1.1 mL) was evacuated and backfilled with argon. Tetrakis(triphenylphosphine)palladium(0) (8.0 mg, 6.85 µmol) was added and the mixture was degassed by ultrasound irradiation under argon for 5 min. The mixture was heated to 100° C. and stirred at this temperature for 10 h. After this time, the reaction mixture was cooled to rt and, partitioned between water (8.0 mL) and EtOAc (40 mL). The aqueous layer was extracted with EtOAc (20 mL) and the organic layers were combined, dried (Na$_2$SO$_4$) and concentrated. Chromatography (SiO$_2$ 230-400 mesh, 1/1 Hex/EtOAc) of the crude afforded 55H (66 mg, 0.13 mmol, 95% yield) as a yellowish oil: LC-MS Anal. Calc'd for $C_{31}H_{30}FN_5O$, 507. found [M+H]=508.

Example 55, Isomer 1 and Isomer 2: Prepared as single enantiomers following the method of Example 28. Example 55, Isomer 1 (yellowish solid, 23.5 mg) Analytical HPLC (Zorbax method): RT=7.71 min, HI: 99%. LC-MS Anal. Calc'd for $C_{31}H_{31}FN_4O_3$ 526. found [M+H] 527. $^1$H NMR (400 MHz, CD$_2$Cl$_2$) δ 7.39 (d, J=2.2 Hz, 1H), 7.35 (s, 1H), 7.32 (d, J=8.3 Hz, 1H), 7.19 (d, J=7.7 Hz, 1H), 7.13-7.03 (m, 5H), 6.95 (dd, J=6.6, 3.3 Hz, 1H), 6.82 (dt, J=8.8, 3.3 Hz, 1H), 6.73 (d, J=2.2 Hz, 1H), 4.41 (d, J=11.0 Hz, 1H), 3.96 (s, 2H), 3.94 (s, 3H), 3.81 (s, 3H), 3.54 (m, 1H), 2.84 (m, 1H), 2.33 (s, 3H), 2.32 (m, 1H), 1.34 (d, J=7.2 Hz, 3H). hGPR40 EC$_{50}$=5630 nM; Example 55, Isomer 2 (yellowish solid, 23.3 mg). Analytical HPLC (Zorbax method): RT=7.71 min, HI: 96%. LC-MS Anal. Calc'd for $C_{31}H_{31}FN_4O_3$ 526. found [M+H] 527. $^1$H NMR (400 MHz, CD$_2$Cl$_2$) δ 7.39 (d, J=2.2 Hz, 1H), 7.35 (s, 1H), 7.32 (d, J=8.3 Hz, 1H), 7.19 (d, J=7.7 Hz, 1H), 7.13-7.03 (m, 5H), 6.95 (dd, J=6.6, 3.3 Hz, 1H), 6.82 (dt, J=8.8, 3.3 Hz, 1H), 6.73 (d, J=2.2 Hz, 1H), 4.41 (d, J=11.0 Hz, 1H), 3.96 (s, 2H), 3.94 (s, 3H), 3.81 (s, 3H), 3.54 (m, 1H), 2.84 (m, 1H), 2.33 (s, 3H), 2.32 (m, 1H), 1.34 (d, J=7.2 Hz, 3H). hGPR40 EC$_{50}$=230 nM.

Example 56

2-((4S,5S)-1-(4-((2'-fluoro-5'-hydroxy-3-methyl-[1,1'-biphenyl]-4-yl)methyl)phenyl)-4-methyl-3-(trifluoromethyl)-4,5-dihydro-1H-pyrazol-5-yl)acetic acid

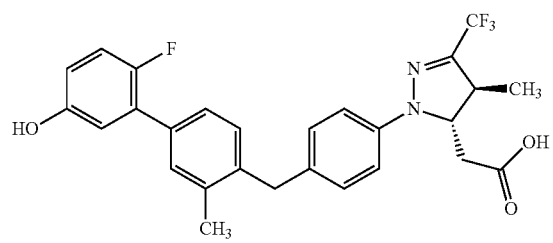 [SMILES: Cc1cc(-c2cc(O)ccc2F)ccc1Cc1ccc(N2N=C(C(F)(F)F)[C@@H](C)[C@@H]2CC(=O)O)cc1]

56A. ethyl 2-((4S,5S)-1-(4-((2'-fluoro-5'-methoxy-3-methyl-[1,1'-biphenyl]-4-yl)methyl)phenyl)-4-methyl-3-(trifluoromethyl)-4,5-dihydro-1H-pyrazol-5-yl)acetate: Example 28N (690 mg, 1.341 mmol) was dissolved in ~1.1M HCl/EtOH, EtOAc solution [52 mL, prepared by addition of AcCl (4.0 mL) to EtOH (48 mL) at 0° C. and then stirring at rt for 1.0 h]. The resulting solution was allowed to stand at rt for 45 h. After this time, the solution was diluted with MeCN (15 mL) and evaporated. The residue was taken up in EtOAc (60 mL) and, washed with 5% NaHCO3 (2×30 mL) and brine (30 mL). The organic layer was dried (Na2SO4) and concentrated. The crude was chromatographed (SiO2 230-400 mesh, 4/1 Hex/EtOAc) to give 56A (725 mg, 1.34 mmol, 100% yield) as a colorless oil: LC-MS Anal. Calc'd for $C_{30}H_{30}F_4N_2O_3$ 542. found [M+H]=543.

56B. ethyl 2-((4S,5S)-1-(4-((2'-fluoro-5'-hydroxy-3-methyl-[1,1'-biphenyl]-4-yl)methyl)phenyl)-4-methyl-3-(trifluoromethyl)-4,5-dihydro-1H-pyrazol-5-yl)acetate: To a stirred solution of 55A (725 mg, 1.336 mmol) in dichloromethane (13.0 mL) at −78° C. was added 1M boron tribromide/$CH_2Cl_2$ (2.9 mL, 2.90 mmol) dropwise. After the addition was complete, the reaction mixture was stirred at −78° C. for 15 min and then allowed to warm to 0° C. over a 4.0 h period. The reaction was quenched at 0° C. with dry EtOH (10 mL) and then allowed to warm up to rt. The mixture was evaporated and, the residue was partitioned between 0.1M HCl (50 mL) and $CH_2Cl_2$ (100 mL). The aqueous layer was extracted with $CH_2Cl_2$ (2×50 mL) and, the combined organic layers were dried ($Na_2SO_4$) and concentrated. The crude was chromatographed ($SiO_2$ 230-400 mesh, 95/5 $CHCl_3$/Ether) to give 56B (578 mg, 1.09 mmol, 82% yield) as a white solid: LC-MS Anal. Calc'd for $C_{29}H_{28}F_4N_2O_3$ 528. found [M+H]=529.

Example 56: To a stirred solution of 56B (44.6 mg, 0.084 mmol) in THF (2.3 mL) and water (0.23 mL) at rt was added 10M aqueous lithium hydroxide (0.23 mL, 0.230 mmol). After stirring at rt for 7.0 h, the rxn mixture was partitioned between water (30 mL) and Hex (15 mL). The aqueous layer was acidified to pH 2 by dropwise addition of 1M HCl, and then extracted with $CH_2Cl_2$ (3×30 mL). The combined organic extracts were dried ($Na_2SO_4$) and concentrated. The residue was dried under vacuum to afford Example 56 (42 mg, 0.084 mmol, 99% yield) as a white solid. Analytical HPLC (Zorbax method): RT=7.28 min, HI: 99%. LC-MS Anal. Calc'd for $C_{27}H_{24}F_4N_2O_3$ 500. found [M+H] 501. $^1$H NMR (400 MHz, $CD_2Cl_2$) δ 7.33 (s, 1H), 7.30 (d, J=7.7 Hz, 1H), 7.19-7.11 (m, 3H), 7.07-6.98 (m, 3H), 6.89 (dd, J=6.6, 3.3 Hz, 1H), 6.75 (dt, J=8.8, 3.3 Hz, 1H), 4.45 (m, 1H), 3.97 (s, 2H), 3.25 (m, 1H), 2.89 (dd, J=16.5, 2.8 Hz, 1H), 2.49 (dd, J=16.5, 10.4 Hz, 1H), 2.31 (s, 3H), 1.33 (d, J=6.6 Hz, 3H). hGPR40 $EC_{50}$=150 nM.

Example 57

(4S,5S)-5-(carboxymethyl)-1-(4-((2'-fluoro-5'-methoxy-3-methyl-[1,1'-biphenyl]-4-yl)methyl)phenyl)-4-methyl-4,5-dihydro-1H-pyrazole-3-carboxylic acid 57A. (4S,5S)-methyl 1-(4-((2'-fluoro-5'-hydroxy-3-methyl-[1,1'-biphenyl]-4-yl)methyl)phenyl)-5-(2-methoxy-2-oxoethyl)-4-methyl-4,5-dihydro-1H-pyrazole-3-carboxylate: To a stirred solution of example 28N (50 mg, 0.097 mmol) in dichloromethane (0.5 mL) at 0° C. was added boron trifluoride-methyl sulfide complex (100 μl, 0.950 mmol). The reaction mixture was allowed to warm to rt and stirred for 2.5 h. The reaction was cooled to 0° C. and quenched with MeOH (5.5 mL) followed by AcCl (0.1 mL). The mixture was allowed to warm to rt, stirred for 13 h and then evaporated The residue was taken up in $CH_2Cl_2$ (40 mL) and washed with water (2×30 mL). The organic layer was dried ($Na_2SO_4$) and concentrated. The crude material was chromatographed ($SiO_2$ 230-400 mesh, 7/3 to 3/2 Hex/EtOAc) to give 57A (43 mg, 0.084 mmol, 87% yield) as a yellowish oil. LC-MS Anal. Calc'd for $C_{29}H_{29}FN_2O_5$ 504. found [M+H]=505.

57B. (4S,5S)-methyl 1-(4-((2'-fluoro-5'-methoxy-3-methyl-[1,1'-biphenyl]-4-yl)methyl)phenyl)-5-(2-methoxy-2-oxoethyl)-4-methyl-4,5-dihydro-1H-pyrazole-3-carboxylate: To a stirred suspension of 57A (42 mg, 0.083 mmol) and cesium carbonate (58 mg, 0.178 mmol) in MeCN (0.5 mL) at rt was added iodomethane (6.0 μl, 0.096 mmol). The mixture was stirred at rt for 14 h and then, diluted with $CH_2Cl_2$ (40 mL) and washed with water (15 mL). The aqueous phase was extracted with $CH_2Cl_2$ (2×20 mL) and the combined organic layers were dried ($Na_2SO_4$) and evaporated. Chromatography ($SiO_2$ 230-400 mesh, 4/1 Hex/EtOAc) of the crude afforded 57B (41.5 mg, 0.079 mmol, 95% yield) as a yellowish oil: LC-MS Anal. Calc'd for $C_{30}H_{31}FN_2O_5$ 518. found [M+H]=519.

Example 57: To a stirred solution of 57B (41 mg, 0.078 mmol) in THF (1.5 mL) and water (0.15 mL) at rt was added 1.0M aqueous lithium hydroxide (0.35 mL, 0.350 mmol) dropwise. After stirring at rt for 3.4 h, the reaction mixture was partitioned between water (30 mL) and Hex (20 mL). The aqueous layer was acidified by addition of 1M HCl (0.25 mL+drops to pH 2) and then extracted with $CH_2Cl_2$ (3×30 mL). The combined organic extracts were dried (Na2SO4) and concentrated. Drying under vacuum afforded Example 57 (38 mg, 0.077 mmol, 98% yield) as a yellow solid: Analytical HPLC (Zorbax method): RT=6.70 min, HI: 99%. LC-MS Anal. Calc'd for $C_{28}H_{27}FN_2O_5$ 490. found [M+H]=491. $^1$H NMR (400 MHz, $CD_2Cl_2$) δ 7.28 (s, 1H), 7.25 (d, J=7.7 Hz, 1H), 7.13-7.05 (m, 5H), 6.99 (dd, J=9.9, 9.3 Hz, 1H), 6.87 (dd, J=6.6, 3.3 Hz, 1H), 6.74 (dt, J=8.8, 3.3 Hz, 1H), 4.48 (dt, J=10.4, 3.3 Hz, 1H), 3.91 (s, 2H), 3.73 (s, 3H 3.23 (m, 1H), 2.83 (dd, J=16.5, 2.8 Hz, 1H), 2.43 (dd, J=16.5, 10.4 Hz, 1H), 2.24 (s, 3H), 1.25 (d, J=6.6 Hz, 3H). hGPR40 $EC_{50}$=6620 nM.

Example 58

2-((4S,5S)-4-methyl-1-(4-((4-methyl-2-phenylpyrimidin-5-yl)methyl)phenyl)-3-(trifluoromethyl)-4,5-dihydro-1H-pyrazol-5-yl)acetic acid

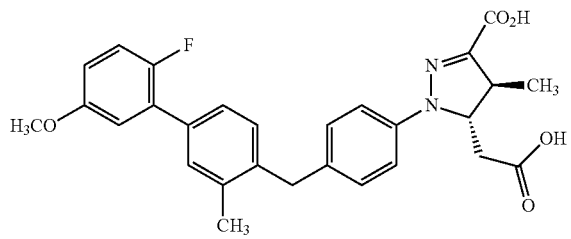 [SMILES: COc1ccc(F)c(-c2ccc(Cc3ccc(N4N=C(C(=O)O)[C@@H](C)[C@@H]4CC(=O)O)cc3)c(C)c2)c1]

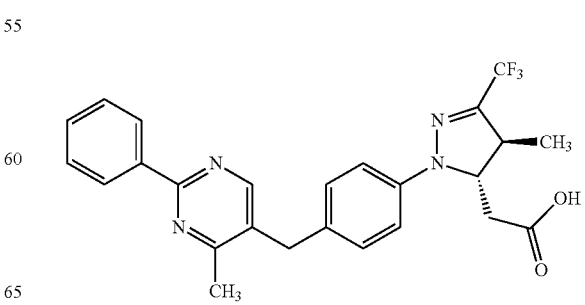

58A. N'-(4-bromophenyl)-2,2,2-trifluoroacetohydrazonoyl chloride: To a stirred solution of example 17A (21.35 g, 85%, 64.1 mmol) in EtOAc (151 mL), at 0° C. and under Ar, was added benzenesulfonyl chloride (10.0 ml, 77 mmol) followed by N,N-diisopropylethylamine (13.6 ml, 78 mmol) dropwise. The mixture was stirred for 2.5 h while slowly warming to 9° C. and then for an additional 6.5 h at rt. The reaction mixture was partitioned between EtOAc (200 mL) and water (200 mL). The organic layer was washed with water (2×150 mL) and sat'd NaCl (100 mL), dried ($Na_2SO_4$) and evaporated. The crude was chromatographed ($SiO_2$ 230-400 mesh, short column, 95/5 to 9/1 Hex/EtOAc) to give 58A (18.9 g, 48.3 mmol, 75% yield) as a brown liquid: LC-MS Anal. Calc'd for $C_8H_5BrClF_3N_2$ 300. found [M−H]=299, 301.

58B. 2-((4S,5S)-1-(4-bromophenyl)-4-methyl-3-(trifluoromethyl)-4,5-dihydro-1H-pyrazol-5-yl)acetonitrile: Example 58B (white solid, 4.99 g) was synthesized from 58A following the sequence used to convert example 281 to 28L: LC-MS Anal. Calc'd for $C_{13}H_{11}BrF_3N_3$ 345. found [M+H]=346, 348.

58C. 2-((4S,5S)-4-methyl-1-(4-(4,4,5,5-tetramethyl-1,3,2-dioxaborolan-2-yl)phenyl)-3-(trifluoromethyl)-4,5-dihydro-1H-pyrazol-5-yl)acetonitrile: A flask containing a suspension of 58B (258 mg, 0.678 mmol), bis(pinacolato) diboron (226 mg, 0.882 mmol) and potassium acetate (105 mg, 1.069 mmol) in toluene (10 mL) was evacuated and backfilled with Ar. Tetrakis(triphenylphosphine)palladium (0) (40 mg, 0.034 mmol) was added to the suspension and the mixture was degassed by ultrasound irradiation under Ar for 5 min. The mixture was heated to 85° C. and stirred at this temperature for 14.0 h. After this time, the reaction mixture was cooled to rt and filtered through Celite. The filter cake was rinsed with EtOAc (80 mL) and, the combined filtrate and rinse were concentrated. Chromatography ($SiO_2$ 230-400 mesh, 4/1 Hex/EtOAc) of the crude afforded 58C (115 mg, 0.26 mmol, 39% yield) as a yellowish solid: LC-MS Anal. Calc'd for $C_{19}H_{23}BF_3N_3O_2$ 393. found [M+H]=394.

58D. 5-(bromomethyl)-4-methyl-2-phenylpyrimidine: To a stirred solution of (4-Methyl-2-phenyl-5-pyrimidinyl) methanol (89.6 mg, 0.447 mmol) and carbon tetrabromide (196 mg, 0.585 mmol) in dichloromethane (2.3 mL) at rt was added triphenylphosphine (152 mg, 0.573 mmol). The mixture was stirred at rt for 22.0 h and then evaporated. The residue was chromatographed ($SiO_2$ 230-400 mesh, 3/2 $CH_2Cl_2$/Hex) to afford 58D (96 mg, 0.36 mmol, 81% yield) as a white solid: LC-MS Anal. Calc'd for $C_{12}H_{11}BrN_2$ 262. found [M+H]=263, 265.

58E. 2-((4S,5S)-4-methyl-1-(4-((4-methyl-2-phenylpyrimidin-5-yl)methyl)phenyl)-3-(trifluoromethyl)-4,5-dihydro-1H-pyrazol-5-yl)acetonitrile: A flask containing a mixture of 58D (37.1 mg, 0.140 mmol), 58C (51 mg, 0.117 mmol), 1.0M potassium carbonate (0.61 mL, 0.610 mmol) and toluene (1.0 mL) was evacuated and backfilled with Ar. Tetrakis(triphenylphosphine)palladium(O) (8.0 mg, 6.85 µmol) was added and the mixture was degassed by ultrasound irradiation under Ar for 5 min. The mixture was heated to 96° C. and stirred at this temperature for 10.0 h. After this time, the reaction mixture was cooled to rt and, partitioned between water (15 mL) and EtOAc (40 mL). The aqueous layer was extracted with EtOAc (20 mL) and the organic layers were combined, dried ($Na_2SO_4$) and concentrated. Chromatography ($SiO_2$ 230-400 mesh, 7/3 Hex/EtOAc) of the crude afforded 58E (43.0 mg, 0.096 mmol, 82% yield) as a yellowish oil: LC-MS Anal. Calc'd for $C_{25}H_{22}F_3N_5$ 449. found [M−H]=450.

58F. methyl 2-((4S,5S)-4-methyl-1-(4-((4-methyl-2-phenylpyrimidin-5-yl)methyl)phenyl)-3-(trifluoromethyl)-4,5-dihydro-1H-pyrazol-5-yl)acetate: Example 58E (43 mg, 0.096 mmol) was dissolved in ~3M HCl/MeOH, $CH_2Cl_2$, MeOAc solution [6.3 mL, prepared by addition of AcCl (1.3 mL) to a 3/2 $CH_2Cl_2$/MeOH solution (5.0 mL) at 0° C. and then stirring at rt for 20 min]. The resulting solution was allowed to stand at rt for 19 h. The solution was evaporated and the remaining oily material was stripped from MeOH (2×4 mL). The residue was dissolved in ~3M HCl/MeOH, MeOAc solution [6.3 mL, prepared by addition of AcCl (1.3 mL) to MeOH (5 mL) at 0° C. and then stirring at rt for 30 min] The resulting solution was heated to 38° C. and allowed to stand at this temperature for 23 h. The solution was cooled to rt, diluted with MeCN (8 mL) and evaporated. The residue was taken up in EtOAc (50 mL) and, washed with 5% $NaHCO_3$ (2×30 mL) and sat'd NaCl (20 mL). The organic layer was dried ($Na_2SO_4$) and concentrated. The crude was chromatographed ($SiO_2$ 230-400 mesh, 4/1 Hex/EtOAc) to give 58F (42 mg, 0.087 mmol, 91% yield) as a colorless oil: LC-MS Anal. Calc'd for $C_{26}H_{25}F_3N_4O_2$ 482. found [M+H]=483.

Example 58: To a stirred solution of 58F (42 mg, 0.087 mmol) in THF (1.9 mL) and water (0.19 mL) at RT was added 1.0M aqueous lithium hydroxide (0.19 mL, 0.190 mmol). After stirring at RT for 4.0 h, most of the THF was evaporated and the remaining mixture was partitioned between water (40 mL) and Hex (20 mL). The aqueous layer was acidified to pH 2 by dropwise addition of 1M HCl, and then extracted with $CH_2Cl_2$ (3×30 mL). The combined organic extracts were dried ($Na_2SO_4$) and concentrated. The residue was dried under vacuum to afford Example 58 (41 mg, 0.087 mmol, quantitative) as a white solid. Analytical HPLC (Zorbax method): RT=7.03 min, HI: 99%. LC-MS Anal. Calc'd for $C_{25}H_{23}F_3N_4O_2$ 468. found [M+H]=469. $^1$H NMR (400 MHz, $CD_2Cl_2$) δ 8.49 (s, 1H), 8.36 (m, 2H), 7.46 (m, 3H), 7.11 (d, J=8.8 Hz, 2H), 7.06 (d, J=8.8 Hz, 2H), 4.45 (m, 1H), 3.95 (s, 2H), 3.24 (m, 1H), 2.86 (dd, J=16.5, 3.3 Hz, 1H), 2.50 (s, 3H) 2.47 (dd, J=16.5, 10.4 Hz, 1H), 1.31 (d, J=7.2 Hz, 3H). hGPR40 $EC_{50}$=4290 nM.

Example 59, Isomer 1 and Isomer 2

2-(1-(4-((2'-fluoro-5'-methoxy-3-methyl-[1,1'-biphenyl]-4-yl)methyl)phenyl)-4-methyl-3-phenyl-4,5-dihydro-1H-pyrazol-5-yl)acetic acid

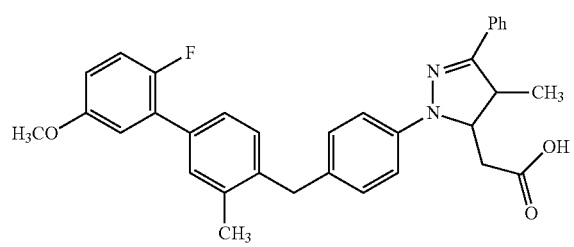 [SMILES: COc1ccc(F)c(-c2ccc(Cc3ccc(N4N=C(c5ccccc5)C(C)C4CC(=O)O)cc3)c(C)c2)c1]

Example 59 was isolated as individual enantiomers according to the method of Example 55: Example 59, Isomer 1 (yellow solid, 5 mg). LC-MS Anal. Calc'd for $C_{33}H_{31}FN_2O_3$ 522. found [M+H] 523. $^1$H NMR (500 MHz, $CDCl_3$) δ 7.77 (d, J=7.2 Hz, 2H), 7.40 (t, J=8.0 Hz, 2H), 7.37-7.31 (m, 3H), 7.19 (d, J=8.0 Hz, 1H), 7.13 (s, 4H), 7.06 (t, J=9.1 Hz, 1H), 6.95 (dd, J=6.2, 3.2 Hz, 1H), 6.82 (dt, J=8.8, 3.4 Hz, 1H), 4.43 (dt, J=10.4, 2.4 Hz, 1H), 3.98 (s, 2H), 3.83 (s, 3H), 3.44 (qd, J=7.1, 1.7 Hz, 1H), 2.91 (dd, J=16.2, 2.8 Hz, 1H), 2.39 (dd, J=16.1, 10.9 Hz, 1H), 2.34 (s, 3H), 1.34 (d, J=7.2 Hz, 3H). Analytical HPLC (orthogonal method): RT=11.1 min, HI: 98%. hGPR40 $EC_{50}$=6470 nM. Example 59, Isomer 2 (yellow solid, 8 mg). LC-MS Anal. Calc'd for $C_{33}H_{31}FN_2O_3$ 522. found [M+H] 523. $^1$H NMR (500 MHz, $CDCl_3$) δ 7.78 (d, J=7.2 Hz, 2H), 7.44-7.38 (m, 2H), 7.38-7.31 (m, 3H), 7.19 (d, J=7.7 Hz, 1H), 7.13 (s, 4H), 7.06 (dd, J=9.9, 9.1 Hz, 1H), 6.96 (dd, J=6.2, 3.2 Hz, 1H), 6.82 (dt, J=8.9, 3.5 Hz, 1H), 4.44 (dt, J=10.4, 2.4 Hz, 1H), 3.98 (s, 2H), 3.83 (s, 3H), 3.44 (qd, J=7.2, 1.7 Hz, 1H), 2.92 (dd, J=16.2, 2.8 Hz, 1H), 2.40 (dd, J=16.2, 10.7 Hz, 1H), 2.35 (s, 3H), 1.34 (d, J=7.2 Hz, 3H). Analytical HPLC (orthogonal method): RT=11.1 min, HI: 96%. hGPR40 $EC_{50}$=6 nM.

Example 60, Isomer 1 and Isomer 2

22-(1-(4-((3-chloro-2'-fluoro-5'-methoxy-[1,1'-biphenyl]-4-yl)methyl)phenyl)-4-methyl-3-(trifluoromethyl)-4,5-dihydro-1H-pyrazol-5-yl)acetic acid

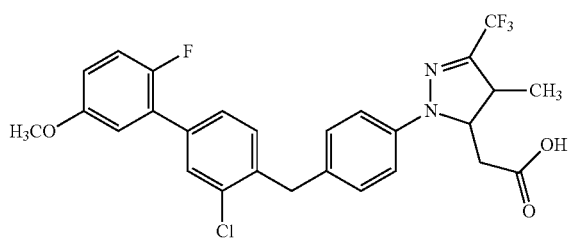 [SMILES: COc1ccc(F)c(-c2ccc(Cc3ccc(N4N=C(C(F)(F)F)C(C)C4CC(=O)O)cc3)c(Cl)c2)c1]

Example 60 was isolated as individual enantiomers according to the method of Example 17: Example 60, Isomer 1 (white solid, 8 mg). LC-MS Anal. Calc'd for $C_{27}H_{23}F_4N_2O_3$ 534. found [M+H] 535. $^1$H NMR (500 MHz, $CDCl_3$) δ 7.58 (s, 1H), 7.37 (d, J=8.0 Hz, 1H), 7.23-7.16 (m, 3H), 7.10-7.02 (m, 3H), 6.91 (dd, J=6.3, 3.0 Hz, 1H), 6.84 (dt, J=9.0, 3.5 Hz, 1H), 4.43 (d, J=10.2 Hz, 1H), 4.09 (s, 2H), 3.82 (s, 3H), 3.22 (d, J=5.0 Hz, 1H), 2.92 (dd, J=16.6, 2.3 Hz, 1H), 2.47 (dd, J=16.6, 10.6 Hz, 1H), 1.35 (d, J=7.2 Hz, 3H). Analytical HPLC (orthogonal method): RT=14.4 min, HI: 98%. hGPR40 $EC_{50}$=970 nM. Example 60, Isomer 2 (white solid, 5 mg). LC-MS Anal. Calc'd for $C_{27}H_{23}F_4N_2O_3$ 534. found [M+H] 535. $^1$H NMR (500 MHz, $CDCl_3$) δ 7.37 (d, J=8.0 Hz, 1H), 7.23-7.15 (m, 3H), 7.10-7.02 (m, 3H), 6.91 (dd, J=6.3, 3.0 Hz, 1H), 6.84 (dt, J=8.9, 3.4 Hz, 1H), 4.43 (d, J=9.9 Hz, 1H), 4.09 (s, 2H), 3.82 (s, 3H), 3.22 (d, J=4.7 Hz, 1H), 2.91 (dd, J=16.5, 1.9 Hz, 1H), 2.47 (dd, J=16.5, 10.5 Hz, 1H), 1.34 (d, J=7.2 Hz, 3H). Analytical HPLC (orthogonal method): RT=14.4 min, HI: 99%. hGPR40 $EC_{50}$=40 nM.

Example 61, Isomer 1 and Isomer 2

2-((4S,5S)-1-(4-((2'-fluoro-5'-methoxy-3-methylbiphenyl-4-yl)methyl)phenyl)-4-methyl-3-(pyrimidin-2-yl)-4,5-dihydro-1H-pyrazol-5-yl)acetic acid

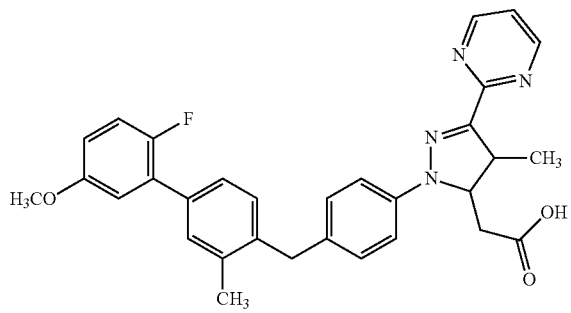 [SMILES: COc1ccc(F)c(-c2ccc(Cc3ccc(N4N=C(c5ncccn5)C(C)C4CC(=O)O)cc3)c(C)c2)c1]

61A: 2-((2-(4-bromophenyl)hydrazono)methyl)pyrimidine. To a mixture of (4-bromophenyl)hydrazine (HCl salt, 2.105 g, 9.44 mmol) and pyrimidine-2-carbaldehyde (1.0 g, 9.25 mmol) in DMF (8.0 mL) was added triethylamine (1.547 mL, 11.10 mmol). After stirred at room temperature for 16 h, the resulting mixture was treated with 20 mL water. The yellow precipitate was collected by filtration and dried under high vacuum to afford 2-((2-(4-bromophenyl)hydrazono)methyl)pyrimidine (2.532 g, 9.14 mmol, 99% yield) as a yellow solid. LC-MS Anal. Calc'd for $C_{11}H_9BrN_4$ 276.00. found [M+3H] 279.0.

61B: N'-(4-bromophenyl)pyrimidine-2-carbohydrazonoyl bromide. To a solution of 2-((2-(4-bromophenyl)hydrazono)methyl)pyrimidine (2.532 g, 9.14 mmol) in THF (10.0 mL) at 0° C. was added n-bromosuccinimide (1.789 g, 10.05 mmol). The reaction mixture was stirred at 0° C. for 3 h, concentrated and purified by chromatography to afford N'-(4-bromophenyl)pyrimidine-2-carbohydrazonoyl bromide (3.27 g, 8.73 mmol, 96% yield) as a yellow solid. LC-MS Anal. Calc'd for $C_{11}H_8Br_2N_4$ 353.91. found [M+3H] 356.9.

61C: 2-(4-methyl-3-(pyrimidin-2-yl)-1-(4-(4,4,5,5-tetramethyl-1,3,2-dioxaborolan-2-yl)phenyl)-4,5-dihydro-1H-pyrazol-5-yl)acetonitrile: racemate. A mixture of 2-(1-(4-bromophenyl)-4-methyl-3-(pyrimidin-2-yl)-4,5-dihydro-1H-pyrazol-5-yl)acetonitrile (100 mg, 0.281 mmol) (prepared by the procedure of example 17), 4,4,4',4',5,5,5',5'-octamethyl-2,2'-bi(1,3,2-dioxaborolane) (114 mg, 0.449 mmol), potassium acetate (83 mg, 0.842 mmol) and 1,1'-Bis(diphenylphosphino)ferrocenepalladium(II) dichloride (11.90 mg, 0.014 mmol) in DMF (2.0 mL) was purge with argon and stirred at 80° C. for 16 h. After cooled to room temperature, the reaction mixture was diluted with water and extracted with DCM. The combined organic extracts were dried over sodium sulfate, filtered and concentrated to give an oil which was purified by chromatography to afford 2-(4-methyl-3-(pyrimidin-2-yl)-1-(4-(1,3,2-dioxaborolan-2-yl)phenyl)-4,5-dihydro-1H-pyrazol-5-yl)acetonitrile (112 mg, 0.264 mmol, 94% yield) as a yellow film. LC-MS Anal. Calc'd for $C_{22}H_{26}BN_5O_2$ 403.22. found [M+H] 404.2.

61D: 2-(1-(4-((2'-fluoro-5'-methoxy-3-methylbiphenyl-4-yl)methyl)phenyl)-4-methyl-3-(pyrimidin-2-yl)-4,5-dihydro-1H-pyrazol-5-yl)acetonitrile: racemate. A mixture of 4'-(bromomethyl)-2-fluoro-5-methoxy-3'-methyl-1,1'-biphenyl (98 mg, 0.317 mmol), 2-(4-methyl-3-(pyrimidin-2-yl)-4,5-dihydro-1H-pyrazol-5-yl)acetonitrile (112 mg, 0.264 mmol), tetrakis(triphenylphosphine)palladium(0) (15.24 mg, 0.013 mmol) and potassium carbonate (1.0M solution) (1.319 mL, 1.319 mmol) in Toluene (2.0 mL) was purged with argon. The resulting mixture was stirred at 110° C. for 16 h. After cooled to RT, the reaction mixture was diluted with water and extracted with EtOAc. The combined organic extracts were dried over sodium sulfate, filtered and concentrated to give a residue which was purified by chromatography to afford 2-(1-(4-((2'-fluoro-5'-methoxy-3-methyl-4-yl)methyl)phenyl)-4-methyl-3-(pyrimidin-2-yl)-4,5-dihydro-1H-pyrazol-5-yl)acetonitrile (111 mg, 0.191 mmol, 72.4% yield) as a yellow foam. LC-MS Anal. Calc'd for $C_{31}H_{28}FN_5O$, 505.23. found [M+H] 506.3.

Example 61: 2-((4S,5S)-1-(4-((2'-fluoro-5'-methoxy-3-methylbiphenyl-4-yl)methyl)phenyl)-4-methyl-3-(pyrimidin-2-yl)-4,5-dihydro-1H-pyrazol-5-yl)acetic acid Prepared by the procedure of Example 17 to give Example 61 isomer 1 (red solid, 15 mg) LC-MS Anal. Calc'd for $C_{31}H_{29}FN_4O_3$ 524.22. found [M+H] 525.3. $^1$H NMR (500 MHz, CDCl$_3$) δ 8.84 (d, J=5.0 Hz, 2H), 7.38-7.30 (m, 2H), 7.27 (d, J=8.8 Hz, 2H), 7.20 (t, J=5.0 Hz, 1H), 7.15 (dd, J=13.5, 8.3 Hz, 3H), 7.05 (dd, J=9.9, 9.1 Hz, 1H), 6.94 (dd, J=6.3, 3.3 Hz, 1H), 6.81 (dt, J=8.9, 3.4 Hz, 1H), 4.59 (dt, J=11.1, 2.4 Hz, 1H), 3.97 (s, 2H), 3.82 (s, 3H), 3.71 (dd, J=7.0, 2.1 Hz, 1H), 2.95 (dd, J=16.0, 2.8 Hz, 1H), 2.50 (dd, J=16.1, 11.1 Hz, 1H), 2.32 (s, 3H), 1.40 (d, J=6.9 Hz, 3H). Analytical HPLC (Zorbax method): RT=7.1 min, HI: 98%. hGPR40 EC$_{50}$>16600 nM; and Example 61, isomer 2 (red solid, 16 mg): LC-MS Anal. Calc'd for $C_{31}H_{29}FN_4O_3$ 524.22. found [M+H] 525.3. $^1$H NMR (500 MHz, CDCl$_3$) δ 8.84 (d, J=5.0 Hz, 2H), 7.38-7.30 (m, 2H), 7.27 (d, J=8.5 Hz, 2H), 7.20 (t, J=4.8 Hz, 1H), 7.18-7.11 (m, 3H), 7.05 (dd, J=9.9, 9.1 Hz, 1H), 6.94 (dd, J=6.3, 3.3 Hz, 1H), 6.81 (dt, J=8.9, 3.4 Hz, 1H), 4.59 (dt, J=10.9, 2.4 Hz, 1H), 3.96 (s, 2H), 3.82 (s, 3H), 3.71 (dd, J=7.2, 2.2 Hz, 1H), 2.95 (dd, J=16.0, 2.8 Hz, 1H), 2.50 (dd, J=16.0, 11.3 Hz, 1H), 2.32 (s, 3H), 1.40 (d, J=7.2 Hz, 3H). Analytical HPLC (Zorbax method): RT=7.1 min, HI: 97%. hGPR40 EC$_{50}$=460 nM.

Example 62, Isomer 1 and Isomer 2

2-(1-(4-((2'-fluoro-5'-methoxy-3-methylbiphenyl-4-yl)methyl)phenyl)-4-methyl-3-(pyridin-2-yl)-4,5-dihydro-1H-pyrazol-5-yl)acetic acid

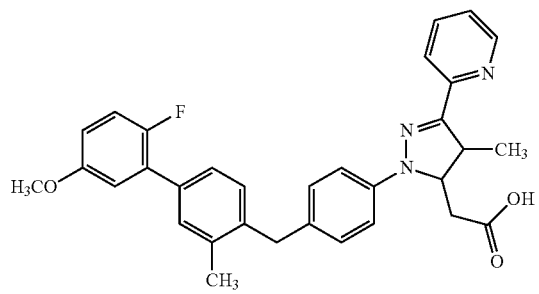 [SMILES: COc1ccc(F)c(-c2ccc(Cc3ccc(N4N=C(c5ccccn5)C(C)C4CC(=O)O)cc3)c(C)c2)c1]

Example 62: 2-(1-(4-((2'-fluoro-5'-methoxy-3-methylbiphenyl-4-yl)methyl)phenyl)-4-methyl-3-(pyridin-2-yl)-4,5-dihydro-1H-pyrazol-5-yl)acetic acid was synthesized according to the method of Example 61 to give Example 62, isomer 1 (orange solid, 6 mg) (6.7 mg, 0.012 mmol, 70.7% yield) as an orange solid. LC-MS Anal. Calc'd for $C_{32}H_{30}FN_3O_3$ 523.23. found [M+H] 524.3. 1H NMR (500 MHz, CDCl$_3$) δ 8.68 (d, J=4.4 Hz, 1H), 8.22 (d, J=8.3 Hz, 1H), 7.78 (td, J=7.8, 1.7 Hz, 1H), 7.40-7.33 (m, 2H), 7.30 (ddd, J=7.4, 5.3, 1.1 Hz, 1H), 7.23-7.18 (m, 3H), 7.18-7.12 (m, 2H), 7.07 (dd, J=9.9, 9.1 Hz, 1H), 6.96 (dd, J=6.3, 3.0 Hz, 1H), 6.82 (dt, J=8.9, 3.5 Hz, 1H), 4.59-4.51 (m, 1H), 4.00 (s, 2H), 3.95 (dd, J=7.2, 1.7 Hz, 1H), 3.83 (s, 3H), 2.91 (dd, J=15.1, 2.8 Hz, 1H), 2.45 (dd, J=15.3, 11.4 Hz, 1H), 2.38-2.31 (m, 3H), 1.38 (d, J=7.2 Hz, 3H). Analytical HPLC (Zorbax method): RT=7.0 min, HI: 98%. hGPR40 EC$_{50}$=1600 nM; example 62, isomer 2 (orange solid, 7 mg) LC-MS Anal. Calc'd for $C_{32}H_{30}FN_3O_3$ 523.23. found [M+H] 524.3. 1H NMR (500 MHz, CDCl$_3$) δ 8.68 (d, J=4.4 Hz, 1H), 8.22 (d, J=8.3 Hz, 1H), 7.78 (td, J=7.8, 1.7 Hz, 1H), 7.40-7.33 (m, 2H), 7.30 (ddd, J=7.4, 5.3, 1.1 Hz, 1H), 7.23-7.18 (m, 3H), 7.18-7.12 (m, 2H), 7.07 (dd, J=9.9, 9.1 Hz, 1H), 6.96 (dd, J=6.3, 3.0 Hz, 1H), 6.82 (dt, J=8.9, 3.5 Hz, 1H), 4.59-4.51 (m, 1H), 4.00 (s, 2H), 3.95 (dd, J=7.2, 1.7 Hz, 1H), 3.83 (s, 3H), 2.91 (dd, J=15.1, 2.8 Hz, 1H), 2.45 (dd, J=15.3, 11.4 Hz, 1H), 2.38-2.31 (m, 3H), 1.38 (d, J=7.2 Hz, 3H). Analytical HPLC (Zorbax method): RT=8.9 min, HI: 98%. hGPR40 EC$_{50}$=63 nM.

Example 63, Isomer 1

2-((4S,5S)-1-(4-((2-(2-fluoro-5-methoxyphenyl)-4-methylpyrimidin-5-yl)methyl)phenyl)-4-methyl-3-(trifluoromethyl)-4,5-dihydro-1H-pyrazol-5-yl)acetic acid

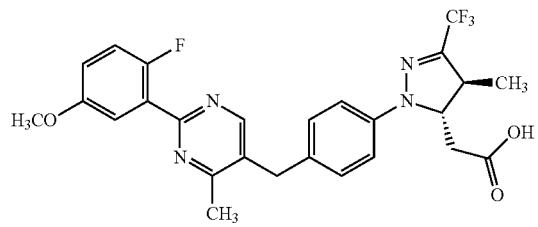

Example 63 (white solid, 75 mg) was synthesized according to the method of Example 17: LC-MS Anal. Calc'd for $C_{26}H_{24}F_4N_4O_3$ 516.18. found [M+H] 517. $^1$H NMR (500 MHz, CDCl$_3$) δ 8.53 (s, 1H), 7.50 (dd, J=6.1, 3.3 Hz, 1H), 7.15-7.04 (m, 5H), 6.96 (dt, J=8.9, 3.5 Hz, 1H), 4.44 (d, J=10.2 Hz, 1H), 3.98 (s, 2H), 3.85 (s, 3H), 3.26-3.16 (m, 1H), 2.86 (dd, J=16.5, 3.0 Hz, 1H), 2.55 (s, 3H), 2.43 (dd, J=16.5, 10.5 Hz, 1H), 1.34 (d, J=6.9 Hz, 3H). Analytical HPLC (Zorbax method): RT=6.2 min, HI: 99%. hGPR40 EC$_{50}$=700 nM.

Example 64

2-((4S,5S)-1-(4-((2-(2-fluoro-5-methoxyphenyl)-4-methylpyrimidin-5-yl)methyl)phenyl)-4-methyl-3-phenyl-4,5-dihydro-1H-pyrazol-5-yl)acetic acid

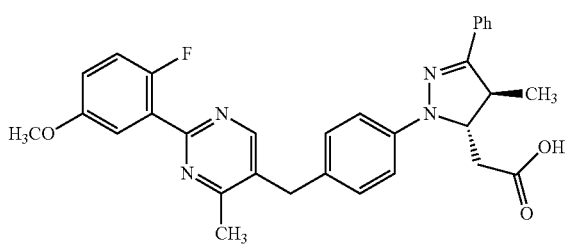 [SMILES: COc1ccc(F)c(-c2ncc(Cc3ccc(N4N=C(c5ccccc5)[C@@H](C)[C@@H]4CC(=O)O)cc3)c(C)n2)c1]

Example 64 (light yellow solid, 17 mg) was synthesized according to the method of Example 58. LC-MS Anal. Calc'd for $C_{31}H_{29}FN_4O_3$ 524.50. found [M+H] 525.3. $^1$H NMR (500 MHz, CDCl$_3$) δ 8.54 (s, 1H), 7.76 (d, J=7.2 Hz, 2H), 7.53 (dd, J=6.1, 3.3 Hz, 1H), 7.43-7.36 (m, 2H), 7.36-7.30 (m, 1H), 7.17-7.11 (m, 2H), 7.09 (d, J=8.3 Hz, 3H), 6.95 (dt, J=8.9, 3.5 Hz, 1H), 4.42 (d, J=9.9 Hz, 1H), 3.96 (s, 2H), 3.89-3.82 (m, 3H), 3.47-3.35 (m, J=6.9 Hz, 1H), 2.83 (d, J=14.3 Hz, 1H), 2.56 (s, 3H), 2.34 (dd, J=16.0, 10.7 Hz, 1H), 1.31 (d, J=6.9 Hz, 3H). Analytical HPLC (Zorbax method): RT=6.2 min, HI: 99%. hGPR40 EC$_{50}$=270 nM.

Example 65

2-((4S,5S)-1-(4-(5-(2-fluoro-5-methoxyphenyl)pyrimidin-2-yloxy)phenyl)-4-methyl-3-(trifluoromethyl)-4,5-dihydro-1H-pyrazol-5-yl)acetic acid

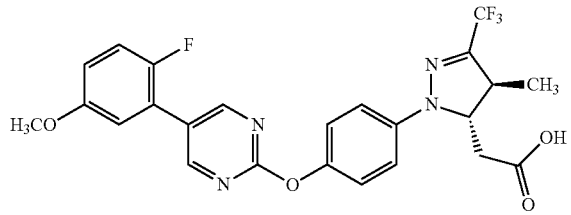 [SMILES: COc1ccc(F)c(-c2cnc(Oc3ccc(N4N=C(C(F)(F)F)[C@@H](C)[C@@H]4CC(=O)O)cc3)nc2)c1]

65A: 2-fluoro-5-(2-fluoro-5-methoxyphenyl)pyrimidine. To a stirred solution of 5-bromo-2-fluoropyrimidine (707 mg, 3.99 mmol) in Toluene (5.0 mL) was added (2-fluoro-5-methoxyphenyl)boronic acid (815 mg, 4.79 mmol), tetrakis(triphenylphosphine) palladium(O) (231 mg, 0.200 mmol) and potassium carbonate (1656 mg, 11.98 mmol). The resulting mixture was purged with argon and stirred at 110° C. for 16 h. After cooled to room temperature, the reaction mixture was diluted with water and extracted with DCM. The combined organic extracts were dried over sodium sulfate, filtered and concentrated to give a solid which was purified by chromatography to afford 2-fluoro-5-(2-fluoro-5-methoxyphenyl)pyrimidine (265 mg, 1.169 mmol, 29.3% yield) as a white solid. LC-MS Anal. Calc'd for $C_{11}H_8F_2N_2O$, 222.06. found [M+H] 223.0.

65B: methyl 2-((4S,5S)-1-(4-(5-(2-fluoro-5-methoxyphenyl)pyrimidin-2-yloxy)phenyl)-4-methyl-3-(trifluoromethyl)-4,5-dihydro-1H-pyrazol-5-yl)acetate. To a stirred solution of 2-fluoro-5-(2-fluoro-5-methoxyphenyl)pyrimidine (103 mg, 0.465 mmol) and methyl 2-((4S,5S)-1-(4-hydroxyphenyl)-4-methyl-3-(trifluoromethyl)-4,5-dihydro-1H-pyrazol-5-yl)acetate (105 mg, 0.332 mmol)(prepared by the procedure of example 17) in DMF (3.0 mL) was added cesium carbonate (325 mg, 0.996 mmol). The resulting mixture was stirred at 65° C. for 16 h. After cooled to room temperature, the reaction mixture was diluted with water and extracted with EtOAc. The combined organic extracts were dried over sodium sulfate, filtered and concentrated to give a residue which was purified by chromatography to afford methyl 2-((4S,5S)-1-(4-((5-(2-fluoro-5-methoxyphenyl)pyrimidin-2-yl)oxy)phenyl)-4-methyl-3-(trifluoromethyl)-4,5-dihydro-1H-pyrazol-5-yl)acetate (215 mg, 0.332 mmol, 100% yield) as a clear oil. LC-MS Anal. Calc'd for $C_{25}H_{22}F_4N_4O_4$ 518.16. found [M+H] 519.2.

Example 65: 2-((4S,5S)-1-(4-(5-(2-fluoro-5-methoxyphenyl)pyrimidin-2-yloxy)phenyl)-4-methyl-3-(trifluoromethyl)-4,5-dihydro-1H-pyrazol-5-yl)acetic acid. Example 65 (white solid, 45 mg) was synthesized from 65B via the method of Example 17; LC-MS Anal. Calc'd for $C_{24}H_{20}F_4N_4O_4$ 504.14. found [M+H] 505.2. $^1$H NMR (500 MHz, CDCl$_3$) δ 8.79 (d, J=0.8 Hz, 2H), 7.20-7.08 (m, 5H), 6.95-6.85 (m, 2H), 4.47 (d, J=10.5 Hz, 1H), 3.83 (s, 3H), 3.28-3.18 (m, 1H), 2.92 (dd, J=16.8, 2.8 Hz, 1H), 2.43 (dd, J=16.8, 10.7 Hz, 1H), 1.35 (d, J=6.9 Hz, 3H). Analytical HPLC (Zorbax method): RT=5.6 min, HI: 100%. hGPR40 EC$_{50}$=1490 nM.

Example 66, Isomer 1 and Isomer 2

2-((4S,5 S)-3-(4-chlorophenyl)-1-(4-((2'-fluoro-5'-methoxy-3-methyl-[1,1'-biphenyl]-4-yl)methyl)phenyl)-4-methyl-4,5-dihydro-1H-pyrazol-5-yl)acetic acid

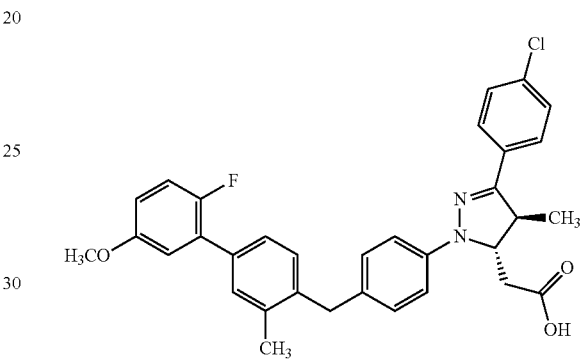

66A. (Z)-1-(4-chlorophenyl)-3-hydroxy-2-methylprop-2-en-1-one: To a solution of Et$_2$O (100 mL) cooled in an ice-water bath was added 1-(4-chlorophenyl)propan-1-one (3.37 g, 20 mmol), ethyl formate (1.930 mL, 24.00 mmol) followed by slow addition of sodium ethoxide (8.96 mL, 24.00 mmol). The orange reaction mixture was stirred at rt for 16 h. After removing most of the solvent under reduced pressure, 20 mL water was added to the orange residue. Then 6 mL 1N HCl was added and the orange solution turned into a clear yellow solution. After separation of the layers, the aqueous layer was further extracted with EtOAc (3×20 mL) and the combined organic layers were washed with water, brine, dried (Na$_2$SO$_4$), filtered and concentrated. Purification by flash chromatography gave 66A (yellow oil, 1.6 g, 8.14 mmol, 40.7% yield). LC-MS Anal. Calc'd for $C_{10}H_9ClO_2$ 196.03. found [M+H] 197.0. $^1$H NMR (400 MHz, CDCl$_3$) δ 15.34 (d, J=4.8 Hz, 1H), 8.62 (d, J=4.5 Hz, 1H), 7.59 (d, J=8.8 Hz, 2H), 7.49-7.38 (m, 2H), 2.00 (s, 3H).

66B. ethyl 5-(4-chlorophenyl)-4-methyl-5-oxopent-2-enoate: To a solution of (Z)-1-(4-chlorophenyl)-3-hydroxy-2-methylprop-2-en-1-one (1.6 g, 8.14 mmol) in Toluene (40 mL) was added ethyl 2-(triphenylphosphoranylidene)acetate (3.12 g, 8.95 mmol). The resulting solution was heated at 70° C. for 2 h. It was cooled to rt and diluted with EtOAc and water. After separating the layers, the aqueous layer was further extracted with EtOAc (2×30 mL), the combined extracts was washed with water, brine, dried (MgSO$_4$), filtered and concentrated. Purification by flash chromatography afforded 66B (light yellow oil, 0.6 g, 2.250 mmol, 27.6% yield) and the other regioisomer ethyl 5-(4-chlorophenyl)-4-methyl-5-oxopent-3-enoate (light yellow oil, 1.4 g, 5.25 mmol, 64.5% yield). LC-MS Anal. Calc'd for $C_{14}H_{15}ClO_3$ 266.07. found [M+H] 267.0. $^1$H NMR (400

MHz, CDCl$_3$) δ 8.00 (d, J=8.8 Hz, 2H), 7.44 (d, J=8.8 Hz, 2H), 6.39 (dd, J=11.4, 9.9 Hz, 1H), 5.89 (dd, J=11.4, 0.9 Hz, 1H), 5.60 (dqd, J=9.8, 6.9, 0.9 Hz, 1H), 4.22 (q, J=7.3 Hz, 2H), 1.40-1.26 (m, 6H).

66C. tert-butyl 1-(4-((2'-fluoro-5'-methoxy-3-methyl-[1,1'-biphenyl]-4-yl)methyl)phenyl)hydrazinecarboxylate: A flask containing aryl iodide example 28D (1 g, 2.313 mmol), tert-butyl hydrazinecarboxylate (0.367 g, 2.78 mmol), cesium carbonate (1.055 g, 3.24 mmol), 1,10-phenanthroline anhydrous (0.083 g, 0.463 mmol) and copper(I) iodide (0.022 g, 0.116 mmol) was evacuated and backfilled with Argon. DMF (2.5 mL) was then added and the mixture was degassed by vigorous stirring and by vacuum/backfill three times. Then the mixture was heated to 80° C. and stirred for 3 h. The rxn mixture was then cooled to rt, diluted with EtOAc (30 mL) and filtered through a pad of Celite. The filter cake was rinsed with EtOAc (2×50 mL) and the combined filtrate and rinse were concentrated. Purification by flash chromatography gave 66C (light yellow oil, 0.9 g, 2.062 mmol, 89% yield). LC-MS Anal. Calc'd for $C_{26}H_{29}FN_2O_3$ 436.22, did not show desired mass. $^1$H NMR (400 MHz, CDCl$_3$) δ 7.45-7.31 (m, 4H), 7.17 (d, J=7.8 Hz, 1H), 7.14-7.02 (m, 3H), 6.95 (dd, J=6.3, 3.3 Hz, 1H), 6.81 (dt, J=9.0, 3.4 Hz, 1H), 4.43 (s, 2H), 4.00 (s, 2H), 3.83 (s, 3H), 2.31 (s, 3H), 1.51 (s, 9H).

66D. ethyl 2-((4S,5S)-3-(4-chlorophenyl)-1-(4-((2'-fluoro-5'-methoxy-3-methyl-[1,1'-biphenyl]-4-yl)methyl)phenyl)-4-methyl-4,5-dihydro-1H-pyrazol-5-yl)acetate: To a solution of tert-butyl 1-(4-((2'-fluoro-5'-methoxy-3-methyl-[1,1'-biphenyl]-4-yl)methyl)phenyl)hydrazinecarboxylate (68.7 mg, 0.157 mmol) and ethyl 5-(4-chlorophenyl)-4-methyl-5-oxopent-2-enoate (35 mg, 0.131 mmol) in DCM (1 mL) was added TFA (1.000 mL). The resulting reddish solution was stirred at rt for 30 min. LC/MS indicated formation of the deprotected hydrazine, then it was heated at 60° C. for 3 h under a refluxing condenser. It was then cooled to rt. After concentration under reduced pressure, purification by flash chromatography gave 66D (yellow oil, 45 mg, 0.077 mmol, 58.6% yield). LC-MS Anal. Calc'd for $C_{35}H_{34}ClFN_2O_3$ 584.22. found [M+H] 585.2. $^1$H NMR (400 MHz, CD$_2$Cl$_2$) δ 7.74-7.66 (m, 2H), 7.44-7.29 (m, 4H), 7.19 (d, J=7.8 Hz, 1H), 7.15-7.01 (m, 5H), 6.95 (dd, J=6.4, 3.1 Hz, 1H), 6.82 (dt, J=9.0, 3.4 Hz, 1H), 4.47-4.36 (m, 1H), 4.13 (q, J=7.3 Hz, 2H), 3.97 (s, 2H), 3.81 (s, 3H), 3.39 (qd, J=7.1, 2.0 Hz, 1H), 2.77 (dd, J=15.8, 3.0 Hz, 1H), 2.43-2.25 (m, 4H), 1.29 (d, J=7.0 Hz, 3H), 1.23 (t, J=7.2 Hz, 3H).

66E. 2-((4S,5S)-3-(4-chlorophenyl)-1-(4-((2'-fluoro-5'-methoxy-3-methyl-[1,1'-biphenyl]-4-yl)methyl)phenyl)-4-methyl-4,5-dihydro-1H-pyrazol-5-yl)acetic acid: ethyl 2-((4S,5S)-3-(4-chlorophenyl)-1-(4-((2'-fluoro-5'-methoxy-3-methyl-[1,1'-biphenyl]-4-yl)methyl)phenyl)-4-methyl-4,5-dihydro-1H-pyrazol-5-yl)acetate (50 mg, 0.085 mmol) was dissolved in THF (2 mL), MeOH (0.500 mL) and water (0.500 mL), sodium hydroxide (0.256 mL, 0.256 mmol) was added. After 1 h it was complete, most MeOH and THF was removed under reduced pressure and the crude was diluted with 2 mL of water, the pH was adjusted using 1N HCl. The aqueous phase was then extracted with EtOAc (3×10 mL) and the combined organic phase was washed with brine, dried (Na$_2$SO$_4$), filtered and concentrated. Purification by preparative HPLC afforded 66E (yellow solid, 25 mg, 0.045 mmol, 52.5% yield). LC-MS Anal. Calc'd for $C_{33}H_{30}ClFN_2O_3$ 556.19. found [M+H] 557.2; $^1$H NMR (400 MHz, CD$_2$Cl$_2$) δ 7.77-7.65 (m, 2H), 7.44-7.28 (m, 4H), 7.19 (d, J=7.8 Hz, 1H), 7.15-7.01 (m, 5H), 6.95 (dd, J=6.3, 3.3 Hz, 1H), 6.81 (dt, J=8.8, 3.5 Hz, 1H), 4.42 (d, J=10.2, 2.6 Hz, 1H), 3.96 (s, 2H), 3.81 (s, 3H), 3.42 (qd, J=7.2, 1.9 Hz, 1H), 2.81 (dd, J=16.2, 3.1 Hz, 1H), 2.42-2.25 (m, 4H), 1.29 (d, J=7.3 Hz, 3H).

Example 66. Chiral separation of 66E gave example 66, isomers 1 and 2 as single enantiomers. Example 66, Isomer 1 (yellow oil, 5.7 mg, 0.01 mmol, 22% yield). LC-MS Anal. Calc'd for $C_{33}H_{30}ClFN_2O_3$ 556.19. found [M+H] 557.2. $^1$H NMR (400 MHz, CD$_2$Cl$_2$) δ 7.69 (d, J=8.5 Hz, 2H), 7.44-7.28 (m, 4H), 7.19 (d, J=7.8 Hz, 1H), 7.16-7.01 (m, 5H), 6.95 (dd, J=6.4, 3.1 Hz, 1H), 6.81 (dt, J=8.8, 3.5 Hz, 1H), 4.43 (d, J=10.0 Hz, 1H), 3.97 (s, 2H), 3.81 (s, 3H), 3.41 (q, J=6.5 Hz, 1H), 2.87 (d, J=14.3 Hz, 1H), 2.46-2.26 (m, 4H), 1.29 (d, J=7.0 Hz, 3H). Analytical HPLC (orthogonal method): RT=14.13 min, HI: 95%. hGPR40 EC$_{50}$=13 nM. Example 66, isomer 2 (yellow oil, 6 mg, 0.01 mmol, 23% yield). LC-MS Anal. Calc'd for $C_{33}H_{30}ClFN_2O_3$ 556.19. found [M+H] 557.2. $^1$H NMR (400 MHz, CD$_2$Cl$_2$) δ 7.68 (d, J=8.5 Hz, 2H), 7.43-7.27 (m, 4H), 7.17 (d, J=8.0 Hz, 1H), 7.14-7.00 (m, 5H), 6.94 (dd, J=6.4, 3.1 Hz, 1H), 6.81 (dt, J=9.0, 3.4 Hz, 1H), 4.41 (d, J=10.0 Hz, 1H), 3.95 (s, 2H), 3.80 (s, 3H), 3.39 (q, J=6.8 Hz, 1H), 2.84 (d, J=15.8 Hz, 1H), 2.44-2.26 (m, 4H), 1.27 (d, J=6.8 Hz, 3H. Analytical HPLC (orthogonal method): RT=11.39 min, HI: 97%. hGPR40 EC$_{50}$=510 nM.

Example 67, Isomer 1 and Isomer 2

2-((4S,5S)-1-(4-((2'-fluoro-5'-methoxy-3-methyl-[1,1'-biphenyl]-4-yl)methyl)phenyl)-3-(4-fluorophenyl)-4-methyl-4,5-dihydro-1H-pyrazol-5-yl)acetic acid

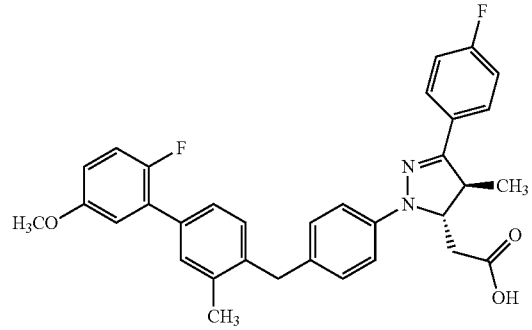 [SMILES: COc1ccc(F)c(-c2ccc(Cc3ccc(N4N=C(c5ccc(Cl)cc5)[C@@H](C)[C@@H]4CC(=O)O)cc3)c(C)c2)c1]

Example 67, Isomer 1 and Isomer 2 were prepared as single enantiomers following the procedure of Example 66. Example 67, isomer 1 (yellow solid, 12 mg). LC-MS Anal. Calc'd for $C_{33}H_{30}F_2N_2O_3$ 540.22. found [M+H] 541.2. $^1$H NMR (400 MHz, CDCl$_3$) δ 7.73 (dd, J=8.0, 5.5 Hz, 2H), 7.43-7.30 (m, 2H), 7.22-7.02 (m, 8H), 6.95 (dd, J=6.3, 3.0 Hz, 1H), 6.81 (dt, J=9.0, 3.4 Hz, 1H), 4.42 (d, J=9.3 Hz, 1H), 3.97 (s, 2H), 3.83 (s, 3H), 3.39 (d, J=5.3 Hz, 1H), 2.92 (d, J=13.1 Hz, 1H), 2.51-2.26 (m, 4H), 1.31 (d, J=6.0 Hz, 3H) Analytical HPLC (orthogonal method): RT=12.3 min, HI: 94%. hGPR40 EC$_{50}$=9 nM. Example 67, isomer 2 (yellow solid, 12 mg). LC-MS Anal. Calc'd for $C_{33}H_{30}F_2N_2O_3$ 540.22. found [M+H] 541.2. $^1$H NMR (400 MHz, CDCl$_3$) δ 7.74 (dd, J=7.8, 5.5 Hz, 2H), 7.43-7.29 (m, 2H), 7.23-7.02 (m, 8H), 6.95 (dd, J=6.3, 3.3 Hz, 1H), 6.82 (dt, J=8.8, 3.5 Hz, 1H), 4.42 (d, J=9.3 Hz, 1H), 3.97 (s, 2H), 3.83 (s, 3H), 3.39 (d, J=5.0 Hz, 1H), 2.92 (d, J=14.6 Hz, 1H), 2.55-2.27

(m, 4H), 1.31 (d, J=6.3 Hz, 3H) Analytical HPLC (orthogonal method): RT=10.5 min, HI: 96%. hGPR40 EC$_{50}$=800 nM.

Example 68, Isomer 1 and Isomer 2

2-((4S,5S)-3-(3-chlorophenyl)-1-(4-((2'-fluoro-5'-methoxy-3-methyl-[1,1'-biphenyl]-4-yl)methyl)phenyl)-4-methyl-4,5-dihydro-1H-pyrazol-5-yl)acetic acid

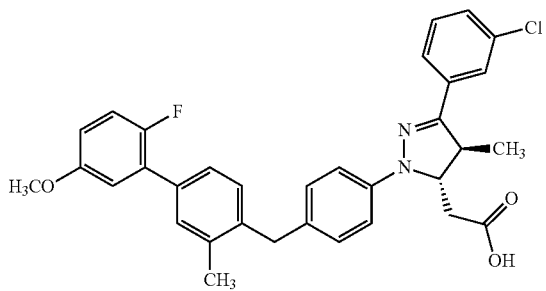 [SMILES: COc1ccc(F)c(-c2ccc(Cc3ccc(N4N=C(c5cccc(Cl)c5)[C@@H](C)[C@@H]4CC(=O)O)cc3)c(C)c2)c1]

Example 68, isomer 1 and isomer 2 were prepared as single enantiomers following the procedure of Example 65. Example 68, isomer 1 (yellow solid, 10.2 mg). LC-MS Anal. Calc'd for C$_{33}$H$_{30}$ClFN$_2$O$_3$ 556.19. found [M+H] 557.3. $^1$H NMR (400 MHz, CDCl$_3$) δ 7.75 (t, J=1.6 Hz, 1H), 7.61 (dt, J=7.3, 1.5 Hz, 1H), 7.43-7.29 (m, 4H), 7.18 (d, J=7.8 Hz, 1H), 7.13 (s, 4H), 7.06 (dd, J=9.9, 8.9 Hz, 1H), 6.95 (dd, J=6.3, 3.3 Hz, 1H), 6.81 (dt, J=8.8, 3.5 Hz, 1H), 4.45 (dt, J=10.5, 2.4 Hz, 1H), 3.98 (s, 2H), 3.83 (s, 3H), 3.50-3.29 (m, 1H), 2.91 (dd, J=16.3, 2.8 Hz, 1H), 2.51-2.27 (m, 4H), 1.33 (d, J=7.0 Hz, 3H) Analytical HPLC (orthogonal method): RT=12.85 min, HI: 98%. hGPR40 EC$_{50}$=15 nM. Example 68, isomer 2 (yellow solid, 6 mg). LC-MS Anal. Calc'd for C$_{33}$H$_{30}$ClFN$_2$O$_3$ 556.19. found [M+H] 557.3. $^1$H NMR (400 MHz, CDCl$_3$) δ 7.75 (t, J=1.5 Hz, 1H), 7.62 (dt, J=7.3, 1.6 Hz, 1H), 7.42-7.29 (m, 4H), 7.18 (d, J=7.8 Hz, 1H), 7.16-7.10 (m, 4H), 7.06 (dd, J=9.8, 9.0 Hz, 1H), 6.95 (dd, J=6.3, 3.3 Hz, 1H), 6.82 (dt, J=8.8, 3.5 Hz, 1H), 4.45 (dt, J=10.5, 2.4 Hz, 1H), 3.98 (s, 2H), 3.83 (s, 3H), 3.51-3.28 (m, 1H), 2.91 (dd, J=16.2, 2.9 Hz, 1H), 2.48-2.27 (m, 4H), 1.33 (d, J=7.0 Hz, 3H) Analytical HPLC (orthogonal method): RT=12.84 min, HI: 97%. hGPR40 EC$_{50}$=8460 nM.

Example 69, Isomer 1 and Isomer 2

2-((4S,5S)-1-(4-((2'-fluoro-5'-methoxy-3-methyl-[1,1'-biphenyl]-4-yl)methyl)phenyl)-4-methyl-3-(5-methylisoxazol-3-yl)-4,5-dihydro-1H-pyrazol-5-yl)acetic acid

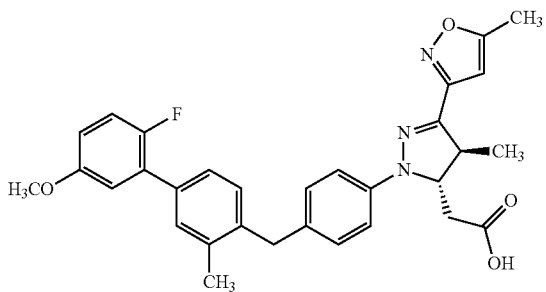 [SMILES: COc1ccc(F)c(-c2ccc(Cc3ccc(N4N=C(c5cc(C)on5)[C@@H](C)[C@@H]4CC(=O)O)cc3)c(C)c2)c1]

69A. 3-hydroxy-2-methyl-1-(5-methylisoxazol-3-yl)prop-2-en-1-one: To a solution of 1-(5-methylisoxazol-3-yl)propan-1-one (560 mg, 4.02 mmol) in EtOH (10 mL) cooled in an ice-water bath was added ethyl formate (0.388 mL, 4.83 mmol) followed by slow addition of sodium ethoxide (1.803 mL, 4.83 mmol). The orange reaction mixture was stirred at rt for 12 h. After removing ethanol under reduced pressure, 20 mL of water was added to the orange residue. Then 5 mL 1N HCl was added. After separating the layers, the aqueous layer was extracted with EtOAc (3×20 mL) and the combined organic layers were washed with water, brine, dried (Na$_2$SO$_4$), filtered and concentrated. Purification by flash chromatography gave 69A (yellow solid, 330 mg, 1.974 mmol, 49.1% yield), LC-MS Anal. Calc'd for C$_8$H$_9$NO$_3$ 167.06. found [M+H] 168.1.

69B. ethyl 4-methyl-5-(5-methylisoxazol-3-yl)-5-oxopent-3-enoate: To a solution of 3-hydroxy-2-methyl-1-(5-methylisoxazol-3-yl)prop-2-en-1-one (330 mg, 1.974 mmol) in Toluene (10 mL) was added ethyl 2-(triphenylphosphoranylidene)acetate (757 mg, 2.172 mmol). The resulting solution was heated at 50° C. for 2 h. It was cooled to rt and concentrated. Purification by flash chromatography afforded 69B as an inseparable E/Z mixture (light yellow oil, 170 mg, 0.645 mmol, 32.7% yield). LC-MS Anal. Calc'd for C$_{12}$H$_{15}$NO$_4$ 237.10, did not show desired mass. $^1$H NMR (400 MHz, CDCl$_3$) δ 7.40-7.29 (m, 1H), 6.33 (s, 1H), 4.18 (q, J=7.0 Hz, 2H), 3.38 (d, J=7.0 Hz, 2H), 2.48 (s, 3H), 1.96 (s, 3H), 1.34-1.20 (m, 3H).

69C. ethyl 2-((4S,5S)-1-(4-bromophenyl)-4-methyl-3-(5-methylisoxazol-3-yl)-4,5-dihydro-1H-pyrazol-5-yl)acetate: To a microwave vial containing a solution of (4-bromophenyl)hydrazine (201 mg, 1.075 mmol) in EtOH (4 mL) was added ethyl 4-methyl-5-(5-methylisoxazol-3-yl)-5-oxopent-3-enoate (170 mg, 0.717 mmol) followed by TFA (2.000 mL). The resulting solution was heated at 90° C. for 12 h. It was then cooled to rt. After removing solvent under reduced pressure, purification by flash chromatography gave 50 mg impure product. Further purification via preparative HPLC gave 69C (yellow oil, 30 mg, 0.074 mmol, 10.31% yield). LC-MS Anal. Calc'd for C$_{18}$H$_{20}$BrN$_3$O$_3$ 405.07. found [M+3H] 408.0. $^1$H NMR (500 MHz, CDCl3) δ 7.49-7.34 (m, 2H), 7.09-6.97 (m, 2H), 6.46 (d, J=0.8 Hz, 1H), 4.43 (dt, J=10.2, 2.8 Hz, 1H), 4.18 (q, J=7.2 Hz, 2H), 3.46 (qd, J=7.2, 2.2 Hz, 1H), 2.78 (dd, J=16.0, 3.0 Hz, 1H), 2.48 (d, J=0.6 Hz, 3H), 2.39 (dd, J=16.0, 10.5 Hz, 1H), 1.37 (d, J=7.2 Hz, 3H), 1.27 (t, J=7.2 Hz, 3H).

69D. ethyl 2-((4S,5S)-1-(4-((2'-fluoro-5'-methoxy-3-methyl-[1,1'-biphenyl]-4-yl)methyl)phenyl)-4-methyl-3-(5-methylisoxazol-3-yl)-4,5-dihydro-1H-pyrazol-5-yl)acetate: To a microwave vial was added zinc dust (10.87 mg, 0.166 mmol) and 0.8 mL THF. The flask was purged with argon, then to the flask was added ethylene dibromide (0.763 μl, 8.86 μmol) and TMS-Cl (0.566 μl, 4.43 μmol). The mixture was heated to 65° C. for 1 h, then to the solution was added 4'-(bromomethyl)-2-fluoro-5-methoxy-3'-methylbiphenyl (34.2 mg, 0.111 mmol) in 0.5+0.2 mL THF dropwise at 65° C. The resulting mixture was then stirred at 65° C. for 2 h. Then to the mixture was added a mixture of ethyl 2-((4S,5S)-1-(4-bromophenyl)-4-methyl-3-(5-methylisoxazol-3-yl)-4,5-dihydro-1H-pyrazol-5-yl)acetate (30 mg, 0.074 mmol) and Pd(PPh$_3$)$_4$ (8.53 mg, 7.38 μmol) in 0.6+0.2 mL THF. The resulting mixture was heated to 80° C. and stirred at the same temperature for 6 h. The mixture was then cooled to rt, filtered through a pad of Celite and concentrated. Purification by flash chromatography afforded 69D (yellow oil, 20 mg, 0.036 mmol, 48.7% yield). LC-MS Anal. Calc'd for C$_{33}$H$_{34}$FN$_3$O$_4$ 555.25. found [M+H] 556.3.

69E. 2-((4S,5S)-1-(4-((2'-fluoro-5'-methoxy-3-methyl-[1,1'-biphenyl]-4-yl)methyl)phenyl)-4-methyl-3-(5-methyl-isoxazol-3-yl)-4,5-dihydro-1H-pyrazol-5-yl)acetic acid: ethyl 2-((4S,5S)-1-(4-((2'-fluoro-5'-methoxy-3-methyl-[1,1'-biphenyl]-4-yl)methyl)phenyl)-4-methyl-3-(5-methyl-isoxazol-3-yl)-4,5-dihydro-1H-pyrazol-5-yl)acetate (20 mg, 0.036 mmol) was dissolved in THF (2 mL), MeOH (0.500 mL) and water (0.500 mL), sodium hydroxide (0.072 mL, 0.072 mmol) was added. After 1 h it was complete, most MeOH and THF was removed under reduced pressure and the crude was diluted with 2 mL of water, the pH was adjusted using 1N HCl. The aqueous phase was then extracted with EtOAc (3×10 mL) and the combined organic phase was washed with brine, dried ($Na_2SO_4$), filtered and concentrated. Purification by preparative HPLC gave 69E (yellow solid, 15 mg, 0.028 mmol, 79% yield. LC-MS Anal. Calc'd for $C_{31}H_{30}FN_3O_4$ 527.22. found [M+H] 528.3. $^1$H NMR (400 MHz, $CDCl_3$) δ 7.43-7.30 (m, 2H), 7.22-7.01 (m, 6H), 6.95 (dd, J=6.2, 3.2 Hz, 1H), 6.82 (dt, J=8.9, 3.4 Hz, 1H), 6.44 (d, J=0.9 Hz, 1H), 4.45 (dt, J=10.7, 2.6 Hz, 1H), 3.98 (s, 2H), 3.83 (s, 3H), 3.49 (qd, J=7.1, 2.3 Hz, 1H), 2.93 (dd, J=16.4, 2.9 Hz, 1H), 2.51-2.37 (m, 4H), 2.34 (s, 3H), 1.39 (d, J=7.2 Hz, 3H).

Example 69. Chiral separation of 69E gave Example 69, isomer 1 and 2 as single enantiomers. Example 69, isomer 1 (yellow solid, 6.2 mg, 0.01 mmol, 38% yield). LC-MS Anal. Calc'd for $C_{31}H_{30}FN_3O_4$ 527.22. found [M+H] 528.3. $^1$H NMR (400 MHz, $CDCl_3$) δ 7.42-7.30 (m, 2H), 7.23-7.02 (m, 6H), 6.95 (dd, J=6.3, 3.3 Hz, 1H), 6.82 (dt, J=9.0, 3.5 Hz, 1H), 6.43 (d, J=0.8 Hz, 1H), 4.45 (dt, J=10.7, 2.7 Hz, 1H), 3.98 (s, 2H), 3.83 (s, 3H), 3.49 (qd, J=7.1, 2.3 Hz, 1H), 2.92 (dd, J=16.3, 2.8 Hz, 1H), 2.50-2.37 (m, 4H), 2.33 (s, 3H), 1.40 (d, J=7.0 Hz, 3H) Analytical HPLC (orthogonal method): RT=9.42 min, HI: 93%. hGPR40 $EC_{50}$=57 nM. Example 69, isomer 2 (yellow solid, 4.5 mg, 0.008 mmol, 29% yield). LC-MS Anal. Calc'd for $C_{31}H_{30}FN_3O_4$ 527.22. found [M+H] 528.3. $^1$H NMR (400 MHz, $CDCl_3$) δ 7.43-7.30 (m, 2H), 7.22-7.02 (m, 6H), 6.95 (dd, J=6.3, 3.3 Hz, 1H), 6.81 (dt, J=8.8, 3.5 Hz, 1H), 6.43 (d, J=1.0 Hz, 1H), 4.45 (dt, J=10.7, 2.7 Hz, 1H), 3.98 (s, 2H), 3.83 (s, 3H), 3.49 (dd, J=7.0, 2.5 Hz, 1H), 2.92 (dd, J=16.3, 3.0 Hz, 1H), 2.52-2.37 (m, 4H), 2.33 (s, 3H), 1.40 (d, J=7.0 Hz, 3H) Analytical HPLC (orthogonal method): RT=11.22 min, HI: 98%. hGPR40 $EC_{50}$=2560 nM.

Example 70

2-((4S,5S)-1-(4-((5'-ethoxy-2'-fluoro-3-methyl-[1,1'-biphenyl]-4-yl)methyl)phenyl)-4-methyl-3-(trifluoromethyl)-4,5-dihydro-1H-pyrazol-5-yl)acetic acid

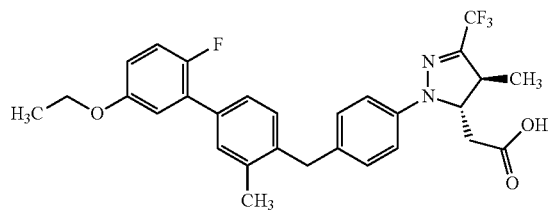 [SMILES: CCOc1ccc(F)c(-c2ccc(Cc3ccc(N4N=C(C(F)(F)F)[C@@H](C)[C@@H]4CC(=O)O)cc3)c(C)c2)c1]

Example 70. A mixture of Example 56A, ethyl 2-((4S,5S)-1-(4-((2'-fluoro-5'-hydroxy-3-methyl-[1,1'-biphenyl]-4-yl)methyl)phenyl)-4-methyl-3-(trifluoromethyl)-4,5-dihydro-1H-pyrazol-5-yl)acetate (39 mg, 0.074 mmol), cesium carbonate (71.2 mg, 0.369 mmol), bromoethane (54.7 µl, 0.738 mmol) and acetonitrile (738 µl) was heated at reflux for 1 h. The reaction mixture was cooled, and sat. aq $NaHCO_3$ (10 mL) was added slowly. The mixture was extracted with EtOAc (2×20 mL), and the combined organic extracts were washed successively with water (20 mL) and brine (20 mL). The organic layer was dried over $Na_2SO_4$, filtered, and concentrated. Purification via silica gel chromatography (0-60% EtOAc in Hexanes) gave ethyl 2-((4S,5S)-1-(4-((5'-ethoxy-2'-fluoro-3-methyl-[1,1'-biphenyl]-4-yl)methyl)phenyl)-4-methyl-3-(trifluoromethyl)-4,5-dihydro-1H-pyrazol-5-yl)acetate (30 mg, 0.054 mmol, 73.0% yield). To a stirred solution of ethyl 2-((4S,5S)-1-(4-((5'-ethoxy-2'-fluoro-3-methyl-[1,1'-biphenyl]-4-yl)methyl)phenyl)-4-methyl-3-(trifluoromethyl)-4,5-dihydro-1H-pyrazol-5-yl)acetate (30 mg, 0.054 mmol) in THF (1.5 mL) and water (0.15 mL) at rt was added 1.0 M aq lithium hydroxide (0.162 mL, 0.162 mmol). The reaction mixture was stirred for 1 h. The reaction mixture was partitioned between water (30 mL) and Hex (15 mL). The aqueous layer was acidified to pH 2.3 by dropwise addition of 1M HCl and the resulting mixture was extracted with $CH_2Cl_2$ (3×30 mL). The combined organic extracts were dried ($Na_2SO_4$), filtered and concentrated. The residue was dried under vacuum to afford Example 70 (25 mg, 0.047 mmol, 87% yield). LC-MS Anal. Calc'd for $C_{29}H_{28}F_4N_2O_3$ 528.20. found [M+H] 529. $^1$H NMR (500 MHz, $CDCl_3$) δ 7.40-7.29 (m, 2H), 7.16-7.08 (m, 3H), 7.07-7.00 (m, 3H), 6.96-6.91 (m, 1H), 6.82-6.76 (m, 1H), 4.42 (d, J=10.3 Hz, 1H), 4.03 (q, J=7.0 Hz, 2H), 3.96 (s, 1H), 3.80-3.73 (m, 1H), 3.26-3.16 (m, 1H), 2.90 (dd, J=16.6, 2.8 Hz, 1H), 2.45 (dd, J=16.6, 10.5 Hz, 1H), 2.33-2.27 (m, 3H), 1.90-1.81 (m, 1H), 1.41 (t, J=7.0 Hz, 3H), 1.34 (d, J=7.0 Hz, 3H). Analytical HPLC (orthogonal method): RT=11.0 min, HI: 99%. hGPR40 $EC_{50}$=120 nM.

Example 71

2-((4S,5S)-4-methyl-1-(4-(3-phenylpropyl)phenyl)-3-(trifluoromethyl)-4,5-dihydro-1H-pyrazol-5-yl)acetic acid

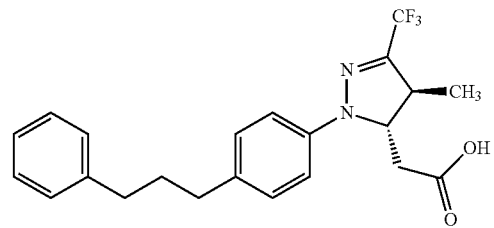 [SMILES: C[C@@H]1C(C(F)(F)F)=NN(c2ccc(CCCc3ccccc3)cc2)[C@H]1CC(=O)O]

71A. methyl 2-((4S,5S)-1-(4-cinnamylphenyl)-4-methyl-3-(trifluoromethyl)-4,5-dihydro-1H-pyrazol-5-yl)acetate was synthesized according to the method of example 58 to give 71A as a purple oil (0.032 g, 0.041 mmol, 93% yield). LC-MS Anal. Calc'd for $C_{23}H_{23}F_3N_2O_2$: 416.2 found [M+H] 415.1.

71B. A solution of methyl 2-((4S,5S)-1-(4-cinnamylphenyl)-4-methyl-3-(trifluoromethyl)-4,5-dihydro-1H-pyrazol-5-yl)acetate (0.032 g, 0.077 mmol) in EtOAc (0.768 ml) was purged 3× with vacuum and argon. Palladium on carbon (4.09 mg, 3.84 µmol) and AcOH (8.80 µl, 0.154 mmol) were added. Purged and stirred overnight under a balloon of $H_2$. The reaction was filtered over Celite, rinsed with EtOAc, and concentrated to methyl 2-((4S,5S)-4-methyl-1-(4-(3- phenylpropyl)phenyl)-3-(trifluoromethyl)-4,5-dihydro-1H-pyrazol-5-yl)acetate (0.015 g, 0.022 mmol, 28.9% yield) as a deep purple oil. LC-MS Anal. Calc'd for $C_{23}H_{25}F_3N_2O_2$: 418.5 found [M+H] 419.1.

Example 71. A solution of methyl 2-((4S,5S)-4-methyl-1-(4-(3-phenylpropyl)phenyl)-3-(trifluoromethyl)-4,5-dihydro-1H-pyrazol-5-yl)acetate (0.015 g, 0.036 mmol) and 0.5M LiOH (0.717 ml, 0.358 mmol) in THF (0.358 ml) stirred 16 h at rt. 1N HCl was added followed by extraction with EtOAc, washed with brine, dried over $Mg_2SO_4$, filtered and concentrated to give 17 mg of a yellow oil. The residue was purified via RP prep HPLC to give example 71 (0.011 g, 0.026 mmol, 73.9% yield) as a clear, colorless oil. LC-MS Anal. Calc'd for $C_{22}H_{23}F_3N_2O_2$: 404.2 found [M+H] 405.1. $^1$H NMR (400 MHz, $CDCl_3$) δ 7.33-7.28 (m, 2H), 7.23-7.17 (m, 3H), 7.13 (d, J=1.0 Hz, 2H), 7.04 (d, J=1.0 Hz, 2H), 4.45 (d, J=10.4 Hz, 1H), 3.22 (br. dd, J=6.9, 1.9 Hz, 1H), 2.91 (dd, J=16.5, 2.7 Hz, 1H), 2.72-2.55 (m, 4H), 2.54-2.36 (m, 2H), 2.01-1.82 (m, J=7.7, 7.7, 7.7, 7.7 Hz, 2H), 1.36 (d, J=7.1 Hz, 3H). Analytical HPLC (orthogonal method): RT=11.4 min, HI: 97%. hGPR40 $EC_{50}$=5760 nM.

Example 72

2-((4S,5S)-1-(4-(3-(3-fluorophenyl)propyl)phenyl)-4-methyl-3-(trifluoromethyl)-4,5-dihydro-1H-pyrazol-5-yl)acetic acid

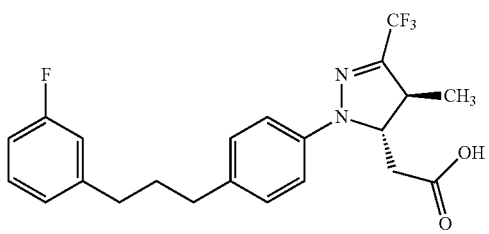 [SMILES: C[C@@H]1C(C(F)(F)F)=NN(c2ccc(CCCc3cccc(F)c3)cc2)[C@H]1CC(=O)O]

Example 72 was synthesized according to the method of Example 71 to give 2-((4S,5 S)-1-(4-(3-(3-fluorophenyl)propyl)phenyl)-4-methyl-3-(trifluoromethyl)-4,5-dihydro-1H-pyrazol-5-yl)acetic acid (yellow oil, 20 mg). LC-MS Anal. Calc'd for $C_{22}H_{22}F_4N_2O_2$: 422.2 found [M+H] 423.1. $^1$H NMR (400 MHz, $CDCl_3$) δ 7.26-7.20 (m, 1H), 7.14 (d, J=1.0 Hz, 2H), 7.05 (d, J=8.8 Hz, 2H), 6.96 (d, J=7.7 Hz, 1H), 6.93-6.85 (m, 2H), 4.45 (br. d, J=10.4 Hz, 1H), 3.29-3.17 (m, J=7.1, 2.2 Hz, 1H), 2.92 (dd, J=16.5, 2.7 Hz, 1H), 2.72-2.56 (m, 4H), 2.55-2.42 (m, 1H), 2.00-1.86 (m, 2H), 1.36 (d, J=7.1 Hz, 3H). Analytical HPLC (orthogonal method): RT=11.4 min, HI: 99.7%. hGPR40 $EC_{50}$=7020 nM.

Example 73

2-((4S,5 S)-1-(4-(3-(3-fluorophenyl)propyl)phenyl)-4-methyl-3-(trifluoromethyl)-4,5-dihydro-1H-pyrazol-5-yl)acetic acid

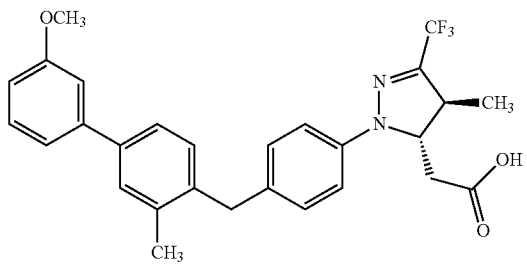 [SMILES: COc1cccc(-c2ccc(Cc3ccc(N4N=C(C(F)(F)F)[C@@H](C)[C@@H]4CC(=O)O)cc3)c(C)c2)c1]

73A. Methyl 2-((4S,5S)-1-(4-bromophenyl)-4-methyl-3-(trifluoromethyl)-4,5-dihydro-1H-pyrazol-5-yl)acetate. A solution of 58B, 2-((4S,5S)-1-(4-bromophenyl)-4-methyl-3-(trifluoromethyl)-4,5-dihydro-1H-pyrazol-5-yl)acetonitrile (170 mg, 0.49 mmol) in 3M HCl/methanol was stirred at 40° C. ovn. The reaction mixture was evaporated and diluted with EtOAc and aq. $NaHCO_3$. The layers were extracted, and the organic layer was dried ($Na_2SO_4$), filtered and concentrated. Purification via silica gel chromatography gave 100 mg (55%) of methyl 2-((4S,5S)-1-(4-bromophenyl)-4-methyl-3-(trifluoromethyl)-4,5-dihydro-1H-pyrazol-5-yl)acetate as a clear oil. LC-MS Anal. Calc'd for $C_{14}H_{14}BrF_3N_2O_2$: 378.02 found [M+H] 379, 381. $^1$H NMR (400 MHz, $CDCl_3$) δ 7.45-7.36 (m, 2H), 7.03-6.92 (m, 2H), 4.50-4.32 (m, 1H), 3.72 (s, 3H), 3.28-3.08 (m, 1H), 2.79 (dd, J=16.3, 3.0 Hz, 1H), 2.41 (dd, J=16.3, 10.3 Hz, 1H), 1.41-1.28 (m, 3H).

73B. methyl 2-((4S,5S)-1-(4-(4-chloro-2-methylbenzyl)phenyl)-4-methyl-3-(trifluoromethyl)-4,5-dihydro-1H-pyrazol-5-yl)acetate. A mixture of zinc dust (<10 μm) (27 mg, 0.42 mmol) in THF (0.5 mL) in a microwave vial was evacuated and refilled with Ar (3×), then treated with ethylene dibromide (2 μl, 0.02 mmol) and TMS-Cl (1 μl, 0.011 mmol), heated to 65° C. and stirred for 1 hr. Then, a solution of 1-(bromomethyl)-4-chloro-2-methylbenzene (60 mg, 0.28 mmol) in THF (0.5 mL) was added and the reaction was stirred at 65° C. for another hour. The reaction was then treated with a mixture of 73A (70 mg, 0.19 mmol) and tetrakis(triphenylphosphine)palladium(0) (21 mg, 0.018 mmol) in THF (1 mL), heated to 80° C. and stirred for 2 hrs. The reaction mixture was filtered through Celite and washed with EtOAc, then concentrated. The residue was purified via silica gel chromatography to give methyl 2-((4S,5S)-1-(4-(4-chloro-2-methylbenzyl)phenyl)-4-methyl-3-(trifluoromethyl)-4,5-dihydro-1H-pyrazol-5-yl)acetate (65 mg, 0.15 mmol, 80% yield) as a colorless oil.

73C. methyl 2-((4S,5S)-1-(4-((3'-methoxy-3-methyl-[1,1'-biphenyl]-4-yl)methyl)phenyl)-4-methyl-3-(trifluoromethyl)-4,5-dihydro-1H-pyrazol-5-yl)acetate. A mixture of methyl 2-((4S,5S)-1-(4-(4-chloro-2-methylbenzyl)phenyl)-4-methyl-3-(trifluoromethyl)-4,5-dihydro-1H-pyrazol-5-yl)acetate (25 mg, 0.057 mmol), (3-methoxyphenyl)boronic acid (17 mg, 0.11 mmol), 2-dicyclohexylphosphino-2',6'-dimethoxy-1,1'-biphenyl (19 mg, 0.046 mmol), palladium (II) acetate (5 mg, 0.023 mmol), and $K_3PO_4$ (31.4 mg, 0.148 mmol) in dioxane (1 mL) and water (0.10 mL) in a microwave vial was evacuated and refilled with Ar (3×), and was heated to 100° C. ovn. The reaction mixture was filtered and washed with EtOAc, then concentrated. The residue was purified via silica gel chromatography to give 72C methyl 2-((4S,5S)-1-(4-((3'-methoxy-3-methyl-[1,1'-biphenyl]-4-yl)methyl)phenyl)-4-methyl-3-(trifluoromethyl)-4,5-dihydro-1H-pyrazol-5-yl)acetate (19 mg, 0.037 mmol, 65% yield).

Example 73. A solution of methyl 2-((4S,5S)-1-(4-((3'-methoxy-3-methyl-[1,1'-biphenyl]-4-yl)methyl)phenyl)-4-methyl-3-(trifluoromethyl)-4,5-dihydro-1H-pyrazol-5-yl) acetate (19 mg, 0.037 mmol) in THF (0.5 mL) and water (0.500 mL) was treated with sodium hydroxide (0.037 mL, 0.037 mmol) and a few drops of MeOH, then stirred at rt overnight. Additional sodium hydroxide (0.074 mL, 0.074 mmol) was added and the reaction was stirred ovn. The reaction mixture was evaporated to remove THF, and was acidified with 1 N HCl and extracted with EtOAc (3×). The combined organic extracts were dried ($Na_2SO_4$), filtered, and concentrated. The residue was dissolved in MeOH, filtered and purified by reverse phase HPLC to afford Example 73 (10 mg, 0.020 mmol, 54.1% yield) as a colorless oil. LC-MS Anal. Calc'd for $C_{28}H_{27}F_3N_2O_3$: 496 found [M+H] 497.2. $^1$H NMR (400 MHz, $CDCl_3$) δ 7.41-7.32 (m, 3H), 7.19-7.10 (m, 5H), 7.08-7.02 (m, 2H), 6.88 (dd, J=8.3, 2.5 Hz, 1H), 4.44 (d, J=10.5 Hz, 1H), 3.97 (s, 2H), 3.87 (s, 3H), 3.22 (d, J=5.3 Hz, 1H), 2.91 (dd, J=16.6, 2.8 Hz, 1H), 2.47 (dd, J=16.4, 10.4 Hz, 1H), 2.32 (s, 3H), 1.35 (d, J=7.0 Hz, 3H). Analytical HPLC (orthogonal method): RT=14.7 min, HI: 99.9%. hGPR40 $EC_{50}$=37 nM.

Example 74

2-((4S,5 S)-1-(4-(4-(5-fluoro-2-methoxypyridin-4-yl)-2-methylbenzyl)phenyl)-4-methyl-3-(trifluoromethyl)-4,5-dihydro-1H-pyrazol-5-yl)acetic acid

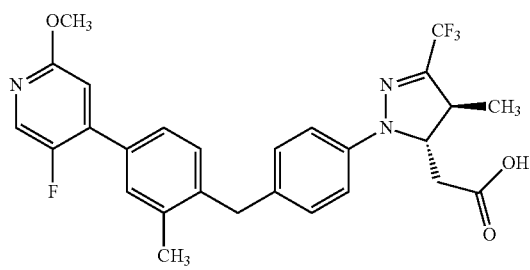 [SMILES: COc1cc(-c2ccc(Cc3ccc(N4N=C(C(F)(F)F)[C@@H](C)[C@@H]4CC(=O)O)cc3)c(C)c2)ccn1]

Example 74 (yellow oil, 3 mg) was synthesized according to the method of Example 72. LC-MS Anal. Calc'd for $C_{27}H_{25}F_4N_3O_3$: 515.2 found [M+H] 516.3. $^1$H NMR (400 MHz, $CD_3OD$) δ 8.03 (d, J=2.5 Hz, 1H), 7.44-7.36 (m, 2H), 7.24 (d, J=7.8 Hz, 1H), 7.14-7.04 (m, 4H), 6.88 (d, J=5.5 Hz, 1H), 4.49 (d, J=9.8 Hz, 1H), 4.00 (s, 2H), 3.91 (s, 3H), 2.81-2.62 (m, 2H), 2.40 (dd, J=16.2, 9.9 Hz, 1H), 2.30 (s, 3H), 1.31 (d, J=7.0 Hz, 3H). Analytical HPLC (orthogonal method): RT=15.4 min, HI: 98%. hGPR40 $EC_{50}$=210 nM.

Example 75

2-((4S,5S)-1-(4-(4-(2-methoxypyridin-4-yl)-2-methylbenzyl)phenyl)-4-methyl-3-(trifluoromethyl)-4,5-dihydro-1H-pyrazol-5-yl)acetic acid

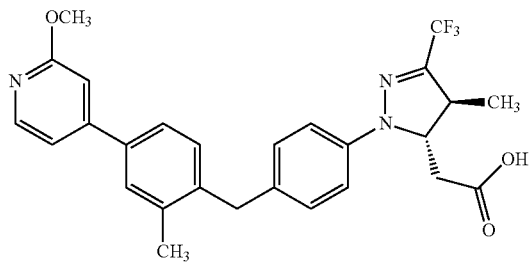

Example 75 (light yellow solid, 4 mg) was synthesized according to the method of Example 72. LC-MS Anal. Calc'd for $C_{27}H_{26}F_3N_3O_3$: 497.2 found [M+H] 498.3. $^1$H NMR (400 MHz, $CD_3OD$) δ 8.19 (d, J=5.8 Hz, 1H), 7.61-7.54 (m, 2H), 7.40 (dd, J=5.8, 1.5 Hz, 1H), 7.31-7.24 (m, 2H), 7.14-7.04 (m, 4H), 4.55-4.42 (m, 1H), 4.05 (s, 3H), 4.01 (s, 2H), 2.77 (dd, J=16.3, 3.0 Hz, 1H), 2.40 (dd, J=16.1, 10.0 Hz, 1H), 2.34 (s, 3H), 1.32 (d, J=7.0 Hz, 3H). Analytical HPLC (orthogonal method): RT=12.7 min, HI: 100%. hGPR40 $EC_{50}$=430 nM.

Example 76

2-((4S,5 S)-4-methyl-1-(4-(2-methyl-4-(pyrazin-2-yl)benzyl)phenyl)-3-(trifluoromethyl)-4,5-dihydro-1H-pyrazol-5-yl)acetic acid

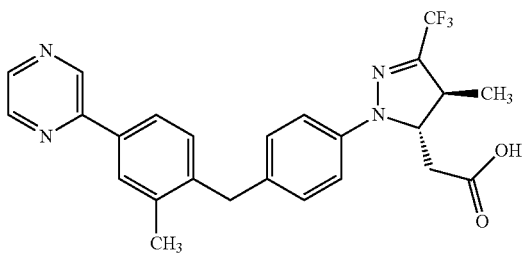 [SMILES: Cc1cc(-c2cnccn2)ccc1Cc1ccc(N2N=C(C(F)(F)F)[C@@H](C)[C@@H]2CC(=O)O)cc1]

Example 76 (yellow solid, 3 mg) was synthesized according to the method of Example 72. LC-MS Anal. Calc'd for $C_{25}H_{23}F_3N_4O_2$: 468.2 found [M+H] 469.2. $^1$H NMR (400 MHz, $CD_3OD$) δ 9.12-9.03 (m, 1H), 8.68-8.59 (m, 1H), 8.49 (d, J=2.5 Hz, 1H), 7.88 (s, 1H), 7.84 (d, J=8.0 Hz, 1H), 7.28 (d, J=8.0 Hz, 1H), 7.09 (q, J=8.7 Hz, 4H), 4.48 (d, J=9.5 Hz, 1H), 4.01 (s, 2H), 2.77 (dd, J=16.1, 3.0 Hz, 1H), 2.40 (dd, J=16.2, 9.9 Hz, 1H), 2.34 (s, 3H), 1.31 (d, J=7.0 Hz, 3H). Analytical HPLC (orthogonal method): RT=12.2 min, HI: 99.4%. hGPR40 $EC_{50}$=1620 nM.

Example 77

2-((4S,5S)-1-(4-(4-(2-methoxypyridin-3-yl)-2-methylbenzyl)phenyl)-4-methyl-3-(trifluoromethyl)-4,5-dihydro-1H-pyrazol-5-yl)acetic acid

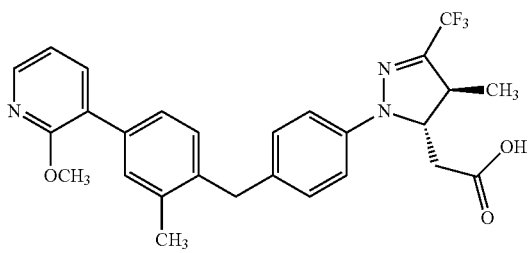 [SMILES: COc1ncccc1-c1ccc(Cc2ccc(N3N=C(C(F)(F)F)[C@@H](C)[C@@H]3CC(=O)O)cc2)c(C)c1]

Example 77 (1.2 mg) was synthesized according to the method of Example 72. LC-MS Anal. Calc'd for $C_{27}H_{26}F_3N_3O_3$: 497.2 found [M+H] 498; HI: 98%. hGPR40 $EC_{50}$=5370 nM.

Example 78

2-((4S,5S)-4-methyl-1-(4-(2-methyl-4-(pyridin-4-yl)benzyl)phenyl)-3-(trifluoromethyl)-4,5-dihydro-1H-pyrazol-5-yl)acetic acid

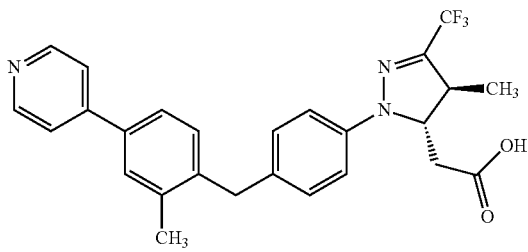 [SMILES: Cc1cc(-c2ccncc2)ccc1Cc1ccc(N2N=C(C(F)(F)F)[C@@H](C)[C@@H]2CC(=O)O)cc1]

Example 78 (1.2 mg) was synthesized according to the method of Example 72. LC-MS Anal. Calc'd for $C_{26}H_{24}F_3N_3O_2$: 467.2. found [M+H] 468; HI: 93%. hGPR40 $EC_{50}$=8330 nM.

What is claimed is:
1. A compound of Formula (I):

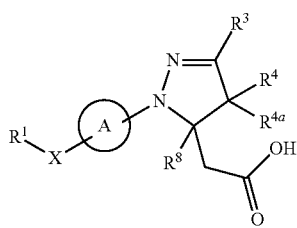

or a stereoisomer, a tautomer, or a pharmaceutically acceptable salt thereof, wherein:
X is independently selected from: O, S, $CH_2$, and $CH(C_{1-4}$ alkyl);

ring A is independently

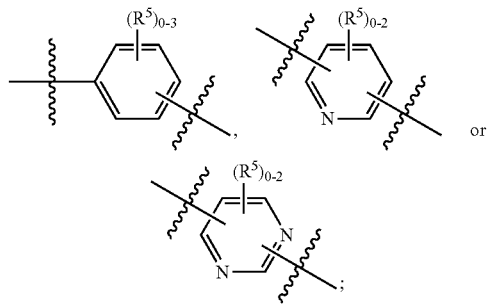

$R^1$ is

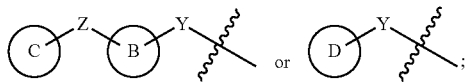

Y is independently selected from: a bond, $C_{1-4}$ alkylene, $C_{2-4}$ alkenylene, and $C_{2-4}$ alkynylene;
Z is independently selected from: a bond, W, $C_{1-4}$ alkylene, W—$C_{1-4}$ alkylene, and $C_{1-4}$ alkylene-W;
W is independently selected from: O, S and NH;
ring B and ring D are independently phenyl, naphthyl or a 5- to 6-membered heteroaryl containing carbon atoms and 1-4 heteroatoms selected from N, $NR^{11}$, O, and S; wherein said phenyl, naphthyl and heteroaryl are each substituted with 0-3 $R^2$;
ring C is independently phenyl, naphthyl or a 5- to 10-membered heteroaryl containing carbon atoms and 1-4 heteroatoms selected from N, $NR^{11}$, O, and S; wherein said phenyl, naphthyl and heteroaryl are each substituted with 0-3 $R^6$;
$R^2$, at each occurrence, is independently selected from: $C_{1-6}$ alkyl substituted with 0-2 $R^a$, $C_{2-6}$ alkenyl substituted with 0-2 $R^a$, $C_{1-6}$ alkoxy substituted with 0-2 $R^a$, $C_{1-6}$ alkylthio substituted with 0-2 $R^a$, halogen, $CHF_2$, $CF_3$, $OCF_3$, $OCHF_2$, $SCF_3$, CN, $NO_2$, $NH_2$, $NH(C_{1-4}$ alkyl), $N(C_{1-4}$ alkyl$)_2$, and a $C_{3-10}$ carbocycle substituted with 0-3 $R^b$;
$R^3$ is independently selected from: H, halogen, CN, OH, $CO_2H$, $C_{1-4}$ alkyl, $C_{1-4}$ alkenyl, $C_{1-4}$ alkynyl, $C_{1-4}$ haloalkyl, $OR^9$, $SR^9$, $C(O)OR^9$, $CO_2R^9$, $S(O)R^9$, $SO_2R^9$, $CONHR^9$, $CON(C_{1-4}$ alkyl$)_2$, —(O)$_n$—$(CH_2)_m$-phenyl, —$(CH_2)_m$-(5- to 10-membered heteroaryl containing carbon atoms and 1-4 heteroatoms selected from N, $NR^{11}$, O, and S); wherein said phenyl and heteroaryl are substituted with 0-2 $R^{10}$;
$R^4$ is independently selected from: H, $C_{1-4}$ alkyl substituted with 0-1 $R^c$, and —$(CH_2)_m$—$C_{3-6}$ carbocycle substituted with 0-2 $R^c$;
$R^{4a}$ is independently selected from: H, halogen, $C_{1-4}$ alkyl, and —$(CH_2)_m$—$C_{3-6}$ carbocycle;
$R^5$, at each occurrence, is independently selected from: halogen and $C_{1-4}$ alkyl;
$R^6$, at each occurrence, is independently selected from: halogen, OH, $C_{1-4}$ alkylthio, CN, $SO_2(C_{1-2}$ alkyl), $N(C_{1-4}$ alkyl$)_2$, $C_{1-4}$ haloalkyl, $C_{1-4}$ haloalkoxy, $C_{1-6}$ alkyl substituted with 0-1 $R^7$, $C_{1-4}$ alkoxy substituted with 0-1 $R^7$, —(O)$_n$—$(CH_2)_m$—$(C_{3-10}$ carbocycle substituted with 0-2 $R^7$), and —$(CH_2)_m$-(5- to 10-membered heteroaryl containing carbon atoms and 1-4 heteroatoms selected from N, NR$^{11}$, O, and S; wherein said heteroaryl is substituted with 0-2 R$^7$;

R$^7$, at each occurrence, is independently selected from: halogen, OH, C$_{1-4}$ alkyl, C$_{2-4}$ alkenyl, C$_{1-4}$ alkoxy, C$_{1-4}$ alkylthio, C$_{1-4}$ haloalkyl, C$_{1-4}$ haloalkoxy, SCF$_3$, CN, NO$_2$, NH$_2$, NH(C$_{1-4}$ alkyl), N(C$_{1-4}$ alkyl)$_2$, SO$_2$(C$_{1-2}$ alkyl), and phenyl;

R$^8$ is independently selected from: H and C$_{1-4}$ alkyl;

R$^9$, at each occurrence, is independently selected from: C$_{1-4}$ alkyl, C$_{1-4}$ haloalkyl and —(CH$_2$)$_m$-phenyl;

R$^{10}$, at each occurrence, is independently selected from: halogen, CN, C$_{1-4}$ haloalkyl, C$_{1-4}$ haloalkoxy, SCF$_3$, NO$_2$, and CO$_2$(C$_{1-4}$ alkyl);

R$^{11}$, at each occurrence, is independently selected from: H, C$_{1-4}$ alkyl and benzyl; R$^a$, at each occurrence, is independently selected from: OH, C$_{1-4}$ alkoxy, C$_{1-4}$ alkylthio, halogen, C$_{1-4}$ haloalkyl, C$_{1-4}$ haloalkoxy, SCF$_3$, CN, NO$_2$, NH$_2$, NH(C$_{1-4}$ alkyl), N(C$_{1-4}$ alkyl)$_2$, SO$_2$(C$_{1-2}$ alkyl) and phenyl;

R$^b$, at each occurrence, is independently selected from: OH, C$_{1-4}$ alkyl, C$_{2-4}$ alkenyl, C$_{1-4}$ alkoxy, C$_{1-4}$ alkylthio, halogen, C$_{1-4}$ haloalkyl, C$_{1-4}$ haloalkoxy, SCF$_3$, CN, NO$_2$, NH$_2$, NH(C$_{1-4}$ alkyl), N(C$_{1-4}$ alkyl)$_2$, and SO$_2$(C$_{1-2}$ alkyl);

R$^c$, at each occurrence, is independently selected from: OH, C$_{1-4}$ alkoxy, halogen, CF$_3$, OCF$_3$, and CN;

m, at each occurrence, is independently 0, 1, or 2; and n, at each occurrence, is independently 0 or 1.

2. A compound according claim 1, wherein the compound is of Formula (II):

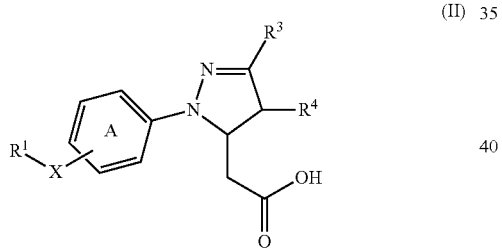

(II)

or a stereoisomer, a tautomer, or a pharmaceutically acceptable salt thereof, wherein:

X is independently selected from: O, S, CH$_2$, and CH(C$_{1-4}$ alkyl);

ring A is independently

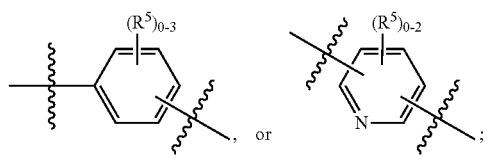

, or

R$^1$ is

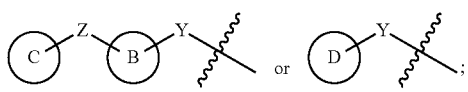

or

Y is independently selected from: a bond, C$_{1-4}$ alkylene, C$_{2-4}$ alkenylene, and C$_{2-4}$ alkynylene;

Z is independently selected from: a bond, W, C$_{1-4}$ alkylene, W—C$_{1-4}$ alkylene, and C$_{1-4}$ alkylene-W;

W is independently selected from: O, S and NH;

ring B and ring D are independently phenyl, naphthyl or a 5- to 6-membered heteroaryl containing carbon atoms and 1-4 heteroatoms selected from N, NR$^{11}$, O, and S; wherein said phenyl, naphthyl and heteroaryl are each substituted with 0-3 R$^2$;

ring C is independently phenyl, naphthyl or a 5- to 10-membered heteroaryl containing carbon atoms and 1-4 heteroatoms selected from N, NR$^{11}$, O, and S; wherein said phenyl, naphthyl and heteroaryl are each substituted with 0-3 R$^6$;

R$^2$, at each occurrence, is independently selected from: C$_{1-6}$ alkyl substituted with 0-2 R$^a$, C$_{2-6}$ alkenyl substituted with 0-2 R$^a$, C$_{1-6}$ alkoxy substituted with 0-2 R$^a$, C$_{1-6}$ alkylthio substituted with 0-2 R$^a$, halogen, C$_{1-4}$ haloalkyl, C$_{1-4}$ haloalkoxy, SCF$_3$, CN, NO$_2$, NH$_2$, NH(C$_{1-4}$ alkyl), N(C$_{1-4}$ alkyl)$_2$, and a C$_{3-10}$ carbocycle substituted with 0-3 R$^b$;

R$^3$ is independently selected from: H, halogen, CN, SO$_2$(C$_{1-4}$ alkyl), CONH(C$_{1-4}$ alkyl), CON(C$_{1-4}$ alkyl)$_2$, C$_{1-4}$ alkyl, C$_{1-4}$ alkoxy, C$_{1-4}$ alkylthio, C$_{1-4}$ haloalkyl, C$_{1-4}$ haloalkoxy, phenyl, benzyl, phenoxy, and a 5- to 10-membered heteroaryl containing carbon atoms and 1-4 heteroatoms selected from N, NR$^{11}$, O, and S; wherein said phenyl, benzyl, phenoxy and heteroaryl is substituted with 0-2 R$^{10}$;

R$^4$ is independently selected from: H, C$_{1-4}$ alkyl substituted with 0-1 R$^c$, and —(CH$_2$)$_m$—C$_{3-6}$ carbocycle substituted with 0-2 R$^c$;

R$^5$, at each occurrence, is independently selected from: halogen and C$_{1-4}$ alkyl;

R$^6$, at each occurrence, is independently selected from: halogen, OH, CH$_2$OH, C$_{1-4}$ alkylthio, CN, SO$_2$(C$_{1-2}$ alkyl), N(C$_{1-4}$ alkyl)$_2$, C$_{1-6}$ alkyl substituted with 0-1 R$^7$, C$_{1-4}$ alkoxy substituted with 0-1 R$^7$, C$_{1-4}$ haloalkyl, C$_{1-4}$ haloalkoxy, —(CH$_2$)$_m$-(phenyl substituted with 0-2 R$^7$), —O(CH$_2$)$_m$-(phenyl substituted with 0-2 R$^7$), —(CH$_2$)$_m$-(naphthyl substituted with 0-2 R$^7$), and —(CH$_2$)$_m$-(5- to 10-membered heteroaryl containing carbon atoms and 1-4 heteroatoms selected from the group consisting of N, O, and S; wherein said heteroaryl is substituted with 0-2 R$^7$;

R$^7$, at each occurrence, is independently selected from: OH, C$_{1-4}$ alkyl, C$_{2-4}$ alkenyl, C$_{1-4}$ alkoxy, C$_{1-4}$ alkylthio, halogen, C$_{1-4}$ haloalkyl, C$_{1-4}$ haloalkoxy, SCF$_3$, CN, NO$_2$, NH$_2$, NH(C$_{1-4}$ alkyl), N(C$_{1-4}$ alkyl)$_2$, SO$_2$ (C$_{1-2}$ alkyl), and phenyl;

R$^{10}$, at each occurrence, is independently selected from: halogen, CN, C$_{1-4}$ haloalkyl, C$_{1-4}$ haloalkoxy, SCF$_3$, NO$_2$, and CO$_2$(C$_{1-4}$ alkyl);

R$^{11}$, at each occurrence, is independently selected from: H, C$_{1-4}$ alkyl and benzyl; R$^a$, at each occurrence, is independently selected from: OH, C$_{1-4}$ alkoxy, C$_{1-4}$ alkylthio, halogen, C$_{1-4}$ haloalkyl, C$_{1-4}$ haloalkoxy, SCF$_3$, CN, NO$_2$, NH$_2$, NH(C$_{1-4}$ alkyl), N(C$_{1-4}$ alkyl)$_2$, SO$_2$(C$_{1-2}$ alkyl) and phenyl;

R$^b$, at each occurrence, is independently selected from: OH, C$_{1-4}$ alkyl, C$_{2-4}$ alkenyl, C$_{1-4}$ alkoxy, C$_{1-4}$ alkylthio, halogen, C$_{1-4}$ haloalkyl, C$_{1-4}$ haloalkoxy SCF$_3$, CN, NO$_2$, NH$_2$, NH(C$_{1-4}$ alkyl), N(C$_{1-4}$ alkyl)$_2$, and SO$_2$(C$_{1-2}$ alkyl);

$R^c$, at each occurrence, is independently selected from: OH, $C_{1-4}$ alkoxy, halogen, $C_{1-4}$ haloalkyl, $C_{1-4}$ haloalkoxy, and CN; and m, at each occurrence, is independently 0, 1, or 2.

3. A compound according to claim 1, wherein:

X is independently selected from: O, S, and $CH_2$;

ring A is independently

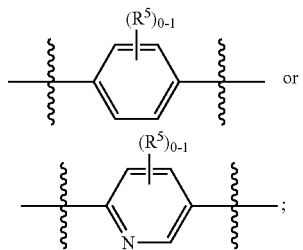

Y is independently selected from: a bond, $CH_2$, $CH_2CH_2$, and $-CH=CHCH_2-$;

Z is independently selected from: a bond, O, $CH_2$, $CH_2CH_2$, and $OCH_2$;

ring B and ring D are independently phenyl substituted with 0-3 $R^2$, or a heteroaryl substituted with 0-1 $R^2$ and selected from: thiazolyl, oxazolyl, pyrazolyl, pyridinyl, pyrimidinyl, pyrazinyl, and pyridazinyl;

ring C is independently phenyl substituted with 0-3 $R^6$ or a heteroaryl substituted with 0-2 $R^6$; wherein said heteroaryl is selected from: furanyl, oxazolyl, thiazolyl, pyrazolyl, pyridinyl, pyrimidinyl, pyrazinyl, and pyridazinyl;

$R^2$, at each occurrence, is independently selected from: $C_{1-6}$ alkyl, $C_{1-6}$ alkoxy, halogen, CN, cyclopropyl, and 5,5-diMe-cyclopent-1-enyl;

$R^3$ is independently selected from: halogen, CN, $CF_3$, $CF_2CF_3$, $CO_2H$, $SO_2(C_{1-4}$ alkyl), $CONH(C_{1-4}$ alkyl), $CON(C_{1-4}$ alkyl)$_2$, oxazolyl,

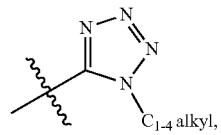

5-$C_{1-4}$ alkyl-isoxazol-3-yl, 1-$C_{1-4}$ alkyl-pyrazol-3-yl, pyridyl, pyrimidinyl, and phenyl substituted with 0-1 halo; and $R^6$, at each occurrence, is independently selected from: halogen, OH, $CH_2OH$, $C_{1-4}$ alkylthio, CN, $SO_2(C_{1-2}$ alkyl), $N(C_{1-4}$ alkyl)$_2$, $C_{1-6}$ alkyl, $C_{1-4}$ alkoxy, $C_{1-4}$ haloalkyl, and $C_{1-4}$ haloalkoxy.

4. A compound according to claim 1, wherein:

ring A is

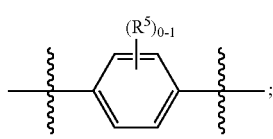

ring B and ring D are independently phenyl substituted with 0-3 $R^2$, pyridinyl substituted with 0-2 $R^2$ or pyrimidinyl substituted with 0-2 $R^2$;

ring C is independently phenyl substituted with 0-3 $R^6$, pyridinyl substituted with 0-2 $R^6$, pyrimidinyl substituted with 0-2 $R^2$, or pyrazinyl substituted with 0-2 $R^6$; and $R^4$ is independently selected from: H, $C_{1-4}$ alkyl substituted with 0-1 $R^c$, $C_{3-6}$ carbocycle and $-CH_2-C_{3-6}$ carbocycle.

5. A compound according to claim 1, wherein the compound is of Formula (III):

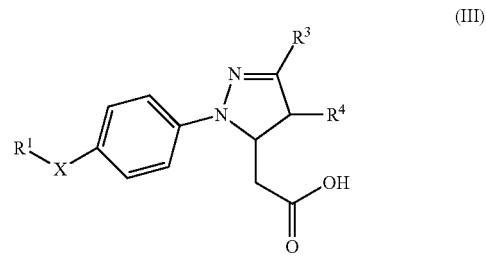

or a stereoisomer, a tautomer, or a pharmaceutically acceptable salt thereof, wherein X is independently selected from: O and $CH_2$;

$R^1$ independently selected from: phenyl substituted with 0-3 $R^2$, benzyl substituted with 0-3 $R^2$,

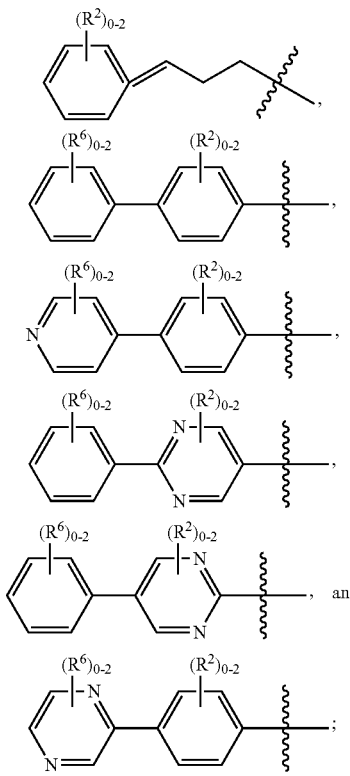

$R^2$, at each occurrence, is independently selected from: halogen, $C_{1-4}$ alkyl, and $C_{1-4}$ alkoxy;

$R^3$ is independently selected from: CN, $CF_3$, $SO_2(C_{1-4}$ alkyl), $CON(C_{1-4}$ alkyl)$_2$, oxazol-2-yl,

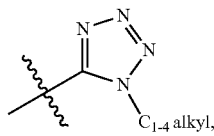

1-$C_{1-4}$ alkyl-pyrazol-3-yl, 5-$C_{1-4}$ alkyl-isoxazol-3-yl, pyrid-2-yl, pyrimidin-2-yl, and phenyl substituted with 0-1 halogen;

$R^4$ is independently selected from: H, $C_{1-4}$ alkyl substituted with 0-1 $R^c$, $C_{3-6}$ cycloalkyl, —CH$_2$—$C_{3-6}$ cycloalkyl, and Ph; and $R^6$, at each occurrence, is independently selected from: halogen, OH, CN, $C_{1-4}$ alkyl, $C_{1-4}$ alkoxy, $C_{1-4}$ haloalkyl, and $C_{1-4}$ haloalkoxy.

6. A compound according to claim 5, wherein:
$R^1$ is independently

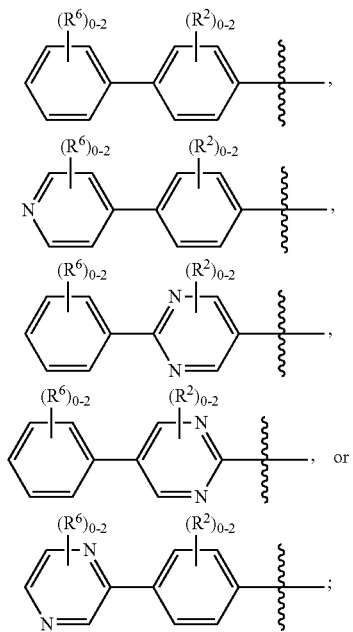

$R^2$, at each occurrence, is independently selected from: halo and $C_{1-4}$ alkyl;

$R^3$ is independently selected from: CN, CF$_3$, Ph, 3-halo-Ph, 4-halo-Ph, oxazolyl, 5-$C_{1-4}$ alkyl-isoxazol-3-yl, pyridyl and pyrimidinyl; and $R^6$, at each occurrence, is independently selected from: halogen, OH, CN, CF$_3$, OCF$_3$, $C_{1-4}$ alkyl, and $C_{1-4}$ alkoxy.

7. A compound according to claim 6, wherein:
$R^1$ is independently selected from: 4-(3-$C_{1-4}$ alkoxy-Ph)-2-$C_{1-4}$ alkyl-Ph, 4-(2-halo-5-OH-Ph)-2-$C_{1-4}$ alkyl-Ph, 4-(2-halo-5-$C_{1-4}$ alkoxy-Ph)-2-$C_{1-4}$ alkyl-Ph, 4-(2-halo-5-CN-Ph)-2-$C_{1-4}$ alkyl-Ph, 4-(2-halo-5-$C_{1-4}$ alkoxy-Ph)-3-$C_{1-4}$ alkyl-Ph, 4-(2-halo-5-CF$_3$-Ph)-3-$C_{1-4}$ alkyl-Ph, 4-(2-halo-5-OCF$_3$-Ph)-3-$C_{1-4}$ alkyl-Ph, 4-(2-halo-5-$C_{1-4}$ alkoxy-Ph)-2-halo-Ph, 4-(3-$C_{1-4}$ alkoxy-Ph)-2-$C_{1-4}$ alkyl-5-$C_{1-4}$ alkyl-Ph, 4-(2-halo-5-$C_{1-4}$ alkoxy-Ph)-2-$C_{1-4}$ alkyl-5-$C_{1-4}$ alkyl-Ph, 4-(2-halo-5-$C_{1-4}$ alkoxy-Ph)-2-$C_{1-4}$ alkyl-5-halo-Ph, 4-(2-halo-5-$C_{1-4}$ alkoxy-Ph)-2-$C_{1-4}$ alkyl-6-halo-Ph, 4-(2-$C_{1-4}$ alkoxy-pyrid-4-yl)-2-$C_{1-4}$ alkyl-Ph, 4-(3-halo-6-$C_{1-4}$ alkoxy-pyrid-4-yl)-2-$C_{1-4}$ alkyl-Ph, 4-(pyrazin-2-yl)-2-$C_{1-4}$ alkyl-Ph, 2-Ph-4-$C_{1-4}$ alkyl-pyrimidin-5-yl, 5-(2-halo-5-$C_{1-4}$ alkoxy-Ph)-pyrimidin-2-yl, 2-(2-halo-5-$C_{1-4}$ alkoxy-Ph)-4-$C_{1-4}$ alkyl-pyrimidin-5-yl; and $R^3$ is independently selected from: CN, CF$_3$, Ph, 3-halo-Ph, 4-halo-Ph, oxazol-2-yl, 5-$C_{1-4}$ alkyl-isoxazol-3-yl, pyrid-2-yl and pyrimidin-2-yl.

8. A compound according to claim 7, wherein:
$R^1$ is independently selected from: 4-(3-$C_{1-4}$ alkoxy-Ph)-2-$C_{1-4}$ alkyl-Ph, 4-(2-halo-5-OH-Ph)-2-$C_{1-4}$ alkyl-Ph, 4-(2-halo-5-$C_{1-4}$ alkoxy-Ph)-2-$C_{1-4}$ alkyl-Ph, 4-(2-halo-5-CN-Ph)-2-$C_{1-4}$ alkyl-Ph, 4-(2-halo-5-$C_{1-4}$ alkoxy-Ph)-3-$C_{1-4}$ alkyl-Ph, 4-(2-halo-5-OCF$_3$-Ph)-3-$C_{1-4}$ alkyl-Ph, 4-(2-halo-5-$C_{1-4}$ alkoxy-Ph)-2-halo-Ph, 4-(2-halo-5-$C_{1-4}$ alkoxy-Ph)-2-$C_{1-4}$ alkyl-5-$C_{1-4}$ alkyl-Ph, 4-(2-halo-5-$C_{1-4}$ alkoxy-Ph)-2-$C_{1-4}$ alkyl-6-halo-Ph, 4-(2-$C_{1-4}$ alkoxy-pyrid-4-yl)-2-$C_{1-4}$ alkyl-Ph, 4-(3-halo-6-$C_{1-4}$ alkoxy-pyrid-4-yl)-2-$C_{1-4}$ alkyl-Ph, and 2-(2-halo-5-$C_{1-4}$ alkoxy-Ph)-4-$C_{1-4}$ alkyl-pyrimidin-5-yl;

$R^3$ is independently selected from: CN, CF$_3$, Ph, 3-halo-Ph, 4-halo-Ph, 5-$C_{1-4}$ alkyl-isoxazol-3-yl, pyrid-2-yl and pyrimidin-2-yl; and $R^4$ is independently selected from: H, $C_{1-4}$ alkyl, —CH$_2$OH, —CH$_2$O($C_{1-4}$ alkyl), —CH$_2$CN, $C_{3-6}$ cycloalkyl and —CH$_2$—$C_{3-6}$ cycloalkyl.

9. A compound according to claim 5, wherein:
$R^1$ is independently selected from: 4-(3-$C_{1-4}$ alkoxy-Ph)-2-$C_{1-4}$ alkyl-Ph, 4-(2-halo-5-OH-Ph)-2-$C_{1-4}$ alkyl-Ph, 4-(2-halo-5-$C_{1-4}$ alkoxy-Ph)-2-$C_{1-4}$ alkyl-Ph, 4-(2-halo-5-CN-Ph)-2-$C_{1-4}$ alkyl-Ph, 4-(2-halo-5-$C_{1-4}$ alkoxy-Ph)-2-halo-Ph, 4-(2-halo-5-$C_{1-4}$ alkoxy-Ph)-2-$C_{1-4}$ alkyl-5-$C_{1-4}$ alkyl-Ph, and 4-(3-halo-6-$C_{1-4}$ alkoxy-pyrid-4-yl)-2-$C_{1-4}$ alkyl-Ph;

$R^3$ is independently selected from: CN, CF$_3$, Ph, 3-halo-Ph, 4-halo-Ph, 5-$C_{1-4}$ alkyl-isoxazol-3-yl, and pyrid-2-yl; and $R^4$ is independently selected from: H, $C_{1-4}$ alkyl, —CH$_2$OH, —CH$_2$O($C_{1-4}$ alkyl), $C_{3-6}$ cycloalkyl and —CH$_2$—$C_{3-6}$ cycloalkyl.

10. A compound according to claim 1, wherein the compound is selected from the group consisting of,

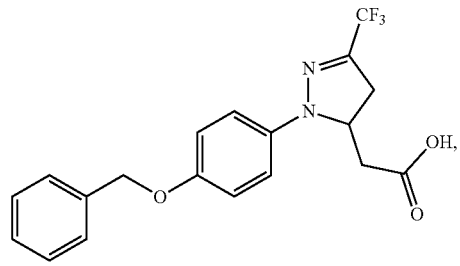

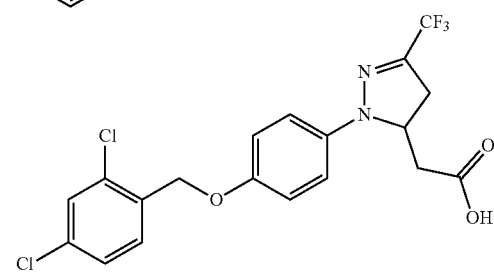

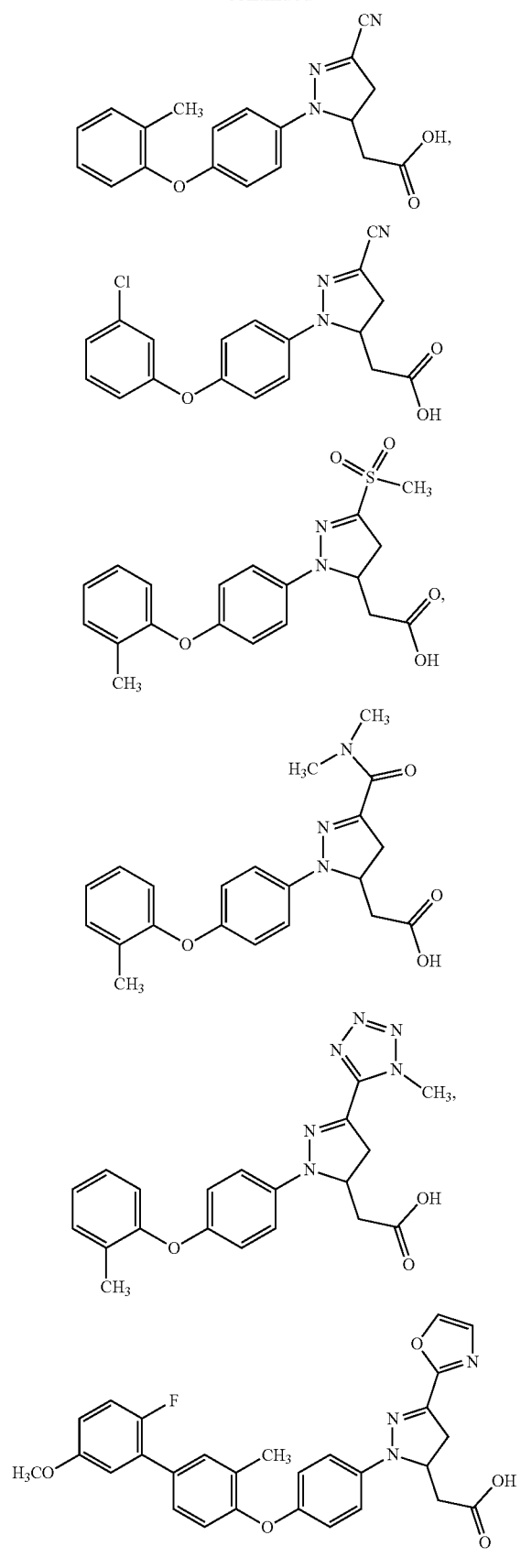
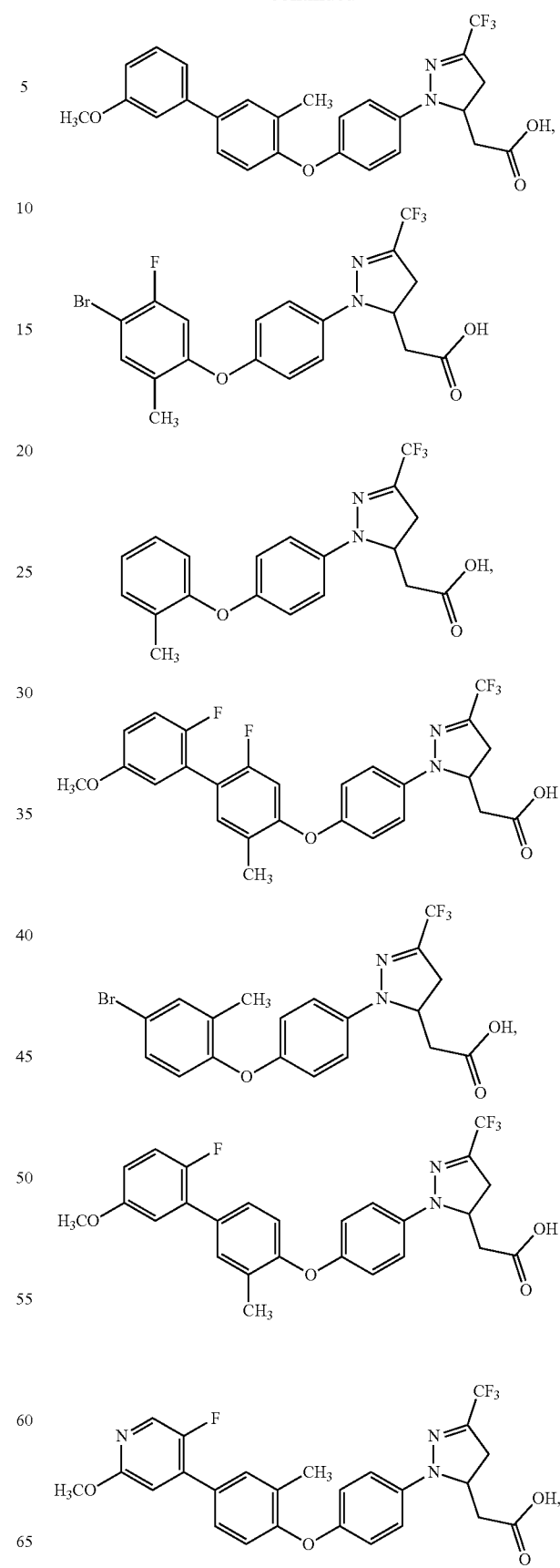

127
-continued
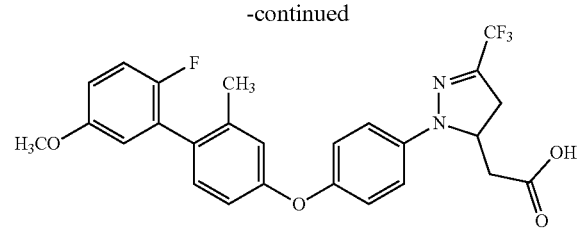
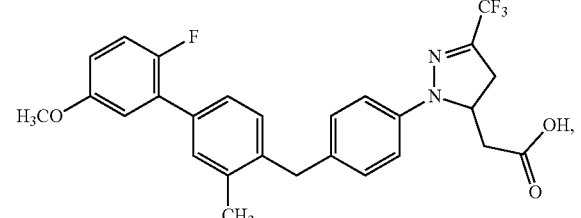
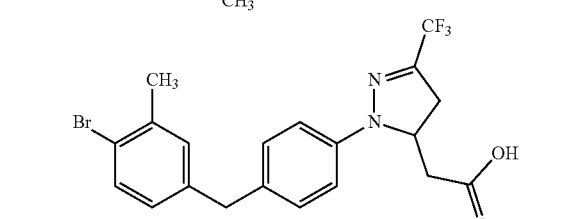
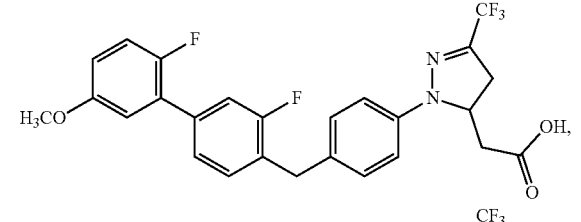
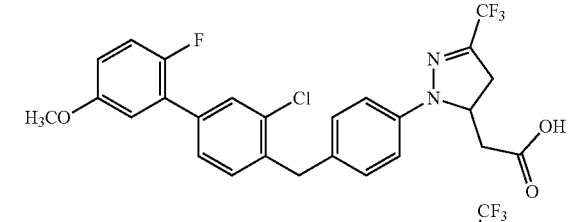
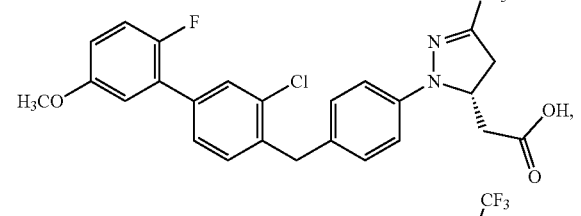
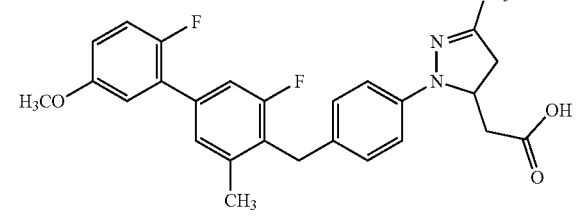
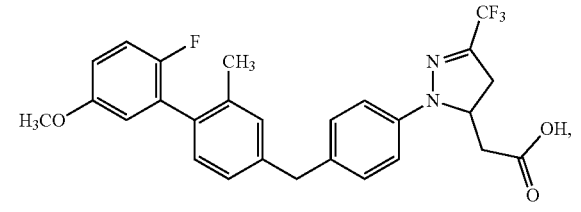
128
-continued
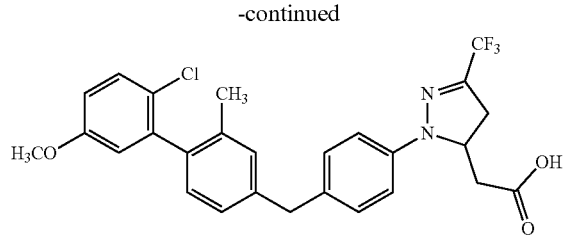
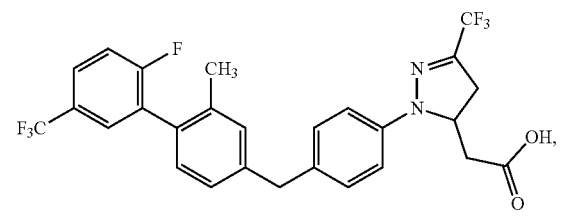
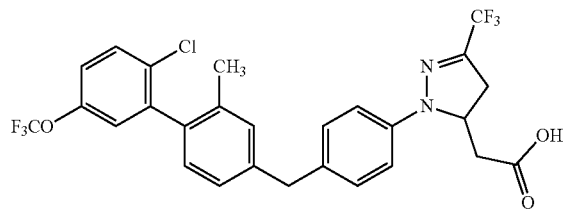
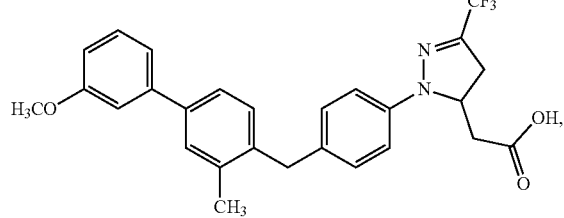
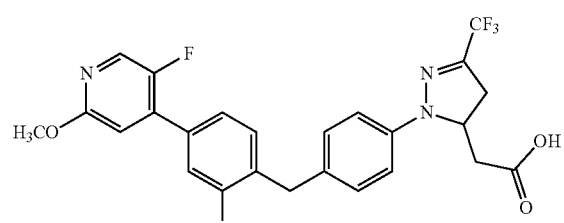
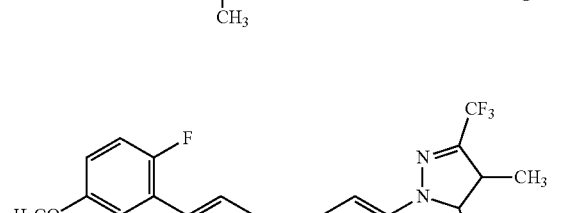
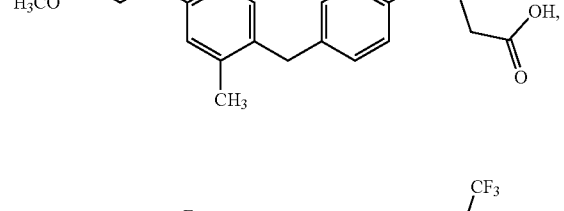
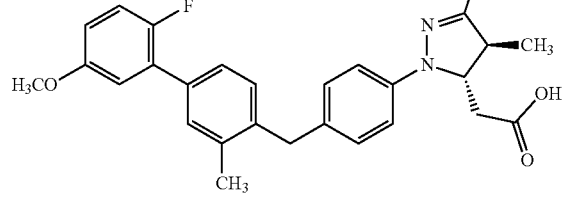

129
-continued
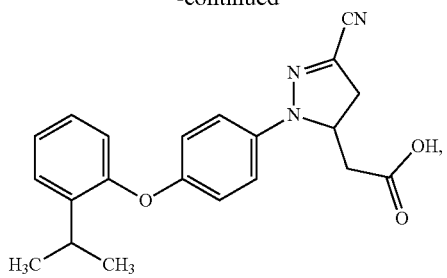
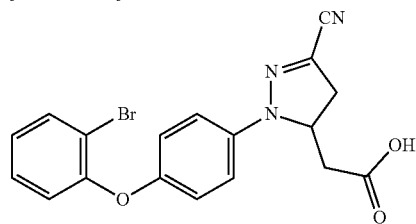
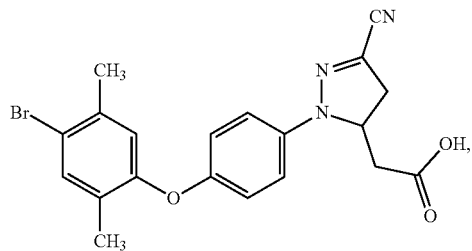
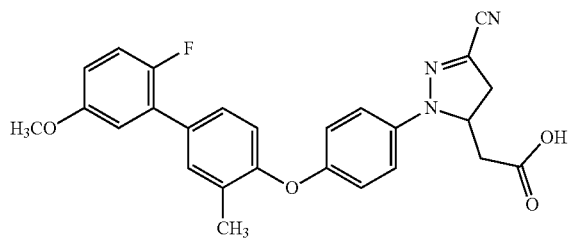
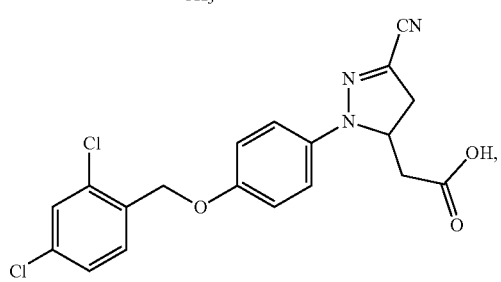
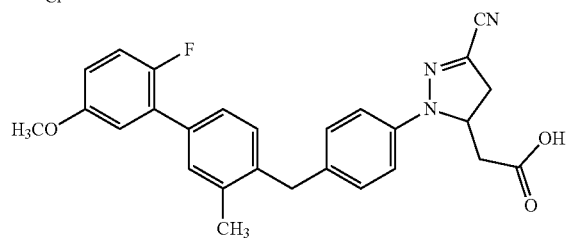
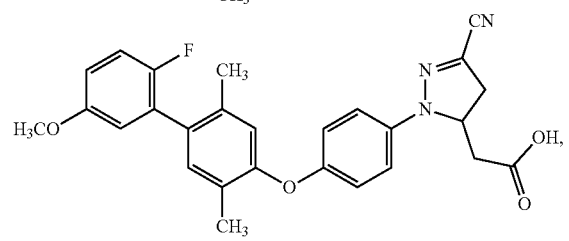
130
-continued
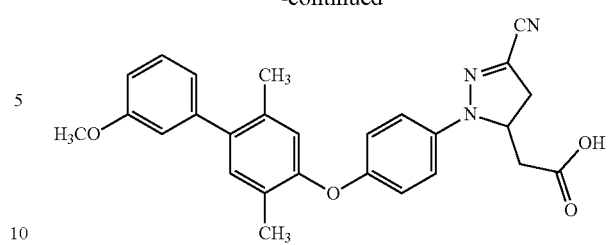
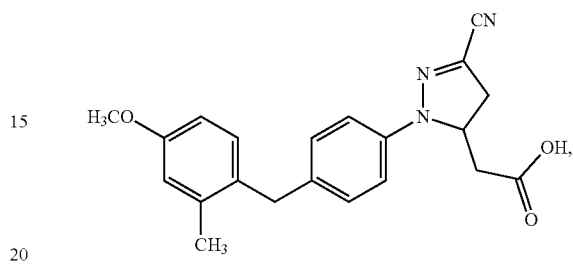
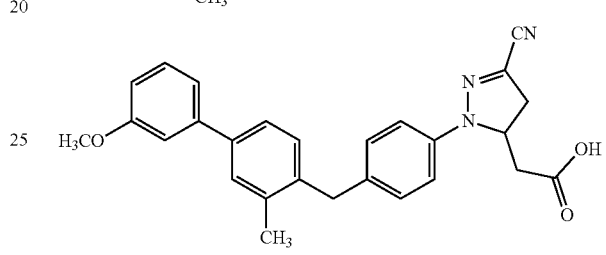
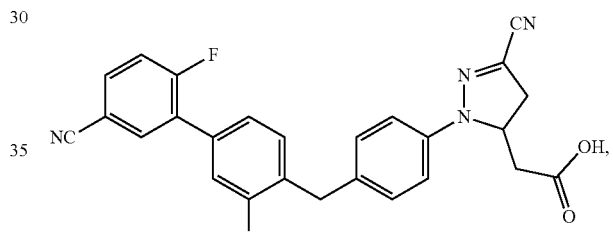
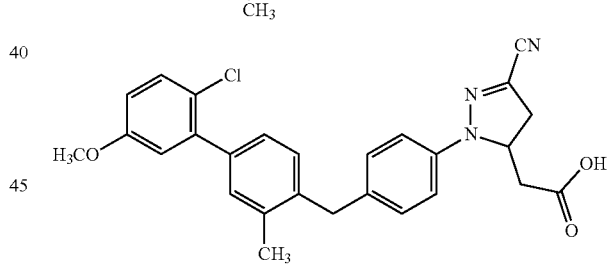
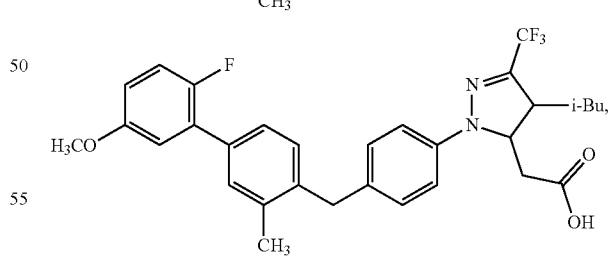
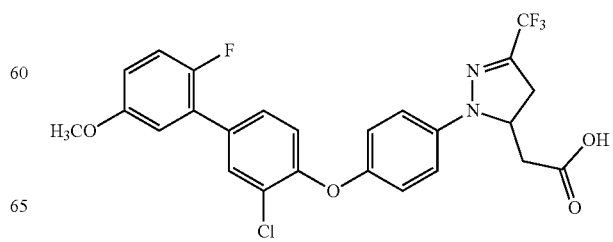

131
-continued
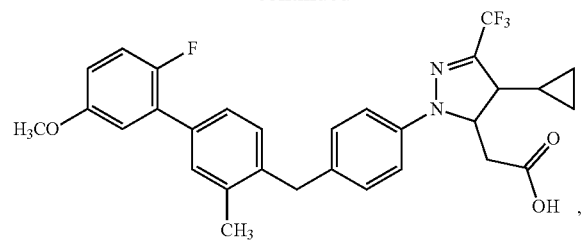
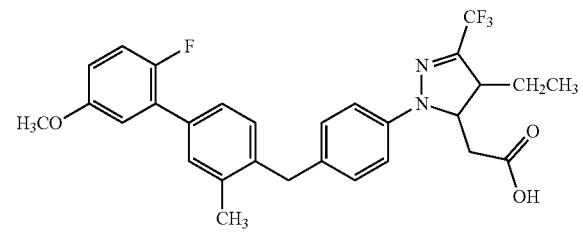
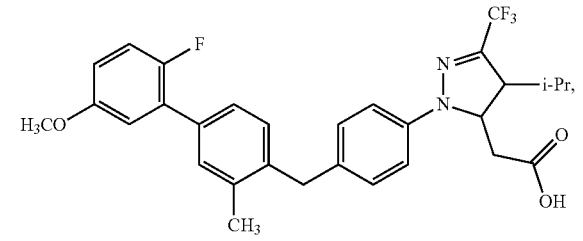
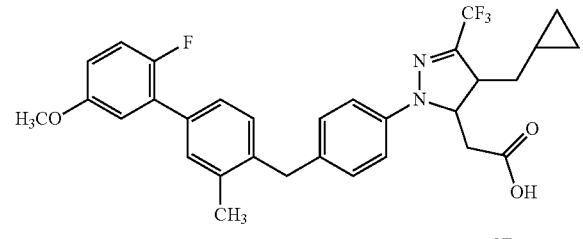
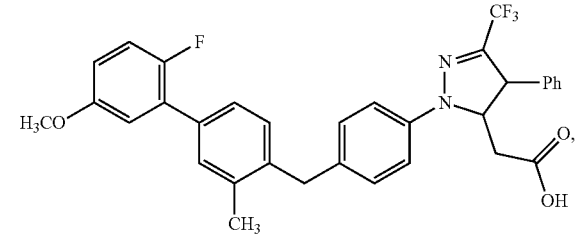
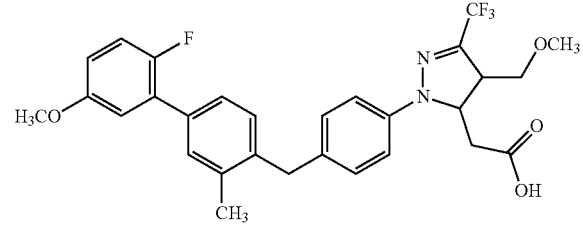
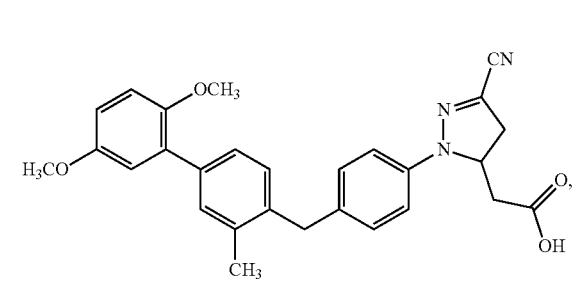
132
-continued
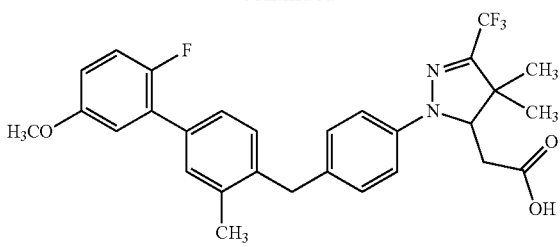
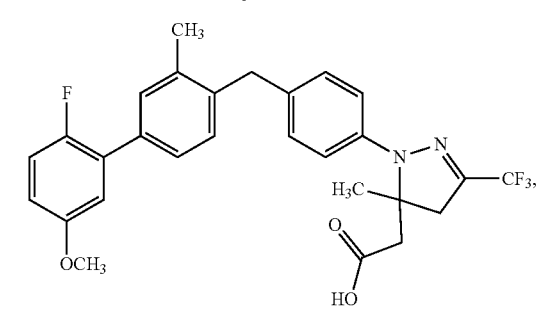
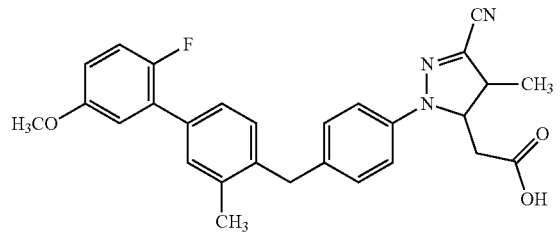
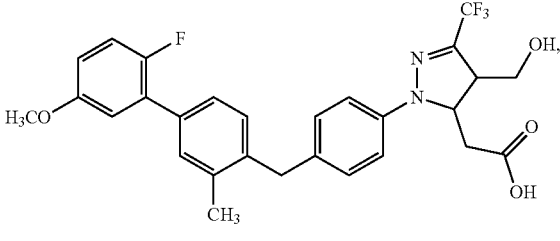
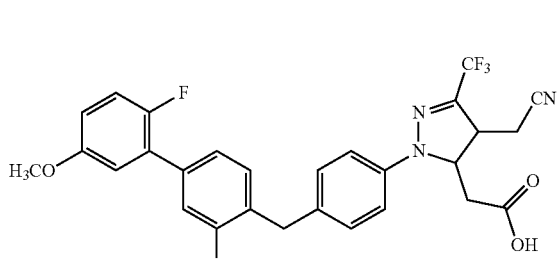
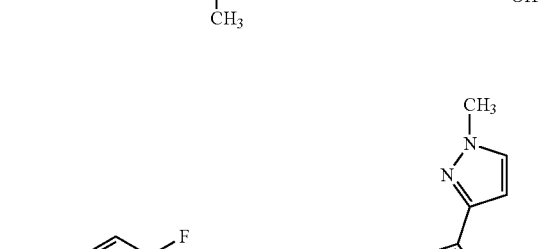
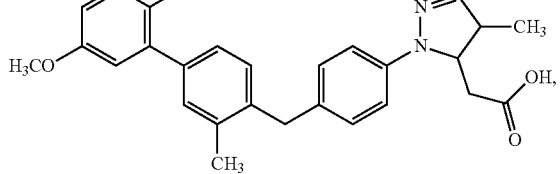

133
-continued
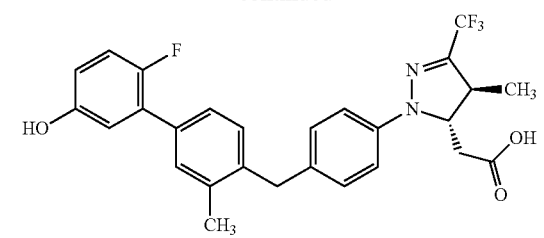
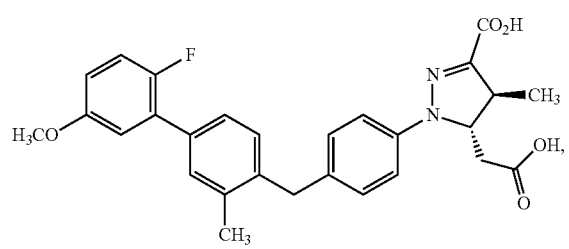
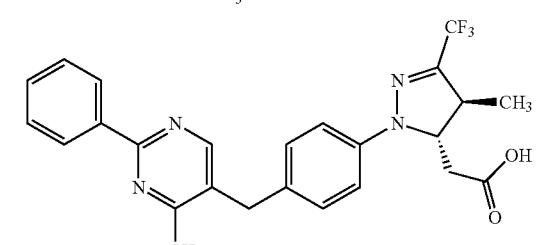
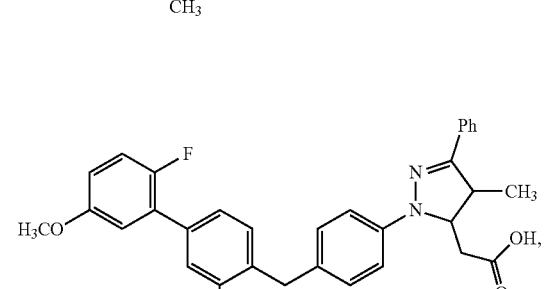
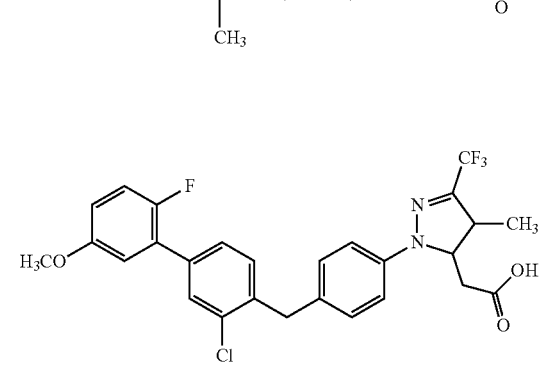
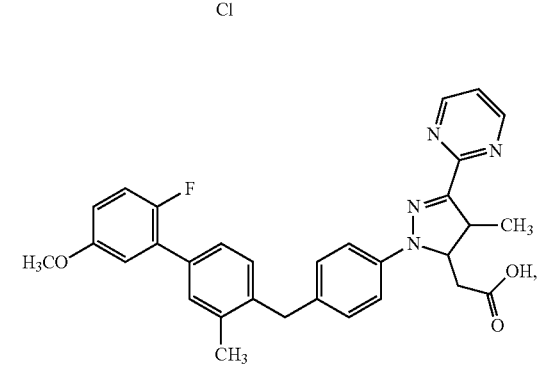
134
-continued
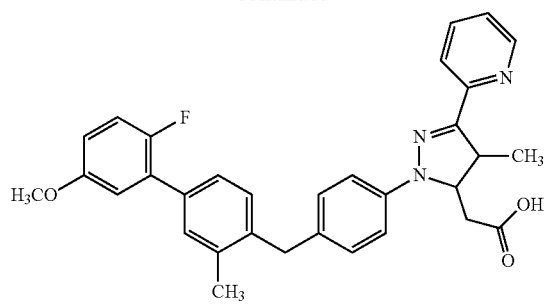
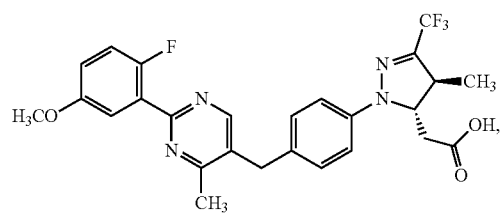
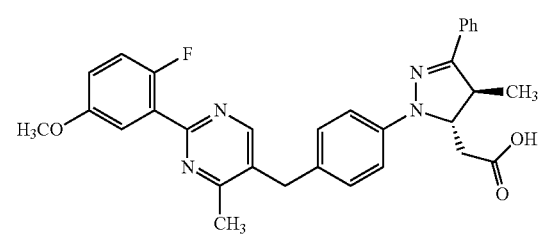
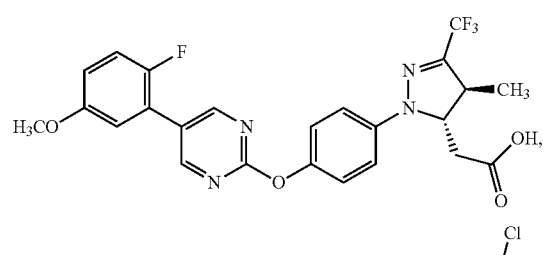
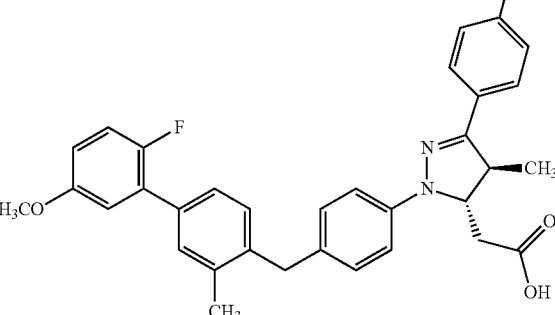
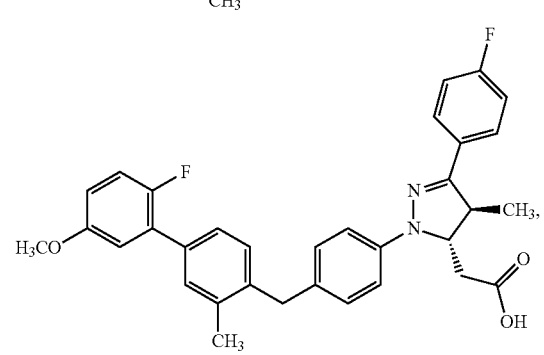

-continued

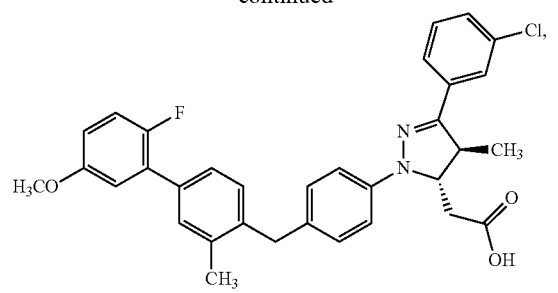
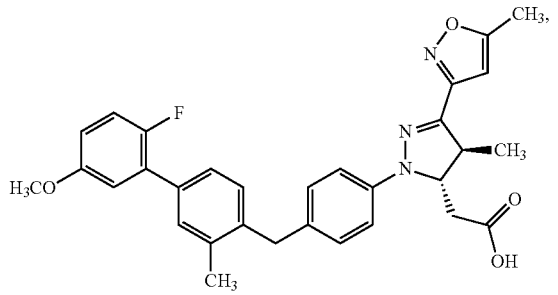
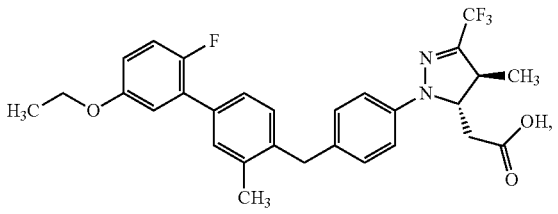
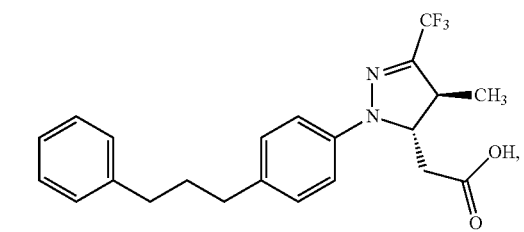
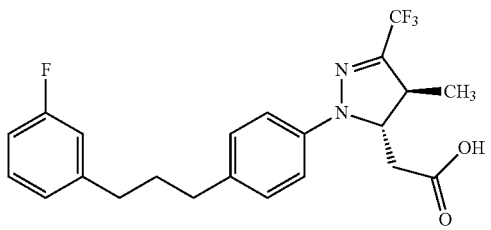
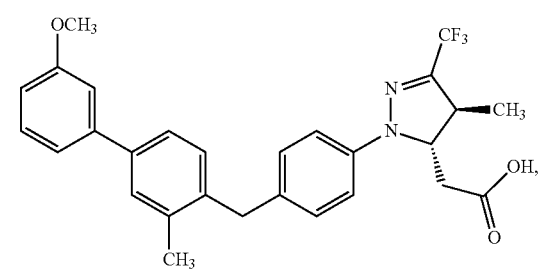

-continued

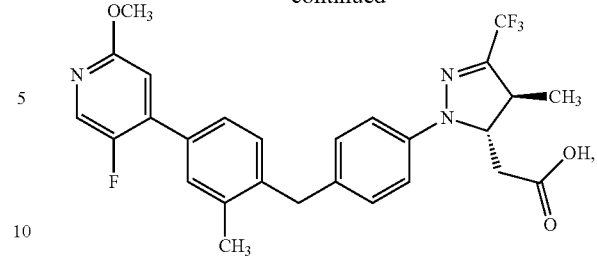
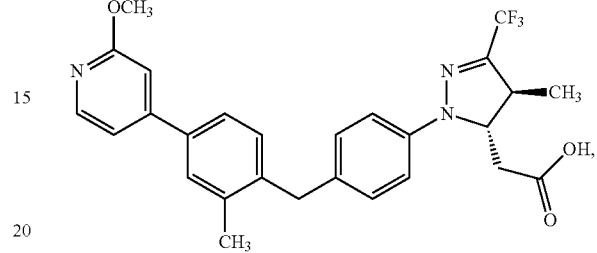
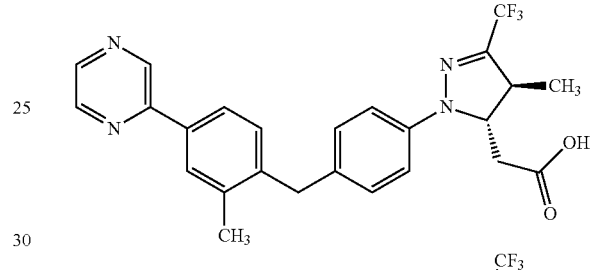
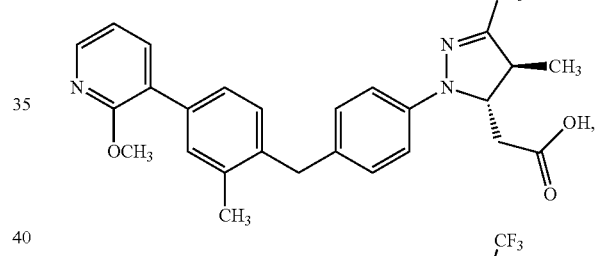
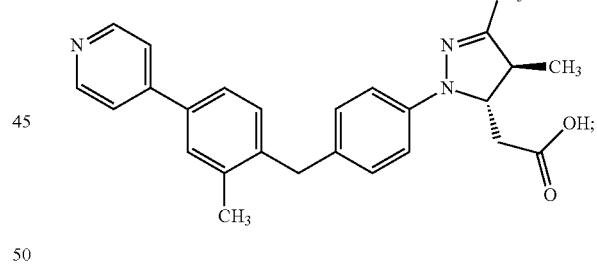

or a pharmaceutically acceptable salt thereof.

11. A pharmaceutical composition, comprising: a pharmaceutically acceptable carrier and a compound of claim 1, or a stereoisomer, a tautomer, or a pharmaceutically acceptable salt thereof.

12. The pharmaceutical composition according to claim 11, further comprising one or more other suitable therapeutic agents useful in the treatment of one or more disorders selected from the group consisting of anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, antidementia agents, cognition promoting agents, appetite suppressants, treatments for heart failure, treatments for peripheral arterial disease and anti-inflammatory agents.

13. The pharmaceutical composition according to claim 11, further comprising a dipeptidyl peptidase-IV inhibitor and/or a sodium-glucose transporter-2 inhibitor.

14. A method of modulating or treating one of more diseases, disorders or conditions comprising administering a compound of claim 1, or a stereoisomer, a tautomer, or a pharmaceutically acceptable salt thereof, to a patient in need thereof; wherein the disease, disorder or condition is selected from the group consisting of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), non-cardiac ischemia, pancreatitis, lipid disorders, neurodegenerative disease, cognitive impairment, dementia, NASH (Non-Alcoholic SteatoHepatitis), NAFLD (Non-Alcoholic Fatty Liver Disease) and liver cirrhosis.

15. The method according to claim 14, wherein an additional therapeutic agent is administered simultaneously, separately or sequentially with the compound of claim 1, or a stereoisomer, a tautomer, or a pharmaceutically acceptable salt thereof.

* * * * *

UNITED STATES PATENT AND TRADEMARK OFFICE
CERTIFICATE OF CORRECTION

PATENT NO. : 9,656,963 B2
APPLICATION NO. : 14/442624
DATED : May 23, 2017
INVENTOR(S) : Andres S. Hernandez et al.

It is certified that error appears in the above-identified patent and that said Letters Patent is hereby corrected as shown below:

In the Claims

Claim 5, Column 122, Lines 31-36:

Delete " 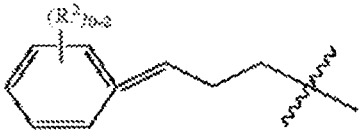 " and insert -- 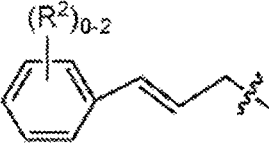 --, therefor.

Signed and Sealed this
Twelfth Day of June, 2018

Andrei Iancu
*Director of the United States Patent and Trademark Office*